US009394571B2

(12) United States Patent
Ramseier et al.

(10) Patent No.: US 9,394,571 B2
(45) Date of Patent: Jul. 19, 2016

(54) METHOD FOR RAPIDLY SCREENING MICROBIAL HOSTS TO IDENTIFY CERTAIN STRAINS WITH IMPROVED YIELD AND/OR QUALITY IN THE EXPRESSION OF HETEROLOGOUS PROTEINS

(75) Inventors: Thomas M. Ramseier, Carmel, IN (US); Russell J. Coleman, San Diego, CA (US); Jane C. Schneider, San Diego, CA (US); Charles D. Hershberger, Fremont, CA (US); Diane M. Retallack, Poway, CA (US); Charles H. Squires, Poway, CA (US)

(73) Assignee: PFENEX INC., San Diego, CA (US)

( * ) Notice: Subject to any disclaimer, the term of this patent is extended or adjusted under 35 U.S.C. 154(b) by 475 days.

(21) Appl. No.: 12/109,554

(22) Filed: Apr. 25, 2008

(65) Prior Publication Data

US 2008/0269070 A1    Oct. 30, 2008

Related U.S. Application Data

(60) Provisional application No. 60/914,361, filed on Apr. 27, 2007.

(51) Int. Cl.
| | | |
|---|---|---|
| G01N 33/554 | (2006.01) | |
| C12N 1/20 | (2006.01) | |
| C12N 15/00 | (2006.01) | |
| C12P 21/04 | (2006.01) | |
| C12P 21/06 | (2006.01) | |
| C07H 21/04 | (2006.01) | |
| C12Q 1/68 | (2006.01) | |
| C12N 15/78 | (2006.01) | |

(52) U.S. Cl.
CPC ......... *C12Q 1/689* (2013.01); *C12N 1/20* (2013.01); *C12N 15/78* (2013.01)

(58) Field of Classification Search
CPC ........... C12N 1/20; C12N 15/78; C12Q 1/689
See application file for complete search history.

(56) References Cited

U.S. PATENT DOCUMENTS

| | | |
|---|---|---|
| 3,844,893 A | 10/1974 | Hitzman |
| 3,878,093 A | 4/1975 | Kanani et al. |
| 4,169,010 A | 9/1979 | Marwil |
| 4,432,895 A | 2/1984 | Tarnowski |
| 4,511,503 A | 4/1985 | Olson et al. |
| 4,551,433 A | 11/1985 | DeBoer |
| 4,595,658 A | 6/1986 | Zinder et al. |
| 4,637,980 A | 1/1987 | Auerbach et al. |
| 4,680,264 A | 7/1987 | Puhler et al. |
| 4,695,455 A | 9/1987 | Barnes et al. |
| 4,755,465 A | 7/1988 | Gray et al. |
| 4,861,595 A | 8/1989 | Barnes et al. |
| 4,888,274 A | 12/1989 | Radding et al. |
| 4,963,495 A | 10/1990 | Chang et al. |
| 5,023,171 A | 6/1991 | Ho et al. |
| 5,043,430 A | 8/1991 | Yoshikawa |
| 5,055,294 A | 10/1991 | Gilroy |
| 5,082,783 A | 1/1992 | Ernst et al. |
| 5,084,559 A | 1/1992 | Profy |
| 5,085,862 A | 2/1992 | Klein et al. |
| 5,128,130 A | 7/1992 | Gilroy et al. |
| 5,151,350 A | 9/1992 | Colbert et al. |
| 5,165,927 A | 11/1992 | Kaslow |
| 5,169,760 A | 12/1992 | Wilcox |
| 5,169,772 A | 12/1992 | Zimmerman et al. |
| 5,173,616 A | 12/1992 | Hinooka |
| 5,232,840 A | 8/1993 | Olins |
| 5,264,365 A | 11/1993 | Georgiou et al. |
| 5,281,532 A | 1/1994 | Rammler et al. |
| 5,292,507 A | 3/1994 | Charley |
| 5,292,658 A | 3/1994 | Cormier et al. |
| 5,348,867 A | 9/1994 | Georgiou et al. |
| 5,399,684 A | 3/1995 | Davie et al. |
| 5,418,155 A | 5/1995 | Cormier et al. |
| 5,441,934 A | 8/1995 | Krapcho et al. |

(Continued)

FOREIGN PATENT DOCUMENTS

| | | |
|---|---|---|
| EP | 0121352 | 10/1984 |
| EP | 0155189 | 9/1985 |

(Continued)

OTHER PUBLICATIONS

Wu et al., 2002, Cell-biological applications of transfected-cell microarrays, Trends in Cell Biology, 12(10): 485-488.*
Baneyx, F., and G. Georgiou, "Construction and Characterization of *Escherichia coli* Strains Deficient in Multiple Secreted Protease: Protease III Degrades High-Molecular-Weight Substrates In Vivo," *J. Bacteriol.*, Apr. 1991, pp. 2696-2703, vol. 173, No. 8.
Thomas, J.G., et al., Molecular Chaperones, Folding Catalysts, and the Recovery of Active Recombinant Proteins from *E. coli*—To Fold or to Refold, *Applied Biochemistry and Biotechnology*, 1997, pp. 197-238, vol. 66.
Wall, G.J., and Pluckthun, A., "Effects of Overexpressing Folding Modulators on the in vivo Folding of Heterologous Proteins in *Escherichia coli*," *Current Opinion in Biotechnology*, Jan. 1, 1995, pp. 507-516, vol. 6, London, GB [XP002092905].

(Continued)

*Primary Examiner* — Yong Pak
(74) *Attorney, Agent, or Firm* — Wilson Sonsini Goodrich & Rosati

(57) ABSTRACT

The present invention provides an array for rapidly identifying a host cell population capable of producing a heterologous protein with improved yield and/or quality. The array comprises one or more host cell populations that have been genetically modified to increase the expression of one or more target genes involved in protein production, decrease the expression of one or more target genes involved in protein degradation, or both. One or more of the strains in the array may express the heterologous protein of interest in a periplasm compartment or may secrete the heterologous protein extracellularly through an outer cell wall. The strain arrays are useful for screening for improved expression of any protein of interest including therapeutic proteins, hormones, growth factors, extracellular receptors or ligands, proteases, kinases, blood proteins, chemokines, cytokines, antibodies and the like.

13 Claims, 3 Drawing Sheets

(56) References Cited

U.S. PATENT DOCUMENTS

| | | |
|---|---|---|
| 5,508,192 A | 4/1996 | Georgiou et al. |
| 5,527,883 A | 6/1996 | Thompson et al. |
| 5,552,302 A | 9/1996 | Lewis et al. |
| 5,558,862 A | 9/1996 | Corbin et al. |
| 5,559,015 A | 9/1996 | Capage et al. |
| 5,571,694 A | 11/1996 | Makoff et al. |
| 5,595,898 A | 1/1997 | Robinson et al. |
| 5,610,044 A | 3/1997 | Lam et al. |
| 5,621,074 A | 4/1997 | Bjørn et al. |
| 5,622,846 A | 4/1997 | Kiener et al. |
| 5,641,671 A | 6/1997 | Bos et al. |
| 5,641,870 A | 6/1997 | Rinderknecht et al. |
| 5,643,774 A | 7/1997 | Ligon et al. |
| 5,662,898 A | 9/1997 | Ligon et al. |
| 5,677,127 A | 10/1997 | Hogan et al. |
| 5,683,888 A | 11/1997 | Campbell |
| 5,686,282 A | 11/1997 | Lam et al. |
| 5,686,283 A | 11/1997 | Gaffney et al. |
| 5,698,425 A | 12/1997 | Ligon et al. |
| 5,698,435 A | 12/1997 | Robinson et al. |
| 5,710,031 A | 1/1998 | Gaffney et al. |
| 5,728,574 A | 3/1998 | Legg |
| 5,731,280 A | 3/1998 | Nielsen et al. |
| 5,736,379 A | 4/1998 | Davie et al. |
| 5,741,663 A | 4/1998 | Russell |
| 5,741,668 A | 4/1998 | Ward et al. |
| 5,756,087 A | 5/1998 | Ligon et al. |
| 5,757,051 A | 5/1998 | Wu et al. |
| 5,766,926 A | 6/1998 | Blanchette et al. |
| 5,773,600 A | 6/1998 | Burnette, III |
| 5,776,730 A | 7/1998 | Stuart |
| 5,777,079 A | 7/1998 | Tsien et al. |
| 5,795,759 A | 8/1998 | Rosazza et al. |
| 5,804,387 A | 9/1998 | Cormack et al. |
| 5,824,472 A | 10/1998 | Betlach et al. |
| 5,834,250 A | 11/1998 | Wells et al. |
| 5,840,554 A | 11/1998 | Thompson et al. |
| 5,869,038 A | 2/1999 | Leifert et al. |
| 5,874,304 A | 2/1999 | Zolotukhin et al. |
| 5,876,995 A | 3/1999 | Bryan |
| 5,891,688 A | 4/1999 | Gaffney et al. |
| 5,914,233 A | 6/1999 | Mundy et al. |
| 5,914,254 A | 6/1999 | Mascarenhas et al. |
| 5,919,445 A | 7/1999 | Chao |
| 5,922,576 A | 7/1999 | He et al. |
| 5,925,558 A | 7/1999 | Tsien et al. |
| 5,932,435 A | 8/1999 | Atkins et al. |
| 5,942,387 A | 8/1999 | Hollinshead |
| 5,948,681 A | 9/1999 | Scanlin et al. |
| 5,948,889 A | 9/1999 | de Boer et al. |
| 5,952,208 A | 9/1999 | Darzins et al. |
| 5,952,236 A | 9/1999 | Thompson et al. |
| 5,955,348 A | 9/1999 | Ligon et al. |
| 5,958,713 A | 9/1999 | Thastrup et al. |
| 5,968,738 A | 10/1999 | Anderson et al. |
| 5,968,773 A | 10/1999 | Heddle et al. |
| 5,968,779 A | 10/1999 | Campfield et al. |
| 5,985,577 A | 11/1999 | Bulinski |
| 5,989,808 A | 11/1999 | Young et al. |
| 5,993,778 A | 11/1999 | Firestein et al. |
| 5,994,071 A | 11/1999 | Ross et al. |
| 5,994,077 A | 11/1999 | Valdivia et al. |
| 6,001,557 A | 12/1999 | Wilson et al. |
| 6,013,447 A | 1/2000 | Nilsen et al. |
| 6,015,557 A | 1/2000 | Tobinick et al. |
| 6,020,192 A | 2/2000 | Muzyczka et al. |
| 6,025,192 A | 2/2000 | Beach et al. |
| 6,027,881 A | 2/2000 | Pavlakis |
| 6,037,133 A | 3/2000 | Li |
| 6,040,138 A | 3/2000 | Lockhart et al. |
| 6,051,383 A | 4/2000 | Thomashow et al. |
| 6,054,321 A | 4/2000 | Tsien et al. |
| 6,060,247 A | 5/2000 | Miller et al. |
| 6,066,476 A | 5/2000 | Tsien et al. |
| 6,071,738 A | 6/2000 | Johnson et al. |
| 6,077,707 A | 6/2000 | Tsien et al. |
| 6,080,576 A | 6/2000 | Zambrowicz et al. |
| 6,083,690 A | 7/2000 | Harris et al. |
| 6,090,919 A | 7/2000 | Cormack et al. |
| 6,093,808 A | 7/2000 | Li |
| 6,096,717 A | 8/2000 | Jarvik |
| 6,096,865 A | 8/2000 | Michaels |
| 6,110,711 A | 8/2000 | Serafini et al. |
| 6,117,670 A | 9/2000 | Ligon et al. |
| 6,121,247 A | 9/2000 | Huang et al. |
| 6,124,128 A | 9/2000 | Tsien et al. |
| 6,130,313 A | 10/2000 | Li et al. |
| 6,133,429 A | 10/2000 | Davis et al. |
| 6,136,538 A | 10/2000 | Olivo et al. |
| 6,136,539 A | 10/2000 | Basbaum et al. |
| 6,136,566 A | 10/2000 | Sands et al. |
| 6,140,132 A | 10/2000 | Tsien et al. |
| 6,146,826 A | 11/2000 | Chalfie et al. |
| 6,150,176 A | 11/2000 | Tsien et al. |
| 6,153,409 A | 11/2000 | Bentley et al. |
| 6,156,313 A | 12/2000 | Burton et al. |
| 6,156,552 A | 12/2000 | Okkels et al. |
| 6,172,188 B1 | 1/2001 | Thastrup et al. |
| 6,180,343 B1 | 1/2001 | Anderson et al. |
| 6,184,440 B1 | 2/2001 | Shoseyov et al. |
| 6,194,194 B1 | 2/2001 | Molloy |
| 6,197,928 B1 | 3/2001 | Tsien et al. |
| 6,203,986 B1 | 3/2001 | Singer et al. |
| 6,204,023 B1 | 3/2001 | Robinson et al. |
| 6,210,910 B1 | 4/2001 | Walt et al. |
| 6,210,922 B1 | 4/2001 | Cote et al. |
| 6,214,563 B1 | 4/2001 | Negulescu et al. |
| 6,214,567 B1 | 4/2001 | Allen-Hoffmann et al. |
| 6,218,185 B1 | 4/2001 | Shirk et al. |
| 6,221,612 B1 | 4/2001 | Knapp et al. |
| 6,225,082 B1 | 5/2001 | Carson et al. |
| 6,228,639 B1 | 5/2001 | Gaitanaris |
| 6,232,107 B1 | 5/2001 | Bryan et al. |
| 6,246,543 B1 | 6/2001 | Baumgart et al. |
| 6,248,550 B1 | 6/2001 | Tsien et al. |
| 6,248,558 B1 | 6/2001 | Lin et al. |
| 6,251,384 B1 | 6/2001 | Tan et al. |
| 6,251,582 B1 | 6/2001 | Littman et al. |
| 6,251,602 B1 | 6/2001 | Young et al. |
| 6,251,677 B1 | 6/2001 | Wilson et al. |
| 6,255,071 B1 | 7/2001 | Beach et al. |
| 6,255,558 B1 | 7/2001 | Haseloff et al. |
| 6,258,560 B1 | 7/2001 | Leung et al. |
| 6,261,760 B1 | 7/2001 | Fielding et al. |
| 6,261,776 B1 | 7/2001 | Pirrung et al. |
| 6,265,548 B1 | 7/2001 | Pavlakis et al. |
| 6,268,201 B1 | 7/2001 | Alland et al. |
| 6,268,549 B1 | 7/2001 | Sailland et al. |
| 6,270,958 B1 | 8/2001 | Olivo et al. |
| 6,274,354 B1 | 8/2001 | Wilson et al. |
| 6,277,625 B1 | 8/2001 | Huang et al. |
| 6,280,934 B1 | 8/2001 | Madden et al. |
| 6,284,496 B1 | 9/2001 | Litman et al. |
| 6,284,519 B1 | 9/2001 | Young et al. |
| 6,291,175 B1 | 9/2001 | Sevigny et al. |
| 6,291,177 B1 | 9/2001 | Madden et al. |
| 6,303,373 B1 | 10/2001 | Bogan et al. |
| 6,319,669 B1 | 11/2001 | Tsien et al. |
| 6,329,172 B1 | 12/2001 | Rhee et al. |
| 6,344,316 B1 | 2/2002 | Lockhart et al. |
| 6,403,957 B1 | 6/2002 | Fodor et al. |
| 6,410,229 B1 | 6/2002 | Lockhart et al. |
| 6,420,108 B2 | 7/2002 | Mack et al. |
| 6,447,770 B1 | 9/2002 | Raaijmakers et al. |
| 6,451,536 B1 | 9/2002 | Fodor et al. |
| 6,495,357 B1 | 12/2002 | Fuglsang et al. |
| 6,506,559 B1 | 1/2003 | Fire et al. |
| 6,509,181 B1 | 1/2003 | Danielsen et al. |
| 6,524,827 B2 | 2/2003 | Moller et al. |
| 6,528,298 B1 | 3/2003 | Svendsen et al. |
| 6,532,462 B2 | 3/2003 | Balaban |
| 6,551,784 B2 | 4/2003 | Fodor et al. |
| 6,558,939 B1 | 5/2003 | Madsen et al. |
| 6,567,540 B2 | 5/2003 | Balaban et al. |

(56) References Cited

U.S. PATENT DOCUMENTS

| | | |
|---|---|---|
| 6,573,099 B2 | 6/2003 | Graham |
| 6,576,424 B2 | 6/2003 | Fodor et al. |
| 6,600,031 B1 | 7/2003 | Fodor et al. |
| 6,607,885 B1 | 8/2003 | Larossa et al. |
| 6,608,018 B1 | 8/2003 | Shinohara |
| 6,617,143 B1 | 9/2003 | Fukuyama |
| 6,642,030 B1 | 11/2003 | English et al. |
| 6,673,580 B2 | 1/2004 | Koren et al. |
| 6,687,692 B1 | 2/2004 | Balaban et al. |
| 6,696,561 B1 | 2/2004 | Pompejus et al. |
| 6,800,738 B1 | 10/2004 | Carter et al. |
| 6,979,556 B2 | 12/2005 | Simmons et al. |
| 7,112,324 B1 | 9/2006 | Dorken et al. |
| 7,175,840 B2 | 2/2007 | Kim et al. |
| 7,189,389 B2 | 3/2007 | Yanai et al. |
| 7,217,796 B2 | 5/2007 | Wang et al. |
| 7,235,641 B2 | 6/2007 | Kufer et al. |
| 7,270,993 B2 | 9/2007 | Smit et al. |
| 7,338,794 B2 | 3/2008 | Gaertner et al. |
| 7,381,804 B2 | 6/2008 | Osslund |
| 7,399,463 B2 | 7/2008 | Shirley et al. |
| 7,411,050 B2 | 8/2008 | Anderson |
| 7,416,849 B2 | 8/2008 | Allen et al. |
| 7,427,596 B2 | 9/2008 | Keyt et al. |
| 7,439,063 B2 | 10/2008 | Digicaylioglu et al. |
| 7,439,323 B2 | 10/2008 | Bielicki |
| 7,445,772 B2 | 11/2008 | West et al. |
| 7,452,971 B2 | 11/2008 | Vitetta et al. |
| 7,459,540 B1 | 12/2008 | Thomason et al. |
| 7,491,697 B2 | 2/2009 | Beals et al. |
| 7,504,237 B2 | 3/2009 | Jensen et al. |
| 7,524,931 B2 | 4/2009 | Van Den Hazel et al. |
| 7,537,771 B2 | 5/2009 | Williamson et al. |
| 7,544,519 B2 | 6/2009 | Hsu et al. |
| 7,547,821 B2 | 6/2009 | Moloney et al. |
| 7,553,940 B2 | 6/2009 | Fares et al. |
| 7,553,941 B2 | 6/2009 | Fares et al. |
| 7,556,817 B2 | 7/2009 | Steward et al. |
| 7,560,112 B2 | 7/2009 | Chen et al. |
| 7,563,443 B2 | 7/2009 | Grant et al. |
| 7,566,566 B2 | 7/2009 | Alitalo et al. |
| 7,566,769 B2 | 7/2009 | Browning et al. |
| 7,575,923 B2 | 8/2009 | Dorken et al. |
| 7,576,190 B2 | 8/2009 | Glaesner et al. |
| 7,582,607 B2 | 9/2009 | Frye et al. |
| 7,585,942 B2 | 9/2009 | Harrison et al. |
| 7,618,799 B2 | 11/2009 | Coleman et al. |
| 7,985,564 B2 | 7/2011 | Retallack et al. |
| 8,288,127 B2 | 10/2012 | Schneider et al. |
| 8,603,824 B2 * | 12/2013 | Ramseier et al. ............ 435/471 |
| 9,109,229 B2 * | 8/2015 | Ramseier et al. |
| 2003/0013150 A1 | 1/2003 | Manosroi et al. |
| 2003/0044906 A1 | 3/2003 | Habermann et al. |
| 2003/0064435 A1 | 4/2003 | Weiner et al. |
| 2003/0108923 A1 | 6/2003 | Tuschl et al. |
| 2003/0114409 A1 | 6/2003 | Mello et al. |
| 2003/0157069 A1 | 8/2003 | Lyman et al. |
| 2003/0180937 A1 | 9/2003 | Georgiou et al. |
| 2004/0028705 A1 | 2/2004 | Ballard et al. |
| 2004/0138127 A1 | 7/2004 | Davidson et al. |
| 2004/0157289 A1 | 8/2004 | Salerno et al. |
| 2005/0214321 A1 | 9/2005 | Rasochova et al. |
| 2006/0008877 A1 | 1/2006 | Retallack et al. |
| 2006/0040352 A1 * | 2/2006 | Retallack et al. ............ 435/69.1 |
| 2006/0062784 A1 | 3/2006 | Grant et al. |
| 2006/0110747 A1 | 5/2006 | Ramseier et al. |
| 2006/0149041 A1 | 7/2006 | Silence |
| 2006/0211088 A1 | 9/2006 | Hermans et al. |
| 2006/0234346 A1 | 10/2006 | Retallack et al. |
| 2006/0246477 A1 | 11/2006 | Hermans et al. |
| 2007/0077249 A1 | 4/2007 | Silence et al. |
| 2007/0123479 A1 | 5/2007 | Kufer et al. |
| 2007/0178082 A1 | 8/2007 | Silence et al. |
| 2007/0224205 A1 | 9/2007 | Powell et al. |
| 2007/0237769 A1 | 10/2007 | Silence et al. |
| 2007/0269422 A1 | 11/2007 | Beirnaert et al. |
| 2008/0096223 A1 | 4/2008 | De Groot et al. |
| 2008/0107601 A1 | 5/2008 | Lauwereys et al. |
| 2008/0107673 A1 | 5/2008 | Ballard et al. |
| 2008/0193974 A1 | 8/2008 | Coleman et al. |
| 2008/0267949 A1 | 10/2008 | Revets et al. |
| 2008/0269070 A1 | 10/2008 | Ramseier et al. |
| 2009/0022721 A1 | 1/2009 | Silence et al. |
| 2009/0028880 A1 | 1/2009 | Beirnaert et al. |
| 2009/0062143 A1 | 3/2009 | Ramseier et al. |
| 2009/0074770 A1 | 3/2009 | Lasters et al. |
| 2009/0148438 A1 | 6/2009 | Nuttal et al. |
| 2009/0191186 A1 | 7/2009 | Bebbington et al. |
| 2009/0226432 A1 | 9/2009 | Lutterbuse et al. |
| 2009/0226444 A1 | 9/2009 | Rau et al. |
| 2009/0238829 A1 | 9/2009 | Silence et al. |
| 2009/0252681 A1 | 10/2009 | Laeremans et al. |
| 2010/0137162 A1 | 6/2010 | Retallack et al. |
| 2014/0162279 A1 | 6/2014 | Ramseier et al. |

FOREIGN PATENT DOCUMENTS

| | | | |
|---|---|---|---|
| EP | 0177343 A1 | 4/1986 | |
| EP | 0288451 A2 | 10/1988 | |
| EP | 0 404 097 | 12/1990 | |
| EP | 0207459 B1 | 3/1991 | |
| EP | 1709170 | 10/2006 | |
| FR | 2567540 | 1/1986 | |
| JP | 2001-299360 A | 10/2001 | |
| JP | 2004502929 A | 1/2004 | |
| JP | 2006-501811 | 1/2006 | |
| JP | H9-506508 | 6/2009 | |
| KR | 10-2003-0074654 | 9/2003 | |
| WO | WO-87-05937 | 10/1987 | |
| WO | WO-87-05938 | 10/1987 | |
| WO | WO-89-10971 | 11/1989 | |
| WO | WO-90-03438 | 4/1990 | |
| WO | WO-92-15673 | 9/1992 | |
| WO | WO-93-11161 | 6/1993 | |
| WO | WO-95-03395 | 2/1995 | |
| WO | WO-95-07463 | 3/1995 | |
| WO | WO-96-17943 | 6/1996 | |
| WO | WO-97-22687 A1 | 6/1997 | |
| WO | WO-98-14605 | 4/1998 | |
| WO | WO-98-24919 | 6/1998 | |
| WO | WO-98-26277 | 6/1998 | |
| WO | WO-99-09834 | 3/1999 | |
| WO | WO-99-15650 | 4/1999 | |
| WO | WO-99-49019 | 9/1999 | |
| WO | WO-99-53035 | 10/1999 | |
| WO | WO-00-15761 | 3/2000 | |
| WO | WO-00-29604 | 5/2000 | |
| WO | WO-00-59537 | 10/2000 | |
| WO | WO-01-21662 | 3/2001 | |
| WO | WO-01-27258 | 4/2001 | |
| WO | WO 01/32844 * | 5/2001 | ............ C12N 9/00 |
| WO | WO 01/32844 A | 5/2001 | |
| WO | WO 2002-002794 | 1/2002 | |
| WO | WO-02-14551 | 2/2002 | |
| WO | WO-2002-16940 | 2/2002 | |
| WO | WO-2002-40696 | 5/2002 | |
| WO | WO-2002-48376 A2 | 6/2002 | |
| WO | WO-02-068660 | 9/2002 | |
| WO | WO-03-006477 | 1/2003 | |
| WO | WO-03-012052 | 2/2003 | |
| WO | WO-03-023015 | 3/2003 | |
| WO | WO-03-056022 | 7/2003 | |
| WO | WO-03-064435 | 8/2003 | |
| WO | WO-03-064621 | 8/2003 | |
| WO | WO-03-068926 A2 | 8/2003 | |
| WO | WO-03-070966 | 8/2003 | |
| WO | WO-03-079007 | 9/2003 | |
| WO | WO-03-089455 A2 | 10/2003 | |
| WO | WO-2004-005221 A2 | 1/2004 | |
| WO | WO-2004-006657 | 1/2004 | |
| WO | WO-2004-011628 | 2/2004 | |
| WO | WO-2004-055206 | 7/2004 | |
| WO | WO-2004-087864 | 10/2004 | |
| WO | WO-2005-014639 A2 | 2/2005 | |

(56) References Cited

FOREIGN PATENT DOCUMENTS

| WO | WO-2005-052151 A1 | 6/2005 |
|---|---|---|
| WO | WO-2005-069913 | 8/2005 |
| WO | WO-2005-089093 | 9/2005 |
| WO | WO-2005-103077 | 11/2005 |
| WO | WO-2005-115622 | 12/2005 |
| WO | WO 2006/014899 * | 2/2006 |
| WO | WO 2006-059701 | 6/2006 |
| WO | WO-2006-066001 | 6/2006 |
| WO | WO-2008-017906 | 2/2008 |
| WO | WO-2008-134461 | 7/2008 |
| WO | WO-2008-094986 | 8/2008 |

OTHER PUBLICATIONS

Canadian Patent Application CA2553503 Exam Report dated Apr. 29, 2014.
Canadian Patent Application CA2685326 Office Action dated May 22, 2014.
Japanese Patent Application 2006-549690 Office Action mailed Mar. 11, 2014.
Japanese Patent Application 2011-132011 Office Action mailed Mar. 25, 2014.
Korean Patent Application 10-2009-7024636 Office Action dated Nov. 26, 2014 (with English language reporting letter from the foreign associate).
U.S. Appl. No. 11/038,901 Supp. RR mailed Oct. 10, 2014.
U.S. Appl. No. 14/071,273 Non Final Office Action mailed Oct. 9, 2014.
Ada, Gordon, et al., Overview of Host Defense Mechanisms with Special Reference to Viral Infections, Gamma Interferon in Antiviral Defense, 1997, Chapter 1, pp. 1-18, R.G. Landes Group.
Ahn Jung Hoon, et al., Homologous Expression of the Lipase and ABC Transporter Gene Cluster, tliDEFA, Enhances Lipase Secretion in Pseudomonas spp., Appl. Environ. Microbiol., Dec. 2001, pp. 5506-5511, vol. 67, No. 12, American Society for Microbiology.
Akao, et al., "Unique synthetic peptides stimulating streptolysin S production in streptococci," 1999, J. Biochem. 125(1):27-30.
Altschul, Stephen F., et al., Basic Alignment Search Tool, J. Mol. Biol., 1990, pp. 403-410, vol. 215.
Ames, et al., "Simple, Rapid, and Quantitative Release of Periplasmic Proteins by Chloroform," 1984, J. Bacteriol., 160(3): pp. 1181-1183.
Andersen, D.C. et al., "Production technologies for monoclonal antibodies and their fragments." Current Opinion in Biotechnology, London, GB, vol. 15, No. 5, Oct. 1, 2004, pp. 456-462.
Anderson, et al., 1997, "A homologue of the TNF receptor and its ligand enhance T-cell growth and dendritic-cell function," Nature 390 (6656), 175-179.
Anderson, Kevin P., et al., Enhancement of a Secondary Antibody Response to Vesicular Stomatitis Virus G Protein by IFN-γ Treatment at Primary Immunization, The Journal of Immunology, 1988, pp. 3599-3604, vol. 140, No. 10, The American Association of Immunologists.
Appa Rao, et al., "High-Level Expression of Ovine Growth Hormone in Escherichia coli: Single-Step Purification and Characterization," Protein Expr Purif, 1997, vol. 1, No. 2, pp. 201-208.
Ariga, et al., "Release of Thermophilic α-amylase from Transformed Escherichia coli by Addition of Glycine," 1989, J. Ferm. Bioeng., 68:243-246.
Arthur, et al., High Level expression of interleukin-1beta in a recombinant Escherichia coli strain for use in a controlled bioreactor. Journal of Biotechnology, Elsevier Science Publishers, 1990, vol. 13, No. 1, pp. 29-46.
Asai, et al., "DNA microarray analysis of Bacillus subtilis sigma factors of extracytoplasmic function family," 2003, FEMS Microbiol. Ltrs. 220(1):155-160.
Asami et al., "Synchronized disruption of Escherichia coli cells by T4 Phage Infection," 1997, J. Ferment and Bioeng., 83: pp. 511-516.
AU Patent Application 2008245696 Office Action issued Oct. 24, 2012.
AU Patent Application 2005269527 Office Action issued Nov. 3, 2010.
AU Patent Application 2005206951 Office Action issued Jan. 16, 2009.
Babiuk, L.A., et al., Symposium Immunobiology of Cytokines and Their Application in Disease Prevention in Dairy Cattle, J. Dairy Sci., 1991, vol. 74, pp. 4385-4398, Veterinary Infectious Disease Organization.
Bagdasarian, M. and Timmis, K., "Host: Vector Systems for Gene Cloning in Pseudomonas." 1982, Curr. Topics Microbial. Immunol., pp. 47-67, vol. 96.
Bagdasarian, M., et al., Specific-purpose plasmid cloning vectors II. Broad host range, high copy No. RSF1010-derived vectors, and a host-vector system for gene cloning in Pseudomonas, 1981, Gene, pp. 237-247, vol. 16, Elsevier/North-Holland Biomedical Press.
Baldwin, G.S., Comparison of Transferrin Sequences From Different Species. 1993, Comp. Biocherm Physiol., pp. 203-218, vol. 106B. No. 1, Pergamon Press Ltd.
Baneyx, Francois, "Recombinant protein expression in Escherichia coli," 1999, Curr. Op. Biotech. 10:411-421.
Bardwell, et al., "Pathways of Disulfide Bond Formation in Proteins in Vivo," 1994, Phosphate Microorg. Chapter 45, pp. 270-275.
Bellini, et al., "Production processes of recombinant IL-1beta from Bacillus subtilis: comparison between intracellular and exocellular expression," Journal of Biotechnology, Elsevier Science, 1991, vol. 18, No. 3, pp. 177-192.
Benoist & Chambon, "In vivo sequence requirements of the SV40 early promoter region," (1981) Nature 290:304-310.
Berrow, N.S. et al., "Recombinant protein expression and solubility screening in Escherichia coli: a comparative study," 2006, Biological Crystallography. 62: 1218-1226.
Blattner, et al., "The Complete Genome Sequence for Escherichia Coli K-12," 1997, Science 277 (5331): 1453-74.
Bohnsack, R.N., "Site-directed mutagenesis using positive antibiotic selection," 1996, Meth. Mol. Biol. 57,1-12.
Foss, FM, 2001, "Interleukin-2 fusion toxin: targeted therapy for cutaneous T cell lymphoma," Ann N Y Acad Sci. 941:166-76.
Brosius, Jurgen, "Toxicity of an overproduced foreign gene product in Escherichia coli and its use in plasmid vectors for the selection of transcription terminators," 1984, Gene 27(2): 161-72.
Broxmeyer, H.E., Monocyte-Macrophage-Derived Acidic Isoferritins: Nomal Feedback Regulators of Granulocyte-Macrophage Progenitor Cells In Vitro, Blood, 1982, pp. 595-607, vol. 60, American Society of Hematology.
Butte, A., "The use and analysis of microarray data," 2002, Nat Rev Drug Discov 1:951-60.
Canadian Patent Application CA2553503 Exam Report dated May 10, 2011.
Canadian Patent Application CA2553503 Exam Report dated May 2, 2012.
Canadian Patent Application CA2574953 Office Action dated Jun. 27, 2012.
Carrier, M.I., et al., Expression of Human IL-1B in Salmonella Typhimurium A Model System for the Delivery of Recombinant Therapeutic Proteins in Vivo, The Journal of Immunology, 1992, pp. 1176-1181, vol. 148, No. 4, The American Association of Immunologists.
Carter, et al., "High Level Escherichia coli expression and production of a bivalent humanized antibody fragment,"1992, Bio/Technology, 10: 163-167.
Casavant, et al., "Use of a site-specific recombination-based biosensor for detecting bioavailable toluene and related compounds on roots." Environmental Microbiology, Apr. 2003, pp. 238-249, vol. 5, No. 4, Society for Applied Microbiology.
Cerretti, Douglas Pat., et al., Cloning, Sequence, and Expression of Bovine Interferon-γ, The Journal of Immunology, 1986, pp. 4561-4564, vol. 136, No. 12, The American Association of Immunologists.
Chalfie, et al., "Green fluorescent protein as a marker for gene expression," 1994, Science 263(5148):802-805.
Chang and Cohen, "Construction and Characterization of Amplifiable Multiopy DNA Cloning Vehicles Derived from the P15A Cryptic Miniplasmid," 1978, Journal of Bacteriology, vol. 134, No. 3, p. 1141-1156.

(56) References Cited

OTHER PUBLICATIONS

Chew, et al., "Production of Recombinant Proteins. Novel Microbial and Eucaryotic Expression Systems," 2005, G. Gellissen, Weinheim, Wiley-VCH: 45-66.
Chiou, et al., "Cobra venom cardiotoxin (cytotoxin) isoforms and neurotoxin: Comparative potency of protein kinase C inhibition and cancer cell cytotoxicity and modes of enzyme inhibition," 1993, Biochemistry, 32 (8), pp. 2062-2067.
Cho, Won-Kyung, et al., "Production and In Vitro Refolding of a Single-Chain Antibody Specific for Human Plasma Apolipoprotein A-I". Journal of Biotechnology, 2000, pp. 169-178, vol. 77, Elsevier Science B.V.
Choi, et al., "Enhanced Production of Insulin-Like Growth Factor I Fusion Protein in *Escherichia coli* by Coexpression of the Down-Regulated Genes Identified by Tanscriptome Profiling," 2003, App. Envir. Microbio 69, pp. 4737-4742.
Clark-Curtiss, Josephine, et al., "Analysis of Recombinant DNA Using *Escherichia coli* Minicells," Methods in Enzymology, 1983, vol. 101, pp. 347-362, Academic Press, Inc.
CN200580032245 Office Action dated Apr. 12, 2012.
CN200880022208 Secord Office Action dated Jul. 16, 2012.
Cosman, "A Family of Ligands for the TNF Receptor Super family," Stem Cells, 1994: 12:440-455.
Dabora and Cooney, "Intracellular lytic enzyme systems and their use for disruption of *Escherichia coli*." 1990, Advances in Biochemical Engineering/Biotechnology, vol. 43, A. Fiechter, ed. (Springer-Verlag: Berlin), pp. 11-30.
Dammeyer, et al., "Efficient production of soluble recombinant single chain Fv fragments by a *Pseudomonas putida* strain KT2440 cell factory," 2011, Microbial Cell Factories, vol. 10, pp. 1-8.
Davis, Bernard D., et al., Mutants of *Escherichia Coli* Requiring Methionine or Vitamin B12, 1950, J. Bact., vol. 60, pp. 17-28.
De Marco, Arto, et al., Native folding of aggregation-prone recombinant proteins in *Escherichia coli* by osmolytes, plasmid- or benzyl alcohol-overexpressed molecular chaperones, 2005, Cell Stress and Chaperones, 10(4), pp. 329-339, Cell Stress Society International.
Deng, W.P. and Nickoloff, J.A., "Site-directed mutagenesis of virtually any plasmid by eliminating a unique site," (1992) Anal. Biochem. 200, 81.
Dolinski, et al., "Peptidyl-prolyl isomerases—an overview of the cyclophilin, FKBP and parvulin families in Guidebook to Molecular Chaperones and Protein-Folding Catalysts," (1997) Gething M-J Ed. Oxford University Press Inc. New York. pp. 359-369.
Doudoroff, M., et al., Gram-Negative Aerobic Rods and Cocci, 1974, Bergey's Manual of Determinative Bacteriology, pp. 217-289, edited by Buchanan and Gibbons.
Dulebohn, D., "Trans-Translation: The tmRNA-Mediated Surveillance Mechanism for Ribosome Rescue, Directed Protein Degradation, and Nonstop mRNA Decay." Biochemistry, 2007, 46 (16): 4681-4693.
Elbashir, et al., "Duplexes of 21-nucleotide RNAs mediate RNA interference in cultured mammalian cells," 2001, Nature 411(6836): 494-8.
Elbashir, et al., "RNA interference is mediated by 21-and 22-nucleotide RNAs," (2001) Genes & Development 15(2):188-200.
EP 05705852 Supplementary European Search Report dated Mar. 18, 2008.
EP05705852 European Search Report dated Oct. 5, 2011.
EP05774619 Examination Report dated Oct. 29, 2010.
EP05774619 International Search Report dated Apr. 4, 2009.
EP08746833.6 Exam Report dated Feb. 15, 2012.
EP11173331.7 Extended search report dated Apr. 18, 2012.
EP11173331.7 Partial Search Report dated Dec. 27, 2011.
EP11176612 Extended European Search Report dated Jul. 18, 2012.
EP11176612 Partial European Search Report dated Jan. 25, 2012.
EP11173331.7 Examination Report issued Dec. 19, 2012.
Espejo, A., "Protein-domain microarrays Processes." 2004, Mol Biol., 264:173-81.
Eymann, C., et al., "*Bacillis subtilis* Functional Genomics: Global Characterization of the Stringent Response by Proteome and Transcriptome Analysis," 2002, J Bacteriol 184(9), pp. 2500-2520.
Fathallah-Shaykh, H.M., "Microarrays: applications and pitfalls," 2005, Arch. Neurol. 62(11):1669-1672.
Fire, A., et al., "Potent and specific genetic interference by double-stranded RNA in Caenorhabdtis elegans," 1998, Nature 391:806-11.
Fleer, et al., "High-level secretion of correctly processed recombinant human interleukin-1 beta in *Kluyveromyces lacti*," Gene, Elsevier, 1991, vol. 107, No. 2, pp. 285-295.
Fox, L.K., et al., The Effect of Interferon-γ Intramammary Administration on Mammary Phagocyte Function, J. Vet. Med., 1990, pp. 28-30. Paul Parcy Scientific Publishers.
Fransen, Lucie, et al., Recombinant Tumor Necrosis Factor: Species Specificity for a Variety of Human and Murine Transformed Cell Lines, Cellular Immunology, 1986, pp. 260-267, vol. 100, Academic Press, Inc.
French, et al., "Development of a simple method for the recovery of recombinant proteins from the *Escherichia coli* periplasm." 1996, Enzyme and Microb. Tech., 19: 332-338.
Friedman, Robert M., et al., Interferon with Special Emphasis on the Immune System, Advances in Immunology, pp. 97-140, 1983, vol. 34, Academic Press Inc.
Frishman, Dmitrij, et al., Starts of bacterial genes: estimating the reliability of computer predictions, Gene vol. 234, 1999, Elsevier Science B.V., pp. 257-265.
Furlong and Sundstrom, "Immobilized cell bioreactors for producing immobilized protein bioadsorbers," Developments in Industrial Microbiology vol. 30, 1989, pp. 141-148.
Gaertner, Frank H., CellCap: An Encapsulation System for Insecticidal Biotoxin Proteins, Advanced Engineered Pesticides, Marcel Dekker, New York, 1993, pp. 73-83.
Gaertner, Frank H., et al., Amended recombinant cells (ARCs(TM)): An economical and surprisingly effective production and delivery vehicle for recombinant bovine IFN-γ, Journal of Controlled Release, vol. 107, Elsevier B.V., Oct. 2005, pp. 189-202.
Gardiner, et al., "Bioinformatic and expression analysis of the putative gliotoxin biosynthetic gene cluster of Aspergillus fumigatus," 2005, FEMS Microbiol. Lett. 248(2):241-248.
Gardy, et al., 2005 PSORTb v.2.0 expanded prediction of bacterial protein subcellular localization and insights gained from comparative proteome analysis. Bioinformatics 21(5): 617-623.
Gellison, ed. Production of Recombinant Proteins, Novel Microbial and Eukaryotic Expression Systems, Wiley-VCH 2005, pp. 47-48.
Gene Ontology Consortium 2004. The Gene Ontology (GO) database and informatics resource. Nucleic Acids Research 32: D258-D261.
Georgiou, et al., "Preparative expression of secreted proteins in bacteria: status report and future prospects," 2005, Current Opinion in Biotechnology, vol. 16, pp. 538-545.
Gill, et al., "Genomic Analysis of High-Cell-Density Recombinant *Escherichia coli* Fermentation and "Cell Conditioning" for Improving Recombinant Protein Yield," 2001, Biotech. Bioengin 72, pp. 85-95.
Gillette, W.K., et al., Pooled ORF Expression Technology (POET), Molecular and Cellular Proteomics, 4: 1657-1652 (2005).
Goeddel, et al., "Expression in *Escherichia coli* of chemically synthesized genes for human insulin," Jan. 1979, Proc. Nat. Acad. Sci. USA, vol. 76, No. 1, pp. 106-110.
Gottesman, S., et al. "The ClpXP and ClpAP proteases degrade proteins with carboxyl-terminal peptide tails added by the SsrA-tagging system," 1998, Genes Dev 12, pp. 1338-1347.
Gottesman, Susan, "Proteases and their Targets in *Escherichia coli*," 1996, Annu. Rev. Genet 30, pp. 465-506.
Gough, R.E., et al., Further Studies on the Adjuvant Effect of an Interferon Inducer (BRL 5907) on Newcastle Disease and Avian Influenza Inactivated Vaccines, Research in Veterinary Science, 1975, vol. 19, pp. 185-188.
Graslund, S., et al., Protein production and purification, Nature Methods, 5:135-146 (2008).

(56) References Cited

OTHER PUBLICATIONS

Graupner, S. & Wackernagel, W., "A broad-host-range expression vector series including a Ptac test plasmid and its application in the expression of the dod gene of *Serratia marcescens* (coding for ribulose-5-phosphate 3-epimerase) in *Pseudomonas stutzeri*," 2000, Biomolecular Engineering, vol. 17, Elsevier Science B.V., pp. 11-16.
Gray, et al, "Structure of the human immune interferon gene," (1982) Nature 298:859-63.
Gray, et al. "Pseudomonas Aeruginosa Secretes and Correctly Processes Human Growth Hormone," Bio/Technology, Feb. 1984, pp. 161-165.
Greenfield, L., et al., "Nucleotide sequence of the structural gene for diphtheria toxin carried by corynebacteriophage beta," 1983, Proc. Natl. Acad. Sci. USA, 80(22):6853-6857.
Gresser, Ion, et al., Anti-Tumor Effects of Interferon in Mice Injected with Interferon Sensitive and Interferon-Resistant Friend Leukemia Cells. VI. Adjuvant Therapy After Surgery in the Inhibition of Liver and Spleen Metastases, Int. J. Cancer, 1987, pp. 789-792, vol. 39, Alan R. Liss, Inc.
Gruss, P., et al., "Simian virus 40 tandem repeated sequences as an element of the early promoter." 1981, Proc. Nat. Acad. Sci. USA 78:943-947.
Gubler, U., et al., "Recombinant Human Interleukin 1-Alpha Purification and Biological Characterization," Journal of Immunology, 1986, vol. 136, No. 7, pp. 2492-2497.
Guzman, M., et al., "Tight Regulation, Modulation and High-Level Expression by Vectors Containing the Arabinose PBAD Promoter," 1995, Journal of Bacteriology 177(14):4121-30.
Gygi, et al., "Quantitative analysis of complex protein mixtures using isotope-coded affinity tags," Nat. Biotech, Oct. 1999, 17:994-999.
Hamilton, et al. "New Method for generating deletions and gene replacements in *Escherichia Coli*," 1989, Journal of Bacteriology 171(9): 4617-4622.
Han, et al., "Engineering *Escherichia coli* for Increased Productivity of Serine-Rich Proteins Based on Proteome Profiling," 2003, Applied Env. Microbiol. 69(10):5772-5781.
Hayase, N., et al., "Secretion of Human Epidermal Growth Factor (EGF) in Autotrophic Culture by a Recombinant Hydrogen-Utilizing Bacterium, *Pseudomonas psedollava*, Carrying Broad-Host-Range EGF Secretion Vector pKSEGF2," Applied and Environmental Microbiology, Sep. 1994, pp. 3336-3342, vol. 60, No. 9, American Society for Microbiology.
Heffron, F., et al., "Translocation of a plasmid DNA sequence which mediates ampicillin resistance: Molecular nature and specificity of Insertion." Sep. 1975, Proc. Nat. Acad. Sci., pp. 3623-3627, vol. 72, No. 9.
Heim and Tsien, "Engineering green fluorescent protein for improved brightness, longer wavelengths and fluorescence resonance energy transfer," (1996) Curr. Biol.6:178-182.
Herman, C., et al., "Degradation of carboxy-terminal-tagged cytoplasmic proteins by the *Escherichia coli* protease HflB (FtsH)," 1998, Genes Dev 12, pp. 1348-1355.
Hochuli, Erich, "Purification of Recombinant Proteins with Metal Chelate Absorbent," 1990, Genetic Engineering, vol. 12, pp. 87-91.
Hockney, Robert C., "Recent developments in heterologous protein production in *Escherichia coli*," 1994, Trends BioTechnology, 12: pp. 456-463.
Holliday, R., "A Mechanism for Gene Conversion in Fungi," Genet Res. 5:282 (1964).
Holliger, et al., "Diabodies": Small bivalent and bispecific antibody fragments, 1993, Proc. Natl. Acad. Sci. USA, 90:6444-6448.
Holtwick, R., et al., "A novel rolling-circle-replicating plasmid from Pseudomonas putida P8: molecular characterization and use as a vector." 2001, Microbiology, vol. 147, Pt. 2, pp. 337-344.
Horton, et al., "Gene splicing by overlap extension: tailor-made genes using the polymerase chain reaction," 1990, BioTechniques 8(5): 528-30, 532, 534-5.
Hsieh et al., "Pairing o f homologous DNA sequences by proteins: evidence for three-stranded DNA," 1990, Genes & Development 4: 1951-1963.

Hsiung, et al., "Use of Bacteriocin Release Protein in *E. Coli* for Excretion of Human Growth Hormone into the Culture Medium," 1989, Bio/Technology 7:267-71.
Hancock and I. Poxton, "Isolation and Purification of Cell Walls," Bacterial Cell Surface Techniques, 1988, Chapter 3, John Wiley & Sons Ltd., p. 55.
Ikehata, O., et al., Primary structure of nitrite hydratase deduced from the nucleotide sequence of a *Rhodococcus* species and its expression in *Escherichia coli*, 1989, Eur. J. Biochem, vol. 181, pp. 563-570.
Indian Patent Application 3608/DELNP/20 Exam Reported dated Apr. 29, 2011.
Indian Patent Application 523/DELNP/07 Office Action issued Sep. 6, 2012.
Ishii, T., et al., Elastase gene expression in non-elastase-producing *Pseudomonas* aeruginosa strains using novel shuttle vector systems, 1994, FEMS Microbiology Letters, vol. 116, Federation of European Microbiological Societies, pp. 307-314.
Japanese Patent Application 2006-549690 Office Action mailed Sep. 11, 2012.
Japanese Patent Application 2007-523707 Office Action dated May 17, 2011.
Japanese Patent Application 2010-0506503 Office Action dated Jun. 5, 2012.
Jeong K.J. and Lee S.Y., "Excretion of Human β-Endorphin into Culture Medium by Using Outer Membrane Protein F as a Fusion Partner in Recombinant *Escherichia coli*," 2002, Appl. Environ. Microbio 68: vol. 10, pp. 4979-4985.
Jin, H., et al., "Soluble periplasmic production of human granulocyte colony-stimulating factor (G-CSF) in *Pseudomonas fluorescens*," 2011, Protein Expression and Purification, vol. 78, No. 1, pp. 69-77.
Jones, Jonathan D.G., et al., An Efficient Mobilizable Cosmid Vector, pRK7813, and its Use in a Rapid Method for Markler Exchange in Pseudomonas Flourescens Strain HV37a, Gene, 1987, Elsevier Science Publishers B.V., pp. 299-306.
Joseph-Liazun, et al., "Human recombinant interleukin-1β isolated from *Escherichia coli* by simple osmotic shock," 1990, Gene 86:291-295.
Kabir, et al., "Gene expression patterns for metabolic pathway in pgi knockout *Escherichia coli* with and without phb genes based on RT-PCR," 2003, J. Biotech. 105 (1-2):11-31.
Kaster, K.R. et al., "Analysis of a bacterial hygromycin B resistance gene by transcriptional and translational fusions and by DNA sequencing," 1983, Nucleic Acids Res. (19):6895-911.
Keown, et al., (1990) "Methods for Introducing DNA into Mammalian Cells." Processes in Enzymology. vol. 185. pp. 527-537.
Khoury, G. and Gruss, P., "Enhancer Elements." 1983, Cell, vol. 33:313-314.
Knight Jr., E., Antiviral and Cell Growth Inhibitory Activities Reside in the Same Glycoprotein of Human Fibroblast Interferon, Nature, 1976, vol. 262, Nature Publishing Group, pp. 302-303.
Knight, et al., Construction and initial characterization of a mouse-human chimeric anti-TNF antibody, Mol Immunol. Nov. 1993;30(16):1443-53.
Kodama, T., et al., "The Initial Phosphate Burst in ATP Hydrolysis by Myosin and Subfragment-1 as Studied by a Modified Malachite Green Method for Determination of Inorganic Phosphate," 1986, J. Biochem., vol. 99, pp. 1465-1472.
Korean Patent Application 10-2006-7014191 Office Action dated Apr. 24, 2012.
Korean Patent Application 10-2006-7014191 Office Action dated Sep. 8, 2011 (English Translation only).
Korean Patent Application 10-2007-7004418 Final Rejection dated Sep. 11, 2012.
Korean Patent Application 10-2007-7004418 Exam Report dated Dec. 22, 2011.
Korean Patent Application 10-2007-7004418 Exam Report dated Nov. 26, 2012.
Korean Patent Application 10-2012-7013463 Office Action dated Sep. 2, 2012 (Office Action in Korean only).
Kumar, et al., "The highly efficient productions of full-length and mutant rat brain calcium-binding proteins (calbindins-28K) in a bacterial expression system," Arch Biochem Biophys, 1994, vol. 308, No. 1, pp. 311-317.

(56) References Cited

OTHER PUBLICATIONS

Kunkel, T.A., et al., Rapid and efficient site-specific mutagenesis without phenotypic slection. 1987, Meth. Enzymol 154, p. 367.

Kunkel, Thomas A., "Rapid and efficient site-specific mutagenesis without phenotypic selection," 1985, Proc. Natl. Acad. Sci. USA, vol. 82, pp. 488-492.

Landry, T., et al., "Safety evaluation of an α-amylase enzyme preparation derived from the archaeal order *Thermococcales* as expressed in *Pseudomonas fluorescens* biovar I," 2003, Regulatory Toxicology and Pharmacology, vol. 37, pp. 149-168, see whole article, particularly pp. 151-152.

Lawn, R., et al., "The sequence of human serum albumin cDNA and its expression in *E. Coli*," 1981, Nucleic Acids Research, vol. 9, No. 22, IRL Press Limited, London, pp. 6103-6114.

Lee, et al., "Global Analyses of Transcriptomes and Proteomes of a Parent Strain and an L-Threonine-Overproducing Mutant Strain," 2003, J. Bacteriol. 185(18):5442-5451.

Lee, S., et al. "Effect of Overproduction of Heat Shock Chaperones GroESL and DnaK on Human Procollagenase Production in *Escherichia coli*," 1992, Journal of Biological Chemistry vol. 267, No. 5, pp. 2849-2852.

Lee, M.H., "Bacterial Expression and in Vitro Refolding of a Single-Chain Fv Antibody Specific for Human Plasma Apolipoprotein B-100," 2002, Protein Expression and Purification, pp. 166-173, vol. 25, Elsevier Science USA.

Lewis, M.K. and Thompson, D.V., "Efficient site directed in vitro mutagenesis using ampicillin selection," 1990, Nucl. Acids Res. 18, No. 12, pp. 3439-3443.

Lloubes, R. et al., "Colincin A lysis protein promotes extracellular release of active human growth hormone accumulated in *Escherichia coli* cytoplasm," 1993, Biochimie 75: pp. 451-458.

Lockhart, et al., "Expression monitoring by hybridization to high-density oligonucleotide arrays," 1996, Nat Biotechnol 14:1675-80.

Lofthouse, S.A., et al., Cytokines as Adjuvants for Ruminant Vaccines, International Journal of Parasitology, 1996, pp. 835-842, vol. 26, No. 8/9, Elsevier Science.

Lombardo, et al, "*Escherichia coli* PapD in Guidebook to Molecular Chaperones and Protein Folding Catalysts," Gething M-J Ed. Oxford University Press Inc. New York, 1997, pp. 463-465.

Lombillo, Vivian A., Antibodies to the Kinesin Motor Domain and CENP-E Inhibit Microtubule Depolymerization-dependent Motion of Chromosomes in Vitro, 1995, The Journal of Cell Biology, vol. 128, Nos. 1 & 2, The Rockefeller University Press, pp. 107-115.

Lopez, et al., "Homologous recombination intermediates between two duplex DNA catalysed by human cell extracts," 1987, Nucleic Acids Res. 15:5643-5655.

Lundell, et al., "Cytoplasmic and periplasmic expression of a highly basic protein, human interleukin 4, in *Escherichia coli*." 1990, J. Indust. Microbio. 5: pp. 215-228.

Lushnikov, A.A., et al., "Shuttle Vector for *Escherichia Coli, Pseudomonas putida*, and *Pseudomonas Aeruginosa*," 1985, Basic Life Sci., pp. 657-662, vol. 30.

MacBeath, G. & Schreiber, SL, "Printing proteins as microarrays for high-throughput function determination," 2000, Science 289:1760-1763.

Magnan, et al., SOLpro: accurate sequence-based prediction of protein solubility, 2009, Bioinformatics 25(17): 2200-2207.

Manduchi, E., et al., "Comparison of different labeling processes for two-channel high-density microarray experiments." 2002, Physiol Genomics 10:169-79.

Manoil, Colin, "Tagging Exported Proteins Using *Escherichia coli* Alkaline Phosphatase Gene Fusions," 2000, Methods in Enzymol. 326: 35-47.

Martineau, Pierre, et al., Expression of an Antibody Fragment at High Levels in the Bacterial Cytoplasm, J. Mol. Biol., 1998, pp. 117-127, vol. 280, Academic Press.

McCarthy, et al., (1990) "Translational Control of Prokaryotic Gene Expression," Trends in Genetics 6:78-85.

Menne, et al., "A comparison of signal sequence prediction methods ising a t test set of signal peptides," 2000, Bioinformatics, vol. 16, No. 8, pp. 741-742.

Messing, et al., "Genetic Engineering of Plants: An Agricultural Perspective," (1983) Edited by Kosuge et al., eds. pp. 211-227.

Mezghani-Abdelmoula, et al., "Invasive Behavior and Depolarization Effect of Pseudomonas Fluorescens on Rat Cerebellar Granule Neurons," African Journal of Clinical and Experimental Microbiology, Jan. 2005, pp. 1-13.

Michalski, Wojtek, et al., Recombinant Chicken IFN-γ Expressed in *Escherichia coli*: Analysis of C-Terminal Truncation and Effect on Biologic Activity, Journal of Interferon and Cytokine Research, 1999, vol. 19, Mary Ann Liebert, Inc., pp. 383-392.

Miksch, O., et al., "The kil gene of the ColE1 plasmid of *Escherichia coli* controlled by a growth-phase-dependant promoter mediates the secretion of a heterologous periplasmic protein during the stationary phase," 1997 Arch. Microbiol. 167:143-150.

Missiakas, D., et al., "Indentification and characterization of HsIV HsIU (ClpQ ClpY) proteins involved in overall proteolysis of misfolded proteins in *Escherichia coli*," 1996, Embo J. 15:6899-909.

Morrison, D.A., Transformation in *Escherichia coli*: Cryogenic Preservation of Competent Cells, Journal of Bacteriology, Oct. 1977 vol. 132, No. 1, American Society for Microbiology, pp. 349-351.

Mukhija, Reema, et al., High-Level Production and One-Step Purification of Biologically Active Human Growth Hormone in *Escherichia Coli*, Gene, 1995, vol. 165, Elsevier Science B.V., pp. 303-306.

Mukhopadhyay, Pradip, et al., "Construction of a Stable Shuttle Vector for High-Frequency Transformation in Pseudomonas syringae pv. syringae." Journal of Bacteriology, Jan. 1990, , vol. 172, No. 1, American Society for Microbiology, pp. 477-480.

Mulder, et al., "InterPro, progress and status in 2005," Nucleic Acids Res., 2005, 33, Database Issue: D201-5.

Nagahari, Kenji, et al., "RSF1010 Plasmid as a Potentially Useful Vector in *Pseudomonas* Species." Journal of Bacteriology, Mar. 1978, pp. 1527-1529, vol. 133, No. 3, American Society for Microbiology.

Nagahira, et al., Humanization of a mouse neutralizing monoclonal antibody against tumor necrosis factor-alpha (TNF-alpha), J Immunol Methods. Jan. 1, 1999;222(1-2):83-92.

Naglak and Wang, "Recovery of a foreign protein from the periplasm of *Escherichia coli* by chemical permeabilization."(1990) Enzyme Microb. Technol., 12:603-611.

Nakamaye, K. and Eckstein F., "Inhibition of restriction endonuclease Nci I cleavage by phosphorothioate groups and its application to oligonucleotide-directed mutagenesis," 1986, Nucl. Acids Res. 14, 9679-98.

Nakashima, Nobutaka, et al., "Cell-free protein synthesis using cell extract of Pseudomonas fluorescens and CspA promoter." Biochemical and Biophysical Research Communications, Jun. 2004, pp. 671-676, vol. 319, No. 2., Elsevier.

Nedospasov, et al., 1986, "Tandem arrangement of genes coding for tumor necrosis factor (TNF-alpha) and lymphotoxin (TNF-beta) in the human genome," Cold Spring Harb. Symp. Quant. Biol. 51 Pt 1, 611-624.

Needleman, Saul B., et al., "A General Method Applicable to the Search for Similarities in the Amino Acid Sequence of Two Proteins." J. Mol. Biol., 1970, pp. 443-453, vol. 48.

Neu and Heppel, "The release of enzymes from *Escherichia coli* by osmotic shock and during the formation of spheroplasts," (1965) J. Biol. Chem., 240:3685-3692.

Neu and Heppel, "The Release of Ribonuclease into the Medium when *Escherichia coli* Cells are converted to Spheroplasts," (1964) J. Biol. Chem 239: 3893-3900.

Nielsen, Henrik, et al., Short Communication—"Identification of Prokaryotic and Eukaryotic Signal Peptides and Prediction of their Cleavage Sites," Protein Engineering 1997, pp. 1-6, vol. 10, No. I, Oxford University Press.

Nieto, C., et al., "Cloning Vectors, Derived From a Naturally Occurring Plasmid of Pseudomonas Savastanoi, Specifically Tailored for Genetic Manipulation in Pseudomonas," Gene, 1990, pp. 145-149, vol. 87, Elsevier.

(56) References Cited

OTHER PUBLICATIONS

Nishihara, et al., "Chaperone coexpression plasmids: differential and synergistic roles of DnaK-DnaJ-GrpE and GroEl-GroES in assisting folding of an allergen of Japanese cedar pollen, Cryj2, in *Escherichia coli*," Appl. Environ. Microbiol. 64:1694 1998.
Niwa, et al., "An Efficient Gene-Trap Method Using Poly a Trap Vectors and Characterization of Gene-Trap Events," 1993, J. Biochem 113:343-349.
Nomine, Yves, et al., "Formation of Soluble Inclusion Bodies by HPV E6 Oncoprotein Fused to Maltose-Binding Protein, Protein Expression and Purification." 2001, pp. 22-32, vol. 23, Academic Press.
Nossal and Heppel, "The Release of Enzymes by Osmotic Shock from *Escherichia Coli* in exponential phase," 1966, J. Biol. Chem., 241: 3055-3062.
Olekhnovich, Igor N., el al., "Controlled-Expression Shuttle Vector for Pseudomonads Based on the trpIBA genes of Pseudomonas Putida," Gene, 1994, pp. 63-65, vol. 140, Elsevier Science.
Opdenakker, G., et al., Interaction of Interferon With Other Cytokines, Experientia, 1989, pp. 513-520, vol. 45, Birkhauser Verlag, Switzerland.
Park, S., et al., "Secretory production of recombinant protein by a high density culture of a protease negative mutant *Escherichia coli* strain," 1999, Biotechnol. Progr 15, pp. 164-167.
Patra, Ashok K., et al., "Optimization of Inclusion Body Solubilization and Renaturation of Recombinant Human Growth Hormone from *Escherichia Coli*," Protein Expression and Purification, 2000, pp. 182-192, vol. 18, Academic Press.
PCT/US05/01549 International Search Report mailed Jul. 19, 2005.
PCT/US05/26390 Search Report dated Jul. 17, 2006.
PCT/US08/61483 Search Report dated Nov. 7, 2008.
Pearson, William R., et al., "Improved Tools for Biological Sequence Comparison." Proc. Natl. Acad. Sci., Apr. 1988, pp. 2444-2448, vol. 85.
Peluso, P., et al., "Optimizing antibody immobilization strategies for the construction of protein microarrays," 2003, Anal Biochem 312:113-124.
Perussia, Bice, et al., "Immune Interferon Induces the Receptor for Monomeric IgG1 on Human Monocytic and Myeloid Cells," J. Exp. Med., 1983, pp. 1092-1113, vol. 158, Rockefeller University Press.
Pestka, Sidney, et al., "Interferons and Their Actions." Annu. Rev. Biochem., 1987, pp. 727-777, vol. 56, Annual Reviews, Inc.
Pierce, et al., "Expression and Recovery of cominant periplasmically secreted or amyase derived from Streptomyces thermoviolaceus." (1995) Icheme Research Event 2: 995-997.
Pighetti, Gina M., et al., Specific Immune Responses of Dairy Cattle Atter Primary Inoculation with Recombinant Bonvine Interferon-y as an Adjuvant When Vaccinating Against Mastitis, American Journal of Veterinary Research, 1996, pp. 819-824, vol. 57, No. 6.
Pilon, et al., "High-Level expression and efficient recovery of ubiquitin fusion proteins from *Escherichia coli*," Biotechnol Prog., 1996, vol. 12, No. 3, pp. 331-337.
Puehler, et al., 1984, Advanced Molecular Genetics New York, Heidelberg, Berlin, Tokyo, Springer Verlag.
Quevillon et al., "InterProScan: protein domains identifier," 2005, Nucleic Acids Research 33: W116-W120.
Radding, C.M., "Homologous pairing and strand exchange in genetic recombination," 1982, Ann. Rev. Genet. 16: 405.
Ralph, Peter, "Human B Cell-Inducing Factor(s) for Production of IgM, IgG and 19A; Independence From IL 2(1)." The Journal of Immunology, Apr. 1984, pp. 1858-1862, vol. 132, No. 4, The American Society of Immunologists.
Ranson, et al., "Chaperonins," 1998, BioChem. J. 333, 233-242.
Rao, et al., "Stable three-stranded DNA made by RecA protein," 1991, PNAS 88: pp. 2984-2988.
Rawlings, et al., "MEROPS: the peptidase database." 2006, Nucleic Acids Res., vol. 34, D270-D272, Database issue doi:10.1093/nar/gkj089.
Retallack, Diane, et al., "Reliable protein production in a Pseudomonas fluorescens expression system." Protein Expression and Purification, 2012, vol. 81, No. 2, pp. 157-165.
Retallack, Diane, et al., "Pseudomonas fluorescens—a robust expression platform for pharmaceutical protein production," Microbial Cell Factories, 2006, p. S28, vol. 5 (Suppl. 1), BioMed Central.
Retallack, Diane, et al., "Transport of heterologous proteins to the periplasmic space of Pseudomonas fluorescens using a variety of native signal sequences," Biotechnology Letters, 2007, pp. 1483-1491, vol. 29, Springer Science+Business Media B.V.
Riesenberg, D., et al., "High Cell Density Cultivation of *Escherichia Coli* at Controlled Specific Growth Rate," Journal of Biotechnology, 1991, pp. 17-28, vol. 20, Elsevier Science Publishers, B.V.
Rosenberg, et al. "Vectors for selective expression of cloned DNAs by T7 RNA polymerase." 1987, Gene, 56(1): 125-35.
Ruiz-Taylor, LA, et al., "Monolayers of derivatized poly(L-lysine)-grafted poly(ethylene glycol) on metal oxides as a class of biomolecular interfaces," 2001, Proc Natl Acad Sci USA, 98:852-857.
Ruiz-Taylor, LA, et al., "X-ray photoelectron spectroscopy and radiometry studies of biotin-derivatized poly(L-lysine)-grafted-poly(ethylene glycol) monolayers on metal oxides," 2001, Langmuir, 7313-7322.
Sabina, J., et al., "Interfering with Different Steps of Protein Synthesis Explored by Transcriptional Profiling of *Escherichia coli* K-12," 2003, J. Bacteriol 185, pp. 6158-6170.
Saiki, Osamu, et al., Induction of Human Immunoglobulin Secretion—I. Synergistic Effect of B Cell Mitogen Cowan I Plus T Cell Mitogens or Factors. The Journal of Immunology, Sep. 1981, pp. 1044-1047, vol. 127, No. 3, The American Association of Immunologists.
Sanchez-Romero & V. De Lorenzo, (1999) Manual of Industrial Microbiology and Biotechnology (A. Demain & J. Davies, eds.) pp. 460-474.
Schein, C.H., "Production of Soluble recombinant Proteins in Bacteria." Bio/Technology (1989), 7:1141-1149.
Schena, M., et al., "Quantitative monitoring of gene expression patterns with a complementary DNA microarray,"1995, Science 270:467-70.
Schneider, et al., (2005) "Auxotrophic markers pyrF and proC can replace antibiotic markers on protein productions plasmids in high-cell-density Pseudomonas fluorescens fermentation." 2005a, Biotechnology Progress 21(2): 343-348.
Schweizer, Herbert P., et al., Vector Design and Development of Host Systems for Pseudomonas, Genetic Engineering, (2001), pp. 69-81, vol. 23, Kluwer Academic/Plenum Publishers.
Schweizer, Herbert P., Vectors to Express Foreign Genes and Techniques to Monitor Gene Expression in Pseudomonads, Current Opinion in Biotechnology, 2001, pp. 439-445, vol. 12, Elsevier Science Ltd.
Service, R.F. et al., "Tapping DNA for structures produces a trickle." Science 298:948-950 (2002).
SG200906987-3 Exam Report dated Sep. 26, 2011.
Shine and Dalgarno, "The 3'-terminal sequence of *Escherichia coli* ribosomal RNA: complementarity to nonsense triplets and ribosome binding sites," (1974) Proc. Natl. Sci. USA 71:1342-1346.
Shokri, et al., "Growth rate-dependent changes in *Escherichia coli* membrane structure and protein leakage," 2002, App. Microbiol. Biotechnol 58:386-392.
Simmons, et al., "Expression of full-length immunoglobins in *Escherichia coli*: rapid and efficient production of aglycosylated," 2002, J. Immun. Meth. 263:133-147.
Singleton, et al., 2000, "Cloning, expression, and characterization of pyrrolidone carboxyl peptidase from the archaeon Thermococcus litoralis" Extremophiles 4(5), 297-303.
Singleton, Paul & Sainsbury, Diana: "Dictionary of Microbiology," 1978, John Wiley & Sons Ltd., Chichester, UK, XP002667935, pp. 332-333.
Slater, Robert J., and Williams,Ross, "The Expression of Foreign DNA in Bacteria," 2000, Molecular Biology and Biotechnology, Fourth Edition, Chapter 4, pp. 125-154, The Royal Society of Chemistry, Cambridge, UK.

(56) References Cited

OTHER PUBLICATIONS

Smith & Waterman, Michael S., "Comparison of Biosequences." 1981, Adv. Appl. Math 2:482-489.
Smits, et al., "New Alkane-responsive expression vectors for *Escherichia coli* and pseudomonas," Plasmid, 2001, vol. 46, p. 16-24.
Song, K.Y., et al., "Accurate modification of a chromosomal plasmid by homologous recombination in human cells." (1987) Proc. Natl. Acad. Sci. USA 84:6820-6824.
Sordillo, L.M., Controlling Acute *Escherichia Coli* Mastitis During the Periparturient Period with Recombinant Bovine Interferon-Gamma, Veterinary Microbiology, 1991, pp. 189-198, vol. 28.
Southern, P. and P. Berg, "Transformation of mammalian cells to antibiotic resistance with a bacterial gene under control of the SV40 early region promoter." (1982) J. Mol. Appl. Genet. 1:327-341.
Squires, et al., "Heterologous protein production in P. Fluorescens," Bioprocess International, 2004, vol. 2, No. 11, pp. 54-56, 58-59.
Stabel, et al., "Periplasmic location of Brucella abortus Cu/Zn superoxide dismutase." (1994) Veterinary Microbiol. 38: 307-314.
Stauber, et al., "Development and applications of enhanced green fluorescent protein mutants." (1998) Biotechniques 24(3):462-471.
Steidler, L., et al., Mucosal Delivery of Murine Interleukin-2 (IL-2) and IL-6 by Recombinant Strains of Lactococcus Lactis Coexpressing Antigen and Cytokine, Infection and Immunity, 1998, pp. 3183-3189, vol. 66, No. 7.
Steidler, L., In Situ Delivery of Cytokines by Genetically Engineered Lactococcus Lactis, Antonie van Leeuwenhoek, 2002, pp. 323-331, vol. 82.
Steinbeck, M.J., et al., Activation of Bovine Neutrophils by Recombinant Interferon-y, Cell. Immunol., 1986, pp. 137144, vol. 98.
Stewart, Russell J., et al., Direction of Microtubule Movement is an Intrinsic Property of the Motor Dotrnins of Kinesin Heavy Chain and Drosophila Ned Protein, Proc. Natl. Acad. Sci., 1993, pp. 5209-5213, vol. 90.
Studier, F.W. and B.A. Moffatt, "Use of bacteriophage T7 RNA polymerase to direct selective high-level expression of cloned genes." 1986, Journal of Molecular Biology 189(1):113-30.
Suzek, Baris E., et al., "A Probalistic Method for Identifying Start Codons in Bacterial Genomes." Bioinformatics, 2001, pp. 1123-1130, vol. 17, No. 12, Oxford University Press.
Taguchi, et al., "Comparison of secretory expression in *Escherichia coli* and Streptomyces subtilisin inhibtor (SSI) gene," (1990) Biochimica Biophysica Acta 1049: 278-85.
Takara Bio Inc., Product Information Bulletin, "Chaperone Plasmid Set," pp. 1-8, Catalog #3340, Version 0401, publication date unknown.
Tanji, et al., "Controlled Expression of Lysis Genes Encoded in T4 Phage for the Gentle Disruption of *Escherichia coli* cells," (1998) J. Ferment and Bioeng., 85:74-78.
Taub, Dennis D., "Cytokine, growth factor, and chemokine ligand database," Current Protocols in Immunology, 2004, XP002677096, DOI: 10.1002/0471142735.im0629s61, [Retrieved from the Internet: URL:http://onlinelibrary.wiley.com/doi/10.1002/0471142735.im0629s61/full [retrieved on Jun. 1, 2012].
Taylor, J.W. et al., "The use of phosphorothioate-modified DNA in restriction enzyme reactions to prepare nicked DNA," 1985, Nucl. Acids Res. 13, No. 24, pp. 8749-8764.
Te Riele H., et al., "Consecutive inactivation of both alleles of the pim-1 proto-oncogene by homologous recombination in embryonic stem cells," (1990) Nature 348:649-651.
Toogood, H.S., et al., "A thermostable L-aminoacylase from Thermococcus litoralis: cloning, overexpression, characterization, and applications in biotransformations," 2002, Extremophiles 6(2): 111-122.
Tsuda & Nakazawa, "A mutagenesis system utilizing a Tn1722 derivative containing an *Escherichia coil*-specific vector plasmid: application to *Pseudomonas* species," (1993) Gene 136 (1-2): 257-62.
U.S. Appl. No. 12/109,554 Non Final Office Action mailed Dec. 30, 2010.
U.S. Appl. No. 12/109,554 Final Office Action mailed Jun. 15, 2011.
U.S. Appl. No. 11/189,375 Non Final Office Action mailed Feb. 7, 2008.
U.S. Appl. No. 11/189,375 Non Final Office Action mailed Sep. 9, 2009.
U.S. Appl. No. 11/189,375 Final Office Action mailed Jun. 16, 2010.
U.S. Appl. No. 11/189,375 Final Office Action mailed Mar. 19, 2009.
U.S. Appl. No. 11/189,375 Non Final Office Action dated Sep. 14, 2012.
U.S. Appl. No. 12/610,207 Office Action mailed Jun. 11, 2012.
U.S. Appl. No. 12/610,207 Final Office Action issued Nov. 30, 2012.
U.S. Appl. No. 11/038,901 Office Action mailed Nov. 25, 2011.
U.S. Appl. No. 11/038,901 Non Final Office Action mailed Apr. 15, 2011.
U.S. Appl. No. 11/038,901 Final Office Action mailed Sep. 17, 2009.
U.S. Appl. No. 11/038,901 Non Final Office Action mailed Aug. 6, 2008.
U.S. Appl. No. 11/038,901 Final Office Action mailed Feb. 27, 2008.
U.S. Appl. No. 11/038,901 Non-Final Office Action mailed Jul. 27, 2007.
U.S. Appl. No. 11/400,840 Office Action mailed Feb. 14, 2008.
U.S. Appl. No. 11/400,840 Office Action mailed Sep. 17, 2008.
U.S. Appl. No. 11/400,840 Office Action mailed Dec. 24, 2009.
Vale, Ronald D., et al., "Identification of a Novel Force-Generating Protein, Kinesin, Involved in Microtubule-Based Motility," Cell, Aug. 1985, pp. 39-50, vol. 42, MIT.
Vera, Andrea, et al., "The Conformational Quality of Insoluble Recombinant Proteins is Enhanced at Low Growth Temperatures," Biotechnology and Engineering, Apr. 15, 2007, pp. 1101-1106, vol. 96, No. 6.
Vincentelli, Renaud, et al., "Medium-Scale Structural Genomics: Strategies for Protein Expression and Crystallization," Ace. Chem. Res., 2003, pp. 165-172, vol. 36, No. 3.
Vinogradov, Alexi A, et al., Solubilization and Refolding of Inclusion Body Proteins in Reverse Micelles, Analytical Biochemistry, 2003, pp. 234-238, vol. 320, Elsevier Science.
Wackemagel et al., "The periplasmic endonuclease I of *Escherichia coli* has amino-acid sequence homology to the extracellular Dnases of Vibrio cholerae and aeromon as hydrophila," (1995) Gene 154: 55-59.
Wan and Baneyx, "TolAIII Co-overexpression facilitates the recovery of periplasmic recombinant proteins into the growth medium of *Escherichia coli*," (1998) Protein Expression Purif. 14:3-22.
Wang et al., 1985, "Molecular cloning of the complementary DNA for human tumor necrosis factor," Science 228 (4696), 149-154.
Waterman, Michael S., Comparison of Biosequences, Advances in Applied Mathematics, 1981, pp. 482-489, vol. 2, Academic Press, Inc.
Wei, Y., et al., "High-density microarray-mediated gene expression profiling of *Escherichia coli*," 2001, J. Bacteriol 183(2), pp. 545-556.
Wesolowski, et al., 2009, "Single domain antibodies: promising experimental and therapeutic tools in infection and immunity," Med Microbiol Immunol. 198(3): 157-174.
Wilson, D.S. et al., "The use of mRNA display to select high-affinity protein-binding peptides," 2001, Proc Nat Acad Sci USA 98:3750-3755.
Witholt et al., "How does lysozyme penetrate through the bacterial outer membrane?" 1976, Biochim Biophys. Acta, 443: 534-544.
Wood, David O., et al., "Versatile Cloning Vector for *Pseudomonas aeruginosal*," Journal of Bacteriology, Mar. 1981, pp. 1448-1451, vol. 14, No. 3.
Yang, Funmet, et al., Human Transferrin: cDNA Characterization and Chromosomal Localization, Proc. Natl. Acad. Sci. USA, May 1984, pp. 2752-2756, vol. 81.
Yasuda, et al., "Osteoclast differentiation factor is a ligand for osteoprotegerin/osteoclastogenesis-inhibitory factor and is identical to TRANCE/RANKL," 1998, Proc. Natl. Acad. Sci. U.S.A. 95(7), 3597-3602.
Yilma, T., et al., Enhancement of Primary and Secondary Immune Responses by Interferon-Gamma, Adv. Exp. Med. Biol., 1989, pp. 145. 152, vol. 251.
Yilma, T.K., et al., Expression of an Adjuvant Gene (Interferon-y) an Infectious Vaccinia Virus Recombinants, Vaccines, 1987, pp. 393-396, vol. 87.

(56) References Cited

OTHER PUBLICATIONS

Yoshida, et al., "A new strategy of gene trapping in ES cells using 3'RACE," Transgenic Research 4:277-287 (1995).
Zapata, et al., 1995, "Engineering linear F(ab ')2 fragments for efficient production in Escherichia coli and enhanced antiproliferative activity," Protein Eng. 8(10): 1057-1062.
Zhu, H. et al., "Global analysis of protein activities using proteome chips," 2001, Science Express.
Zinder and Arndt, "Production of Protoplasts of Escherichia Coli by ysozyme Treatment," Proc. Mathl. Acad. Sci. USA 1956, 42: 586-590.
Zuffa, A., et al., Protection of Cattle Vaccinated with Inactivated Oil-Adjuvant Infectious Bovine Rhino Trachetis Vaccine Against Experimental Infection, Zbl. Vet. Med. G., 1989, pp. 725-733, vol. 27.
Abdullah et al., "System-48" high-throughput cloning and protein expression analysis, Methods Mol Biol 498:117-127 (2009).
Akao et al., "Purification and Characterization of a Peptide Essential for Formation of Streptolysin S by Streptococcus pyogenes," Infection and Immunity 60(11):4777-4780 (1992).
Amitani et al., "Purification and Characterization of Factors Produced by Aspergillus fumigatus Which Affect Human Ciliated Respiratory Epithelium," Infection and Immunity 63(9):3266-3271 (1995).
Aricescu et al., "Eukaryotic expression: developments for structural proteomics," Acta Cryst D62:1114-1124 (2006).
Aricescu et al., "A time—and cost-efficient system for high-level protein production in mammalian cells," Acta Cryst D62:1243-1250 (2006).
Bahia et al., "Optimisation of insect cell growth in deep-well blocks: development of a high-throughput insect cell expression screen," Protein Expression and Purification 39:61-70 (2005).
Baldwin et al., "Subunit Vaccine against the Seven Serotypes of Botulism," Infection and Immunity 76(3):1314-1318 (2008).
Bebbington and Yarranton, "Antibodies for the treatment of bacterial infections: current experience and future prospects," Curr Op Biotech 19(6):613-619 (2008).
Boettner et al., "High-throughput screening for expression of heterologous proteins in the yeast Pichia pastoris," J Biotech 99:51-62 (2002).
Buzzi et al., "CRM197: reduction of atherosclerosis stenoses in carotids of three elderly patients," Therapy 4(3):293-298 (2007).
Calvete et al., "The disulfide bond pattern of catrocollastatin C, a disintegrin-like/cysteine-rich protein isolated from Crotalus atrox venom," Protein Science 9:1365-1373 (2000).
Cosman, D., "A Family of Ligands for the TNF Receptor Superfamily," Stem Cells 12:440-455 (1994).
Damasceno et al., "Cooverexpression of chaperones for enhanced secretion of a single-chain antibody fragment in Pichia pastoris," Appl Microbiol Biotechnol 74:381-389 (2007).
Duetz et al., "Methods for Intense Aeration, Growth, Storage, and Replication of Bacterial Strains in Microtiter Plates," Appl Env Microbiol 66(6):2641-2646 (2000).
Duetz and Witholt, "Oxygen transfer by orbital shaking of square vessels and deepwell microtiter platesof various dimensions," Biochem Eng J 17:181-185 (2004).
Edmond et al., "Optimized and automated protocols for high-throughput screening of amylosucrase libraries," J Biomol Screen 12:715-723 (2007).
Fang et al., "Development of a high-throughput yeast two-hybrid screening system to study protein-protein interactions in plants," Mol Genet Genomics 267:142-153 (2002).
Fischer and Montal, "Crucial Role of the Disulfide Bridge between Botulinum Neurotoxin Light and Heavy Chains in Protease Translocation across Membranes," J Biol Chem 282(40):29604-29611 (2007).
Georgopoulos, "Toothpicks, Serendipity and the Emergence of the Escherichia coli DnaK (Hsp70) and GroEL (Hsp60) Chaperone Machines," Genetics 174:1699-1707 (2006).

Giannini et al., "The amino-acid sequence of two non-toxic mutants of diphtheria toxin: CRM45 and CRM 197," Nucl Acids Res 12(10):4063-4069 (1984).
Gonzalez Barrios et al., "Autoinducer 2 controls biofilm formation in Escherichia coli through a novel motility quorum-sensing regulator (MqsR, B3022)," J Bacteriol 188:305-316 (2006).
Halling et al., "Genomic cloning and characterization of a ricin gene from Ricinus communis," Nucl Acids Res 13(22):8019-8033 (1985).
Holz et al., "A micro-scale process for high-throughput expression of cDNAs in the yeast Saccharomyces cerevisiae," Protein Expression and Purification 25:372-378 (2002).
Hsu et al., "Engineering the Assembly Pathway of the Baculovirus-Insect Cell Expression System," Annals New York Academy of Sciences 721:208-217 (1994).
Jarvis et al., "Influence of different signal peptides and prosequences on expression and secretion of human tissue plasminogen activator in the baculovirus system," J Biol Chem 268:16754-16762 (1993).
Kim et al., "Glycosyltransferase—a specific marker for the discrimination of Bacillus anthracis from the Bacillus cereus group," J Med Microbiol57:279-286 (2008).
Larsen et al., "Expression of Candida antarctica lipase B in Pichia pastoris and various Escherichia coli systems," Protein Expression and Purification 62:90-97 (2008).
Makarenkova et al., "Dendritic cells and natural killer cells interact via multiple TNF family molecules," J Leukocyte Biol 77:408-413 (2005).
Mitamura et al., "Diphtheria Toxin Binds to the Epidermal Growth Factor (EGF)-like Domain of Human Heparin-binding EGF-like Growth Factor/Diphtheria Toxin Receptor and Inhibits Specifically Its Mitogenic Activity," J Biol Chem 270(3):1015-1019 (1995).
Montgomerie et al., "Improving the accuracy of protein secondary structure prediction using structural alignment," BMC Bioinformatics 7:301 (2006).
Naamati et al., "ClanTox: a classifier of short animal toxins," Nucl Acids Res 37:W363-W368 (2009).
Niwa et al., "Bimodal protein solubility distribution revealed by an aggregation analysis of the entire ensemble of Escherichia coli proteins," PNAS 106(11):4201-4206 (2009).
Novak et al., "Bacterial growth properties at low optical densities," Antonie Van Leeuwenhoek 96(3):267-274 (2009).
Orr et al., "Expression and Immunogenecitity of a Mutant Diphtheria Toxin Molecule, CRM 197, and Its Fragments in Salmonella typhi Vaccine Strain CVD 908-htrA," Infection and Immunity 67(8):4290-4294 (1999).
Papini et al., "Cell Penetration of Diphtheria Toxin," J Biol Chem 268(3):1567-1574 (1993).
Randolph et al., "Amino acid sequence of fibrolase, a direct-acting fibrinolytic enzyme from Agkistrodon contortrix contortrix venom," Protein Science 1:590-600 (1992).
Schiavo et al., "An Intact Interchain Disulfide Bond is Required for the Neurotoxicity of Tetanus Toxin," Infection and Immunity 58(12):4136-4141 (1990).
Shu et al., "The structure of spider toxin huwentoxin-II with unique disulfide linkage: Evidence for structural evolution," Protein Science 11:245-252 (2002).
Smialowski et al., "Protein solubility: sequence based prediction and experimental verification," Bioinformatics 23(19):2536-2542 (2007).
Tsai and Rapoport, "Unfolded cholera toxin is transferred to the ER membrane and released from protein disulfide isomerase upon oxidation by Ero 1," J Cell Biol 159(2):207-215 (2002).
Tsunawaki et al., "Fungal Metabolite Gliotoxin Inhibits Assembly of the Human Respiratory Burst NADPH Oxidase," Infection and Immunity 72(6):3373-3382 (2004).
Usami et al., "Primary structure of two-chain botrocetin, a von Willebrand factor modulator purified from the venom of Bothrops jararaca," PNAS USA 90:928-932 (1993).
Vad et al., "Engineering of a Pichia pastoris expression system for secretion of high amounts of intact human parathyroid hormone," J Biotechnology 116:251-260 (2005).
Yuan et al., "Discovery of a Distinct Superfamily of Kunitz-Type Toxin (KTT) from Tarantulas," PLoS One 3(10):e3414 (2008).

(56) References Cited

OTHER PUBLICATIONS

Zhang et al., "Enhanced Secretion of Heterologous Proteins in Pichia pastoris Following Overexpression of Saccharomyces cerevisiae Chaperone Proteins," Biotechnol Prog 22:1090-1095 (2006).
Canadian Patent Application CA2553503 Exam Report dated May 2, 2013.
Canadian Patent Application CA2574953 Office Action dated Jul. 23, 2013.
EP11173331.7 Office action dated Nov. 6, 2013.
EP12198545 Extended European Search Report dated Jun. 14, 2013.
Japanese Patent Application 2011-132011 Office Action mailed Jul. 9, 2013.
Japanese Patent Application 2010-506503 Office Action dated May 14, 2013.
Japanese Patent Application 2007-523707 Office Action dated Feb. 28, 2014.
Korean Patent Application 10-2007-7004418 Exam Report dated Jun. 25, 2013.
Korean Patent Application 10-2013-7002343 Office Action dated Feb. 25, 2014.
U.S. Appl. No. 11/038,901 Office Action mailed Dec. 17, 2013.
U.S. Appl. No. 11/189,375 Final Office Action mailed Mar. 29, 2013.
U.S. Appl. No. 11/400,840 Office Action mailed Mar. 28, 2014.
Canadian Patent Application No. 2,685,326 Office Action mailed Jul. 30, 2015.
European Patent Application No. 05705852.1 Invitation pursuant to Article 94(3) dated May 26, 2015.
European Patent Application No. 11176612.7 Communication dated Nov. 20, 2015.
India Patent Application No. 6791/DELNP/2009 First Examination Report dated May 26, 2015.
U.S. Appl. No. 11/038,901 Office Action dated May 4, 2015.
U.S. Appl. No. 11/400,840 Office Action dated Apr. 30, 2015.
U.S. Appl. No. 11/400,840 Office Action dated Jan. 12, 2016.
U.S. Appl. No. 12/610,207 Office Action dated Aug. 3, 2015.

\* cited by examiner

US 9,394,571 B2

SEQUENCE LISTING

<160> NUMBER OF SEQ ID NOS: 137

<210> SEQ ID NO 1
<211> LENGTH: 42
<212> TYPE: DNA
<213> ORGANISM: Artificial Sequence
<220> FEATURE:
<223> OTHER INFORMATION: oligonucleotide primer

<400> SEQUENCE: 1
atatactagt aggaggtaac ttatggctga cgaacagacg ca    42

<210> SEQ ID NO 2

```
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 2
atattctaga ttacaggtcg ccgaagaagc                                    30

<210> SEQ ID NO 3
<211> LENGTH: 291
<212> TYPE: DNA
<213> ORGANISM: Pseudomonas fluorescens

<400> SEQUENCE: 3
atgaagcttc gtcctctgca cgaccgcgtc gtaatccgtc gcagcgaaga agaaaagaaa    60
accgctggcg ggatcgttct gccaggttcg gctgctgaaa aagccaacca cggtgtaatc   120
gtcgctgctg gcccaggcaa aaccctggag aatggtgatg tacgcgcact ggccgtgaaa   180
gtgggtgaca aggttgtttt cggcccttac tccggcagca acactgtgaa agtagacggc   240
gaagacctgc tggtaatggc tgagaacgaa attctcgccg ttctggaaga c            291

<210> SEQ ID NO 4
<211> LENGTH: 762
<212> TYPE: DNA
<213> ORGANISM: Pseudomonas fluorescens

<400> SEQUENCE: 4
atggctgcta agaagttaa attcggcgac tccgcccgca agaaaatgct cactggcgtc      60
aacgtactgg ctgacgcagt aaaagcgacc ttgggcccga aggccgtaa cgtgatcatc     120 gagaagagct cggcgctcc gaccatcacc aaggatggcg tttccgtagc aaaagaaatc     180
gaactggaag accgtttcga gaacatgggc gcgcagctgg tcaaagacgt tgcctcccgt    240
gccaacgatg acgcaggcga cggcaccacc accgctaccg tcctggctca ggcgatcgtc    300
aacgagggct acaaggccgt cgctgccggc atgaacccga tggacctcaa gcgtggcatc    360
gacaaggcga ccatcgccat cgttgccgag ctgaaaaatc tgtccaagcc atgcgccgac    420
accaaggcca tcgctcaggt aggcaccatc tccgccaact ccgacagctc catcggtgac    480
atcattgccg aagccatgga aaagtcggt aagaaggcg tgatcaccgt tgaagaaggc      540
tcgggcctgg aaaacgaact gtcggttgta gaaggcatgc agttcgaccg tggctacctg    600
tctccgtact cgtcaacaa gcctgagacc atggttgccg agctggacag cccgctgatc    660
ctgctggtcg acaagaagat ctccaacatt cgcgaaatgc tgccagtact ggaagccgtt    720
gccaaagccg ccgtccatt gctgatcgtt tccgaagacg tg                       762

<210> SEQ ID NO 5
<211> LENGTH: 456
<212> TYPE: DNA
<213> ORGANISM: Pseudomonas fluorescens

<400> SEQUENCE: 5
atggctacta ccctgtcgtt ggccccactg ttccgtcaat cggtgggctt tgatcgcttc     60
aatgacctgt tcgagtcggc gctgcgcagc gaggctccga attcctatcc acctcacaat   120
gtggaaaagc acggtgacga cgcgtaccgc attgtcatcg ccgtggctgg cctgaccgag   180
gaggatctgg atatccaggt cgagaggggt gtattgacgg tttctggcgg taaacgcgaa    240
accgacgata aggtcgctta cctgcaccag ggcattgccc aacgtgcgtt ccggttgtcg    300
```

```
ttccgcttgg cggaccatat cgaagtacgt ggcgcatccc tgaccaacgg tttgctcaac    360
atcgacctgc tgcgtgaagt gcctgaagag gccaagccaa aacgcatcat gattggtggc    420
gaggccaaac ctgaactgcg tcaggtcagc ttgcag                              456
```

<210> SEQ ID NO 6
<211> LENGTH: 519
<212> TYPE: DNA
<213> ORGANISM: Pseudomonas fluorescens

<400> SEQUENCE: 6

```
gtgggtactc cttgtcattt cgctttattc gagctgcagc cgagctttcg gctggacctt     60
gagcagcttg ccacgcgcta ccgtgaattg gcgcgtggcg tgcatccgga ccgctttgcc    120
gacgcttccg agcgtgagca acgcttggcg ctggagcaat cggccagcct caacgaagcc    180
tatcagacgc taaaaagccc cccgaaacgc gcacgttatt tactggcgat gacgggcggc    240
gagttgccga tggaagtcac cgtgcatgac ccggacttcc tgatgcagca gatgcagtgg    300
cgcgaagagc tcgaagactt gcaggacgaa gccgatgtgg cgggtgtcgt ggtcttcaag    360
cgccgtctga aggcggccca ggatgagctc aacgaaagct tcgcagcctg ttgggatgat    420
gcggcgcaac gtgagcaggc cgaacgcctg atgcggcgca tgcaattcct cgacaagctc    480
acctacgaag tgcgccagct agaagagcgc ctcgacgat                           519
```

<210> SEQ ID NO 7
<211> LENGTH: 1920
<212> TYPE: DNA
<213> ORGANISM: Pseudomonas fluorescens

<400> SEQUENCE: 7

```
atgggcaaaa ttatcggtat cgacctgggg actaccaact cctgcgtctc cgtgctggaa     60
aacggcgttg caaaagttat tgaaaacgcc gaaggcgcac gtaccacccc gtcgatcatc    120
gcttacgcca acgacggtga atcctcgtc ggccaatcgg ccaagcgtca ggcagtgacc    180
aacccgcaca caccctgta cgcggtaaag cgtctgatcg gtcgtaagtt cgacgaagaa    240
gtcgtacaga aagacatcaa gatggtgcct tacaaaatcg ccaaggccga caacggtgac    300
gcctgggttg aagtgaacgg ccagaagatg tcgccgccac aaatctcggc tgaaatcttg    360
aaaaagatga gaagaccgc cgaagactac ctcggtgaag cagtgactga agcggtgatc    420
accgttccgg cctacttcaa cgacagccag cgtcaggcca ccaaagacgc cggccgcatc    480
gcgggcctgg atgtaaaacg tatcatcaac gaaccaaccg cagctgctct ggcttacggt    540
atggacaagg ccaagggcga tcacaccgtg atcgtttacg acctgggtgg cggtacattc    600
gacgtctccg tgatcgagat cgcagaagtt gacggcgagc accagttcga agtgttggcc    660
accaacggcg acaccttctt gggtggtgaa gactttgaca ttcgtctgat cgactacctc    720
gttgacgaat tcaagaaaga aagcggcatg aacctcaaag gtgacccgct ggccatgcag    780
cgcctgaaag aagccgctga aaaagccaag atcgagctgt cttccgctca gtcgaccgac    840
gtgaacctgc cgtacatcac agcagacgcc actggtccta agcacttgaa cgtgaaaatc    900
tcgcgttcca gctcgaagc gctggttgaa gacctggttc aacgcaccat cgaaccttgc    960
cgcatcgcgc tgaaagactc cggtatcgac gttggctcta tcaacgacgt gatcctggta   1020
ggcggtcaga cccgtatgcc actggttcag aagctggtca ccgaattctt cggcaaagaa   1080
gctcgtaaag acgtgaaccc ggacgaagcc gttgccatgg gtgctgccat ccagggtgcc   1140
```

```
gtactggccg gtgacgtgaa agacgtgttg ctgctggacg taagcccgct gaccctgggt    1200
atcgaaacca tgggtggcgt gatgactgcg ctgatcgaga aaacaccac gattcctacc     1260 aagaaatccc aggtgttctc gactgccgat gacaaccagg gcgccgtgac tatccacgtg    1320
ctgcagggcg agcgtaagca agctgcgcag aacaagtccc tgggcaagtt cgacttggct    1380
gagattccac cagcaccacg tggcgtgcca caaatcgaag tgaccttcga catcgacgcc    1440
aacggcatcc tgcacgtcgg cgcgaaagac aaggccaccg gcaaagagca gaagatcacc    1500
atcaaggcca actccggcct gtctgatgaa gaaattcaac agatgatccg tgatgctgaa    1560
accaatgctg aagccgacaa gaagttcgaa gagttggcgg gcgcccgtaa ccagggtgac    1620
gcgctggttc actcgacgcg caaaatgatc gctgatgctg gcgacaaagt gaccgacgaa    1680
gagaaaaccg caatcgaagc ggcagtggtt gccctggaag ccgccatcaa aggcgacgac    1740
aaggctgcca tcgaagccaa ggttgaggag ctgtcgaaag tctccgcgcc agttgctcag    1800
aaaatgtacg ccgaacaagg ccagccggct gacggcgctg cgcaacaagc agaacctgaa    1860
gccaagcacg acgacgttgt cgatgccgag ttcgaagaag ttaaagacga ccagaagaag    1920
```

<210> SEQ ID NO 8
<211> LENGTH: 1266
<212> TYPE: DNA
<213> ORGANISM: Pseudomonas fluorescens

<400> SEQUENCE: 8

```
atgaaaaacg catccccagc ccgtgcctgc ggcatcgact tcggcacgtc caactccacc      60
gtcggctgga tccgccccgg cgaggagacg ctgatcgcgc tggaggacga caagatcaca    120
ttgccgtcag tggtctttttt caacttcgag gagcgccgcc cggtgtacgg tcgcctggcg    180
ctgcacgaat acttggagaa ctacgaaggc cgcctgatgc gctcgctcaa gagcctgctg    240
ggttccaagc tgatcaagca cgacaccagc gtgctcggca ccgccatgcc cttcaccgac    300
ctgctggccc tgtttatcgg ccaactcaag agccgcgccg aagccaacgc cggccgtgag    360
ttcgaagaag tggtgctggg ccgcccggtg ttcttcgtcg atgacgaccc gatggccgac    420
caggaagcgg aaaacaccct ggtggacgtg gcgcgcaaga tcggcttcaa ggacatctcc    480
tttcagtacg aaccgattgc tgctgccttc gactacgagt ccaccatcac caaagaagag    540
ctggtgctga tcgtcgacat cggcggtggt acctccgact tctccctggt gcgcctgtcg    600
ccggagcgtc gtcacaacga caaccgccag agcgacatcc tcgccaccgg cggcgtgcac    660 atcgcggta ccgacttcga caaacagctc tcgctagccg catgatgcc gctgttcggc      720 tacggcagcc gcatgaaaag cggcgcctac atgcctacca gccaccacat gaacctggcc    780
acctggcata ccatcaactc ggtgtactca caaaaatccc agctggccct gggcagcatg    840
cgctacgaca tcgaagacac cggcggcatc gaccgcctgt tcaagctgat cgaacagcgc    900
gccgggcact ggctggccat ggaagtggaa gagaccaaga tccagctcac ccaggcagac    960
agccgccacg tgccgctgga ccgcatcgaa gccggcctga gcgtagacct gagccgcgcg    1020
ctgttcgagt cgtccattga caatctgctg aacgcgtac gcggcagcgt cacgcagttg     1080
ctcaacgacg cctcggtgag cgtggcgcaa gtggacacgt tgttcttcac cggcggctcc    1140
agcggcatcc cggcactgcg ccacagcatc tcggcaatgc tgccgaatgc gcggcatgtg    1200
gaaggcaata tcttcggcag tattggcagt ggtttggcga ttgaggcgag caagcgctac    1260
ggcagc                                                                 1266
```

<210> SEQ ID NO 9
<211> LENGTH: 1860
<212> TYPE: DNA
<213> ORGANISM: Pseudomonas fluorescens

<400> SEQUENCE: 9

| | | | | | |
|---|---|---|---|---|---|
| atggctctac | tgcaaatcgc | cgaacccggc | caaagccctc | aaccgcacca | gcgtcgcctg | 60 |
| gcggtcggga | ttgacctggg | caccaccaat | tccctggttg | ctgccttgcg | cagcggcctg | 120 |
| tccgagccac | tgcctgacgc | cgatgggcag | gtgatcctgc | cgtccgccgt | gcgttatcac | 180 |
| gccgaccgca | ctgaagtggg | cgaatcggcc | aaattggccg | cgtccgcaga | ccctttgaac | 240 |
| acggtgttgt | cggtcaagcg | cttgatgggt | cgtgggttgt | ccgacgtcaa | gcaattgggc | 300 |
| gaccaactgc | cgtaccgctt | tgtcggcggt | gaatcccata | tgccgttcat | cgacaccgtc | 360 |
| caggggccca | agagcccggt | ggaagtgtcg | gctgatatcc | tcaaggtgct | cgccagcgt | 420 |
| gcagaaagca | ccctgggcgg | tgagctggta | ggggcggtga | tcactgttcc | ggcgtatttc | 480 |
| gatgacgccc | agcgccaagc | caccaaggat | gcggcgaaac | ttgccggctt | gaacgtgctg | 540 |
| cgcttgctca | acgaaccgac | tgcggcggcg | gtggcctacg | gcctcgatca | gcacgctgaa | 600 |
| ggcctggtcg | ctatttatga | cctgggcggc | ggcaccttcg | atatttcgat | cctgcgcctg | 660 |
| accggcggtg | tgttcgaagt | gctcgcgacc | ggcggcgaca | gcgccctggg | tggcgatgat | 720 |
| ttcgatcacg | ctattgctgg | ctggatcatc | agcagtgctg | gcttatcggc | cgacctggac | 780 |
| ccaggcgcgc | agcgcaacct | gctgcaaact | gcctgcgcgg | ccaaagaggc | gctgactgac | 840 |
| gctgcttctg | ttgaagtgtc | ctacggtgac | tggtcggcac | agctgacccg | cgaagccttt | 900 |
| gatgcgctga | tcgagccgat | ggtcgcccgc | agcctcaaag | cctgtcgtcg | tgctgtgcgt | 960 |
| gattccggta | tcgagttgga | agacgtcggt | gcagtggtca | tggtcggcgg | ttccacccgc | 1020 |
| gtgccgcgcg | tgcgcgaagc | ggtcgccgaa | gcctttgggc | gccaaccgct | gaccgaaatc | 1080 |
| gacccggatc | aagtggtcgc | catcggcgct | gccatccagg | ccgataccct | ggctggtaac | 1140 |
| aaacgcgatg | gcggcgaatt | gctgttgctc | gacgtgatcc | cgttgtccct | gggcctggaa | 1200 |
| accatgggtg | gcctgatgga | gaaggtgatt | ccgcgcaaca | ccaccattcc | cgtcgcccgt | 1260 |
| gcccaggact | tttctaccta | caaagacggc | cagacagcga | tgatgattca | tgtgctgcaa | 1320 |
| ggtgagcgcg | agctgatcag | cgactgccgt | tccctggcgc | gctttgaatt | gcgtggcatt | 1380 |
| ccggcgatgg | tggccggtgc | cgccaagatt | cgcgtgacct | tccaggtcga | tgccgatggc | 1440 |
| ttgctcagcg | tggctgcgcg | tgagctggct | tcgggcgtgg | aggccagcat | ccaggtcaag | 1500 |
| ccgtcctacg | gcctcaccga | tggcgaaatc | gccaagatgc | tcaaggattc | gttccagtat | 1560 |
| gccggtgacg | ataaggtcgc | ccgtgtatta | cgcgagcagc | aagtagatgc | ccagcgcctg | 1620 |
| ctcgaagcgg | tgcagggtgc | ccttgaagcc | gatggcgagc | gctgctgga | tgccgaagaa | 1680 |
| cgcatggtca | ttgacctgca | aatgcaggaa | ctggccgaac | tgatgaaagg | caacgatggc | 1740 |
| tacgccatcg | agcaacagac | caagcgcctg | tcgcaagtga | ctgatgcctt | tgccgcccgc | 1800 |
| cgtatggatc | agacggttaa | agccgcgctg | gcgggccgca | acctgaatga | aattgaggaa | 1860 |

<210> SEQ ID NO 10
<211> LENGTH: 936
<212> TYPE: DNA
<213> ORGANISM: Pseudomonas fluorescens

<400> SEQUENCE: 10

| | | | | | |
|---|---|---|---|---|---|
| atggatttca | aagactacta | caagattctc | ggtgtcgagc | cgacggctga | cgacaaggag | 60 |

```
atcaagtcgg cttatcgcaa gctggcgcgt aaatatcacc cggacgtcag caaggaaaag        120
gatgccgaat ccaagttcaa ggatgcgtcc gaggcctatg aagcgctgaa aagtgccgac        180
aaacgcgccg aatacgatga actgcgcaaa tacggccagc atggccagcc gttccagggg        240
ccaccgggtt ggcagagccg tggaggcttt ggtggcggcc aggacgcggg cgattttcg         300 gacttttca gttcgatctt cggttcgcgc ggcgatgcct tcggtggcgg ccagcgccgt         360
cctaccgggc gcaagggcca ggatgtggag atgcagctca tggtttccct ggaggaaacc        420
ctgtccaccg agtccaagca gatcagcttc caggtgccac agtacgatgc ttccggtcgg        480
catgtgagca acaccaccaa aagcctgaac gtgaagatcc cggccggtgt ggccgatggc        540
gagcgcattc ggctcaaggc ccagggcgcg ccgggcattg gtggcgggggc caatggtgat       600 ttgtacctga tcatcaagtt cgcaccccac cccaagttcg aggtggacgg cgaaaacctg        660
atcatcaacc tgccgctggc accctgggaa ctggcgctgg gcacggaagt ggccgtgccg        720
actctcaccg gcaagatcaa cctcaaggtg cctgccggca ccagaacgg ccagcgcatg         780 cgcgccaagg gccatggctt gctgaacaag gccgggcaac gcggctatct gttcatccag        840
ctcaaggcgg tgatgcccaa ggcggcggat gatgaggtca aagcgctgtg ggaggccttg        900
gcacaaaagg ccgcgttcaa tccgcgcgag cagttc                                  936
```

```
<210> SEQ ID NO 11
<211> LENGTH: 1122
<212> TYPE: DNA
<213> ORGANISM: Pseudomonas fluorescens

<400> SEQUENCE: 11
atggcaaagc gtgactatta cgaagtattg ggtgtggagc gtggcgccag cgaggcggag        60
ctgaaaaagg cctaccgtcg cctggcgatg aagcaccacc cggaccgtaa tccggataac        120
aaagaatccg aagagatgtt caaagaggcc aacgaggcct acgaatgcct gtgtgatccc        180
aataagcgtg cagcctacga ccagtatggc catgccggtg tcgacccaag catgggcggc        240
ggcggtgccg gttttggtgg tcagaacttc tccgatattt tcggcgacgt attcagcgac        300
ttcttcggcg gtggccgtgg cggtcagcgt ggcggccctc agcgcggcag cgacctgcgt        360
tacaccctgg aactgaacct ggaagaagcc gtgcgcggca ccagtgtcaa tatccgtgtg        420
ccgacgctgt tcaactgcaa gccgtgcgac ggctcgggtg cgaagaaagg ctcctcgccg        480
atcacgtgcc cgacctgcgg cggtattggg caggtgcgca tgcaacaggg cttcttctcg        540
gtgcagcaaa cctgcccgcg ttgccatggc cagggcaaga tcatttccga tccgtgcgac        600
tcctgccacg gcgaaggccg cgtcgaagag tacaagacgc tgtcggtcaa agtgccggcg        660
ggtgtggata ccggcgatcg tattcgcctg tcgggcgaag gcgaggcggg tgcacagggc        720
ggccctacag gcgacctgta cgtggtgatc aatgtgcgcg agcactcgat cttccagcgt        780
gacggcaagc acttgttctg cgaagtgccg atcagctttg ttgatgcggc cctgggtggc        840
gagctggaga ttccgacgct ggatggtcgg gtcaagctca agattcccga ggggactcaa        900
accggcaagc agttccgcat tcgtggcaaa ggcgttgcgc ccgtgcgtgg tggcggtgct        960
ggcgacctga tgtgtcgtgt ggcggttgaa accccgtga acctgaatcg tcgtcagcgt        1020
gaactgctgg aagagttccg cagctcgctg gaaggcgatg actcgcactc accgaagacc        1080
acaggcttct tcgacggtgt aaaacgcttc ttcggcgacc tg                          1122
```

```
<210> SEQ ID NO 12
<211> LENGTH: 234
```

```
<212> TYPE: DNA
<213> ORGANISM: Pseudomonas fluorescens

<400> SEQUENCE: 12
atgaaagtcg aaccagggct ctaccagcat tacaaggggc cgcagtaccg tgttttcagc      60
gtggcgcgcc actctgaaac cgaagaagaa gtggtgtttt accaagcgct gtatggcgaa     120
tacggctttt gggtgcgccc tttgagcatg ttcctggaga ccgtcgaagt tgacggcgag     180
caggtcccgc gctttgcttt ggtcacggcc gaacccagtc tttttacagg gcaa           234

<210> SEQ ID NO 13
<211> LENGTH: 558
<212> TYPE: DNA
<213> ORGANISM: Pseudomonas fluorescens

<400> SEQUENCE: 13
atggctgacg aacagacgca ggatacgcaa actccagacg ccaattcggc tgccggtgat      60
gaactggcga ctcgtgtgca agtgctcgaa gagcaattgg ccgctgcgca ggatcaatcg     120
ttgcgtgttg ccgccgatct gcagaacgtc cgccgccgtg ccgagcagga tgtagagaag     180
gctcacaagt tcgcgctgga aaaattcgcc ggtgacctgc tgccgatcat cgacagcctg     240
gagcgtggtc ttgagttgtc caacccggac gacgaaaaca tccgcccaat gcgcgaaggc     300
attgagctga ccctgaaaat gttccaggac accctgaagc gttatcagtt ggaagcgatc     360
gatccgcaag ccggcgagcc gttcaatgct gagcatcacc aagccatggc catgcaggaa     420
agccatgacc tggaacccaa tagcgtgatc aaggtgttcc agaagggtta ccagctcaac     480
ggtcgcctga tgcgcccggc aatggtggtg gtgagcaagg ctcctgcacc cgttgcacct     540
tctattgatg agcaggct                                                   558

<210> SEQ ID NO 14
<211> LENGTH: 2268
<212> TYPE: DNA
<213> ORGANISM: Pseudomonas fluorescens

<400> SEQUENCE: 14
atgttaaacc gcgagctcga agtcaccctc aatcttgcct tcaaggaggc tcgttcgaag      60
cgtcatgaat tcatgaccgt cgaacacctt ttgctggcac ttttggataa cgaagctgcc     120
gccaccgttc tacgtgcgtg cggcgccaac cttgacaagc tcaagcatga cctgcaggag     180
tttatcgact ccaccacgcc actgatcccc gtgcatgacg aggaccgcga aacccagcca     240
accctgggct tccagcgggt attgcagcgt gctgtgttcc acgtacagag ctccggtaag     300
cgtgaggtca caggcgcgaa tgtacttgtg gcaattttca gcgaacagga aagccaggcc     360
gtgtttctgc tcaagcagca gagcgttgcc cgtattgatg tggtcaacta catcgcccac     420
ggtatctcca aggtgcctgg gcacggcgat cattccgagg gtgagcagga catgcaggac     480
gaggagggcg gcgagtcttc ttcttccagc aaccgctgg atgcctatgc aagtaacctc     540
aatgaaatgg cgcgccaggg gcggatcgat ccgctagtgg ggcgtgagca tgaggttgag     600
cgtgtagcgc agatcctggc gcgtcgtcgc aagaacaacc cattgctggt gggcgaggcg     660
ggcgtgggta aaccgcgat tgccgaaggc ctggccaagc gcattgtcga caaccaggtg     720
ccagacctgc tggccagcag tgtcgtctac tcccttgacc tgggcgcgtt gctcgccggg     780
accaagtacc gtggcgattt cgagaagcgc ttcaaggcgt tgctcggcga gctgaaaaaa     840
cgcccgcagg ccatcctgtt catcgacgag atccatacca tcattggcgc cggtgcggct     900
```

```
tccggtgggg tgatggacgc ttccaacctg ctcaagccac tgctgtcctc cggtgatatc    960
cgctgcattg gttcgaccac gttccaggaa tttcgcggca tcttcgagaa agaccgcgcc   1020
ctggcgcgtc gcttccagaa agttgacgtg tccgagccct cggttgaaga caccatcggc   1080
atcctgcgcg ggctcaaggg cgttttgaa gcgcaccatg gcatcgagta caccgatgag    1140
gccctgcgtg cggcggctga gctggcgtcg cgctacatca acgaccggca catgccagac   1200
aaagccatcg atgtgatcga cgaggcgggt gcctaccagc cctgcagcc ggtcgagaag    1260 cgcgtgaagc gcatcgacgt gcctcaggtc gaggacatcg tggccaagat cgcgcggatt   1320
ccgccaaaac acgtcaccag ttccgacaag gagttgctgc gtaacctgga gcgcgacctc   1380
aagctcaccg tgtttggtca ggatgcggcc atcgactcgc tgtccacggc gatcaagttg   1440
tcccgtgcgg gcctcaagtc gccggacaag ccagtcggtt cgttcctgtt cgcaggcccg   1500
accggcgtcg gcaagaccga ggcggctcgc cagttggcca aggccatggg catcgagctg   1560
gtgcgtttcg acatgtccga gtacatggag cgccacacgg tgtcgcgttt gatcggcgcg   1620
cctccgggct atgtcggctt cgatcaggg cggcctgtga ccgaggcgat caccaagcag    1680
ccacactgcg tattgctgct cgacgaaatc gaaaaggctc acccggaagt cttcaacctg   1740
ctgttgcagg tcatggacca cggcaccctg accgacaaca acgggcgcaa ggcagacttc   1800
cgcaacgtga tcgtgatcat gaccaccaac gccggtgctg aaaccgcggc gcgtgcttcg   1860
atcggcttta cgcatcagga tcactcgtct gatgccatgg aagtgatcaa gaagagcttc   1920
acgccggagt tccgcaaccg cctggacacc attatccagt ttggtcgcct cagccatgag   1980
gtcatcaaaa gcgtggtgga caagttcctc accgagcttc aagcgcagtt ggaagacaag   2040
cgcgtgcagc tggatgtgac ggaagcggcc cgcagttgga tcgcagaggg cggctacgat   2100
gcggcaatgg gcgcacgccc aatggcgcgt ctgatccagg acaagatcaa gcggccattg   2160
gccgaagaga tcctgttcgg cgaactctcc gaccatggcg gcgtggtgca catcgacctg   2220
aaggacggcg agctgacctt cgagttcgag accacggcgg aaatggcc              2268

<210> SEQ ID NO 15
<211> LENGTH: 2562
<212> TYPE: DNA
<213> ORGANISM: Pseudomonas fluorescens

<400> SEQUENCE: 15
atgcgtattg atcgtttaac cagcaaatta cagttggcat tgtccgactc tcaatctttg     60
gcagtgggcc tcgaccaccc ggccatcgaa cctgcgcact tgatgcaggc actcctggaa   120
cagcaaggtg gttctatcaa gcccttgctg atgcaggtgg gctttgacgt taacagcctg   180
cgcaaggagt tgagtaaaga gctcgaccag ctgccgaaaa tccagaatcc caccggcgac   240
gtaaacatgt cccaggactt ggcgcgcctg ctcaaccagg ccgaccgtct ggcccagcag   300
aaaggtgacc agttcatctc cagtgaattg gtgttgctcg ccgccatgga cgacaacagc   360
aagctcggca agttgttgct gggccagggc gtgagcaaaa aggccctgga aaacgccatc   420
aacaacctgc gtggcggcga agcggtgaac gaccccaacc acgaggagtc gcgccaggcc   480
ctggacaaat acaccgtcga cctgaccaag cgtgccgaag agggcaagct ggaccgggtg   540
atcggccgcg acgatgaaat cgtcgcacc attcaggtgt tgcaacgtcg caccaagaat    600
aacccggtgt tgatcggtga acctggcgtg gtaaaaccg cgattgccga gggcctggcc    660
cagcgcatca ttaatggcga ggtaccgac ggcctcaaag gcaagcgcct gctgtctctg    720
gacatgggct cgttgatcgc cggtgccaag ttccggggtg aattcgaaga gcgcctcaaa    780
```

```
tccttgctta acgaattgtc gaagcaggaa gggcagatca ttctgtttat cgacgaattg      840
cacaccatgg tcggcgccgg taagggcgaa ggctccatgg acgccggcaa catgctcaag      900
cccgccttgg cacggggtga gttgcattgc gtcggtgcga ccacgctcaa cgaataccgt      960
cagtacatcg aaaaggacgc agcgcttgag cgtcgcttcc agaaagtcct ggtggaagag     1020
ccgagcgaag aagacaccat cgcgatcctg cgtggcctga agagcgcta tgaggtccac      1080 cataaagtgg cgatcaccga cggtgcgatc attgcggcgg ccaaattgag ccatcgctat     1140
atcaccgatc gtcagttgcc ggacaaggcg atcgacctga tcgacgaagc ggccagccgt     1200
atccgtatgg agatcgactc caagccgaaa gtgctggatc gtctggatcg gcgcctgatt     1260
caactgaaag tcgaatccca ggcgctgaag aaagaagaag acgaagcggc caagaaacgc     1320
ctggaaaaac tccaggaaga aattgtccgc ctggaacgtg agtattcgga cctcgaagaa     1380
atctggacct cggaaaaagc cgaagtacag ggttcggcgc agatccagca aaaaatcgag     1440
cagtcccgcc aggaactgga agccgcgcgc cgcaaaggcg acctgaaccg catggccgag     1500
ttgcagtacg gggtgatccc ggacctggaa cgcagcctgc agatggtcga ccagcacggc     1560
aaacctgaaa accagttgct gcgcagcaag gtgaccgagg aagaaattgc cgaagtggtc     1620
tccaagtgga ccggtattcc cgtgtcgaag atgctcgaag gcgagcgcga caagctgttg     1680
aagatggaaa gcctgctgca tcagcgcgtc atcggccagg aagaggcggt ggtggcggtg     1740
tccaacgccg tacggcgttc gcgggcgggt ttgtccgacc cgaaccgtcc aagcggctcg     1800
ttcatgttcc tcggcccgac cggtgtaggt aagaccgagt tgtgcaaggc cctggccgag     1860
ttcctctttg atacggaaga ggccatggtg cggatcgata tgtccgaatt catggagaaa     1920
cactcggtgg ctcgcctgat cggtgcacca ccaggctatg tgggttacga agagggcggt     1980
tatctgaccg aagccgtgcg gcgtaagcct tactcggtga tcctgctgga tgaggtcgag     2040
aaggcgcacc cggatgtgtt caacatcttg ctgcaggtgc tggaggatgg tcgcttgacg     2100
gacagccacg ggcgtacggt ggacttccgt aatacggtga tcgtgatgac ctccaacctg     2160
ggctcggcgc agatccagga attggtgggt gatcgtgaag cccagcgtgc ggcggtgatg     2220
gacgcgttga ccacgcactt ccgtccgaaa ttcatcaacc gggtcgatga agtggtgatc     2280
ttcgagcctc tggcgcggga tcagatcgcg ggcatcaccg agatccagtt gggccgcctg     2340
cgtagccgcc tggctgagcg cgagctggac ctggagctga gcggcgaagc gttggacaag     2400
ctgatcgcgg tcggttacga cccagtgtat ggcgcacggc cacttaaacg tgcgatccag     2460
cgctggatcg agaacccact ggcgcagttg atcctgtcgg gcagctttat gcctggcact     2520
cgcgtcacgg cgacggtgaa agacgacgaa atcgtcttcc at                       2562
```

<210> SEQ ID NO 16
<211> LENGTH: 1281
<212> TYPE: DNA
<213> ORGANISM: Pseudomonas fluorescens

<400> SEQUENCE: 16

```
atgactgaca cccgcaacgg cgaggacaac ggcaagctgc tctattgctc cttctgtggc       60
aaaagccagc atgaagtacg caaattgatt gccggcccct cggtgtttat ctgcgacgaa      120
tgcgtcgacc tgtgcaatga catcatccgt gaggaggtgc aggaagccca ggccgagagc      180
agtgcgcata aattaccttc gcctaaagaa atcagtggca tccttgacca atacgtcatt      240
ggtcaagagc gtgcaaaaaa ggttctggcc gtagcggtgt acaaccacta caagcgcttg      300
```

```
aaccagcgtg acaagaaagg tgacgaggtt gaactcggca agagcaacat cttgctgatc    360
ggtcctacag gctcgggtaa aaccctgctt gcagaaaccc tcgctcgcct gctgaacgtt    420
ccgttcacca tcgccgacgc caccaccctc accgaggctg gctacgtggg tgaagatgtc    480
gagaacatca ttcagaaact gctgcagaag tgcgactacg acgtagagaa agcccagatg    540
ggtattgtct acatcgacga gatcgacaag atctcgcgca agtcggacaa cccgtcgatc    600
actcgggacg tttccggtga aggcgtgcag caggccctgt tgaagctgat cgaaggcacg    660
gttgcgtccg taccgccgca aggtggtcgc aagcacccgc agcaggaatt ccttcaggtt    720
gatacgcgca acatcctgtt catttgtggc ggtgcgttct cgggtctcga aggtgatt     780
cagcagcgtt ccacccgtgg cggcattggt ttcagtgcgg aagtgcgtag caaggaagaa    840
ggcaagaagg tgggcgagtc cctgcgtgaa gtcgagcctg acgatttggt caagttcggt    900
ctgatcccgg aattcgttgg ccgtctgccg gtcctggcca cgttggacga gttggatgag    960
gcggctttga tccagatcct caccgaaccg aaaaacgccc tgaccaagca atacggcaaa   1020
ttgttcgaga tggaaggtgt agacctggag ttccgtaccg acgcgctgaa atcggtggcc   1080
aagcgggcac tggagcgcaa gaccggtgca cgtggtctgc gttctatcct cgaaggcgtg   1140
ttgctcgaca ccatgtacga aatcccctcg cagtccgagg tgagtaaagt ggtgatcgac   1200
gaaagcgtta tcgaaggcaa gtccaagccg ctgtatatct atgaaaacag tgagccggct   1260
gccaaggctg cacccgacgc g                                             1281

<210> SEQ ID NO 17
<211> LENGTH: 633
<212> TYPE: DNA
<213> ORGANISM: Pseudomonas fluorescens

<400> SEQUENCE: 17
atgttccgta attcctatat tcagcagaac tctgatatcc aggccgcagg cggcctggtc     60
ccgatggttg tcgagcagtc cgctcgtggc gaacgcgcct acgacatcta ctcgcgcctg    120
ctcaaggagc gagtgatctt tctggttggc ccggtagagg actacatggc caacctgatc    180
tgtgcgcagc tgctgttcct tgaagcggaa aacccggaca aggacatcca tctctacatt    240
aattcgccgg gtggttcggt gactgcgggc atgtcgatct acgacaccat gcagttcatc    300
aagccaaacg tgtcgaccac ctgtattggc caggcgtgca gcatgggcgc cttcctgctg    360
accgcgggtg ccgaaggcaa gcgtttctgc ctgccgaact cgcgcgtgat gattcaccag    420
ccactgggcg gtttccaggg ccaggcgtcg gacatcgaaa tccacgccaa ggaaatcctc    480
ttcattcgtg agcgtctcaa cacgctgatg gccaagcaca gcgggcgcac cctggaagaa    540
atcgagcgcg ataccaaccg tgacaatttc atgagcgctg aagccgccaa ggaatacggg    600
ttgatcgacg cagtgatcga caagcgcccc gca                                 633

<210> SEQ ID NO 18
<211> LENGTH: 1335
<212> TYPE: DNA
<213> ORGANISM: Pseudomonas fluorescens

<400> SEQUENCE: 18
atgtccatga ctccccgcga aatcgtccat gaactcaatc gccatatcat cggccaggac     60
gatgccaagc gcgccgttgc cattgcgctg cgtaaccgct ggcgccggat gcaactgccg    120
gaagaactgc gcgttgaagt aacgcccaag aacatcctga tgatcggccc caccggcgtg    180
ggtaaaaccg agatcgcccg gcgcctggcc aaactggcca atgcaccgtt catcaaggtc    240
```

```
gaagcgacca agttcaccga agtcggctat gtgggccgcg atgtcgagtc gatcattcgt      300
gacctggctg acgccgccct gaagatgctg cgcgaacagg aagtaaccaa ggtcagccac      360
cgcgccgaag acgccgctga agagcgcatc ctcgacgccc tgttgccacc ggcacgcatg      420
ggtttcaacg aagacgccgc accggctacc gattccaaca ctcgccagct gttccgcaag      480
cgcctgcgtg aaggccagct ggatgacaag gaaatcgaga tcgaagtggc tgaagtgtcc      540
ggcgtggata tttctgcccc gcctggcatg aagaaatga ccagccagct gcagaacctg       600
ttcgccaaca tgggcaaggg caagaagaaa gccgcaagc tcaaggtgaa agaggcgctc       660 aagtcgtgc gcgacgaaga agccgggcgc tggtcaatg aggaagaact caaggccaag        720
gccctggaag cggtcgagca acatggcatc gtgtttatcg acgagatcga caaagtggcc      780
aagcgaggca actcaggcgg cgtggatgtg tcccgcgaag gcgtgcagcg cgatttgctg      840
ccgctgatcg agggctgcac ggtcaacacc aagctgggca tggtcaagac tgaccacatc      900
ctgtttatcg cttccggtgc tttccacctg agcaagccca cgacctggt gcccgagctg       960 caaggccgct tgccgattcg ggtggagctc aaggcgctga cgccgggcga cttcgagcgc     1020
atcctcagcg agccgcatgc ctcgctcacc gagcagtacc gcgagttgct gaaaaccgaa     1080
gggctgggta tcgaattcca ggcagacggg atcaagcgcc tggcggagat cgcctggcag     1140
gtcaacgaga agaccgagaa catcggtgcc cgtcgcctgc ataccttgct tgagcgcctg     1200
ctggaggaag tgtccttcag tgccggcgac atggccggtg cgcagaatgg cgaagcgatc     1260
aagatcgatg ctgattacgt caacagccac ttgggcgaat tggcgcagaa cgaagatctg     1320
tctcgttata tcctg                                                     1335

<210> SEQ ID NO 19
<211> LENGTH: 528
<212> TYPE: DNA
<213> ORGANISM: Pseudomonas fluorescens

<400> SEQUENCE: 19
ttgaccacca tcgtttcagt acgtcgccac ggcaaagttg tcatgggcgg cgacggccag       60
gtttccctgg gcaacaccgt gatgaaaggc aacgccaaga agtgcgccg cctgtaccac       120 ggccaggtgc ttgccggctt cgcaggcgca accgccgacg cctttaccct gttcgagcgt      180
ttcgaaggcc agcttgagaa acaccagggc cacctggtgc gcgccgctgt ggaactagcc      240
aaagaatggc gcaccgaccg ctccctcagc cgcctggagg ccatgctcgc ggttgcgaac      300
aaagacgctt ccctgatcat cactggcaac ggcgacgtgg ttgaacccga gcatggcctg      360
atcgccatgg gttccggcgg cggctacgcc caggctgcgg ccagcgcgct gttgaagaaa      420
accgacctgt cggcccgtga aatcgtcgag accgccctgg gtatcgctgg cgatatctgc      480
gtgttcacca accacaacca gaccattgag gagcaggacc tcgccgag                   528

<210> SEQ ID NO 20
<211> LENGTH: 900
<212> TYPE: DNA
<213> ORGANISM: Pseudomonas fluorescens

<400> SEQUENCE: 20
atgactgatc taccggatac cgacttcacc caacgcttca tcttcgatga gagcgatgcc       60
cgcggcgaga tggtttcgtt ggagctcagc tatgccgaag tccttgccaa acacgcctat      120
ccggagccgg tcgcgcaatt gctcggcgag ttgatggccg ccgcggcgct gctggtgggc      180
```

| | |
|---|---|
| accatgaagt tcgacggttt gctgatcttg caggcgcgtt ccgaagggcc ggtgcccatg | 240 |
| ttgatgatcg agtgctcgag cgagcgcgag atccgtggcc tggctcgtta tgacgctgag | 300 |
| cagattgctg cagacgctac cctggccgac ctgatgccca acggcgtcct ggcactgact | 360 |
| gtcgacccga ccgaaggcca gcgctaccag ggtattgtcg acctcgacgg ccagaccctg | 420 |
| tcggaatgct tcaccaacta cttcgtcatg tcccagcaag tgggcaccaa gttctggctt | 480 |
| aacgccgacg gcaagcgcgc tcgcggtttg ctggtgcaac aactgccggc cgatcgcatc | 540 |
| aaggatgagg atgaccgtgc cgaaagctgg cggcatatca tcgccctggc cgacaccttg | 600 |
| aaggccgaag aactgctggg cctggacaac gaaaccatcc tgcaccgcct ctaccacgaa | 660 |
| gaagccgtgc gcctgttcga cgcacaaggc ctgcgcttca attgcagctg ctcgcgcgag | 720 |
| cgttccggca acgcgctggt cagtctgggc ctggaagatg cgcaaaatct ggtggtggaa | 780 |
| cacggcggcc atatcgagat cgactgccag ttctgcaacc agcgctacct gttcgatgcg | 840 |
| gctgatgtag cgcaattgtt cgctggcgca ggcagcgaca ccccttccga cacccgccac | 900 |

<210> SEQ ID NO 21
<211> LENGTH: 1902
<212> TYPE: DNA
<213> ORGANISM: Pseudomonas fluorescens

<400> SEQUENCE: 21

| | |
|---|---|
| atgagtgtgg aaactcaaaa ggaaaccctg ggcttccaga ccgaggtgaa gcaactgctg | 60 |
| cacctcatga tccattcgct gtattccaac aaggaaattt ccttcgcga attgatctcg | 120 |
| aacgcctctg acgctgtcga caaattacgt ttcgaagccc tgtccaagcc tgagttgctg | 180 |
| gaaggcggcg cggaactgaa gatccgtgtg agctacgaca agacgccaa accgtcacc | 240 |
| ctcgaagaca acggtatcgg catgagccgt gacgatgcga tcacccacct ggggaccatc | 300 |
| gccaaatccg gcactgcaga tttcatgaag aacctgtcgg gcgaccagaa aaagagactct | 360 |
| cacctgatcg gccaattcgg cgtgggcttc tattcggcct tcatcgtcgc cgacaaggtt | 420 |
| gaagtcttca gccgccgcgc cggcctcgac gccagcgaag gcgtgcactg ggcctccaag | 480 |
| ggcgaaggcg aattcgaaat cgccacgatc gacaaggctg accgcggcac ccgcatcgtg | 540 |
| ctgcacctga agccggtga agatgaattc gccgatggct ggcgcctgcg caacatcatc | 600 |
| aagaagtact ccgaccatat cgcgttgccg atcgagttgc ccaaggaaca gaccgttgcc | 660 |
| gaaggcgaag aagccccggc ggcggagtgg gaaaccgtca accgcgccag cgccctgtgg | 720 |
| acccgtccgc gtaccgagat caaggacgag gaataccagg agttctacaa gcacatcggg | 780 |
| cacgattacg agaacccgct gagctggagc cacaacaagg ttgaaggcaa gctcgaatac | 840 |
| agctcgctgc tctacgtccc ggcccgtgct ccgttcgacc tgtaccagcg tgaagcgcca | 900 |
| aaaggcctga agctctacgt acagcgcgtg ttcgtgatgg accaggcgga atccttcctg | 960 |
| ccgctgtacc tgcgctttat caaaggtgtg gtcgactcca cgacctgtc gctgaacgtg | 1020 |
| tcgcgggaaa tactgcagaa agaccgatt atcgactcca tgaagtcggc gctgaccaag | 1080 |
| cgcgtgctcg acatgctgga aaagctggcg aagaacgagc ctgagcaata caagagcttc | 1140 |
| tggaaaaact cggccaggt catgaaagaa ggccgggcag aagattttgc caacaaggaa | 1200 |
| aagattgccg gtttgctgcg ttttgcctcg actcaaggcg aagatggcga gcaggttgtg | 1260 |
| tccctggctg attacctggc acgtgccaag gaaggtcagg acaagatcta ctacctgacc | 1320 |
| ggcgaaacct acgctcaggt caagaacagc ccgcacctgg aagtgttccg caagaaaggc | 1380 |
| atcgaagtgc tgctgctgac cgaccgtatc gatgagtggc tgatgagcta cctcaccgag | 1440 |

```
ttcgacggca aaaccttcgt cgacgtggcc cgtggtgacc tagacctggg taacctggac    1500
tccgaagaag agaagaaaga agccgaagaa gtcgccaagt ctaaagaggg cctggttgag    1560
cgcatcaagg cttccctggg cgaagcggtg agtgaagtgc gggtttccca ccgcctgacc    1620
gactctcctg cgatcctggc catcggcgag caggacctgg gcatgcagat gcgccagatc    1680
ctggaagcca gcggccagaa agtgccggat tccaagccga tcttcgaatt caacccgtct    1740
cacccgctga tcgagaaact cgatggcgag cagagcgaag agcggtttgg tgacctgtcg    1800
cacatcctct tcgaccaggc cgccctggca gccggcgaca gcttgaagga cccggccgcg    1860
tatgtgcgcc gactgaacaa gctgttggtt gaattgtcgg tt                      1902
```

<210> SEQ ID NO 22
<211> LENGTH: 477
<212> TYPE: DNA
<213> ORGANISM: Pseudomonas fluorescens

<400> SEQUENCE: 22

```
atgactgatc aacagaacac cgaagcagcg caagaccaag ccccacagtt ctcgctgcag     60
cggatctatg tgcgtgacct gtcgttcgaa gcgccaaaaa gcccggccat cttccgtcag    120
gagtggaccc caagcgttgc gctggacctg aacactcgtc agaaatccct ggaaggtgac    180
ttccacgaag tggtgctgac cctgtcggtc accgtcaaga atggtgaaga agtcgctttc    240
atcgctgaag tgcaacaggc cggtatcttc ctgatccagg gcctggacga agcgtccatg    300
agccacaccc tgggcgcgtt ctgcccgaac atcctgttcc cgtatgcccg tgagaccctg    360
gacagcctgg tcacccgtgg ctcgttcccg gcactgatgc tggcgccggt taacttcgat    420
gccctgtacg ctcaagagct gcagcgcatg caacaggaag gcgcgccgac cgttcag      477
```

<210> SEQ ID NO 23
<211> LENGTH: 588
<212> TYPE: DNA
<213> ORGANISM: Pseudomonas fluorescens

<400> SEQUENCE: 23

```
atgagtaaaa ccctggagtt tttctttgat ctcggcagcc ccgccactta cctggcctat     60
acccggttgc cggcgctgtg tgccgaaacc ggcgcacagg tggtgtatca acccatgcta    120
ttgggcggtg tattcaaggc cacgggcaat gcctcgccga tcacggtgcc cgccaagggt    180
cgctacatgc tcgatgacct ggcgcgttac gccaaacgct acaacgtgcc gctcaggttc    240
aacccgcact ttcccatcaa taccttgctg ctgatgcgcg ctgtcaccgg cattcaaatc    300
caccagcctg agcgcttcct cgacttcatc ggctgccttt tccgagcact ctgggtggaa    360
ggccgtcact tgggcgaccc agaggtcgtg gccaatgtgc tcaccgaaca ggggttcgat    420
cccgagcagg tactggccct gtcaaacgat gcagccgtca aggacgctct caaggacaaa    480
accgaacaag ccattaagcg cggcgtgttc ggcgctccca gtttctttgt aggaaaccag    540
ctgttcttcg gccaggaccg tctggacttt gtgcgtgaag cgctcagc                588
```

<210> SEQ ID NO 24
<211> LENGTH: 651
<212> TYPE: DNA
<213> ORGANISM: Pseudomonas fluorescens

<400> SEQUENCE: 24

```
atgagtactc ccctgaaaat cgatttcgtc agcgacgtat cctgcccctg gtgcatcatc     60
```

```
ggcctgcgcg gcttgaccga agccctcgac cagctcggca gcgaggtgca ggccgagatt    120
cattttcaac cgttcgaact gaacccgaac atgcccgccg aaggtcagaa catcgtcgag    180
cacattaccg aaaagtacgg ctccacggct gaagagtccc aggctaatcg tgcgcgtatc    240
cgtgacatgg gcgccgcgtt gggctttgct tttcgcaccg atggccagag ccgtatctac    300
aacaccttcg acgcgcaccg tctgttgcac tgggccgggt tggaaggctt gcagtacaac    360
ctcaaggaag cgctgttcaa ggcgtacttc agcgatggcc aggacccttc cgaccacgcg    420
accttggcga tcatcgccga aagcgtcggg ctggaccttg cgcgcgccgc cgagattctt    480
gccagcgatg aatacgccgc cgaggtccgc gagcaggagc agctgtgggt ttcccgtggg    540
gtgagttcgg tgccgaccat tgtcttcaat gaccaatatg cggtgagcgg tgggcaaccg    600
gctgaagcct tcgtgggtgc gattcgccag atcatcaacg aatccaaatc c             651
```

<210> SEQ ID NO 25
<211> LENGTH: 633
<212> TYPE: DNA
<213> ORGANISM: Pseudomonas fluorescens

<400> SEQUENCE: 25

```
atgcgtaatc tgatcctcag cgccgctctc gtcactgcca gcctcttcgg catgaccgca     60
caagctgccg atgtgccgct tgaagccggt aaaacctatg ttgagctggc taacccggtt    120
cccgttgcag tgccgggcaa gatcgaagtg gtggagctgt tctggtacgg ctgccccgcat   180 tgctacgcct tcgagccgac tatcaaccca tgggctgaaa agctgcccaa ggacgttaac    240
ttccgtcgca ttcccgccat gttcggtggc ccatgggacg cccacggcca gctgttcctg    300
accctggaag ccatgggtgt tgagcacaag gtccacaacg ctgtcttcga agcgatccag    360
aaacaaggca agcgcctgac caagccggac gaaatggctg acttcgttgc cactcagggt    420
gtcgacaagg acaagttcct ggcgaccttc aactccttcg ctatccaggg ccagatcaaa    480
caggccaagg aactcgcgca gaagtacggc gtgcaaggct tccaaccct gatcgtcaac    540 ggcaaatacc gtttcgacct gggcagcacc ggtggtcctg aagcgaccct gaacgttgct    600
gaccagctga ttgccaaaga acgcgctgcc aag                                 633
```

<210> SEQ ID NO 26
<211> LENGTH: 729
<212> TYPE: DNA
<213> ORGANISM: Pseudomonas fluorescens

<400> SEQUENCE: 26

```
atgcgcttga cccagattat tgccgccgca gccattgcgt tggtttccac ctttgcgctc     60
gccgatgatg cggccgagca gaccatccgc aagagcctgg ccaacctggc gctcgacacg    120
cctatcgaaa gcattagcgc cagccccatg gccggcctgt acgaagtcaa gctcaagggc    180
agccgcgtgc tgtacgccag tgccgatggc cagtacatcg tccagggcta cctgttccag    240
ctcaaggacg gcaagccggt caacctgacc gagaaggccg agcgcctggg cgtgtccaag    300
ctgatcaacg gcatcccggt ggctgaaacc gtggtttacc cggccattgg cgaaaccaag    360
acccacatca ccgtgttcac cgacaccacc tgcccgtact gccacaagct gcacgctgaa    420
atcccggcac tgaacaagct gggcgtggaa gtgcgctacg tcgcgttccc cgcgcagggc    480
ctgggttcgc cgggtgacga gcagttgcaa gccgtatggt gttcggccga caaaaaggcg    540
gccatggaca agatggtcga cggcaaggaa atcaaatcgg ccaaatgcgc caacccggtt    600
tccaagcagt tcgccctggg ccagtccatt ggtgtgaacg gtacaccggc catcgttttg    660
```

```
gccgacggcc aggtgattcc gggctaccag ccggcgccgc aagttgccaa actggcactg    720
ggtgccaag                                                            729

<210> SEQ ID NO 27
<211> LENGTH: 759
<212> TYPE: DNA
<213> ORGANISM: Pseudomonas fluorescens

<400> SEQUENCE: 27
atgcctcgcc tccgccacct gctgaccctg ctgccgttga cgctagccgc tgcgctggcc     60
caggccgaag acctgccggc cccgatcaaa cagatcgaag ccaaaggtgc caagatcatc    120
ggcaaattcg acgccccag cggcctcacc ggctacgcag cccagtacca gaaccgtggc    180
atggccctgt acttgaccgc cgacggcaaa aacgtcatcg ccggcaacct gtacgacgcc    240
cagggcaatg acctgagcac cgcgcccctg aaaaactgg tgtacgcgcc gatggccaag    300
gaagtctggg ccaagatgga aaacagcagc tggatccagg acggcgacaa aaacgccccg    360
cgcaccatct acctgttcag cgaccccaac tgcccgtact gcaacatgtt ctgggaacag    420
gcccgcccgt gggtcaaggc cggcaaggtg cagttgcgcc acatcatggt cggcatcatc    480
cgcgaagaca gccccggcaa atccgccgcc ctactcgccg ccaaagaccc gcaaaaagcc    540
ctgcaagacc acgaagcggc cggcaagggc agcaagctca aggcgctgga aaagatcccg    600
gccgaggtag aggccaagct tgatgcgaat atgaagttga tggatgaact ggagttgtcg    660
gcgacgccgg cgattttcta tctggatgac aaaggggggt tgcagcagca gcaaggcgcg    720
ccttcgccgg ataagttggt gaagatactg gggccgaag                           759

<210> SEQ ID NO 28
<211> LENGTH: 561
<212> TYPE: DNA
<213> ORGANISM: Pseudomonas fluorescens

<400> SEQUENCE: 28
atgctgaaaa aaatcgcctt atttgccggt tccgccttgt tcgctgccaa cctgatggcg     60
gctgagccgg ccaaggcgcc acatgttttg ctcgacacca ccaacggcca gattgaaatc    120
gaactggacc cggtcaaggc gccgatcagc accaagaact tccttgagta cgtcgacagc    180
ggcttctaca ccaatacgat tttccatcgc gtgatcccgg gcttcatggt ccagggcggc    240
ggcttcaccc agcaaatgca acagaaagac acgaaggcac cgatcaagaa cgaggccagc    300
aacggcctgc ataacgtgcg cggtacgctg tcgatggccc gcacctcgaa cccgaactcg    360
gccaccagcc aattcttcat caacgtggct gacaatgcct tcctcgaccc gggccgcgat    420
gccggttatg ccgtgttcgc caaagtggtc aagggcatgg acgtcgtcga catcatcgtc    480
aactcccaga ccaccaccaa acaaggcatg cagaacgtgc caatcgatcc tgtgttgatc    540
aagtcggcca agcgcatcga c                                              561

<210> SEQ ID NO 29
<211> LENGTH: 504
<212> TYPE: DNA
<213> ORGANISM: Pseudomonas fluorescens

<400> SEQUENCE: 29
atgactcaag tcaaactgac caccaaccac ggtgacatcg tcatcgagct gaacgccgat     60
aaagcgccga tcaccgtcgc caacttcatc gaatacgtca agccggcca ctacgaaaac    120
```

```
accgttttcc accgtgtcat cggtaacttc atgatccagg gcggcggttt cgagcctggc      180
atgaaagaaa agaaagacaa gcgtccaagc atccagaacg aagcggacaa cggccttttcc    240 aacgacaagt acaccgtcgc catggcccgt accatggagc cgcattcggc ctccgcgcag     300
ttcttcatca acgtcgccga caacgccttc ctgaaccaca gcggcaaaaa cgtgcagggt     360
tggggctacg cggtgttcgg taaagtcacc caaggcaccg acgttgtcga caagatcaaa     420
ggcgtatcga ccacctccaa ggccggtcac caggacgttc cagccgaaga cgtgatcgtc     480
gagaaagccg agatcatcga agcg                                            504
```

```
<210> SEQ ID NO 30
<211> LENGTH: 729
<212> TYPE: DNA
<213> ORGANISM: Pseudomonas fluorescens

<400> SEQUENCE: 30
atgtccgaag ttaatctgtc caccgacgaa acccgcgtca gctacggtat cggccgtcag      60
ttgggcgacc aactgcgtga caacccgcca ccggcgtca gcctggacgc gatcctggcc      120
ggcctgaccg acgcgttcgc aggcaagcca agcgtgttg accaagagca aatggcggcc      180
agcttcaaag tgatccgcga aatcatgcaa gccgaagccg ctgccaaggc tgaagctgca     240
gcaggcgctg gcctggcttt cctggcggaa aacgccaagc gtgatggcat caccaccctg     300
gcttccggcc tgcaatttga agtgctgacg gctggtaccg cgccaagcc gacccgtgaa      360 gaccaagtgc gtactcacta ccacggcacc ctgatcgacg gcactgtgtt cgacagctcc     420
tacgagcgcg ccagcctgc agaattcccg gttggcggg tgatcgccgg ctggaccgaa       480
gccctgcaac tgatgaatgc cggcagcaaa tggcgcgtgt acgtgccgag cgaactggct     540 tacgcgctc aaggcgttgg cagcatcccg ccgcacagcg ttctgtattc gacgtcgagc     600
tgctcgacgt tctgtaaaac tgctggtta cctgttggga cgaacgcgtt cgccccaaca     660
ggcgtttgcc agtttcttca tggatggaac ttgccattga gctccgtcgc cgggcgcaac    720
gctcgtgca                                                             729
```

```
<210> SEQ ID NO 31
<211> LENGTH: 738
<212> TYPE: DNA
<213> ORGANISM: Pseudomonas fluorescens

<400> SEQUENCE: 31
atgaaacagc atcggttggc ggcggcggtg gccctggtta gcctggtact tgcgggttgt      60
gattcgcaga ccagcgtaga gctgaaaacc ccggcgcaaa aagcttccta cggcatcggc     120
ctgaacatgg gcaagagcct tgcccaagaa ggcatggacg acctggactc caaagctgtt     180
gcccagggca tcgaagatgc cgtcggcaag aaagagcaga agctcaagga cgatgagctg     240
gttgaagcgt ttgccgcact gcaaaagcgt gctgaagaac gcatgaccaa atgagcgaa      300 gagtcggcag ccgctggcaa gaaattcctc gaagacaacg ccaagaaaga cggtgtcgtc     360
accaccgctt ccggcctgca gtacaagatc gtgaagaagg ccgacggcgc ccagcctaag    420
ccgaccgacg tggtgactgt tcactacacc ggcaagctca ccaacggcac caccttttgac    480 agctccgtag atcgcggtag cccgatcgac ctgccggtca gcggcgtgat cccggggttgg    540 gtcgaaggcc tgcaactgat gcacgtgggc gagaaggttg agctgtacat cccgtccgac    600
ctggcctacg cgcccagag cccgagccg gcgatcccag cgaactccgt gctggtattc       660
gacctggaac tgctgggcat caaggaccca gccaaggcag aagcggctga cgcacctgct    720
```

```
gcaccagccg ccaagaag                                                      738

<210> SEQ ID NO 32
<211> LENGTH: 675
<212> TYPE: DNA
<213> ORGANISM: Pseudomonas fluorescens

<400> SEQUENCE: 32
atgtcgcgtt acctttttct agtgttcggc ttggcgatct gcgtggccga tgcaagcgag    60
caaccttcgt caaacatcac cgacgcaacc ccgcacgacc ttgcctatag cctgggcgca   120
agccttggcg aacggttgcg ccaggaagtc cccgacctgc agatacaggc tctgctcgac   180
ggactcaaac aagcctacca aggcaaacca ctggcgctgg ataaggcgcg catcgaacag   240
atcctctccc agcatgaagc gcagaacacc gccgacgccc aactgccgca agcgaaaaa    300 gcactggccg ccgaacagca atttctcact cgggaaaaag ccgccgccgg cgttcgtcag   360
ctagccgacg gtatcctgct caccgagctg gcaccgggca ctggcaacaa gccgttggcc   420
agcgatgaag tacaggtgaa atacgtgggc cgactgcctg acgggactgt cttcgacaaa   480
agtacgcaac cgcaatggtt tcgcgtcaac agcgtgatca gcggttggag cagtgcattg   540
caacagatgc cggtgggtgc gaaatggcgc ctggtgattc cttcggccca ggcctatggc   600
gcagacggcg caggtgagtt gatcccaccc tatacgccgc tggtgttcga atcgaactg    660 ctcggcactc gccac                                                     675

<210> SEQ ID NO 33
<211> LENGTH: 483
<212> TYPE: DNA
<213> ORGANISM: Pseudomonas fluorescens

<400> SEQUENCE: 33
atgacgatcg ccgctaacaa ggctgtctcc atcgactata ccctgaccaa cgacgctggt    60
gaggtcatcg acagctcctc cggcggcgcg ccgctggttt acctgcaagg cgcaggcaac   120
atcatcccgg gcctggaaaa ggctctggaa ggcaagagcg tcggtgacga actgaccgtc   180
gccgtagaac ctgaagatgc ctacggcgaa tactccgccg aactggtcag taccttgagc   240
cgcagcatgt tcgaaggtgt tgatgagctg gaagtgggca tgcagttcca cgcttcggcg   300
ccggacggcc aaatgcagat cgtcaccatc cgcgacctgg acggcgatga cgtgaccgtt   360
gacggcaacc accctctggc tggccagcgc ctgaacttcc aagtgaagat cgtagccatc   420
cgcgacgctt cccaggaaga agtggctcac ggccacgtcc acggtgaagg cggccatcac   480
cat                                                                  483

<210> SEQ ID NO 34
<211> LENGTH: 1308
<212> TYPE: DNA
<213> ORGANISM: Pseudomonas fluorescens

<400> SEQUENCE: 34
atgcaagttt ctgttgaaaa tactactgct ctcgagcgcc gcctgagcat caccgtgccg    60
gcagagcgta tcgagactgc ggtcaacaag cgtctgcagc agactgccca aaaggccaag   120
atcgctggtt tccgtccagg caaagtgccg atgagcgaaa tcaagcgtcg ttttggtgcc   180
gatgcgcgcc aggaagctgt aggtgacgtg atccaggctt cttttctacga agccgttgtc   240 gagcaaaagc tgaacccggc tggctcgcct tcgatcgagc ccagtccct ggaagcgggc    300
```

```
aaggacctgg aatacgttgc cgtattcgaa gtgttcccgg aatttgaagt ggccggtttc      360
gacggtatcg aaatcgagcg tctgagcgcc gaagtggctg attcggacct ggacaacatg      420
ctggaaatcc tgcgcaagca gaacactcgt ttcgaagtgg ccgaccgtgc cgcccagaac      480
gaagaccaac tgaacatcga tttcgttggc aaggttgacg gcgaagtctt cgctggcggc      540
tccgccaagg gcactcagct ggtgctgggt tccaaccgca tgatccctgg tttcgaagac      600
ggcctggttg cgccaaagc cggcgaagag cgcgttctga acctgacgtt ccctgctgac       660
taccagaacc tggacctggc tggcaaagcc gccgagttca ccgtgaccgt caacagcgtt      720
tccgagccta agctgccaga gctgaacgaa gagttcttcg cccagttcgg catcaaggaa      780
accggcatcg aaggcttccg caccgaagtt cgcaagaaca tggagcgtga gctgcgccag      840
gccatcaagt ccaaggtcaa gaaccaggtc atggacggtc tgctggccgc caaccctatc      900
gaagtgccta aggccctgct gtccaacgaa gtggatcgcc tgcgtgttca agcggttcag      960
cagtttggtg gcaacatcaa gcctgaccag ctgccggccg agctgttcga agagcaagcc     1020
aagcgccgcg ttgtgctggg cctgatcgtg gctgaagtgg tcaagcagtt cgacctcaag     1080
ccagacgaag accgcgtccg cgaaatgatc caggaaatgg cttcggccta ccaggagcct     1140
gagcaggtcg tggcttggta ctacaagaat gagcagcaga tgaacgaagt acgttcggtt     1200
gtgctggaag aacaagttgt ggatactgtt ctgcagaagg ctaaggtgac cgataaagcg     1260
gtctcttacg aagaagcagt caaaccggcg gaagcagcac aagccgac                 1308

<210> SEQ ID NO 35
<211> LENGTH: 450
<212> TYPE: DNA
<213> ORGANISM: Pseudomonas fluorescens

<400> SEQUENCE: 35
atgactgatc aggtattggc tgagcaacgc atcggccaga acacggaagt cactttgcat       60
tttgcattgc gcctggaaaa tggcgacacg gtcgacagcc ccttcgacaa agccccggcg      120
accttcaagg ttggcgacgg taacctgctg cctggttttg aagcggcatt gttcgggttc      180
aaggcgggcg acaagcgcaa cctgcagatc ctgccggaaa acgccttcgg ccagcccaac      240
ccgcaaaacg tgcagatcat cccgcgttcg cagtttgaag gcatggacct gtcggaaggc      300
ttgctggtga tcttcaatga tgcggcgaat accgaattgc ccggagtggt taaagcgttc      360
gatgatgcgc aagtgaccat cgacttcaac catccgttgg ccggtaaaac cttgacgttt      420
gatgttgaaa tcatcgacgt taaagcgctc                                      450

<210> SEQ ID NO 36
<211> LENGTH: 450
<212> TYPE: DNA
<213> ORGANISM: Pseudomonas fluorescens

<400> SEQUENCE: 36
atgcattcca gcgaacggtt caccatcacg ctggccattc ccctgcactt gccaaacccca      60 tccgattctg ggaaaacccc agcccttcac cccttcaatg agaaccccat gagcaacgac      120
gaactgcagg tcaccgacat ccgcctgggc gacggcaaag ccgtggtcaa gggcgcgctg      180
atcaccaccc aatacaccgg caccctggaa gatggcacgg tgttcgattc ctcctgggag      240
cggggcaaac cgttccagtg cgtgatcggc actggccgcg tgatcaaggg gtgggaccag      300
ggcttgatgg gcatgcaggt tggcggcctg cgcacgttgt atgtaccggc gcacctggcc      360
tatggcgagc gctcgatggg cgcgcatatc aaacccaaca gtaacctgcg tttcgagatc      420
```

```
gaattgttgg aagtgctgac gcgggatgat                                      450
```

<210> SEQ ID NO 37
<211> LENGTH: 759
<212> TYPE: DNA
<213> ORGANISM: Pseudomonas fluorescens

<400> SEQUENCE: 37

```
atgaaaccaa gttttcgtta cacccacctg gtctattcgc tattagtgtt aactttgagc     60
cagagtgcca gtgcggcaat cggattagat cgtacccgtc tggtatttga gggcagcaaa    120
gacgctgtca gcgtcaacat cgtcaacaat aacacccaat taccttactt agctcaaggc    180
tggattgagg atgaaaaagg tgccaaaatc accactccgt tgattgtgct gccaccggtt    240
caacggctgg agccgggtaa gaaaagtcag gtaaaagtcc aggcgctgcc agcagccaag    300
ttgctgccgc aagaccgcga aactgtctac tacttcaatc taagagaaat tccgccgcgt    360
agtgataaag ccaacacctt gcaaattgcc ttgcagaccc gggtcaaatt gttttaccgg    420
ccagctgcta ttacgcctag tcagcaggat atctccaatc catggcagga gaaactcaca    480
ttgacccgcg atggcgaccg ttatcaggtg cataacccta cgccttatta cgtgactttg    540
gtggatgccc gtagcaataa ggacggagaa accgctccag atttccagcc tgtgatggta    600
ccacctaaag gttccttaca cctgggccca agcgctagag cgcttggcac tacaccttac    660
ctgacctacg ttaacgacta cggcggtcgc ccggtactgg cctttacctg cagtggcaat    720
acctgcgaag taaaaccaga cgctaaaccg agcaatgag                           759
```

<210> SEQ ID NO 38
<211> LENGTH: 702
<212> TYPE: DNA
<213> ORGANISM: Pseudomonas fluorescens

<400> SEQUENCE: 38

```
atgacgacga cattctcaaa caccgctgtc ggcctgattg ccttgctctt gatgctcggc     60
gatcaggtaa agccgacgg tatggtcccg gacacctccg tggtgatcgt gcacgaggcc    120
gaaggcgaag cgtccgtgtc ggtgaccaac accgacagcc agctcgcgct gctgcatgtg    180
accttgcagg acattccgga agacaccgag ccgctgctgg tggtgacgcc gcccctttca    240
cgggtggaag cgtccaaatc ccaactggtg cgtttcattc tgcaaaacca gcagccgtta    300
ctgacccagc ggcttaagcg cgcggtgttc gaaggcatgc ccagggccg cgccgccaca    360
gccgccgggc atgcccgcgt gggcgtgacc gtgcgccaga acctgccggt gattgtgcac    420
cccaagggcc tggcgcccaa ccgcacgccc tggaccgacc tgacctggac actgcgcgaa    480
ggccagttac aggtgcgcaa cgacacgccg tacgtggtgc gtctggcgca ggagctgcaa    540
ctgctgcccg gtgacggcaa ggcgttgctg cctcggacct atgtgctgcc cggcgaagcc    600
ttgagcgtgc cggccagcag cagccaggcc aagacggtca ggctgcagcc ggccacggtg    660
tacgggttcg cggtcaaggc ttacgacgca ccaatcagct tc                      702
```

<210> SEQ ID NO 39
<211> LENGTH: 786
<212> TYPE: DNA
<213> ORGANISM: Pseudomonas fluorescens

<400> SEQUENCE: 39

```
atggggtgtg ctttgcgacg gttatgcacc gtgggtttcg ccttgggggc gttgtgctcg     60
```

```
gcggggtttg tacaggcagc cagttcggtg ctgatctggc ccatcgaccc ggtgctggag      120
gccgaccaac aggccagcgc gctgtggctg gagaaccgtg gcaccgagac cgccaacctg      180
cagatccgcg tgtttgcctg gagccagaat ggctttgacg agcagtacca gaaccagcgc      240
gatgtgatcg gcagcccgcc cgtggccaaa atcgagccgg ccagaaaca  actggtgcgc      300 ctgacccgca cccgggaagt gccgccggga caggagctgg cctatcgcat catcattgat      360
gaaattccct cggcgcttca ggtgcccacg ccgccggagg gcaagaacac ggcggcggcg      420
attcgctttc agatgcgtta ttcggtgccg ttgtttgcct acggcgccgg cttgtggagc      480
aaggacgacg ctacccgcca acgcgatccc aagggcgcgg gcaagccgca gttgagctgg      540
cagaaggtca acgtggcagg gcgcaactac atcgaggtgc gcaaccaggg cgccgtgcat      600
gcgcggctta ccgatgcgtc attcaaacag ggcgggcaga cccggccgtt ggtgacggt       660 ttgctcggct atgtgctgcc gggcgcgagc atgcgctggc cggtgccgga tgccgtatcg      720
gccgaccagc cgttgcaggt acgcgtcaac ggcgcgccgc aactggaaag cctggcgccc      780
aagcga                                                                786
```

```
<210> SEQ ID NO 40
<211> LENGTH: 744
<212> TYPE: DNA
<213> ORGANISM: Pseudomonas fluorescens

<400> SEQUENCE: 40
atgtcgtgca cacgtgcatt caaaccactg ctgctgatcg gcctggccac actgatgtgt      60
tcccatgcat tcgctgcagt ggtgattacc ggtacgcgcc tggtctatcc ggcggaccag     120
aaagaaatca ccgtaaaact gaacaataac ggcacgttgc ccgcactggt ccaatcatgg     180
atcgacaccg gcagcgtcga atcgacaccc accagctcca aggcgccgtt cctattgtcg     240
cccccggtgg cgcgcattga cccgaccaag ggccaaagct tgcgagtgct ctttaccggc     300
gcgcctttgg cgcaggacaa agagtcggtg ttctggctca acgttctcga aatcccgccc     360
aaacccgagg cgggtgcaga cctcaacacg ctgcaaatgg cttttccgttc gcgcatcaag     420 ctgttctatc gcccggtcgg cttgcctgga aatcccaatg aggcggttga gcaggtgcag     480
tggcaattgg ttacggcacg cgatggccaa ggcctggcgc tgaaggcgta caacccgtcg     540
gcgttccacg tctcgctgat cgagttggac ctggtggcgg gtaaccaacg ctatcgcagt     600
gaggacggca tggtcggccc tggggaaacc cggcagttcg cgctgcccac gctcaaggcc     660
aggccgtcga gccaggcaca agtggagttc agcgccatca cgattacgg  cgcgttggtc     720 ccgacccgca acacgctgca gccc                                           744
```

```
<210> SEQ ID NO 41
<211> LENGTH: 723
<212> TYPE: DNA
<213> ORGANISM: Pseudomonas fluorescens

<400> SEQUENCE: 41
atgggctgcg ttcccttacc cgaccatgga attaccgtgt tcatgtttct actcagaatg      60
gtgctgctgg cctgcgggtt gctggtgctt gcgccccgc  ctgccgatgc ggcgctgaag     120
atcgaaggca cccgcctgat ctatttcggc caggacaagg ccgccggtat cagcgtggtc     180
aaccaggcct cgcgggaagt ggtggtgcaa acctggatca ccggcgagga cgaatcagcc     240
gaccgcaccg tgcccttttgc cgccaccgag ccattggtac aactgggcgc cggggagcat     300
cacaagctgc gcatcctgta tgccggtgag ggcttgccca gcgatcggga atcgctgttc      360
```

```
tggctcaata tcatggagat cccgctcaag cctgaagacc ccaacagcgt gcagttcgcg    420
atccgccagc ggctcaagct gttctatcgg ccccccgcac tccagggcgg ctcggccgag    480
gcggtgcagc aattggtatg gagcagcgac gggcgcacgg tgacggtcaa caaccccagc    540
gccttccacc tgtcgctggt caacctgcga atcgacagcc agacgctcag cgattacctg    600
ctgctcaagc cccatgaacg caaaaccctg accgcgctcg acgctgtgcc caagggcgcc    660
actctccact tcaccgaaat caccgatatc ggtttgcaag cccgtcatag cacggcgctc    720
aac                                                                  723

<210> SEQ ID NO 42
<211> LENGTH: 738
<212> TYPE: DNA
<213> ORGANISM: Pseudomonas fluorescens

<400> SEQUENCE: 42
atgccgcctc gttctatcgc cgcatgtctg gggctgctgg gcttgctcat ggctacccag     60
gccgccgcca gcatttcatt gaatgccacc cgtatcgtgt ttgacggtga ccacaaggaa    120
gccaacatta ccgtgcgtaa tggtaaccag gatgtattga ttcaatcctg ggtcgacatg    180
aacgacgcca gcgccagccg cgcgccgttt gccgtcaccc cgccactggc acgggtattc    240
gccaaggaac aacaactgct gcgcattctg tatgaaggca ccggcatgcc cacggaccgc    300
gagtcggtgg tgtggctcaa tgtgcaggaa atccccaagg ccagcgaggc cgagaacacc    360
ttgcagttgg ccatccgcca acgcatcaag atttctctac cgccctgccgg tcttaccggc    420 agcgcgctgc aagcccctgc gcagcttgaa tggacgctgg ccaaacacgg cagccaaacc    480
ctgttgcagg tgaaaaaccc gacattgtac cacgtgtcca tggccgacat caaagtgcag    540
gcggtcttgg ccagcgactc caccatgatt gcgcccggcg agcaaaaaca gtttgcgctc    600
agtgctccag ttgccagtgg gccggtgcag ttgtcgtttt ccagcatcaa tgactacggc    660
gcgcagaatc actacagcgc gccgctgacc agcggcactg cgctaccggc gcatgcgact    720
gaatcgcgcc tcaaccccc                                                 738

<210> SEQ ID NO 43
<211> LENGTH: 771
<212> TYPE: DNA
<213> ORGANISM: Pseudomonas fluorescens

<400> SEQUENCE: 43 atgcttttc gcacattact ggcgagcctt acctttgctg tcatcgccgg cttaccgtcc      60
acggcccacg cgggagtggt gatcgatggc acacggcaca tctacccca gcagcgccgt    120 gaaatcaccc tgcgcctgag caacgacgat aaacgggcac cgcgcctggt ccaggtgtgg    180
ctggatcaag gcgatgccac tccagatccc tcccatagcg acgtgccgtt cagcctctcg    240
cccccagtgt ttcgcctgga tccagggaga agccagggtg tgcggctggt ctacacccag    300
gatccgttgc cgccagatcg agagtccttg ttctggctta atgccttgga ggtcccccg    360 aaaatcagtg cggccgaact cggtgaacaa gcccctgaag ggaatcatct gcagtttgct    420
tttcgtatcc gcaccaaagt gttttttcgc cccgtcatt tgcctggcag tgcagaccag    480
gcccccgcgc aactgcgctg gagtctgagg cgcaccgagc gcgcagccgt actgcgcgta    540
cacaacccta cggcctttca cgtgaccttc aacgaggtgg cactggcgct gggccctcgg    600
cctgacgccc acctgatacc ggtacaagaa ggcatggtgc cgccaggtgc cagccttgaa    660
```

```
ctgcctgtac gcggcaccct gccgacgatc cccgcggacg cccaggtgca tttcaaatac      720
atcaatgatt acggcgcatt ctccgcgccg cagcgagccc ccctgaagtt t               771
```

<210> SEQ ID NO 44
<211> LENGTH: 867
<212> TYPE: DNA
<213> ORGANISM: Pseudomonas fluorescens

<400> SEQUENCE: 44

```
atggttggca ggcagcaccg gcaacggcac cttccagatt cccttgaccg cgcgctacat       60
acaaaccggc gccaccgtcc gcccgggcac ggccaacggg ctggcgacct ttactttggc      120
ctatcggtag tcggcgtgat gatccgagtc ttattgacct gcgtgtccgg tctggcactg      180
gcggcatcta tggcgatggt gcaagcgaaa atcgtcattg atcgcacccg gcttatttac      240
ccggccacgg cacgggtggt aaccctcacc ctgcgcaacg aggcggacag cccacggctg      300
gtacaggtat ggatcgatga aggcgacccc cagatggcgc cggaattgag tgacgtaccc      360
tttactgtca caccaccgat tctgcgaatg ggccccggca aggctcaagc gttgcgggtg      420
atttatcacc cggtacccag acaagccatg accgatcctc aggaagtggt gtattggctg      480
aatgtgctag ggatacggcc tactgacgcg gcaagccatc aactgcaact ggcgtttcgc      540
acgcgtatca aactgttcct gcccccaat gcgttgcctg cagggcgga agatgccgtg        600 gcggcgttgc aatggcaact ggcagacgac cgcccggtgc tgcgggtgcg caacccgagt      660
gcctttcatg tgaccttgtc cagcgtggca ctcaaccttg agggcgtcga ataccgccat      720
gaaaacccac cgatgctggc accgcgctca acggccgagt tgatcatgcc gggttgggtt      780
gtaccgtggc gaggtacgcc gacgctgcgc ttcaccacat tggatgacta tggcgcgacc      840
catgagagca cgcagcgcat aggccgg                                         867
```

<210> SEQ ID NO 45
<211> LENGTH: 699
<212> TYPE: DNA
<213> ORGANISM: Pseudomonas fluorescens

<400> SEQUENCE: 45

```
gtgcgtggtt tttaataag ttgtgcgctg ctgtggcatc ttttttttcag tgctgttgcc       60 gccgccgacg gtatgttgcc ggaaacaaca gtggtggtgc tttatgagga agacggcgaa      120
gccaccttga gtatcaagaa caccgatgcg gggccggcac tgttgcattc cgttgttgag      180
aatgtgcctg aagacctgga gccgctactg attgtcacac cgcctgtcac ccgtgtggag      240 gcggggggata cgcagcttgt gcgctttatc agcaccttga acagccgct caagacccag      300 cggctcaagc gcgtgtcgtt cgagggcatc ccccaagcgc gtgctgccgg tggtgcgacc      360
atcggcatca ccctgcggca gaatttgccg ctgatcctgc accccaaagg cctgccacgg      420
caccacacgc cctgggagtt gttgacgtgg aagcgcgtcg gggaccggct cagcgtccac      480
aacgacagcg cctatgtagt gcgcctggcg ccagatgtgc aactgctgcc acaaggcacg      540
ctggcgacat tgccgcgcac ttacatttg ccaggtgagg cattggtggc gaagggcgaa      600
ggtccgttgg gcaatgtggc tcaagtagag atccagcccg ccacggtcta cgggttttcg      660
gtagacaact accgagcgcc ggtcatcacc gatgagggt                            699
```

<210> SEQ ID NO 46
<211> LENGTH: 1455
<212> TYPE: DNA
<213> ORGANISM: Pseudomonas fluorescens

<400> SEQUENCE: 46

```
atgcactttg gaaaatggtt tcacaccagc accctgctgg tcggcttgag ttttgtgctg      60
ggcggctgcg ccagcgtctc ccaaacctcc accccggcaa ccctggataa gctgttgagc     120
gacccggcgc tgcaaggcgc caccgtctcg ctgatggtgc gtgatgcccg cacaggcacc     180
acgctgtatc agcacaaccc acgcaccsgg ctggtgcccg cgtccaacct caagctgttg     240
accacggcgc cagccatgga tgtattgggg ccgcagtacc gcttcgccac gcaactgctg     300
agcaatggcc tacgccaggg cgaccggctg actggcaacc tgtacctgcg tggcttgggc     360
gacccgagta ttcagtttgc cgactatcag gcgctcgccg cgcaattggc cagccagggc     420
gtgcgccagg tgcagggtga cctggtgttc gacgacactt ggttcgatgc cgagcggctg     480
ggcgtggact ggtcccatga tgatgaaacc acctactacg cgcgcagat ttcagcgctg     540
accgtggcgc ccaataccga ctttgatgct ggcagcgtgc tggtcaccgc caaggcgccg     600
ttgcacgtcg gctcgccggt cggcgtggag atctacccgc ccaccgacta cctgcaactg     660
aataaccgcg ccgtcagcgg gccgggtaac agctatggga tcaaccgtcg ccatggcacc     720
aacctgctgc agctcagcgg cgcggtggcg cctggccggc agagccagca attgatcagc     780
gtgtgggagc cgacgcaact ggtggccaac ctgtttgagc aagccttggc gcagcagggc     840
atcaaggtgc tggggcgtcg ggtgatgggc ggggcaagtc ctgctggggt gacggtgctg     900
gccgagcacc aatcggcgcc gttgcaggag ctgatcgtgc cgctgctcaa gctctcgaac     960
aacgccatgt ccgaagccgt gctcaaggcc atgggccgcc agacggccag cagcggcacg    1020
gcggcggcgg gcgccgtggc ggtggccgac tttctcaagc gccaggggct ggacaccagc    1080
gctgtgagcc aagtggacgg ctccggcctg tcgcggcgta acctggtgtc gtcgcaaacc    1140
ctcaccgacc tgctgctggc ggccagcaaa caaccctggt tcgacgcctg gtacaacgcg    1200
ctgccggttg ccggcaatgc cgaccgtatg accggcggca gctgggtta ccgcctgcgc    1260
ggcacggctg cggaaaataa cctgcatgcc aagaccggct ccatggccgg cgtgtcgtca    1320
ttgagcggtt acatcaccga tgctcacggg cgcaagctgg tgttcgcgat gttgaccaac    1380
aactatgtgg tcgctggcgc gcaggtaaaa gccgtggaaa accgcgtcgc cgtggccctg    1440
tcccacagcg aagac                                                     1455
```

<210> SEQ ID NO 47
<211> LENGTH: 1488
<212> TYPE: DNA
<213> ORGANISM: Pseudomonas fluorescens

<400> SEQUENCE: 47

```
atggaattgg ttgtaaaaag cgttagcccc gaaacgttga aaaccgccac cctcgtggtc      60
gctgtcggcg aaggccgcac actcggcgtc gccgccaagc aactggacga actgagcggc     120
ggcgctatca gcgccgtgct caagcgcggc gacctggccg gcaaagtcgg ccagagcctg     180
ctgctgcaga gcctgcccaa ccttaaggcc gagcgcgttt tgctggtggg cgtgggcaag     240
gatgccgaac tgggcgaccg tccgtttcgc aagatcgtca gcagcatcct caccaccctc     300
aagggcctgg gcgcagcga tgcggtgctg gcactcgatg aaatcgtggt caagggccgc     360
gacagctacg gcaagacccg cctgctggcc gagtcgctgg tggacggcgg ctatattttc     420
gaccagttca gagccagaa agccgaaccc gcgccctga gaaaatcac cctgctgacc     480
atcaaggctg cccaggctga agtccagcgc gccgtcaccc acgcccaggc catcgctaac     540
```

| | |
|---|---|
| ggcatgtcgt tcactcgcga cctgggcaac ctgccgccga acatctgcca cccgacattc | 600 |
| ctgggcgaac aggccaaggc actgggcaaa gagttcaagg gcttgaaggt tgaagtgctg | 660 |
| gacgagaaga aaatcaagga cctgggcatg ggctcgttct atgccgtggg ccagggcagc | 720 |
| gaccagccgc cacgcctgat cgtgatgcaa tacaacggcg gcaagaagtc cgagaaacct | 780 |
| tacgccctgg taggtaaagg catcaccttc gacaccggcg gcatcagcct caagccgggt | 840 |
| gccggcatgg acgagatgaa gtacgacatg ggcggcgccg ccagcgtgtt cggcaccctg | 900 |
| cgtgcggtgc ttgagctcaa gctgccgatc aacctggtgt gcattttggc ctgtgccgag | 960 |
| aatatgccga gcggcggcgc ggctcgccca ggcgatatcg tcaccaccat gagcggccag | 1020 |
| actgtggaga tcctcaacac cgacgccgaa ggccgcctgg tgctgtgcga cgcactgacc | 1080 |
| tacgccgagc gcttcaagcc ccaggccgtg atcgacatcg ccactctgac cggtgcctgc | 1140 |
| atcgtggccc tgggctccca cacctcaggc ctgctgggca caacgacga actgatcgag | 1200 |
| caactgctca gcgccggcaa ggccgccgac gaccgcgcct ggcaactgcc gctgttcgat | 1260 |
| gagtaccagg aacagctcga cagcccgttc gccgacatcg ccaacatcgg tggccctaaa | 1320 |
| gccggcacca tcacggcggc ctgcttcctg tcgcgctttg ccaagaactt caactgggct | 1380 |
| cacctggaca tcgccggcac cgcctggacc agcggcggca aggacaaggg cgccactggc | 1440 |
| cgtccggtgc cctgttgac tcaataccctg ctggatcgcg ccaaagct | 1488 |

<210> SEQ ID NO 48
<211> LENGTH: 633
<212> TYPE: DNA
<213> ORGANISM: Pseudomonas fluorescens

<400> SEQUENCE: 48

| | |
|---|---|
| atggataact ggatagcgtt ggtcaaagcc aacatgaaag accgcaaggt cacacaggat | 60 |
| gaactggcgc agcgcctggg catgtcccag ggcggcatcg gccattggct caataaacgc | 120 |
| cgtgtgccga gcctggcgga catgaaccgc gtactggccg aactgggggtt gggtatttg | 180 |
| gaggtggcgc tggaaattcg tgaacgggcc gcgcaagtgc ctgaacggga tcgcactac | 240 |
| aacccgtact tcgttaccc ggtcaacgac tggaagcagg cctgcgagct gcgtgaggag | 300 |
| cgtgcgcctt atagaaccga gcgctacgaa ttgaccgatt accacgcccg aggcaaggca | 360 |
| ttctggctgc cagtgagggg agacgccatg accgcccca cgggcatgag cattgcagct | 420 |
| ggcatgatga tcctggttga cccggcgatc gcgcccgagc ccggtaaatt agtgctggcc | 480 |
| caatgggctg gcaaccccca ggccacctt cgccaattgc aggaagaaag cggccagcac | 540 |
| tacctggtgc cgctcaaccc cacttacccc aaggtgctgc tcaccgacgg ctgtcgcctc | 600 |
| ctgggtgtag tggtgcaggc cacggcgaag ttc | 633 |

<210> SEQ ID NO 49
<211> LENGTH: 2043
<212> TYPE: DNA
<213> ORGANISM: Pseudomonas fluorescens

<400> SEQUENCE: 49

| | |
|---|---|
| atgccgccca gcatttcgc ggctacaatg cgcgcctcaa ccgtgacaag cctgactaaa | 60 |
| aaaactatgt ccttgcccaa gcatcacctg gaattgctca gccctgcccg cgatgtcgcc | 120 |
| attgcgcgcg aggctatctt gcacggcgcc gacgccgttt atatcggcgg gccgagcttc | 180 |
| ggcgcccgcc ataatgcgtg taacgagggtg agcgatatcg ctcaactggt ggaattcgcc | 240 |
| cgccgctacc acgcccgcgt cttcaccacc atcaacacta tcttgcatga caacgagctg | 300 |

```
gagcccgcac gcaagctgat ccatcagctc tacgatgccg gtgtcgatgc gttgatcgtg      360
caagacctgg gcgtgatgga gctggatatt ccgccgatcg agctgcacgc cagcacccag      420
accgacatcc gcacactggg ccgggccagg tttctcgacc aggccggttt ctcgcagttg      480
gtactggccc gcgagttgaa cctgcaagag attcgcgcca ttgccgatga gaccgatgct      540
gccatcgagt tctttatcca cggcgccctg tgcgtagcct tctccggcca gtgcaatatc      600
tcccacgcgc aaaatggccg cagcgccaac cgtggcgact gctcccaggc tgccgcctg       660 ccctacacct aaaagatga ccaaggccgc gttgtagcct ttgaaaagca cctgctgtcg       720
atgaaagaca acaaccagag cgccaacctg cgcgccctgg tcgaagcggg cgtgcgttcg      780
ttcaagatcg aaggccgcta caaggacatg gctatgtga agaacatcac cgcctactac       840
cgccagcgcc tcgacgagat cctcgaagac cgcccgacc tggcccgcgc ttccagcggc       900
cgtaccgcgc acttcttcct gcccgacccg aaaaaacct tccaccgtgg cagcaccgat       960
tactttgtca cgaccgcaa gatcgacatc ggcgcctttg acaccccgac cttcaccggg      1020
ctgcccgtgg caccgtgga aaaagccggc aagcgcgact tgcaggtggt cacccatgag      1080
ccgctgtcca acgcgacgg cctgaatgta ctgatcaagc gtgaagtggt gggctttcgt      1140
gccaacatcg ccgagcccaa gggtgagttc gaggaagacg gtgagaagcg ctaccgctac      1200
cgcgtcgagc ctaacgaaat gccggccggc ctgcatcaac tgcgccccca tcacccgctc      1260
aaccgcaacc tggaccacaa ctggcaacag gccctgctca agacctcggc cgagcgccgt      1320
atcggcttgt catgggtcgc gcgcctgcgt gaagagcagc tgcaaatcac cgcgaccagc      1380
gaagaaggca tcagcgccag cgttatcctg cccggcccgt ttggcgtggc caacaagccg      1440
gaacaggcgc tggacaccct gcgcgacctg ctcggccagc tcggcaccac cgaataccat      1500
gccacccgca tcgagctgga tgcgccgcag gcgttcttca tccccaactc gcagctcaag      1560
gccttgcgcc gtgaagtgat cgaagcgctg actgccgcac gcgtcgccgc gcacccacgg      1620
ggtgggcgca aggctgaaac ctcgccgccg ccggtttacc ctgaggcgca cttgtcgttc      1680
ctggccaacg tctacaacca gaaggcccgg gacttctacc atcgtcacgg cgtaaagctg      1740
atcgacgcag ccttcgaagc ccacgaagaa ccggcgaag tgccggtgat gatcaccaag      1800
cactgcctgc gtttctcgtt caacctgtgc cctaaacagg ccaagggcgt gaccggggtg      1860
aagaccaagg tggcgccgat gcagttgatc catggtgacg aagtgttgac cttgaagttc      1920
gactgcaaac cttgcgagat gcacgtggtg ggcaagatca aggggcatat cctcggcctg      1980
ccgcagccag gcagcgcagt ggagcatttc aacccggaaa accttatcta ccaaggcacg      2040
cac                                                                   2043
```

<210> SEQ ID NO 50
<211> LENGTH: 615
<212> TYPE: DNA
<213> ORGANISM: Pseudomonas fluorescens

<400> SEQUENCE: 50

```
atgtactcca tgacaaacct gactccccgc cgcaccgcca tcctgacctt cattcgcgag       60
cgcatcgcgc aacaaggcca gcctcccagc ctcgccgaga tcgccgaggc gttcggcttc      120
gcctcgcgca gcgtcgcccg caagcatgtg gtggcgctga ccgaagctgg ctttatcgag      180 gtcaaccccca accaggcccg tggcattcgc ttgctaaatc aaccggcgcg tcccgagtgg      240
ctggatgtgc cggtgctcgg ccgcgtggcg gccggtcggc cgattggcgc cgatgccgag      300
```

| | |
|---|---|
| gtgcacagcc gcttgcaact ggaccccgct accttcgcca aaaccccccga ctacctgctg | 360 |
| cgagtgcagg gcgattcgat gattgaagat ggcattctcg atggcgacct ggtgggcgta | 420 |
| cgccgcactg tcgaagcctt gaacgggcag attgtggtgg cgcgcctgga cggtgacgtc | 480 |
| accatcaagc gtttcgagcg ccacggcgac agggttcgcc tgttgccgcg caacccggcg | 540 |
| tatcaaccca tcgtggtcgg gcccgagcag gacctggcca tcgaaggcgt gttctgcggc | 600 |
| ctggtgaggc aaggc | 615 |

<210> SEQ ID NO 51
<211> LENGTH: 903
<212> TYPE: DNA
<213> ORGANISM: Pseudomonas fluorescens

<400> SEQUENCE: 51

| | |
|---|---|
| atgagaatcc tcggcatttt atgcctgcta ctcacattga acggctgcag ctccttactg | 60 |
| ttctaccccg agcccggcct gcccttcact ccggaaaaag cccacctgca ataccgcgac | 120 |
| gtcacgctca ccaccgcaga cggggtgaag ctgcacgctt ggtggttgcc agccaaagcg | 180 |
| ggtgtgccac tcaaaggcac catcctgcat ttgcacggca acggcggtaa cctcgcctgg | 240 |
| cacctggggg gcagttggtg gttgccgagc cagggttatc aagtgttgtt gctggactat | 300 |
| cgcggctatg gctgtcgga aggcaagcca tcgttgccgg cggtctacca ggatatcgac | 360 |
| gccgcattcg gctggatcga caaggcgcct gaaacccagg gtaaaccgct gattattctc | 420 |
| gggcaaagcc tgggcggtgc actggcggtg cattacctgg cagcccaccc ggagcgtcaa | 480 |
| gcccaactca aagctctggt actggacggc gtgccagcca gttatcgtga cgtaggacaa | 540 |
| ttcgccttga gcacttcctg gttaacctgg ccgttgcagg tgccgctgtc atggctggtg | 600 |
| cccgacgccg acagtgcgat caatgccatg ccccgcgtga ccggcgtgcc caagctgctg | 660 |
| ttccacagcc tggatgatcc catcgtgccg gtggccaatg gcatccgcct gtatcaggcc | 720 |
| gcaccgccgc ccagggtgtt gcaactgacc cgtggcggcc atgtgcagac ctttgccgat | 780 |
| aaaacctggc agaccgtgat gctgcgttac ctggacgacc gcagcactt caacggcttg | 840 |
| cgccgcctgg gcgaaattcc gaattaccct attcctaaag ttgattcatc agagagcccg | 900 |
| caa | 903 |

<210> SEQ ID NO 52
<211> LENGTH: 2049
<212> TYPE: DNA
<213> ORGANISM: Pseudomonas fluorescens

<400> SEQUENCE: 52

| | |
|---|---|
| gtgagcgcga acaaccctct tttgcagtcc tacgacctgc cgccgttctc ggcgatccgt | 60 |
| gccgagcacg tgcagccggc catcgaacag atcctcgccg acaaccgcgt ggcaatcgca | 120 |
| gagatcctgc agagccaggg taaaaatccg acgtgggccg gctggtcct ggccatggac | 180 |
| gaactcaatg atcgcctggg tgcggcctgg agcccggtca gccacctcaa tgccgtgtgc | 240 |
| aacagcgccg aactgcgcga agcctatgag gcgtgcctgc cggccttgag cgcttactct | 300 |
| accgaaatgg ccagaaccg tgagctgttc caggccttcg aagccctggc caacagcccg | 360 |
| gaagctgccg gtttcgatgt ggcgcaaaaa accattctgg aacactccct gcgtgacttc | 420 |
| cgcctgtcgg gtatcgactt gccgccggag cagcaaaagc gctacgccga ggtgcagagc | 480 |
| aagtctgtcc agctgggcag caagttctca aaccagttgc tggacgccac ccaggcctgg | 540 |
| accaagcacg tcaccgatga agccaccctt gccggtctga ccgactcggc caaggcacaa | 600 |

```
atggccgccg ccgcccaggc caagggcctc gacggctggc tgatcacctt ggaattcccc      660
agctactacg ccgtcatgac ctacgcccag gaccgtgccc tgcgtgaaga ggtgtacgcc      720
gcctactgca cccgtgcgtc ggaccaaggc ccgaatgccg gtcagaacga taacggcccg      780
gtgatggaac agatcctcga cctgcgtcag gaactggccc aattgttggg ttatgcgtcc      840
ttctccgagc tgagcctggc caccaagatg gccgagtcca gcgaccaggt gctgagcttt      900
ctgcgtgacc tggccaagcg cagcaagccg tttgccgccc aggacctgca acagctcaag      960
gcctatgccg ccgagcaagg ctgccctgat ctgcaaagct gggacagcgg tttctacggc     1020
gaaaaactgc gtgagcagcg ctacagcgtg tcccaggaag cgctacgcgc ctacttcccc     1080
atcgacaaag tgctgggcgg cctgtttgcc attgtgcagc gcctgtacgg catcgagatt     1140
gctgagctca aaggcttcga cacctggcac ccggatgttc gtttgttcga aatcaaggaa     1200
aacggcgagc acgtcgggcg tttcttcttc gacctgtacg cccgcgccaa caagcgtggc     1260
ggtgcctgga tggatggcgc ccgtgaccgc cgccgtaccg ttgatggcgt gctgcaaagc     1320
cccgtcgcca acctggtgtg caacttcacc ccggccgaca gcggcaagcc tgccctgctg     1380
acccacgatg aagtcaccac cctgttccac gaattcggcc atggcttgca tcacctgctc     1440
acccgcgtgg aacatgccgg agtatccggt atcaacggtg tggcgtggga cgcggtggaa     1500
ctgccgagcc aattcatgga gaactggtgc tgggagcctg aaggccttgc gctgatctcc     1560
ggccactacg aaaccggcga gcccctgccc caggacctgc tggagaaaat gctcgcggcg     1620
aaaaacttcc agtccggcct gatgatggtg cgtcagctgg agttctcgct gttcgacttt     1680
gaattgcacg ccacccatgg cgatggtcgc agtgtggccc aggtgctgga aggcgtgcgc     1740
gatgaagtct cggtcatgcg cccaccggcc tacaaccgct cccccaacag cttcgcgcac     1800
atcttcgccg gcggttatgc ggcgggttac tacagctaca gtgggccgga agtgctgtcg     1860
gcggacgcgt tctccaagtt tgaagaagac ggcgtgctca atgccagac cgggcgggcg       1920
ttccgtgaag ccatcctggc ccgtggcggt tcccaggcgc cgatggtgct gttcgtcgac     1980
ttccgcggac gcgcgccgtc gattgacgca ctcttgcgcc acagcggcct gagtgaggac     2040
gcggcagca                                                             2049
```

<210> SEQ ID NO 53
<211> LENGTH: 1155
<212> TYPE: DNA
<213> ORGANISM: Pseudomonas fluorescens

<400> SEQUENCE: 53

```
atgaacatca ccaccttagc caaacgcacg tgcctgctta tctcgctgat catcaccccg       60
gccgcctggg cggttgaaat ggtgccggcc tccccgcaac tggccgccaa gtcgtgggtc      120
ctcatggacg ccgccagtgg caacgtgctg gtcgaaaacg gcggtgatgt acgcctgccg      180
cctgccagcc tgaccaagct gatgaccgct tacatcgcga ccctggaaat ccgtcgcggc      240
cagatcggcg agaacgaccc ggtgaccgtc agcgaaaacg cctggcgtac cggtggttcg      300
cggatgttca tcaaggtggg ttcgcaagtc accgtgagcg acctgctgca cggcatcatc      360
atccagtccg gtaacgacgc cagcgtcgcc ctggccgagc acatcgccgg cagcgaagac      420
gccttcgccg acatgatgaa caaaaccgcc ggtgagttgg gcatgaccaa cagccacttc      480
atgaacccaa ctggcttgcc aaaccccgag cactattcgt cggctcacga catggcgatc      540
ctggcgcgcg cgatcatccg cgttgacccg gtgcactacg cgatctactc ccagaaggaa      600
```

```
ttcttctgga acaacatcaa gcagcctaac cgcaacctgt tgctgtggcg cgacaagacc      660
gtcgatggcc tgaagaccgg ccacaccgac gaagccggct actgcatggt gtcgtccgcc      720
gtacgtgatg ccagcgcct gatcgccgta gtattcggca ccaacagcga gcaggcccgt       780
gcggccgaga cgcaaaaact gctgacttac ggcttccgct tcttcgaaac ccagaccttc      840
taccagaagg gtgctgaact ggcgaccgcg ccggtgtgga agggctcgac ttcgcaagtc      900
aaggccggcc tggccgacga cctgaccctg accatgccta aaggccagct gaaaaagctc      960
gccgccagca tgaccctgaa cccgcaattg gttgcgccaa tcgccaaggg tgatgtgatc     1020
ggtaaggtcg aagtgaagct ggacgacaag gtggtgcaca cgccgacct gatcgcgctg      1080 gacgctgtcg aggaaggtgg tatcttccgc cgcgtatggg atagcatccg tctattcttc     1140
tacggcttgt tcaac                                                      1155
```

<210> SEQ ID NO 54
<211> LENGTH: 1149
<212> TYPE: DNA
<213> ORGANISM: Pseudomonas fluorescens

<400> SEQUENCE: 54

```
atgacggccc atgccgacct ttcgccgacc cttcaacttg ccatcgacct gatccgtcgc       60
ccgtcggtca cgccggtcga tgccgattgc cagaagctga tgatgcagcg cctgggcgac      120
gccggttttg cgcttgaacc gatgcgcatc ttcgacgtgg acaatttctg ggccacccat      180
ggcaagcatg aaggtccggt gctgtgcttt gccggtcaca ccgacgtggt gccgaccggc      240
ccggtgcagg cctggcagaa cgacccgttc gacgcgctga tcgatgaaaa cggcatgctc      300
tgcggccgtg gcgcggccga catgaaaggc agcctggcgg cgatgctggt ggcagcggaa      360
cgtttcgtca cggactaccc ggaccacaag ggttcggtcg ccttcctgat caccagcgac      420
gaagaaggcc cggcgcacca tggcaccaag gccgtgatcg aacgcctggc cgcacgcaag      480
gagcgcctgg actggtgcat cgtcggcgag ccgtcgagca ccagcctggt gggtgacgtg      540
gtcaagaacg ggcgccgtgg ctccctcggt gccaccttga ccgtgcgcgg tgtacaaggc      600
cacgtggctt acccgcacct ggcgaagaac ccgatccacc tggccgcacc ggccctggcc      660
gaactcgccg ccgaacattg ggatgacggc aacaccttct ttccgccgac cagcttccag      720
atttccaacc tcaactccgg taccggcgcc accaacgtga tcccgggtga cctgacggcg      780
gtgttcaact tccgtttttc taccgagtcc accgtcgagg gctgcaaca acgggtcgcg      840 gccattctcg acaagcatgg cctggactgg catgtggagt gggcgctgtc gggcctgccg      900
ttcctcaccg agccgggcgc tctgctcgat gcggtgtcgg ccagcattct ggcgatcacc      960
gggcgtgaga cccaggcatc caccagcggc ggcacctccg atgggcgctt cattgcgacg     1020
ctgggcaccc aggtggtcga actggggccg gtcaacgcga cgatccacca ggtcaacgaa     1080
cgcatcctgg ccagcgacct cgatgtgctg accgaaatct actaccagac cctgatcaag     1140
ttgctcgcc                                                             1149
```

<210> SEQ ID NO 55
<211> LENGTH: 1311
<212> TYPE: DNA
<213> ORGANISM: Pseudomonas fluorescens

<400> SEQUENCE: 55

```
atgctgcatt tgtcccgcct cacttcgctg gccctgacga tcgccctggt gatcggcgcg       60
cctctggctt ttgccgacca ggccgcaccg gctgcacccg ccacggctgc gacgaccaag      120
```

```
gcgccattgc cgctggacga gctgcgtacc tttgccgagg tcatggaccg gatcaaggca    180
gcgtatgtcg aacccgtaga cgacaaggcc ctgctggaaa atgccatcaa gggcatgctc    240
agcaacctcg acccgcactc cgcctacctg ggcccggaag atttcgccga gctgcaggaa    300
agcaccagcg gtgagttcgg cggcctgggc atcgaagtgg gctccgaaga cggccagatc    360
aaagtggtct cgcctatcga cgacaccccg gcgtccaagg ccggtatcca ggccggcgac    420
ctgatcgtga agatcaacgg ccagccaacc cgcggccaga ccatgaccga agccgtcgac    480
aagatgcgcg gcaagctcgg ccagaagatc accctgaccc tggtacgcga cggcggcaac    540
ccgtttgacg tgaccctggc ccgcgcgacc atcacggtca agagcgtgaa agccagctg     600 ctggagtcgg gctacggtta tatccgtatc acccagttcc aggtcaagac cggcgacgaa    660
gtggccaagg ccctggccaa gctgcgcaaa gacaacggca agaagctcaa cggcatcgtg    720
cttgacctgc gcaacaaccc aggcggcgtg ttgcagtcgg cggtcgaggt ggtcgaccac    780
ttcgtcacca agggcctgat cgtctacacc aagggccgta tcgccaactc agagttgcgc    840
ttctcggcca ccggcaacga cctcagcgag aacgtgccac tggcggtatt gatcaacggt    900
ggcagcgcct cggcttcgga aatcgtcgcc ggtgccctgc aagacctcaa gcgcggcgtg    960
ctgatgggca ccaccagctt cggcaaaggc tcggtgcaga ccgtattgcc gctgaacaac   1020
gagcgtgcgc tgaagatcac cacggcgctg tactacacgc ccaacggccg ctcgatccag   1080
gcccagggca tcgtgccgga catcgaagta cgccgcgcca agatcaccaa cgagatcgac   1140
ggcgaatact acaaagaggc cgacctgcaa ggtcacctgg caatggcaa cggcggtgcc    1200 gaccagccaa ccggcagccg cgccaaggcc aagccgatgc cgcaggacga tgactaccaa   1260
ctggcccagg cactcagcct gctcaagggc ttgagcatca cccgcagccg t            1311
```

<210> SEQ ID NO 56
<211> LENGTH: 852
<212> TYPE: DNA
<213> ORGANISM: Pseudomonas fluorescens

<400> SEQUENCE: 56

```
atgtcactaa atttcccgct gttgctggtc attgccgttg ccgtctgtgg tctcctggcg     60
ttgctcgatc tggtgttctt cgccccgcgt cgtcgggcgg ccattgcttc ctatcagggc    120
agcgtcagcc agcccgatgc ggtggtggtc gagaagctga acaaagagcc cttgctggtt    180
gagtacggca agtcgttctt cccggtgttg ttcatcgtgc tggtgttgcg ctcgtttctg    240
gtagagccgt tccagatccc ttcggggtcg atgaaaccga ccctgacgt gggcgacttc     300 atcctggtga acaagttttc ctacggcatt cgtctgccgg tgatcgacaa gaaagtcatc    360
cccgtgggtg acccgcagcg cggcgatgtg atggtgttcc gctacccaag cgacccgaac    420
gtcaactaca tcaagcgtgt ggtcggcctg ccgggcgacg tggtgcgcta caccagtgac    480
aagcgcctgt tcatcaacgg tgagtcggtg gccgagaagc tgctgggcgc cgagccgaac    540
accctgggca gcgccgagct gtaccaggaa aaactcggcg cggtggagca ccaaatccgc    600
aaggaaatga ccgctaccg tgcgatgccg gatggccagt ggaaagtgcc tgccgggcac    660
tactttatga tgggcgacaa ccgcgacaac tccaacgaca gccgctactg ggatgacccc    720
aacattccca agacctgct gggcatggtg cccgacgaga acattgtcgg caaagccttc    780
gcggtctgga tgagttggcc ggaacccaag ctcagccacc tgccgaactt ctcgcgggtc    840
gggctgatca ag                                                         852
```

<210> SEQ ID NO 57
<211> LENGTH: 1158
<212> TYPE: DNA
<213> ORGANISM: Pseudomonas fluorescens

<400> SEQUENCE: 57

| | | | | | |
|---|---|---|---|---|---|
| atgctcaagg | cactgcgttt | ttttggatgg | ccattgttgg | ctggcgtgct | gatcgcgatg | 60 |
| ctgattatcc | agcgttatcc | ccagtgggtg | ggcctgccca | cactggatgt | gaacctgcaa | 120 |
| caggcgccgc | agaccaacac | ggtggtgcag | ggcccggtga | cctatgccga | tgccgtggtc | 180 |
| attgccgcgc | cggcggtggt | caacctgtac | accaccaagg | tcatcaacaa | gcccgcgcat | 240 |
| ccgttgtttg | aagacccgca | atttcgccgc | tatttcggtg | acaacggccc | caagcagcgc | 300 |
| cgcatggaat | ccagcctcgg | ctccggtgtg | atcatgagcc | cgagggcta | catcctcacc | 360 |
| aacaaccacg | tgaccaccgg | cgccgaccag | atcgtggtgg | ccctgcgtga | cggccgcgaa | 420 |
| accctggccc | gcgtggtggg | cagcgacccg | gaaacggatc | tggcggtact | caagattgat | 480 |
| ctgaagaacc | taccggccat | caccctcggc | cgctccgacg | gtttgcgcgt | gggcgatgtg | 540 |
| gcgctggcca | tcggcaaccc | gttcggggtg | ggccagacgg | tgaccatggg | catcatcagc | 600 |
| gccaccgggg | gcaaccagct | gggccttaac | agctacgaag | atttcatcca | gaccgacgcg | 660 |
| gcgatcaacc | ccggcaactc | cggcggtgcg | ctggtggacg | ccaatggcaa | cctgaccggc | 720 |
| atcaacaccg | cgattttttc | caagtccggc | ggttcacagg | gcattgggtt | tgcgatcccg | 780 |
| gtgaagctgg | cgatggaagt | gatgaagtcg | atcatcgagc | acggccaggt | gattcgcggc | 840 |
| tggctgggca | ttgaagtaca | gcccttgacc | aaggaactgg | ccgaatcatt | cggcctgacc | 900 |
| gggcgtccag | gcatcgtggt | agcggggatc | ttccgcgacg | gcccggcgca | gaaggccggc | 960 |
| ctgcaactgg | gcgatgtgat | cctcagcatc | gacggcgccc | cggcgggtga | tggccgcaag | 1020 |
| tcgatgaacc | aggtggctcg | gatcaagccg | accgacaagg | tggcgatcct | ggtgatgcgc | 1080 |
| aacggcaagg | agatcaaact | gtcggcggaa | atcggcctgc | cccaccacc | ggcgaccgcg | 1140 |
| ccagtgaaag | aagagcaa | | | | | 1158 |

<210> SEQ ID NO 58
<211> LENGTH: 1449
<212> TYPE: DNA
<213> ORGANISM: Pseudomonas fluorescens

<400> SEQUENCE: 58

| | | | | | |
|---|---|---|---|---|---|
| atgtcattca | tctttccat | ttcatcttca | aagtcaaaat | tacttatgac | cactgaaccg | 60 |
| tctaaagcgc | cgccgcttta | cccgaagacc | cacctgctcg | ccgcaagtgg | tatcgccgcc | 120 |
| cttctcagcc | tggcactgct | ggtattccct | tccagtgacg | ttgaagccaa | cgaacatcc | 180 |
| ctgagccttg | atctggaaag | cccagttgaa | caactgacac | aagatcaaga | cgcttccgac | 240 |
| gctcaacaag | ccacaaacac | tgcaactgaa | tcaccttcg | cccagatcga | agcacaccc | 300 |
| gaagacaccc | agcaagccgc | ccaggaagca | cctgcagcag | ccaagagtcc | ccagcatcgc | 360 |
| gaagtcatcg | tgggcaaagg | cgacacactc | tcgaccctgt | tcgaaaaagt | tgggttgcct | 420 |
| gccgccgctg | taaatgacgt | gctcgccagc | gataagcaag | ccaagcaatt | cactcagctc | 480 |
| aaacgtggtc | aaaagcttga | atttgagctg | acgccagacg | gccagttgaa | caacctgtac | 540 |
| accagcatca | gtgacttgga | aagcatcagc | ctgagcaaag | gcgccaaagg | cttcgcattc | 600 |
| aacagaatca | ccaccaaacc | cgtcatgcgt | tccgcctacg | tacatggcgt | gatcaacagc | 660 |
| tccctgtcgc | agtcggccgc | gcgtgcgggc | ctgtcgcata | gcatgaccat | ggacatggcc | 720 |

```
agcgtatttg gctacgacat cgacttcgcc caggacatcc gtcaaggcga cgaattcgac      780
gtgatctacg aacagaaagt agccaacgga aaagtggtcg gcactggcaa cattctttct      840
gcacgcttca caaaccgtgg caaaacctac accgccgtgc gctacaccaa caaacaaggc      900
aacagcagct actacacggc tgatggcaac agcatgcgta aggccttcat ccgtacaccc      960
gttgactttg cccgtattag ctcgcgtttc tccatgggcc gcaagcatcc aattctgaac     1020
aaaattcgcg cacacaaggg cgtcgactat gccgcgccgc gtggcacgcc aatcaaagca     1080
gcgggcgacg gcaaggtctt gttggcgggg cgccgtggtg gttacggcaa tacggtgatc     1140
atccagcacg gcaacactta ccgcacgctg tacggccaca tgcaagggtt cgccaagggc     1200
gtcaagacag gcggcaacgt gaaacagggc caagtgatcg gctacatcgg taccaccggc     1260
ctctccaccg gccgcacttt gcactacgag ttccaggtca acggcgtaca cgtcgaccca     1320
ttgggccaga agctgccgat ggccgacccg attgccaagg ccgaacgcgc gcgcttcatg     1380
caacagagcc agccgctgat ggcacggatg gatcaagagc gctccacctt gctggcttcg     1440
gcgaagcgt                                                             1449

<210> SEQ ID NO 59
<211> LENGTH: 996
<212> TYPE: DNA
<213> ORGANISM: Pseudomonas fluorescens

<400> SEQUENCE: 59
atgagtgacg agtggaaagc gcctgaaaag gccgagagca gtgatgataa aagctggaag       60
ctgctggaaa agaccctcct ggccagcgtc caggaacagc ggcgttcgcg cgcgctggggg     120 attttcttca agctgctgac ctttgtgtac ctgcttggga tgctggcgct gttcagcccg      180
ctgatggaca tggaaaagag cgccacccgc ggcagtcatt acaccgcctt gatcgaggtg      240
cgcggcgtga ttgccgacaa ggagcccgcc agtgccgaca atatcgtcac cagcctgcgc      300
gcggcctttg aggaccccaa ggtcaaaggc gtggtcctgc gtatcaacag cccaggcggc      360
agcccggtgc agtcgggcta tgtgtatgac gagattcgtc gtctgcgcgc cttgcatccg      420
gataccaagc tctatgccgt gatctccgac ctgggtgcct cgggcgccta ttacattgcc      480
agtgccgcag accagatcta tgccgacaag gccagcctgg tgggttctat tggtgtgacc      540
gcggccggtt acggttttgt cggtgctatg gagaagctgg ggatagagcg tcgcacctac      600
acctcgggtg agcacaagtc gttcctcgat cctttccagc cgcagaaggc ggatgaaacc      660
gcgttctggc agggcgttct cgacactact catcgtcagt tcatcgccag cgtcaagcag      720
ggccgtgggg atcgtctgaa ggataaagac catccagagc tgttctccgg cctggtctgg      780
tcgggtgaac aggcgttgcc gctgggcctg atcgatggcc tggcagtgc cagttcggtg      840 gcgcgggatg tggtgggtga agaagttg gtgtatttta cggttgagga atcgccgttt      900
gatcgcttct ccaagaagct cggtgccagt gtggcggaga agctagctct gtatatgggc      960
ttccaggggg ccgtccctgc gctgaaacct gaaggc                               996

<210> SEQ ID NO 60
<211> LENGTH: 1365
<212> TYPE: DNA
<213> ORGANISM: Pseudomonas fluorescens

<400> SEQUENCE: 60
atgcgacttt ccaatacgct gcaaagtttt catgcgccgc ttgctggcga tcagcaatca       60
```

| | |
|---|---|
| gcggtggccg atgcgaccct aaggcccaac gacccctctg aatcgaacgt tgataaaccc | 120 |
| tctttcacgg ttgatcaggc cgcgcgtcaa atcactcgaa ccggccatcg ttggtttgac | 180 |
| gccaatcgcg acggcatcac gcagatctcc tattcattca acaagcacgc aagagggcac | 240 |
| acggcgttca atgcgaccca gaaagagcag gcccggcgct cgatgcaatc gtgggaggat | 300 |
| gtcgcgaatg tttcattcca ggaaggcagt cgtcgccccg aggggcttct agcgttctcc | 360 |
| aatagcacgg actacgaggt cgccttcggc cagtatccgg ccaggaagg taaagtgctg | 420 |
| atcaatcccc gattcggcac caatactaac ccggccctgc acaatcatgg gcgaatgacc | 480 |
| ctgacccatg aaattgggca aaccctgggc ctgttacacc caggcaccta taattttggt | 540 |
| aatcccaatt accgcgatca cgccttatat gctcaggata cgcgggctta cagcgtgatg | 600 |
| agctacttcg atgcacctga agcgggtaaa cacttcaatg gaaagttacc gtcggcgccg | 660 |
| atgatggatg atatcgccgc tgcgcagcgg gtttatggtg ccaataacac gacgcgcaat | 720 |
| tcagatacca cctatggctt caactccaat gcgggacgag actatctgga gttgaactcg | 780 |
| cgtcacgata cggccttgtt ttgtgtatgg acggtggtg gtgtcgatac gttggacttt | 840 |
| tccaagtatc accaaaacca gactatcaat ttgcgggcgg agtccttttc ggatgttggc | 900 |
| ggcctggtgg ggaatgtttc cattgccaag ggggttacgc tggagaatgc aatcggcggc | 960 |
| tccgggcatg actcgatcat tggtaaccaa gcaaacaacg tgcttaaagg tggggcgggt | 1020 |
| gcggatcgac tccgaggtgc gggggggcgct gacaccttcg cttacgacaa tgccagcgac | 1080 |
| tccacgccgg aatatcccga tcagattatg gatttgtca cgggtgtgga cagaatcgat | 1140 |
| ctgtcgaacc tgctgggcaa cgcggggggtt gatgccctga ggttcgtcag gcggctgacg | 1200 |
| ggcaaaccag gtgaagcgat tctggattac aaccgtacga ctaacctgtc taggctggcc | 1260 |
| atcgacctca cagggaatgg ccgatttgat tttttcctca aggcttacgg cccgatcaat | 1320 |
| gtgcccgaca tcatcaccgc caatcctggc aggcagcgct acgcc | 1365 |

<210> SEQ ID NO 61
<211> LENGTH: 558
<212> TYPE: DNA
<213> ORGANISM: Pseudomonas fluorescens

<400> SEQUENCE: 61

| | |
|---|---|
| atgagctcgc aactcaacgg caagcacatc ctcgtcatca cctccaacac cggtatcgag | 60 |
| cgcgacgaac tgctcaagcc gctggagacg ctgcgtggct acggcgcgac cgtgacgcac | 120 |
| gcctccagca aggggggcac tacccagaca tttgtcggcg acacggaaaa agaccagacc | 180 |
| gtggaatccg acgtgcaact gtcggatgtt gtcagcgccg acttcgatgc gctggtcatc | 240 |
| ccgggcggca cggtcaatgc cgatacgctg cgccaggatg ccgccgcgtt gcgcttgatc | 300 |
| aatgagttcg tgcaggccgg caagaccatc gcggcaatct gtcacgggcc atggacccctg | 360 |
| atcgacgctg gcgtggtcaa gggcaaaacc ctgactgcct ataaaagcgt gcgcatcgac | 420 |
| cttgaaaacg ccgcgctgc cggcgtggtg gatgccgagg ttaaagagtg ccaggccaat | 480 |
| ggctggacct tgatcaccct cgcgcacgccg gacgatctac cggcgttcaa tgaggcgatt | 540 |
| gccaaggccg tcggcggc | 558 |

<210> SEQ ID NO 62
<211> LENGTH: 1227
<212> TYPE: DNA
<213> ORGANISM: Pseudomonas fluorescens

<400> SEQUENCE: 62

```
atgctcttca ccttcccgcg taccctgttg gccgctaccc tggccttgtc tttcagcctg    60
ccggcctaca gcgccgagcc tcataaacag atccagcaac aggccgaaca atacaaggcc   120
gaagccttga agctgctgga gcgcctggtg aatatcgact cgggctcagg ctacgagccc   180
ggcttgactc aagtgcgcga tatcgccgtg atgagttgaa acagttgggg tttcaccatc   240
gaactggtgc cggataaagc cgccaacaac agccatgtgg tcgccaccct caaaggcact   300
ggcaaggcca agatcctgct gatggcccat atggacaccg tattcaagga aggctcggcc   360
gccgagcgcc ccttccacat caaggacggc cgcgcctacg ccccggcgt gatggatgac    420 aagggcggca tagtcgccgg catctatgcg ctcaaagtcc tcaaaagcca gggcttcaag   480
gactacgcgc agatcacctt cctgctcgac gccagcgaag aaaccgggtc cgacgccgct   540
tccgaactga tccgcaacac tgccaagggc cacgatgtaa ccctgaacct ggaacccggt   600
cgccccgccg acggcctggt ggtgtggcgc aaaggcagcg ctaccgccgt ggtcgaagtc   660
aaaggcaagg ccgcccacgc cggcgtcgcc cggaactgg acgcaacgc cgccatggaa     720 gccgcgcacc agatcctgca actgggcaaa ctcggcgacg aagacaagaa aaccaccatc   780
aacttcaccg tgctcaaggc tggcgaccgc accaacgtca tccctgacca ggccaccgcc   840
aaggccgacg tgcgtgcggc cttgccggaa gaattcgacc ggatcgagaa agacctggcc   900
cgggtttcag ccaacaaatt gatcccggaa accgaagtga aaaccagcct gcagcgcggc   960
ctgccgccga tgccgcagac ggccgagtcg gataaattgg tggcgatggc ccaagggatt  1020
tatggcgaac tgggacgcaa gttgaccatc gaaggcagcg gcggcgcggc ggatgccagc  1080
ttgtccgccg gtgtaggcac gccgacgttg gatgggtttg gatagtgggg gggcaatatt  1140
cacacggcgg aggaatatgc cgaggtggag agtgttgcgc gcgggttta tttgttgagt   1200 cggatgatca tggagttgtc caagcgc                                       1227
```

<210> SEQ ID NO 63
<211> LENGTH: 1488
<212> TYPE: DNA
<213> ORGANISM: Pseudomonas fluorescens

<400> SEQUENCE: 63

```
atgagtgatc gcaaaaacag ccgcctgatc ctgcccggcc tgatcgccgt caccctgatg    60
gcggccagcg ccgtttactt cttgcgcccc agcgagtcgg tcgccagcca ggccctggac   120
aaggctcaaa cggccagcac cctgcaatcc ctggcggaac tggatggcaa ggcaccgacc   180
aaccgcaagc tcgacgtaca aacctggacc accgccgaag cgccaaggt gctgttcgtc    240 gaagcccatg agttgccgat gttcgacatg cgcctgctgt tcgccgccgg cagcagccag   300
gatggcgacg tgccaggcct ggcgctgatg accaacgcca tgctcaacga aggcgtgccg   360
ggcaaggacg tcagccagat cgccagtggc ttcgaaggcc tggggccga cttttggcaac  420 ggcgcctacc gcgacatggc gctggtgacc ctgcgcagcc tgagcgacag cgccaagcgc   480
gacgccgccc tgtcactgtt caaccaggtg atcggccagc cgactttccc ggcagactca   540
ctggcacgca tcaagaacca gatcctggcc ggtttcgagt accagaagca gaaccccggc   600
aaactggcga gcatcgaact gttcaagcgc ctgtacggcg accacccta cgcacacccg   660 agcgaaggca cccccgagag cgtgccgaag attaccctgg cgcagttgca ggcgttccac   720
gccaaggcct atgcagcggg taacgcggtg attgcagtgg tgggcgacct gacccgcgcc   780
gaagctgaag ccatgacggc caaggtgtcc gcgtcgctgc ccaaaggccc ggctatggcc   840
```

-continued

```
aagatcgccc agccgaccga gccaaaagcc ggcctgagcc gtatcgagtt cccgtccaag    900
caaacccacc tgctgtttgc gcagttgggc atcgaccgtg ccgacccgga ttacgcagcc    960
ttgtccctgg gtaaccagat cctcggcggc ggtggcttcg gcacccgctt gatgagcgaa   1020
gtgcgtgaaa agcgcggcct gacctacggc gtgtattccg gtttctcacc aatgcaggcg   1080
cgcggcccgt tcatgatcaa cctgcagacc cgcgccgaaa tgagcggtgg caccttgcgc   1140
ctggtggagg acgtactggc tgactacctc aagaccggcc cgacgcaaaa ggaactggat   1200
gacgccaagc gcgagctggc cggcagcttc ccgctgtcca ccgccagcaa cgccgatatc   1260
gtcgggcagt tgggcgccat gggtttctac aacctgccgc tgagctatct ggaagatttc   1320
atgaaacaat cccaggccct gaccgtcgat caggtcaagg ctgcaatgaa taaacacttg   1380
agcgccgaca gatggtcat cgtgaccgcc ggcccgacga ttgcgcaaaa gccactaccg   1440 cccccactg ataaacctgc cgagcagccg ctcggggttc cggagcat              1488
```

<210> SEQ ID NO 64
<211> LENGTH: 1353
<212> TYPE: DNA
<213> ORGANISM: Pseudomonas fluorescens

<400> SEQUENCE: 64

```
atgaatgctc tagcccgccg cgccgcaggc ctgctgttca gcacagtttg tctgcctctc     60
tcagctttgg ctgccgatcc acaacccacc catgaattca ccctcgataa cggcctcaag    120
gtggtcgtgc gcgaagatca tcgtgcgccg gtggtggttt cccaggtctg gtacaaggtt    180
ggctcaagct acgaaacccc gggccagacc ggtttgtccc acgccctgga acacatgatg    240
ttcaaaggca cgccaaggt tggccccggc gaagcctcgc tgatcctgcg cgacctgggc    300
gccgaagaaa atgcgttcac cagcgacgac tacaccgcgt actaccaggt attggcccgt    360
gaccgcctgg gcgtggcctt tgagctggaa gccgaccgca tggccagcct cgcctgccg    420 gccgacgagt tcagccgtga aatcgaggta atcaaggaag aacgccgcct cgcaccgac    480 gataacccca tgtccaaggc gttcgagcgc ttcaaggcca tggcgttccc ggccagtggc    540
taccacacgc cgaccattgg ctggatggcc gacctggacc gcatgaaggt cgaggaactg    600
cgccactggt accaatcctg gtacgtgccg aacaacgcca ccctggtggt ggtcggcgac    660
gtgaccccgg acgaggtgaa aaacctcgcc caacgttact tcgggccgat ccccaagcgt    720
gacgtgccac cggcaaaaat cccgatggaa ctggccgagc ccggcgagcg cctgctgacc    780
ctgcacgtgc agacccaact gccgagcgtg atcctgggct tcaacgtgcc cggcctggcc    840
accgccgaag acaaacgctc ggtacaggcc ctgcgcctga tctcggccct gctggacggc    900
ggctacagtg cacggatctc cgagcaactg gaacgcggtg aggagctggt gtccgccgct    960
tccaccaact acgacgccta caccgtggc gacagcctgt caccctctc ggccacgccg   1020 aaccagcaga agaagaaaac cgtcgcccaa gccgaagccg gctgtggcg cctgctcgat   1080 gagctgaagg ccaagccgcc gaccgccgaa gagctggagc gcatccgcgc caagtgatt   1140 gccggcctgg tgtaccagcg tgattccatc accagccagg ccacggccat ggctccctg   1200 gaaaccgtcg gcctgtcctg gaaactcatg gacaccgagc ttgccgacct gcaaagcgtg   1260
accccggaag acatccagaa ggctgcacgc acctatttca cccgcgaacg tctgagcgtc   1320
gcccatgttt tgcctgagga gaccgctcat gag                               1353
```

<210> SEQ ID NO 65
<211> LENGTH: 528

```
<212> TYPE: DNA
<213> ORGANISM: Pseudomonas fluorescens

<400> SEQUENCE: 65
ttgaccacca tcgtttcagt acgtcgccac ggcaaagttg tcatgggcgg cgacggccag    60
gtttccctgg gcaacaccgt gatgaaaggc aacgccaaga agtgcgccgc cctgtaccac   120
ggccaggtgc ttgccggctt cgcaggcgca accgccgacg cctttaccct gttcgagcgt   180
ttcgaaggcc agcttgagaa acaccagggc cacctggtgc gcgccgctgt ggaactagcc   240
aaagaatggc gcaccgaccg ctccctcagc cgcctggagg ccatgctcgc ggttgcgaac   300
aaagacgctt ccctgatcat cactggcaac ggcgacgtgt tgaacccga gcatggcctg   360 atcgccatgg gttccggcgg cggctacgcc caggctgcgg ccagcgcgct gttgaagaaa   420
accgacctgt cggcccgtga atcgtcgag accgccctgg gtatcgctgg cgatatctgc   480
gtgttcacca accacaacca gaccattgag gagcaggacc tcgccgag                528

<210> SEQ ID NO 66
<211> LENGTH: 636
<212> TYPE: DNA
<213> ORGANISM: Pseudomonas fluorescens

<400> SEQUENCE: 66
atgcgaccat ttttcaagac atggctaacc atttgcctat taatgccact ggccgcccac    60
gccaccaatc gtgagcaacg acttccgaac gttaacggtt tcaccccta agtccatagc   120 acgcccagca ctgccaaagc ggcaaagccg accgtcagcc gcccgactca actgagcaag   180
gcccacggca aagtgctttc cacccagctg gccgtgaaca ccaagcaaag cagcaacgtc   240
ttgagccgtg ccgtcaacgt gctcggtaca ccttatcgtt ggggcggcag cagcccaagt   300
aaagggttcg actgcagcgg gctggtgaaa tatgcattta acgatgtaaa agcggtggac   360
ctgccacgca cctccaacgc catggcggcc ggcatgggt tgaaggttga ccgcaaagac   420
ctgaagccgg gcgatctgtt gttcttcaag ttgaagagcc gccaggtgaa ccacgttgcc   480
atctacctgg gcaatgaccg ctttattcac gcaccgcgcc gtggcaagtc ggtgagcatc   540
gacacgctga aaaagccgtt ctgggacaag aactacgtga ttgccaagcg ggtactgcct   600
aaagagcaga acagcaacct gcggatcgtg cagcgc                             636

<210> SEQ ID NO 67
<211> LENGTH: 2040
<212> TYPE: DNA
<213> ORGANISM: Pseudomonas fluorescens

<400> SEQUENCE: 67
atgcctattt ccaccgcacc gattgcccgc aaggcccag gcccagaccc gtacgcctgg    60
ctgcaagaac gcgacaaccc tgaggtgctc gactacctca aggtcgaaaa cgcttggcag   120
gaagcgcaac tggccgatca gcaggcgttg cgcgagaccc tgttcgacga gatcaagggc   180
cgcattttgg aaaccgacct gtccctgccc tccccttggg gcccgtattt gtattacacc   240
cgcaccaccg ccggcgacga atacgcccgc cactaccgct gccgccgccc ggccgatgac   300
agcaaccacg tggacgccag cagcgaagaa ctgttgctgg accctaacgt actggccaat   360
ggcggctttt tctccctggg cgcattcagc atcagccccg accaccaacg cctggcctac   420
agcctcgaca ccagtggcga agagatttac accctgttcg tgaaggaatt ggcgtccgac   480
aaggtcagcg aactggcgtt cgacaactgc gacggcagca tgacctgggc caatgacagc   540
```

```
ctgacgctgt ttttcggtga gctggacgac acccatcgtc cgcacaaact gtatcgctat      600
cgcctggacg gcaccgccgc gcaggaagtc ttccacgagc ccgacggccg tttcttcctg      660
cattgctacc gctcaagctc cgaacgccaa ctgttgctgg ccctgggcag caagaccacc      720
agcgaagtct gggcgctgga cgccgagcaa ccgcacctgg ccttcgcctg cctggcgccg      780
cgggtcgaag accacgaata cgatgtcgac cacggcaagc gcaatggcca gtggacctgg      840
tttatccgca gcaaccgcga cggcatcaac catgcactgt acgtggccgc cgacaccggc      900
acgccgccca ccgaagccga ctggcagaac ctgatccccc acagcgatga ggtcatgctc      960
gacggcgtga gcctgaacgc caacgccatg accttgagcc tgcgcattgg tggcctgccg     1020
gttatcgaag tacaccccga gaacgtgccg gcctatcggg tgcaattgcc tgacgccgcc     1080
tacagccttt acgtgcagaa cagcctggag tttcccagcg acaagatccg cctgcgctat     1140
gaagccttga accgtcccgc ccaagtgcgc cagctcgacc tggcgacagg cgcgcaggtt     1200
gtgctcaagg aaaccccggt gctgggcgt ttcaacgccg atgattacgt cagccaacgc     1260
ctgtgggcca cgtccgccga cggcacccag gtgcccatca gcctggtggt caaacgtgac     1320
cagctcggca agccgacgcc gctgtacctg tatggctacg gggcctacgg ctcaagcctg     1380
gacccgtggt tttcccatgc gcgcctgagc ttgctcgacc gcggggtggc gtttgccatc     1440
gcccatgtgc gcggcggcgg tgagctgggg gaagcctggt atcgcaacgg caagcaggaa     1500
cacaagcaga ataccttcag cgactttatc gcctgcgccg agcatttgat cgcccagggc     1560
ctgaccacct cccggcaact ggcgatcagc ggcggcagtg ccggcggcct gttgatcggc     1620
gcggtgctca accagcgccc ggaattgttc caggcggcga ttgccgaagt accgttcgtc     1680
gacgtgctca acaccatgct cgacccggaa ctgccgctga ccatcaccga gtacgacgaa     1740
tggggcaacc ccgaagaccc cgaggtgtac gcgcgcatca aggcctacgc gccctacgag     1800
aacgtcagcg cccaggctta cccggccacg ctggtgatcg ccggctataa cgacagccgt     1860
gtgcaatatt gggaagccgc caagtgggtg gccaagctgc gtgataccaa gacggacgac     1920
aacctgctgc tgctcaagac cgaactgggc gccggccatg gcggcatgag cgggcgctat     1980
caggggctac gtgacgtcgc cctcgaatat gcctttgtgt tcaaggccct cggcctggtc     2040
```

<210> SEQ ID NO 68
<211> LENGTH: 1311
<212> TYPE: DNA
<213> ORGANISM: Pseudomonas fluorescens

<400> SEQUENCE: 68

```
atgcgcccga taactgcccc cgaactgctc gctcccgccg gcaccctgaa aaacatgcgc       60
tacgccttcg cctacggtgc cgacgcggtc tatgccggcc agccgcgcta cagcctgcgg      120
gtgcgcaata acgagttcga ccacgccaac ctggccctcg gcatccagga agcccatgac      180
cagggcaagc gctttacgt ggtggtgaac attgcgccgc acaacgccaa gctcaagacc      240
ttcctcaaag accttgcgcc cgtgatcgct atgggcccgg atgcgctgat catgtccgac      300
ccggggttga tcatgctggt gcgcgagcac ttcccgcaga tgccaatcca cctgtcggta      360
caggccaata cggtgaactg ggccagcgtg gcgttctggc agcaacaagg catttgcagg      420
gtgattctgt cgcgggagct gtccctggaa gagatcggcg aaatccgcca gcaggtgccg      480
gccatggagt tggaggtgtt tgtacatggc gccttgtgca tggcctattc cgggcggtgc      540
ctgctgtcgg gctatatgaa caagcgcgat gccaaccagg gcagttgcac caatgcctgc      600 cgctggaaaat accaggccac gccggcagtg gagaatgtca cggggggatat cgtccatgaa      660
```

```
tatcaaccca cattgggcat cggcgcgccc accgatcagg tgttcctgct acaagaggcc    720
aatcgccccg atgaccccat gcccgctttc gaagacgaac acggcaccta catcatgaac    780
gccaaggacc tgcgcgccgt gcagcatgtg gagcgcctgg cacagatggg cgtgcattcg    840
ttaaagatcg aaggccgcac caaatcgcac ttctactgcg cacgcaccac ccaggtgtat    900
cgccaggcca tcgatgacgc tgtggccggc cgtgcgtttg accgcggctt gatgaccaac    960
ctcgagtccc tggcccaacg tggctacaca gaaggtttcc tgcgccgcca cgtgcatgac   1020
gaataccaga actaccagaa cggcagctcg gtttccgagc ccagcagtt tgtcggggag    1080 ctgaccggcg agcgccgtgg tgcgttggcc gaggtgaagg tgaagaatcg ctttgcgctg   1140
ggcgaccacc tggagttgat gacgcccgcc ggcaactttc actttgactt gccgagcctg   1200
cataacgcca agggcgaagc catcgaggtg gcgccggggg acgggcatac ggtgtatgtg   1260
ccgattccgg cgcagatgga cctgcgtttt ggcttgctga tgcgcgacgt t            1311
```

<210> SEQ ID NO 69
<211> LENGTH: 627
<212> TYPE: DNA
<213> ORGANISM: Pseudomonas fluorescens

<400> SEQUENCE: 69

```
gtgcaaagcg tattgctgac gggcttcgag ccctttgata cgccccgat taacccctcg     60 tgggaggctg tgcgtcggtt ggatggcgtg cagttgagcg aaggtgtgca aattgttgcg    120
cgttgtttgc cctgcgcatt tgcctccgct gccgagacct tactgcaatt gatcaacgaa    180
ctgcagccgg caatggtcat cgccacgggc ttggggcctg ggcgcggtga tatttccatc    240
gagcgcgttg cgatcaacgt taacgatgcg cgtattcccg acaatctggg cgcgcagccg    300
attgatatcg cggtagtgga tggcggcccg gcggcgtatt tctcgacgtt gccgatcaag    360
ggcatggtca aggcggtgcg tgaggccggt attacgtcct cggtgtcgca gacggcgggg    420
acgtttgtgt gtaaccaggt gttttaccgc ttgcagcatg cgttggcggg gactggggtg    480
cgcagtgggt ttattcacgt tcccggcttg cctggatcgg gcgagccgtc gatggcgtta    540
tcgatgaccg tggaagggtt gcgtgtagcg gcgttggccg cctggcaaac ccaggcggat    600
atcgttctta ccggtggcca gatcagc                                       627
```

<210> SEQ ID NO 70
<211> LENGTH: 1722
<212> TYPE: DNA
<213> ORGANISM: Pseudomonas fluorescens

<400> SEQUENCE: 70

```
atgaaatacc aacccttgag tcacacgttg attgcgaccg cgctggtctt gacggtcaac     60
ggtgtgcacg cagcttccca agccccggtt gcgggtgaaa atggcatggt ggtcacggcc    120
cagcacctgg caaccacgt gggtgtcgat gtgctcaagg ccggcggcaa cgcggtcgat    180
gcggcggtgg cggtaggtta cgcgctggcg gtggtgtacc cggcggcggg caacctgggc    240
ggcggtggtt tcatgaccgt gcaactggcg gacgggcgca agaccttcct cgacttccgc    300
gaaaaagccc cgttggcggc aacggccgac atgtacctcg acaaggccgg caatgtggtc    360
gaaggcctca gcgccaaagg ccatttggcg gtcggcgtac cgggcacggt gtctggcatg    420
gagctggccc tgagcaagta cggcaccctc aagcgcgcgc aagtgattgc cccggcgatc    480
aagttggccg aaaacggctt tgcgctggag cagggcgata tcgacctgtt gcacactgcc    540
```

```
accggtgagt cgaaaaaga ccaggacatg cgcgggatct tcctgcacaa cggaaaaccg    600
atgcaggtgg gtcagaagct ggtgcagaag gacctggcca agaccctcaa ggaaatctcg    660
gccaagggca ccgacggttt ctataaaggc tgggttgcca aggcggtggt ggattccagc    720
caggccggca aggcatcat cacccaggcc gacctgacg cctacaaaac ccgcgaactg    780
gcccccatcg agtgcgacta ccgtggctac catgtggtct cggcaccgcc acccagctcg    840
ggcggtgtag tgatctgcca gatcatgaac atcctgaag gctacccgat ggccgatctg    900
ggctatcact cggcccaggg cctgcactac cagatcgaag cgatgcgcca tgcctacgtg    960
gaccgcaaca gctacctggg tgatccggac ttcgtgaaga cccccatcga gcatctgctg   1020
gacaagaact acgcggccaa gctacgcgct gccatcgagc cgcagaaggc cggtgactcc   1080
caggcgatca gccaggtgt gtcgccccac gaaggcaata acaccaccca ctattccatc   1140
gtcgacaagt ggggcaacgc ggtctcggtg acctataccc tcaatgactg gtttggcgcc   1200
gggtgatgg ccagcaagac cggggtgatt ctcaacgatg aaatggatga cttcaccgtc   1260
aaggtcggcg tgccgaatat gtatgggctg gtgcagggcg aagccaacgc catcgcaccg   1320
ggcaaggcgc cgttgtcatc gatgagcccg accatcgtca ccaaggacgg taaggcagta   1380
atggtcgttg gcacaccggg gggcagccgc attatcaccg cgaccttgct gaccatcctg   1440
aatgtcatcg actacaagat gaacatccag gaagccgtgg acgcaccgcg cttccaccag   1500
caatggatgc cggaaaccac caaccttgag acctttgcgg tcagcccgga cacccagaag   1560
atcctcgaaa gctggggcca aagtttgcc ggcccgcaag atgccaacca cctggccgcc   1620
atcctggtag gcgcgccttc cctggacggc aagccggtgg gtaacaaccg tttctatggg   1680
gccaatgacc cgcggcgcaa cacgggcttg tcgttgggct ac                      1722

<210> SEQ ID NO 71
<211> LENGTH: 579
<212> TYPE: DNA
<213> ORGANISM: Pseudomonas fluorescens

<400> SEQUENCE: 71
atgtctttta cgctcaccgg cttttgcgag tttcgtgaag aaatacgcaa aagtcgcttt     60
atcaccttgg cggcgccgat taccagcccg caggacgccc aagcgttttt cgagcagcac    120
agcgacctca cgccacaca caactgctgg gcctggaagc tgggcgatca ataccgcagc    180
agcgatgacg gcgaacccgg aggcaccgcc gggcgcccga ttcttgcggc catcgaggcc    240
cagggctttg atcaggtggc cgtcttggtg atccgctggt acggcggcat tcaactgggc    300
acgggtggat tggcccgggc ctatggcggc ggggccaata aatgcctgca gaatgccgaa    360
cgcatcgagc tgatcagccg cgtccccctg cgttgcgcct gcgggttctc cgaactgaac    420
ctggtgaagc tgcgtgtcgc tgaactcggc gggcttttgg tggaagaaac cttcaccgcc    480
aacggcgtag agctgcagct cgccctgggg gaggcgcaca tcgacaccct gcaaacccag    540
ctcgccgacc tgagccgtgg gcgcatcctg ctcgaacgc                           579

<210> SEQ ID NO 72
<211> LENGTH: 975
<212> TYPE: DNA
<213> ORGANISM: Pseudomonas fluorescens

<400> SEQUENCE: 72
atgagcccag ccgagttgca cgccgacagc atcgttatcg acggtctgat tattgccaag     60
tggaaccgcg acctgttcga agacatgcgc aaaggtggcc tcaccgccgc caattgcacg    120
```

```
gtgtcggtgt gggaaggctt ccaggccacg atcaataaca tcgttgccag ccagaccctg      180
atccgcgaaa acagcgacct ggtgatcccg gtgaaaacca ccgccgacat ccgccgcgcc      240
aaggagctgg gcaagactgg catcatcttc ggcttccaga atgcccatgc ctttgaggac      300
cagctcggct atgtcgagat cttcaagcag ctcggcgtgg gcgtggtgca gatgtgctac      360
aacacccaga acctggtggg caccggttgc tacgagcgcg atggcggcct gtcgggtttc      420
gggcgtgaga tcgtcggcga gatgaaccgc gtcggcatca tgtgcgacct gtcccacgtg      480
ggctccaaga ccagcgaaga ggtcatcctc gaatcgaaaa agccggtgtg ctactcccac      540
tgtctgccgt ccgggcttaa agagcacccg cgcaacaagt ccgatgaaga gctgaagttc      600
atcgccgacc atggcggatt tgtcggtgtg accatgttcg cgccgttttt ggccaagggc      660
atcgactcga ctatcgacga ctatgccgaa gccatcgaat acaccatgaa catcgtcggc      720
gaagacgcca tcggcatcgg caccgacttc acccagggcc atggccagga tttcttcgaa      780
atgctcaccc atgacaaggg ctacgcccgc cgcctgacca gcttcggcaa gatcatcaac      840
ccgctgggca tccgcaccgt gggtgagttc cccaacctca ccgagaccct gctcaagcgc      900
ggccacagcg agcgcgtggt gcgcaagatc atgggcgaga actgggtcaa cgtgctcaag      960
gacgtctggg gcgaa                                                      975

<210> SEQ ID NO 73
<211> LENGTH: 1353
<212> TYPE: DNA
<213> ORGANISM: Pseudomonas fluorescens

<400> SEQUENCE: 73
atggcaatga caaaatcacg ttcgaaaaag gcgctgtata tcggcctgcc gctggccctg       60
gctatcggcg ccggggcggg ctttctggtc tgggatcagt ggttcaaggg caacgccggc      120
tacccgctgg aggtgatcaa gcaggccaat gaaatgcagg atcgcctgtt gtcattcgac      180
agccacatca ccctgcccct ggatttcggc acggcgggca acgaggccga caaggatggc      240
agcggccagt tcgacctggc caaggccgcc cgcgggcgat tgtcgggcgc cgcgctgacg      300
atattcggct ggccggaaat ctggaacggc gccaacgccc cgcacaagcc caccgacggt      360
tttgtcgagg aggcccgcca cgagcaggag gtgcgctata agatcatctc cggcatggtg      420
cgcgactttc ccaaccaggt gggcatcgcc tacaccccgg acgatatgcg acgcctacac      480
ggcgaaggca agttcgcgat ttttatcagc atgctcaacg cctacccccct gggcaatgac      540 ctgaaccagc tggacctgtg gccgcacgc ggcatgcgca tgttcgggtt cagctacatc      600
ggcaataacg cctggtccga ctcgtcgcgc ccgctgccgt ttttcaatga ctcccccgac      660
gcccttgaag gctgtcgcc gatcggccag caagcggtgc atcgcctcaa tgacctgggg      720
gtgatcatcg acgtgtcgca gatgtcgacc aaggccctgg aacaagtcgc gcagttgagc      780
cgtacgccga tggtggcgtc ccactcggcg ccacgggcat cggtgacat cccgcgcaac      840 ctcagtgaca aggaactgca actgatcaag aacagcggcg gcgtggtgca agtggtgggc      900
ttccccgcct acctgcggcc cttgagccag ccgacccagg acaagctcaa cgccctgcgc      960
gcacgcttcg acctgccgcc actgcccaat ctggccatgg ctctgatgcc cggcgacgcg     1020
atcattgccg cctggcccga gcaacgcttc ggccagtacg ccagcgcgct gtacggcatc     1080
ctcgaggaag aacccaaggc caccctcaag gacctgggcg acgccatcga ctacaccgtg     1140
cgcaagatcg gcatcgatca tgtcggtatt gcctcggact tcaacgacgg cggcggcctc     1200
```

| | |
|---|---|
| cagggctggg agaacgtcgg cgaagtgcgc aacgtcaccg ccgaactgat ccagcgcggc | 1260 |
| tactccgaag ccgatatcgc caaactgtgg ggaggcaact tcctgcgggt gtgggagcag | 1320 |
| gtacaaaaat ccgccaagcc attggccaat cgc | 1353 |

<210> SEQ ID NO 74
<211> LENGTH: 2064
<212> TYPE: DNA
<213> ORGANISM: Pseudomonas fluorescens

<400> SEQUENCE: 74

| | |
|---|---|
| atgtcagcca ttacaaatta tcatccctcg tacgtaaaac ctcaaactta cccgctctcg | 60 |
| gccgacgccc caacagccga tccacttgca ccttcgttat cggacaaggt tgcacgagac | 120 |
| cttactcgcg acaatttgaa attaaaagat aaaaatggcg acggcaaact aacagtttca | 180 |
| tataaatttt tagaccaggg cgcaggtgag ttcagccagg ccagaaagaa agcgttcaag | 240 |
| agcgccatca aggcttggga agacgtggtc aaagtcaagt tcaccgaaaa cgccaaggag | 300 |
| gctgatgcgt tttttgtact tcatgccaat ccgggcgttg gtggatatgc cgtcatgcca | 360 |
| aatgaccaag gaactgcaag cattggcatc ggcgtcggcg ataagaactc gcccctgcac | 420 |
| tctgccatga tccatgagct tggtcatagt ttgggattag accatccaac cggagattac | 480 |
| ccagaaaaca accatactca tactgccatg agttacagta caaatggtg gctacccaca | 540 |
| gacaatccta ggcttcgtat ttcggactat aacttgactc cagcaatgca cgacatcgca | 600 |
| ggcattcatc gcttatacga acccaattat gaaacccgaa agataatac aacctacggc | 660 |
| tttaactcca cactgagcg cgatcattat acgttgacct ccgccgacga cctgaccaac | 720 |
| ttttgtgtct gggacaacgg cggcgaagac acgttggact tttccggctt caagcagaac | 780 |
| caaaagataa acctggccgc cgagacactc tcggatgtgg gcggccgcgt gggcaacgtg | 840 |
| tccatcgcca agggcgttgt gatggagaac gccatcggtg gctcagggca tgacgtactg | 900 |
| atcggcaatc acgtcaataa cagactaacc ggcggagccg tcgcgacaa actgataggc | 960 |
| ggcggtggtg ctgataccct tgtttataac aaagccagcg actccacccc tgggaatccg | 1020 |
| gacatacttg aagactttac cagcggcgtc gacaagatcg acctgtccag ggtgctcaac | 1080 |
| gacgccggca ttgaaaagcc ggagctggtt agcgtactca ccggtcgcaa aggcgagctg | 1140 |
| acgctcagct acgatgaaaa tgccaagatg cacaaactgg ttctgaatgt gagcggcaaa | 1200 |
| cctgactctg cactactgat tctgagcaaa ggacctatag cgctggacga catcctggcc | 1260 |
| cacgcggatt caaagcccga gcctgggccc gagccagaac ctgagccagc ccccaaaccc | 1320 |
| aggcctgaac cagaaccgaa gcccaggccc aagcgtgaac ccaagcccaa gcagaaccca | 1380 |
| gagcccaggc ccacccccagt atcatgcccc cgacccgaca cgcgcgacac ggtctatggt | 1440 |
| ttcaatgcaa ataccggacg ccccagtaca accctcacct ctgcctgcga caaaccttat | 1500 |
| ttcagcgtgg acgacagaaa aggcaacgac accgtggact tctctggttt ctatcaagac | 1560 |
| caacagattg atctgacacc cggtactcgc tccagcgtag gtgggctacg cgacaatgtg | 1620 |
| tttattacgc aaacaaccgt catcgaaaac gccataggtg gcaagggtaa cgaccgtatc | 1680 |
| agcggaaata gcgccgataa catcctgatc ggtggtgcag gcgcggacca tctgaccggc | 1740 |
| aatggaggct ttaatacctt cagctaccat tttgcctgcg attctccacg caacaacgcg | 1800 |
| gacaccctct tggacttcac cacgggcaaa gacaagattg atttgagaaa aatgagcgaa | 1860 |
| aatgcccaag tcaaactcaa ctatgtcaac cagtaccgca accagcccgg cgacacgatc | 1920 |
| atcgtgcaca acccattcac cggcaggtac ttcctgggcg ttgacctgac gggcgatggc | 1980 |

```
aagaccgatt ttctgatcaa gagtacccgc cccatcagca acgaagacgt gatcggactg   2040
aacatccagg atgacggtta cctg                                          2064
```

<210> SEQ ID NO 75
<211> LENGTH: 1320
<212> TYPE: DNA
<213> ORGANISM: Pseudomonas fluorescens

<400> SEQUENCE: 75

```
atgatccata tccccaaagc ggaatacacc cggcgccgca aggcgctcat ggcgcagatg     60
gaacccaaca gcatcgcgat cctgccggcc gccgccgtgg ccatccgcaa ccgtgatgtc    120
gagcatgttt accgccagga cagcgatttc caatacctga gcggtttccc cgagcccgaa    180
gcggtgatcg tgctgatgcc cggtcgccag cacggcgagt acgtgctgtt ctgccgcgag    240
cgcaatgccg agcgcgaatt gtgggacggc ctgcgtgccg gcaccgaggg cgcgattcgc    300
gactttggcg ctgacgacgc attccccatt accgatatcg cgacatcct gcccggcctg     360 atcgaaggtc gcgaccgcgt gtactcggcc atgggcagca atgccgagtt cgaccggcat    420
gtgatggagt ggatcaacgt gatccgttcc aaagcgcacc tgggcgccca gccgccgaac    480
gaattcgttg ccctggatca tttgcttcac gatatgcgcc tgtataaatc ggcggcagaa    540
gtgagggtga tgcgcgaggc ggcgcgaata tcctgtgcag cccatgtacg ggcgatgcag    600
gccagccgtg ccggcctgca tgagttcagc ctggaagccg agctggatta cgagtttcgc    660
aaaggcggtg cgaaaatgcc ggcctatggc tccatcgtcg ccgctgggcg caacagctgc    720
atcctgcatt accagcagaa tgacgcggtg ctcaaagacg gcgacctggt gctgatcgat    780
gctgggtgcg agatcgattg ctacgccagc gacatcaccc gtacctggcc ggtcaatggc    840
aagttctcgc ccgagcagaa ggcgatctac gagattgtgc tggcctccca ggaagccgcc    900
ttcaagcaga tcgcgccgaa caaacattgg aaccaggccc acgaggcgac cgtgcaggtc    960
atcaccgccg gcttggtaaa gctggggttg ttgcaaggtg acgttgacga actgatcgcc   1020
agcgaagcct accgcgcctt ctacatgcac cgtgccggcc actggctggg catggatgtg   1080
catgatgtgg gcgagtacaa agtgggcggt gaatggcgcg tgctggaagt gggcatggcc   1140
ttgaccgtgg agccgggcat ctatatttcc ccggacaacc agaacgtggc aaagaaatgg   1200
cgtggcattg gcgtgcgcat cgaggacgac gtggtagtga ccaagcaagg ctgtgaaatc   1260
ctgaccggcg gcgtgcccaa gaccgttgcc gagatcgaag cgttgatggc ggctgcccga   1320
```

<210> SEQ ID NO 76
<211> LENGTH: 684
<212> TYPE: DNA
<213> ORGANISM: Pseudomonas fluorescens

<400> SEQUENCE: 76

```
atgagcaccc tgctggccct ggacaccgcg actgaagctt gctccgttgc cttgctgcac     60
gatggcaagg tcacgagcca ctacgaggtg atcccgcgcc tgcacgcgca gaaattgttg    120
ccgatgatca agcaactgct tgaagacgcc ggtaccaccc tggcggcggt ggatgccatc    180
gcgtttggcc gtgccccgg tgcattcact ggcgtgcgca tcgccattgg cgtggtgcag    240
ggcctggctt ttgccctgga gcgtccggtg ttgccagtgt ccaaccttgc ggtactggcc    300
cagcgcgcgt tgcgtgagca cggggcgtcg caggtgcag cggcgattga tgcacgcatg    360
gatgaagtct actggggttg ctaccgtgag atcgcaggcg aaatgcgcct ggtcggtgcc    420
```

```
gaagcggtgc tggcccccga agcggcgcag ttgcccgctg atgccagcgg cgattggttc      480
ggtgccggca cgggctgggg ttatggcgaa cgcatcaaga tgacgtgtac gcagcaggac      540
gcggcgatgt tgccccacgc tgaagacctg ctggcgttgg cgcgtttcgc attcgagcgc      600
ggcgaagcga ttgcggcgga ccaggcagca ccggtgtatc tgcgcgataa agtcgcacaa      660
accaaggccg agcgcgggat tatt                                             684

<210> SEQ ID NO 77
<211> LENGTH: 588
<212> TYPE: DNA
<213> ORGANISM: Pseudomonas fluorescens

<400> SEQUENCE: 77
atgagtctgg cgctattccc cctcaacact gtgctgttcc caggctgcac cctcgacctg       60
cagatattcg aggcgcgcta cctggacatg atcggccgtt gcatgaaaaa gggcgaaggc      120
tttggtgtgg tgtgcatcct ggatggctca gaggtgggcg cggcccctga cggttatgcg      180
cttgtcggtt gtgaagcgct gattcgtgac ttcaaacagc aggagaacgg cctgctgggc      240
attcgcgtcg aaggtggccg tcgtttccgc gtgcgtgaag ctggcgtgca aaaagaccag      300
ttgctggtgg ccgacgtgca atggctgcaa gagttgccgg accagccgct gggcgaagaa      360
gacgccgact tgctggcgtt gcttgaggcc ctggccgagc acccgatggt ggcttcgctg      420
gacatgggcg gtgacgtcga aggccagcaa gccctgggca accggttggc ctatctgctg      480
ccgtttaccg aggccgacaa aatcgacttg ctgcaactgg acgacccaca gcaacggctg      540
gatgcgatcc agatgttgct cgatgaactg cagggcgagc tgttcacc                   588

<210> SEQ ID NO 78
<211> LENGTH: 768
<212> TYPE: DNA
<213> ORGANISM: Pseudomonas fluorescens

<400> SEQUENCE: 78
atgatcaaga cccccgcaca gttggccgta atgcgtgaag ccgggcgcct gttggcgcag       60
gtcttcgaca tgctcgacgg cttcgtcgcc gccggccgct ctaccctgga gctggacagc      120
gccgtcgaag ccttcatccg caatgacctc aaggcccgcc ctgccagcct ggggcagtac      180
gactacccct tctgcatcaa cacctcgatc aacgaagtgg tgtgccacgg catgcccagc      240
gccaagcaat tgctcaagga cggcgacatc atcaacatcg acatcaccct ggaaaaaggc      300
ggcttcattg ccgactccag caagatgtac atgatcggca acgtgacgcc caaggccagg      360
cgcctggtgg acatgacctt cgaggcgatg tgggccggta tccgccaggt caagcccggc      420
gcgcgcctgg gcgatatcgg ccatgcgatc cagagccacg cgcaagccaa tggctacagc      480
gtggtgcgcg aatactgcgg ccacggcatc ggccggcaaa tgcacgaaga accgcaaatc      540
ctgcacttcg gccgcccggg caccggcctg gaactgcgcg aaggcatggt gtttaccatc      600
gagccgatgc tcaaccaggg cagcgccaaa acccgcagcc tgaaagacgg ttggacggtg      660
gtcaccaagg acaacagcct ctcggcgcaa tgggaacata ccgtggcggt gacggcggat      720
gggtttgaag tgctgacctt gcaaaccccct caaaaccttc acaccctg                  768

<210> SEQ ID NO 79
<211> LENGTH: 606
<212> TYPE: DNA
<213> ORGANISM: Pseudomonas fluorescens

<400> SEQUENCE: 79
```

```
atgctaaaac tgacgccacg ccaagctgag attctggctt ttatcaagcg ctgccttgat    60
gacaatggtt acccgcctac ccgtgcggag attgccctgg agctggggtt caaatccccg   120
aacgccgccg aggaacacct caaggccctc gctcgcaaag gtgcgatcga gatgacccca   180
ggtgcttcgc ggggtattcg tatccctggc ttcgaagcca aggccgacga gtcgacattg   240
ccgatcatcg gccgcgtcgc cgcaggtgcg ccgatcctgg cgcagcagca cgtcgaggaa   300
tcctgcaaca tcaacccgac cttcttccat ccccgcgccg actacctgtt gcgcgttcac   360
ggcatgagca tgaaggacgt gggcatcttt gacggtgacc tgctggcggt ccataccacc   420
cgcgaagctc gcaatggcca gatcgtcgtg gcccgtatcg cgacgaggt cacggtcaaa    480 cgcttcaaac gcgaaggcag caaggtctgg ctcctggccg aaaaccctga gtttgccccg   540
atcgaagtca acctgaaaga ccaggacctg gtgatcgaag gcttgagtgt cggcgtcatt   600
cgccgc                                                               606

<210> SEQ ID NO 80
<211> LENGTH: 2373
<212> TYPE: DNA
<213> ORGANISM: Pseudomonas fluorescens

<400> SEQUENCE: 80
atgcctgcgc cggttcaccc tcatcccgtt cacctgaccc tcgccaatgg cctgcgggtt    60
tgcctgcgcc atgcgccgcg cttgaagcgc tgcgccgccg ttttacaggt ggctgccggc   120
agccatgacg tgccattggc ctggcctggg ctggcgcatt ttcttgagca cttgctgttt   180
ctcggtaccg agcgctttcc agccggcgaa gggctgatgg cctacgtgca acgacacggt   240
gggcaggtca atgccagcac ccgtgagcgc accaccgagt ttttctttga actgccggtg   300
ccggttttta cagacgggct gatgcggttg gcggatatgc tgactcaccc acgcctggcc   360
ctcgacgatc aacagcgtga gcgcgaagtg ctcgacgcgg agttcatcgc ctggtcccag   420
gatgccaagg cccaacaaca gtggcgctg ctgcaaggct tggcagcaga tcatccgttg    480
cgcggttttc atgccggcaa ccgcgacagc ctgccggtgg aaagcgaggc ctttcagcaa   540
gccttgcgcg ggttccacgc acactttat caaagcgggc agatgacttt gagccttgcc    600
ggcccacaat cgctgaccga cctgcaggcc atgcccagc agttcagtga ccaactgaca    660
cccgggccat tgcaccccgca ggccgctcca ccggccttga tgcaaggctc cgcacgctgc   720
tatcaacacg ccgccgatcg ccacctgcat caggtcatta cctgtgacgc accacgggaa   780
gcgttggcgt ttctctgcac ctggctcaac gcctcggccc ccggcggggt gctcgccgaa   840
ctgcaagctc gacgactggc caccgcgctg caggcgtccg tgctgtacca gtttgcggat   900
caagccgtgc tggatatcca cttcactctc ggcagcgagc gcgaaccggc cacgcagatc   960
gaagagttac tgcacgactg gctgagcttc ttcgcacaca gcgactggac agcgttacgc  1020
gaagaattcg ccttgctcaa tgctcgccag caacaggtcc aaggcgccct ggccttggcg  1080
cgcaacgacg cccacgatct gtcggaacaa ggcgccgctg ccctcaaggc catgctcgat  1140
tcactgcacc tgcccgcctc ccggcacccct tggcaactgc cgcctaacaa tcctttgctt  1200
cgtgcgcccg ccaaggaaga acgcgccggc ctgattcgcg ccaaaccag cgcccatcgt   1260 ggcttgcgta cctttgccca ggatcgctca cggggccgac gggagctgtc ggcgctgacc  1320
ttcagccagg cgttggcgga tgacacgggc gaaggtgcgc tgtacctgca ctggcggttt  1380
gactcggcgg tacccaccgg gctggaaagc ctgttgcggc cgttgtgcga acaggcacgg  1440
```

```
caggcgggcg tcgagttgtc ttgcgaaacg atcgccactg actggcaggt aaagatgcac    1500
ggcctccacg agcccatgcc ggcggtgctc gaagcgttgg cgcggtgtct gagtgactcg    1560
aatggacctt tgccaccgcc cgctcccgtg ccgatgatcg ccatccggga actgctcaag    1620
gcgttgcctg cttgctgtgc cggtgttcaa cccgagcctc aggggacgac agcgtcctgg    1680
gccacagcac gctggcaggg gctggtcaca ggcttgcccg ccagctgtga agcggcgatc    1740
aaagccgcag cggcccggtt gcctgggcaa ccggcaactc tgcctttcac acctcaggcc    1800
cttgacgggc aaaagcgctg gcacgcagtc aacaccgaat ccagcgaggc ggcgctactg    1860
ctattttgcc caacgcctgt gcaaaccctc gccgatgaag ccaactggcg gttactcggg    1920
cacgtgctgc aagggccgtt ctaccagcgc ttgagagtcg aactgcaaat cggctacgcc    1980
gtgttcagtg gcatccgaca aatcaacggc caaaccggcc tgctgtttgg ggtgcaatcg    2040
cccagcactt ctctggacgg catcgtcgaa cagttgcagg ccttcctcga caactgccg     2100
tcgttgatcg agcgctgccc cgacttgggt aaccaggccc ttgcgcagca gttcgcggcc    2160
caggcgctac ccgtcaacca ggctgccgag ttgctctggc atgcgcactt ggcaggtcat    2220
tcgtcgggtt atctggatca gcttcaacag ttgattcaac agcgcacacg cgaggatgtg    2280
cagcacgccg cgcagcaact caatgacgcc gcaggcggct ggcaatgcgt ggccaacggg    2340
cggtgtatca acgacgactg gcaagcgacg tcg                                2373

<210> SEQ ID NO 81
<211> LENGTH: 2007
<212> TYPE: DNA
<213> ORGANISM: Pseudomonas fluorescens

<400> SEQUENCE: 81
atgaggcgcg cattgtgcaa agggtctggg cttgaacgtc cccctcacct caaggaagac      60
cttgtgataa agcctctagc cctcgccatc agcgttgccg gtgccctgtt gcccacccat     120
agccaggcgt acgattacgg ccagcacgcc aacaccaccc tggaaaagct gatcaacgat     180
taccctggcc gttatcgcgg cacggccaat tttgccgggg cagccgactg gatgcagagc     240
cagatgggca cggcctataa catcagccgc caggatttca cctggaacaa cggcagccgg     300
gcttcgcaaa acgtggtggc ctctgccgct ggcaccaagg cccagtacgt ggtgattggc     360
gcgcatttcg atacctactt cggccgcccc accctacaag gcctggatga caacggttcc     420
ggcgccagcg tgttgactga ggtggcgaag aacctcggcg gcctgtcact ggaaaatggc     480
ctgcaaatcg ttggcttcgg cgccgaagaa gaaggcctgc gtggctcgcg ggccttttgtc    540
gactcactca gcgccagcca gcgcgccaac atgctcgcga tgatcaacct cgacagcctg     600
atcaccggtg acatgatgta tgcccacgcc ggccagaaca gcaccgctaa cccggcgttg     660
gcctccttgc gtgagcacac cttccagatc gccagggaac tgaacatccc cttgttcagc     720
aaccccggcc tggacccgca gtacccaaag ggcaccggct gctgcagcga tggtgaagcg     780
ttcgaaccgc tgaatatccc cgatcctttat atagaggcca ccaactggga actgggcgac    840
ctggacggtt acacccagac cgacaacccg aaaatccccg gcggctcgac ctggcacgac     900
cccaccgaag acaacaaagc cgtgctgacc gatgcattcg ccaggcgcg catcgaccag      960
cgcctgcgtg actattcacg cctgctcagc cgcctggtgc tggaactgac caacgccgac    1020
ctgatggcct cgaccgcttc cggcggtgcc gttgcgcgca atatgcaaga caacctgcaa    1080
cgccagcatc aggccctggt acgcctgcat gatcgccgct ggctgaccct gcaagcggcc    1140
agccgcgagg tgggcagctt tgatggcgag atcggcgtgg atggcgaata caacccggac    1200
```

```
agcggcttcg acagcgcccc aaccccgaa gcccggcgct tgggcctgca tgccctcggc      1260
gactaccaac tgacttcaag cctgaatatg ggcgccagcc tcagctacct caatgggcgc      1320
gacaaactgg agcatcgcgg caagctcgac agcgacacct ggcaggcagc cgtctatgca      1380
ctgctcaacg atggtgggcc aagctggctg gccggtgacc tgagcgtggg ccacacgcgc      1440
ttcgattcca agcgcaacct ggtcatccag gccaatggcg ggccgatcct gctcaaccag      1500
caactgacgg cgacaccga tgccctggcg ctgggcgcac gggtgctggg tggctatgac      1560
tttgactttg gcgcgatcaa gagcgggccg ttcgccggcc tggactacag ccattaccgc      1620
atcgacaagt tccacgaaaa gcagaacctg cgcacggccc tggaatacga agagcagtct      1680
ttcgactccc tggaagccag cctcggctgg gcgtgcgcg gcgctgttgc cctgccctat       1740
ggcctgaacc tgatgcccta cggcgacatc gcctgggtca aggaattggc cgacggccgc      1800
ctggacgacc tgcaactcac cgcgcacgcc gatggccagg cccgcaacgc caggctgggc      1860
tcagtggata gagctttgc tcgtgcacaa ctcggcagcc aactggcgat caccccacag       1920
ttgggcgtgt tgccgaggt caatggccgc ctcgggcatg ctgaaggcag ccagaccggt       1980
tattcgctgg gtgtgcagtg gatgttc                                         2007

<210> SEQ ID NO 82
<211> LENGTH: 1380
<212> TYPE: DNA
<213> ORGANISM: Pseudomonas fluorescens

<400> SEQUENCE: 82
atgcgtcgcc tgttactcgc ctgcctgctc ttgggctcgg cacacgcctt tgcctttgac      60
cgtctgcaag tcgagggcta caccttgccc aacggcctgc aactgctgct caaaccgggc      120
accgagcgtg ggcatgtcgc tattcgcctg gtggttggtg tgggcctgga cgacttcggt      180
tgcgaagaaa aagaactgcc gcacttgttc gagcacttgc tgttcagcgg catcgacggc      240
ggcggcgagg gcgacctcga agaccgcatg caagccctgg gcggcgagtg gaacgcctac      300
accagcaacg ccgataccac cttcgtgatc gaggcgcccg cgcagaacca acgcaaggtg      360
ctggacctgc tgctggcaat cctcacgcgc acgaactga ccgacgccca tatcaacgcc       420
gccaaacagg tggtggagcg cgaagacggc ggccattact cacacttgca acgcctgctg      480
gaccgccagg acctcggtca gcgccagc aaccaattgg ccgtggagtt gggcctcaag       540
tgcgccgaac gcgccgaggt cagccacctc acccgcgatc agttggagaa gctgcgcaac      600
gaatggtacg cgccgaacaa catgaccctg atcgtcgtcg gcgatctcga caaactgctg      660
cctgcctacc tggaacgcac ctatggtcaa ctcgaccccg tggagccgag cgaacatcgc      720
ccgcttccgg aaatccagca caccgccgcc agccaccgcg acctgatccg cggctgggtg      780
ggcgatggcg ccaagctgca ctggctgttc cccgagccgg tgttggatga ccagcatgat      840
gaaacctaca acctgctcaa ggattacctc gactgggcac tgtaccggca actgcgcctc      900
aagcacggtt tgtcctacgg cccctgggta gaacgcgaag tgctcggcgg cgttggattc      960
ctcagcttga atgccgacct tgagcgagaa aacctccctg aagctgagca ggtcttgcaa      1020
gacctcaagg cccaactgct caaggacggc ctcgacccaa cagtattcac acgcctgcag      1080
caagccgcca ttgcccggca ggcttgggcg gtgcagggca acagcgcgct ggccgactat      1140
tattggagtg cggccggcga ctacagcaac gggcgtttca gcgatccggt caaacgcatc      1200
aaggctgtaa gcctggcgca aaccaaccag gccatgcgcg aagcgttcca gcagccgggc      1260
```

```
tactggcgca tcgaaaaacc gctgttgagt tatgacgcgt tgacctggat cggtgcgggc   1320
gtgctgggcc tgatcatcct tggtttgatc ggcttgaggc tttatcgcaa acctgttgag   1380
```

<210> SEQ ID NO 83
<211> LENGTH: 819
<212> TYPE: DNA
<213> ORGANISM: Pseudomonas fluorescens

<400> SEQUENCE: 83

```
atgccacgcc tactgagcct gttgatgctg ttgtgcctca cgtttaacgc ccacgccgac    60
agctacatca cgcgaaccct gaacaaaccc gtgcctggcg gcgtggccgt cgtcgaacta   120
ggcccttcgg ccacagcgcc gaaagccacc taccagggca agccggtgct ggtggtcaag   180
gagcaggaca actggctggc gattgtcggc atcccgttga cggtcaagcc tgcaacgag    240 cgcatcagca gcggggggcg caacctgccg tttatcgtcg gctacaagaa gtatccggaa   300
caacgcatca ccttgaagaa caaaagccag gtcaaccccg accggcccca gctcaagcgc   360
atcgaaggcg aattggcagt gcagctcaag gcttaccgca gcttcagccc gaatttgccg   420
agcaatctgg tgctggataa accggtgaac gggccgctgt cgagcaagtt cggggtgcga   480
cgcttcttca acggcgaaga gcgcaacccg cactcgggcc tggacttcgc cgtaccggcc   540
ggcacaccga tcaagacacc cgccaatggc aaggtgattc tggtcggcaa ttacttcttc   600
aacggcaata ccgtgtttgt cgaccatggc caggggttta tcagcatgtt ctgccatatg   660
tcgaagatcg atgtgagggt gggtcagcaa ctggtgcgcg gtgcggtagt cggcaaagta   720
ggctcgacag gccgggccac tgggccgcat atgcactgga acgtcagcct gaacgatgca   780
cgggtagatc cggcgatttt tatcggcgcg tttcaaccc                          819
```

<210> SEQ ID NO 84
<211> LENGTH: 789
<212> TYPE: DNA
<213> ORGANISM: Pseudomonas fluorescens

<400> SEQUENCE: 84

```
atgattgctt tgccctggct gtacctcacc ctactttcca ttggctatgt cgtggccttg    60
atctacggcc aactgggcgt actggcggcg gtctccatcg cactgctgct ggtggccggg   120
tacgccgtgc gccagcaacg caaccccttgg gcgcgctacc tgggtcacgg cttgtttatt   180
gtcctggccc tgggcctggc gatgcactgg ctgccgggtt tctataacgg ccgcggtatt   240
gcgccccagc gttttactcc ggactcagtg cccttctcga tgtacctgaa ccaggacaaa   300 ccctgatcg gcttctggct gttgctggcc tgcccatgga ttgtggcgcg acgctcattg   360
cgcctgtcga tctgcgtcac ggccgtggcc ctgaccctgg ccgccatcgc cgccctgggt   420
ggcgcagcgc tgctagggat gatcagttgg gcgccgaaat ggccggacga ggcgtggctg   480
tgggtgttga ataacctgct gctggtgacg ttggtcgaag aagcgctgtt tcgcgggtat   540
atccagggcg gcctgagccg acgcttcaaa cacctgccct atggcgagaa cctcgcgctg   600
ctgctggcct cactgttatt cggcctggtg cattttgctg cggggttggca gtggatgctg   660 ctggcgagta ttgctggcgt gggttacggc ctggcctatc gctttggtgg cttgggcgcg   720
gcgattgcca cgcactttgg cttgaatctg ctgcacttcg gcctgttcac ctacccgatg   780
ctcgccggc                                                           789
```

<210> SEQ ID NO 85
<211> LENGTH: 1737

<212> TYPE: DNA
<213> ORGANISM: Pseudomonas fluorescens

<400> SEQUENCE: 85

```
atgcactttc cactgaaaaa actggtggct gccaccttgt tcgccgcgag cctgtcggca    60
gttgccactc ccgcatccgc taacatcacc gcagaccaaa gcgcagccat cttgaagcag   120
ttcagcgaga cctcggtcac cgattttcgc agtttcctcg gcaccctggc taagggcgag   180
ttcggcaaat cggctgacac cggcactgct atcagcgcgt ttctgggcaa caaaaccctg   240
agcgccgagc agcagaacga gatcaatcgc ctgctgggca tttacacccg cgttaaatat   300
ggcaaagccg cgctcgaaac cctgcgtgaa ctggtggaga tccctacgtt taacgtagac   360
ggcctgccgc aatacaataa cccggaattc ctcaagatcg ccgcgaagat cgaggccctg   420
gccaagtcct tcaacctgaa cttccgtaac gtcgataacc gcgtctacga aatccctg    480
gaaggcagcg gtgatgaagt cgtgggggtg catgctcacg ccgacgtggt gccggtcacc   540
ccggaaaact gggtgctgca agacggcacc aaactcgacc cgttcaaggt cacgctgatc   600
ggcgaccgca tgtatggccg cggtaccgag gatgacaaga acggcatcgt ggtgacgatg   660
tacgccatga aggtgatcaa ggaagaaaag ctgccactgg cgcgcacgtt caagctgctg   720
gtggacacca ccgaagaaac ttccggtgag gctattcctt actatttcga gcgcaatccc   780
gtgccgcaat acaacctggc gctggatggc ggttacccgg tggtgattgc cgagaaaggc   840
tcggggacgg tcatggccac cttccgggtg cgcaaaggcg aaggcaaagg cgcagagatc   900
atcgcgatga ccggcggcaa ggcgaacaac cagatcccat cggcctcggt agccacgctg   960
gtcagcgata caccgccga attggccgcc agcctgcaac aggccggtgc cgactatgcc  1020
aagcgcaacg gtggcaattt ccaggtgacg gccaaggtcg atggcaagga cgtcaaactc  1080
acggtgaccg gcgtgtccgc gcactcctcc gagcccgaaa ccggagtcaa cccggtggcg  1140
cgcatgctgg agttgatcca tagcctggat ggcaaggtcg ccctcaagca caaccacatc  1200
accgacgccg cgcggtatgc cgccgacaac tggggcctgg attacctggg cggcaaattg  1260
ggtgtgggct acgcggatga tttcatgggc ccgctgacca cctcgctgac gtttgtgggc  1320
caagatgaca aagccttcaa actggcagtg aacctgcgcg cgccgaaagg taaaaccct  1380
gattcactca aggcgcagat tgagcagaag ctcactgcct ggaaccagga tgccaaggtc  1440
aaggtgaact tcacgtactc gctcgacacg ccgatgtacc gcaaccctga aggcgagtgg  1500
gtcaaggcct tgttggcggt ggccacggaa aacctgggga tggcacacaa gttcggcact  1560
tcagccggcg caacctccgt gcatgacctg cccaacggcg tgcaattcgg cctggcgcgc  1620
ccggaagaga gtacaccgg gcacacggac agcgagttca agacggttga gcagttcttg  1680
ctggacctgc agatcgtcac cgaaatgatg ggccgcgtcg ggcaattgcc gaagctc     1737
```

<210> SEQ ID NO 86
<211> LENGTH: 1431
<212> TYPE: DNA
<213> ORGANISM: Pseudomonas fluorescens

<400> SEQUENCE: 86

```
atgtcaaaag taaagacaa agctattgta tctgccgcgc aagccagcac tgcttactcg    60
caaatcgata gcttcagcca tttgtatgac cgtggcggta acctcacagt caatggcaaa   120
ccgtcctaca ccgtggacca ggcagcgacc cagctgctgc gggatggtgc tgcgtaccgg   180
gactttgatg gcaacggcaa gatcgatctg acctacacct tcctcacctc ggctacccag   240
```

```
agcaccatga caaacatgg catctcgggg ttcagccagt caacaccca gcagaaagca    300 caggccgcac tggccatgca atcctgggcg gatgttgcca acgtgacctt taccgaaaag    360
gcttccggcg gtgacggcca catgacgttc ggtaactaca gcagtggcca ggacggcgcc    420
gcggccttcg cttacctgcc cggtaccggt gcaggctacg acggcacctc gtggtacctg    480
acaaacaaca gctacacgcc gaacaagacc ccggacctga caactatgg ccggcagacc    540 ctgacccacg aaatcggcca caccctgggc ctggctcacc ctggcgacta caacgccggg    600
aacggcaacc cgacctataa cgacgcaacc tatggacagg acacgcgtgg ttatagcctc    660
atgagttact ggagcgagag caacaccaac cagaacttca gcaaaggcgg cgtcgaagct    720
tacgcttccg gcccgctgat cgacgacatt gccgcgatcc agaagctcta cggtgccaac    780
ctcagcaccc gcgccacgga caccacctac gggttcaact ccaacaccgg gcgtgatttc    840
ctcagcgcca cgtccaacgc cgacaagctg gtgttctcgg tatgggacgg tggcggcaac    900
gacaccctgg acttctccgg tttcacccag aaccagaaga tcaacctcac ggccacctcg    960
ttctctgatg tgggcggcct ggtgggcaac gtgtccatcg ccaagggcgt caccatcgag   1020
aacgcgttcg gcggcgcggg caacgacctg attattggta accaagttgc caacaccatc   1080
aagggcgggg ccggcaacga cctcatctac ggcggcggcg gtgcggacca actgtggggc   1140
ggcgcgggca gcgatacatt cgtgtacggt gccagttccg actccaagcc agggctgcg    1200 gataagatct tcgacttcac gtccggttcg gacaagatcg acctgtctgg tatcaccaag   1260
ggtgcgggcg tgaccttcgt caacgccttt accgggcatg ccggcgatgc tgtactgagc   1320
tatgcctcgg gtaccaacct gggcaccttg gccgtggact tttccgggca cggcgtggcg   1380
gatttcctcg tcaccaccgt tggccaggcg gctgccagtg acatcgtagc c            1431

<210> SEQ ID NO 87
<211> LENGTH: 1827
<212> TYPE: DNA
<213> ORGANISM: Pseudomonas fluorescens

<400> SEQUENCE: 87
atgaacggag ttcagcgcgt gtttttgatt tcccgccgca gcctgacagt catcgccgca     60
gccctggccc tcgccgcctg ccacacgccg gtcaacgaac agccaccggc cccggagctg    120
ggctcgggct atcgcaccga cctgagcacc cgccacgccg agcgccatat ggccgccgcc    180
gccaaccctc tggccgctga agccgggcgt gagatgttgc gccaaggcgg ttcggctatt    240
gatgctgcga ttgctatgca agcgatattg accctggtgg aaccgcagtc gtccggcatc    300
ggcggcggtg cattcatcat gctgtgggat gggcacaacg tgcaggctta cgacggccgc    360
gaaactgcgc cggccgggc gacggagcgc ttgttcctga agggcgacgg tacgccgatg    420
gcgttcacgg atgcgcagat tggcgggcgc tcggtgggca cgccaggggt attgcgcgcc    480
ctggagatgg cgcacaaaaa gagcggccac ttgccatggg ccaagctgtt cgagccggcg    540
attcgcttgt cggagcaagg cttcgccatt tccccgcgct tgcacagctt gatcgccgca    600
gaccgcttta tcgcgcaatc gcccgacatg gcggcgtact tcctgaatgc cgatggctcg    660
ccaaaagcca ccggcacgct gctgaaaaac ccggcactgg ccgtcgtgtt caagcgcatc    720
gccaaggaag ggccggacgc gctgtaccaa ggcccgattg ccgaggagat cgcacgcaag    780
gtgcagggcc atcgcaatgc cggcagcctg tcccaggctg atctcaaggg ctacaccgcc    840
aagcaacgcg caccgctgtg caccgactac aaacaatgga aggtctgcgg catgccaccg    900
ccgtcctcgg gcgggattgc cgtggcgcag atcctcggga cactgcaggc gctggaaacc    960
```

```
cgcaccccgc gcctggccat cgcccctatg acaccggtca agagtgcctc gccggccggg      1020
cttgagccga cacccgaggc cgtgcacctg ctcgccgaag ccgggcgcct ggcctttgcc      1080
gaccgcgcgc tgtacgtggc cgatgcagac ttcaccccg  tacccgtcgc cggcctcgtc      1140
gcaccgagtt acctggcgca gcgcgccacg ctgatcggcg aacgcagcat gggcatcgcc      1200
aagcccggcc aacccgccgg tattcaggta gcgtatgcgc cagaccgctc gccgctgcgc      1260
atctccacct cacaggtggt ggcggtggac gaccagggcg cgccgtgtc  gatgaccacc      1320 acggttgaag cggcattcgg ctctcatgtg atggtccagg cttttttgct caacaaccag      1380
atgaccgact tctccttcat ccccgaagaa acggccagc  ctgtggccaa ccgcgtgcaa      1440
ccgggcaaac gcccacgctc ggccatggcg ccgaccttgg tgttcgaccg caactcgggc      1500
gaactgctgg ctaccgtcgg ctcccccggc ggctcgcaga tcatcgagta cgtgagtaaa      1560
tccctggtgg ccatgctcga ctggaagctc gacccgcagg cggccatcag cctgcccaac      1620
ttcggcagtc gcaatggtgc taccgagttg gaagctgggc tgttcagccc ggcgcttaaa      1680
caggcgctca aggacaaggg ccacgccctg agcgagatcg agatgaccag cggcgtgcag      1740
gccatcgtgc gcacacggga tgcccaaggc aagtgacgc  tcagtggtgg cgcggaccct      1800
cggcgtgaag gtgaggcgtt gggtgat                                         1827

<210> SEQ ID NO 88
<211> LENGTH: 1647
<212> TYPE: DNA
<213> ORGANISM: Pseudomonas fluorescens

<400> SEQUENCE: 88
atgacggtgg tgaaggtctt ttcaatgtgg gagctttatc gggctgacaa cggagcagtc        60
ggcatcggta actcgcatat atggacggtt aactttccac tgttcagagt atcaaagcac       120
atgcatatcc ctgttaggca gtcttcttac tcgcgtcctt cagataagtt acagcccgat       180 cttcacccg  atgaacacca agttgttctc tgggccaaca ataaaaaatc tttcaccacg       240
gatcaggccg cgaaacacat cacccgcggt ggcttcaagt tcatgatcg  caacaatgat       300 ggaaaaatcg tcgtgggtta aactttgcg  gcggcttca  atgcggctca gaaagaacgg       360
gccaggcaag cccttcagta ctgggcggat gttgctaata tcgaatttgt tgaaaatggc       420
ccgaacacgg atggcacaat aagcatcaag ggtgttccgg ttcggcagg  cgtcgcgggg       480 ttgcccaaca aatataattc gaacgtccag gccaatatag gcacccaggg tgggcaaaac       540
ccggcgatgg gcagtcactt cctgggctta ttgatccatg aactggggca taccctgggg       600
ctgagtcatc caggtaaata cgacggccag ggtttcaatt acgatcgggc tgccgaatat       660
gcccaggaca ccaaggctcg cagtgtcatg agctattgga cggagactca tcagccgggg       720
cacaattttg ccggggcgcag cccgggtgcc ccgatgatgg acgatatcgc cgccgcccag       780
cggctctacg gcgccaacac caaaacccgg aataccgaca ccacctacgg cttcaattcc       840
aattcaggcc gggaggctta tagcctcaag caggggagcg acaagccgat cttcaccgtc       900
tgggacggtg gaggtaatga cacgctcgac ttctccgggt tcacccagaa ccaaaccatc       960
aacctcaagg ctgagtcatt ctcggacgtg ggggcttgc  gaggaaatgt gtcgattgcc      1020
aagggtgtga gtgtggaaaa cgccattggc ggtacaggca cgataccttt gacggggaac      1080
gagggcaaca atcggctcac gggcggcaag ggggccgata gctgcacgg  cggagctgga      1140 gcagacacgt ttgtttaccg ccgcgccagc gattcaacgc cgcaggcacc ggacatcatc      1200
```

```
caggacttcc agagcgggag cgacaagatc gacctgaccg gtgttgttca ggaggcgggg    1260
ctcaagtcgc tgagcttcgt cgagaaattc agcggcaagg cgggcgaggc cgtgctcggc    1320
caagacgcga aaaccggccg tttcacgttg gcggtggaca caacgggaaa tggtacggcg    1380
gatctactgg ttgccagcca aagccagatc aaacaggcgg atgtgatctg gaacggtcag    1440
gcgccgacag tgacgccaac gcctgaaccc actgtggtgc ctgtgtcaga tcccgtgccg    1500
acccctactt cagagccgac tgaacctgaa cccacgcctg agcccgcccc tttgcccgtc    1560
ccgactccac ggcctggagg agggtttatc gggaaaattt tttcatcatt caaggggttc    1620
ataaaaaaag tgtggtcgat attcagg                                         1647

<210> SEQ ID NO 89
<211> LENGTH: 2577
<212> TYPE: DNA
<213> ORGANISM: Pseudomonas fluorescens

<400> SEQUENCE: 89
atgagagtgc caggaccaac cgcaacgaat tctaatgcag gcaggtgcc agatccgagg      60 agtggcatca gcccggaggg ccctacgcag gtatatacac taaacagcaa aaaaaccgtc    120
ttcactacga aacaggccgg gaaacatatc acccgcagcg gtttcaagtt tcatgacagt    180
aacggtgatg gcaaaaccac gttgtcctat cgtgtttcca agggctttac cccacagcag    240
gcagatcaag ccaggcaggc actgcaatcc tggcaggatg tcgctaacgt cacattcact    300 gaaaaaggc aggggctga cggccatata gatatcaatg agatgcacgg aacctctggg      360
ggtatggcct cactccccaa ccgctatatg agtcaaactt tcgcaaatgt cggaacagcg    420
aatgcaggtg caaaccctcc acggggtcat tattttcgcg aagttctagt tcacgaaata    480
ggccacacca ttgggctgga acaccgggg gactatgatg gctctggtaa ctatggacgg      540
gacgcagcgt atgccgggga tactcgagcg cgttctgtga tgagttacta ttcggaaaaa    600
aaccagccgg gacatgattt caaatcattg aaccctctg cgccgatgat ggatgatata      660
tcggccgttc agaaactcta tggggcgaat actaaaacgc gtaataccga tacgacgtat    720
ggatttaatt ccaatacaaa ccgtgaagcc tatagtttga agtcggctaa cgacacaccc    780
atttctctgt gtgtggatgg tggtggtaat gacacattgg atttctctgg gtattcacac    840
catcagaaaa tcaacctcaa tgccgagtcc ttttcggatg taggggcgtt gaaaggtaac    900
gtttccgttg ccaagggcgt cacgctggaa aatgcagtgg gcggtaaggg cgacgacaca    960
cttatcggta atcatgttgc caatcgcctc aaaggggggg cgggagccga cagactgtct   1020 gggggggcg gcgcagatac ctttgtttac gaccatgcca gtgattccac cccggataac    1080
cctgatgtca tcctggattt tgcgagtggc gcagataaga ttgatgtatc cgcagtcctt   1140
aaaagagcga atgtcagtgc tctcaagttc gtcgatcgct taactggcca acccggccag   1200
gctgtgatga gttatgacga gggccgcaac gagggggggc tggccctgga tctgacaggc   1260
aacggcaagg ctgatctatt aataaaaagc attggccaga taaagctgc tgatatcttg    1320 gcgcacggcg atacaaccgc gccaaaccct gaacccaaag atcccaagcc gcagccgcgt   1380
cctcaacccg aggagcccaa acccaagcct gaatccaaac gaaggagcc aaaaccggag    1440 gaaccaaaac cgcgtccgga ctcgtgtgaa ccaaagccgc gtccggatcc gtgtgagccg    1500
aagccgcgtc cggatccgtg cgagccgaag ccgcgtccgg attcgtgtga gccaaagccg   1560
cgtccggatc cgtgcgagcc gaagccgcgt ccagatccac gcgaaccgca gccacgtccg   1620
gacccgcgcg agccgcagcc gcgtccagat ccacgcgaac cgcagccacg tccggacccg   1680
```

```
cgcgagccgc agccgcgtcc ggacccgcgc gagccgcagc cgcgtccaga tccacgcgaa 1740
ccgcagccac gtccggaccc gcgcgagccg cagccgcgtc cagatccacg cgaaccgcag 1800
ccacgtccag acccacgtga accgcagcca tgtccggatc cacgcgaacc gcagccgcgt 1860
ccggacccgt gtgagccgca gccgcgtccg gacccgtgtg agccacagcc gcgtccagac 1920
ccacgtgaac cgaggccgcg tccgaaccca cgtgaaccgc agccacgtcc ggacccacgc 1980
gagccgcagc cgcagccgcg tccggaccca cgtgaaccgt acccacgtcc agacccacgt 2040
gaaccgaggc cgcgcccgaa cccacgtgag ccgaggccgc gtccgaaccc acgtgaacca 2100
cagccgcgtc cagacccacg tgagccgagg ccgcgtccgg acccgtgtga gccacagccg 2160
```

```
cgtccagacc cacgtgagcc gaggccgcgt ccgaacccac gtgaaccaca gccgcgtcca 2220
gacccacgtg aaccgcagcc acgcccggac ccgcgtgagc cgaggccgcg tccggaccca 2280
cgtgaaccgc agccacgccc ggacccgtgt gagccacagc cgcgtccgga accatgtgag 2340
ccgagaccgc gtccgaaccc acgtgaaccg caaccacgtc cggacccgtg cgagcctaaa 2400
ccaacccctc gcacagatcc ttgcgagccg aaagctgtca ctcgaaacgt aaggccagcc 2460
tatggcttga gtgcccattc aggcgagtac cgggcgatgc aggcgccagc ctttgatagt 2520
cgtcatttcc agggcgggct tgcaggggaa ttcattcgac gtcagaagcg cgctgaa 2577
```

<210> SEQ ID NO 90
<211> LENGTH: 549
<212> TYPE: DNA
<213> ORGANISM: Pseudomonas fluorescens

<400> SEQUENCE: 90

```
atgcctttac acattatcaa cttcaccgca ccggtcaccg cctccacgtg cagccaactg 60
atcgaaaaag cctcattagc cgtgcagcaa ggtgcccaag gcctggtact gaatatcgcc 120
accatgggcg gcgaatgcag ctacggcttt acgatgtaca actttttatt gtccctgccg 180
atcccggtgc atacccataa cctcggcacc gtggaatcca tgggcaatat catcttcctg 240
gccggtgagc gcaggaccgc ctgcaaacac agcaaattcc tgttccaccc ctttcattgg 300
catgtgcaag gcgcggttga ccactcgcgc atgtctgaat acgcaatgag cctcgactat 360
gacttgcagt tgtacgcacg catcgtcgcc gagcgcaccg ccgatgccgt cgaaaaactg 420
gagaccgaaa aatacctgat cgccgcgcca cgcattctcg acccgcaaca agcgctcatc 480
gccggcttga tccatgggat cgaacttccc gtggtcaagg cggaattcgt gagcagcttc 540
attcattcc 549
```

<210> SEQ ID NO 91
<211> LENGTH: 2022
<212> TYPE: DNA
<213> ORGANISM: Pseudomonas fluorescens

<400> SEQUENCE: 91

```
atgcctgaaa gcaatccact gttactgccc tacgacctgc caccgttctc tgccatccga 60
gcagagcact tggtgcccgc cattgagcag atcatcactg aaagtcgcaa caccaccgcc 120
acgatcattg ccagccagac gccattcccc acctgggacg acctggtgca agcagtggag 180
gcgttggagg ctcgcctgga tggcgttctc aaaatcatcg agctgcttga ctcccacccc 240
caagggcctg catggacgct ggcatcacac cgcagttatg agctggccat gcagtacagg 300
gttgagttgg ccgggaacaa cgacctgtat caactgcacc gacaacttgc cgacagcccg 360
```

```
atcgcgaccc ttttcaatga acaacgccac agcgcgttgc gtaaaatatt gcgcaagtac      420
cacttggctg gccttgatct ttctcctgaa aagcagcgac ggctgaaagc gttgaacctg      480
caaatcgatg aattcagcca cgagttcctg cgtcgtgtga gcgactccag tgacgcatgg      540
cgtaagcaca ttcaagacaa ggcgctgctg agcggactac ctgacgcagc cctggcgcgc      600
ctggagttcg cggctcggga cgcaggcctg ggggatggt tattaaccct ttcgaagcaa       660
tcctttcagg aggtgatgag ctacgccgac catagagcct tgcgccagga aatgatgctg      720
gcttactaca gccgtgccgt gggcacgggg cctgacgcca ttgccactga caatgaagcg      780
gttctgaccg tgttgctcga cagtcgtcac cagaaagcac aattgctggg ctatgccaac      840
ttcgccgagc tggcgctggt ggaacaaatg gctgagacga ccgatgaggt cactgcctgt      900
gtgcatcaac agattgatca ggcacgcacg acatttgccc atgatgcaca acaactgcaa      960
cgctatgccg cgcaacgggg agtcgatgcg ctagaaccgt gggattacga cttttttcgcg    1020 gaaaaaattc gccaggacgt ggcgggtgtc tcccaggacg cagtgcgcct ctacttcccg     1080
ttggagacag tgctgcaacg cttgtgcacg ttcacccaaa cgctgttcgg cgttgagctg     1140
attgaacaag ccacggtcga tacctggcac ccggatgtgc gggtatttga actcagggag     1200
tacgcgcagc cgattggaca tttgtttatt gaccctatc gccgcgtggc gggcggcgaa      1260
attggcgccg ccatgggctt gcgcaatcac cgaatgactg ccgaggggcg cccacaacgg     1320
cccatagccg tgctgcgcag ccagttgcca cgacctacgg cggcccagcc ttgcttgctg     1380
gatcacctgc aattgagggt cctattgcat gagttcggac actgcctgca gcatctgttg     1440
tccgccgccc cctaccgggc gatttcgggc atgggccaat taagccacga tacgacggag    1500
ttcttcggcc tagtgctgga gcagttctgc cttacgccgt cgttcctgat ctatctatcc     1560
gggcatgtgc agacgggaga tcccttgcct gacaaaatgg cgacgcaaat gagccgattt    1620
gctcataccc agaccagtca ggaaaccgcc agtattttgc tcacgggcct cgttgacttc    1680
gagttgcacc gcacctatgg cgacgggcgc acaccgcatg aagtattcac cgacgccaat    1740
gttgaagtcg ggcatttgca gtggcctgat ggcgctcgtc cgatcaacag tttcgaacaa    1800
ccgatgggta gctatggcgc caaactgtat tcctacacgt ggtccggcgt tctggcccgc    1860
caggcgtttg agcggtttga gcgtgatggc ctgttcaacc gcagaccgg gaaagccttc     1920 cgggacgcgt tcatcactga gggcgatacc ggtactctgt tgagcgcact tgcgcttttc    1980 cgggggggacg gcgcgggatg tgtcgggcat tccaccgggg ta                      2022

<210> SEQ ID NO 92
<211> LENGTH: 2394
<212> TYPE: DNA
<213> ORGANISM: Pseudomonas fluorescens

<400> SEQUENCE: 92
atgaagacaa ccatcgaatt gcctctcctg ccgttgcgtg atgtcgtcgt ctatccgcac       60
atggttatcc cgctgttcgt ggggcgcgag aagtctatcg aagccctcga ggccgcgatg     120
acgggcgaca agcaaatcct gctgttggcc cagaagaatc ctgctgatga tgatccgggc     180
gaagatgccc tgtatcgcgt cggcaccatt gccactgtcc tgcaattgct caagctgccc     240
gatggcaccg tcaaggtgct ggtcgaaggc gagcagcgcg gtgccgtaga gcgctttatg     300
gaggtggacg ccaccctgcg cgcggaagtg gcactgatcg aagaagtcga agccccggag    360
cgtgaatccg aggtgttcgt gcgcagcctg ctgtcgcagt tcgagcagta tgtgcagttg     420
ggcaagaaag tcccggctga agtcctgtcg tccctcaaca gcattgatga gccaagccgc    480
```

```
ctggtcgaca ccatggccgc gcacatggcg ctgaaaatcg agcagaagca agacatcctc      540
gaaatcatcg acctgtcggc ccgtgtcgaa cacgtactgg cgatgctgga tggcgaaatc      600
gacctgttgc aggttgaaaa acgcatccgt ggtcgcgtga aaaagcagat ggagcgtagc      660
cagcgcgagt actacctgaa tgagcagatg aaggccattc agaaggaact cggcgacggc      720
gaggaaggcc acaacgaaat cgaagagctg aaaaagcgca tcgatgccgc tggcctgccc      780
aaagacgccc tgaccaaggc caccgccgag ctgaacaagc tcaagcagat gtcgccgatg      840
tcggctgaag ccaccgtggt gcgctcgtat atcgactggc tggtgcaagt gccgtggaag      900
gcccagacca aggtgcgtct ggacctggcc cgtgctgaag agattctcga cgctgaccat      960
tacggcctgg aagaggtcaa ggagcgcatc cttgagtacc tcgctgtaca aaaacgcgtg     1020
aagaaaatcc gcgcccggt gttgtgcctg gttgggcctc cgggcgtggg taaaacctcc     1080
ctggcggaat caattgccag cgcgaccaac cgcaaattcg tgcgcatggc cttgggtggc     1140
gtgcgtgacg aagcggaaat tcgcggtcat cgccgtacct acatcggttc gatgccggga     1200
agattgattc aaaagatgac aaaagtgggt gtacgcaacc cgctgttcct gctcgatgaa     1260
atcgacaaaa tgggcagcga catgcgtggc gacccggcgt cggctttgct cgaagtgctg     1320
gaccctgagc agaaccataa tttcaacgac cattacctgg aagtcgacta cgacttgtct     1380
gacgtaatgt tcctgtgcac ctccaactcc atgaacattc cgccagcctt gctgaccgg      1440 atggaggtga ttcgtctgcc gggctacacc gaagacgaga agatcaacat cgcggtcaag     1500
tacttggcgc ccaagcagat ttcggccaac ggcctgaaga agggcgagat cgaattcgag     1560
gtcgaggcga tccgcgacat cgtgcgctac tacactcgcg aggccggtgt gcggggcctt     1620
gagcgccaga tcgcgaagat ctgccgcaaa gcggtgaagg aacacgcgtt ggaaaaacgc     1680
ttctcggtga agtggttgc cgactccctg gagcacttcc tgggcgtgaa gaaattccgc     1740
tacggcctgg ccgagcaaca ggaccaggtc ggccaggtga ctggcctggc gtggacccag     1800
gtgggtggcg aattgctcac catcgaagct gcggtgattc cgggcaaagg ccagttgatc     1860
aagaccggct ccctgggtga cgtgatggtc gaatccatta ccgccgcgca gaccgtggta     1920
cgcagccgcg cccgcagcct gggcatcccg ctggacttcc acgagaagca cgacacccat     1980
atccacatgc cggaaggggc gaccccccaaa gacggcccta gcgcgggcgt aggcatgtgc     2040
acggccctcg tgtcggcctt gaccggcatt cccgtgcgcg ccgatgtggc gatgaccggg     2100
gaaatcaccc tgcgtggcca ggtattggcg atcggtggtc tcaaagagaa attgctcgcc     2160
gcgcaccggg gtgaatcaa gactgtgatc attcctgaag agaatgttcg cgacttgaag     2220
gaaattcctg acaacatcaa gcaggatctt cagattaaac cggttaaatg gattgacgag     2280
gtcctgcaaa ttgcgctgca atacgcgccg gagcccttgc cggatgtggc cccggagatt     2340
gtcgcgaagg acgaaaaacg cgagtccgat tccaaggaaa gaattagcac gcat           2394
```

<210> SEQ ID NO 93
<211> LENGTH: 921
<212> TYPE: DNA
<213> ORGANISM: Pseudomonas fluorescens

<400> SEQUENCE: 93

```
gtgaaaattc gtctttctat tgtcagcctg ttttttgctt tggcaggcac cttcgcccac       60
gccgccgaat ccaccctggc cccgcgtgac gcctccaagc ttcaaatcgc ctccggcagc      120
gccatgctgg tcgatttgca gaccaataaa gtcatttatt ccagcaaccc cgacgtggtg      180
```

```
gtacctatcg cctcggtgag caagctgatg accggcctga tcgtcctcga agccaagcag    240
aatatggacg agtacatcga catcaacatc accgacacgc ccgagatgaa aggcgtgttc    300
tcccgggtga agatcggcag ccagatgccg cgcaaggaaa tgctgctgat cgcgctgatg    360
tcttcggaaa accgcgccgc tgcgagcctg gcccaccatt atcctggcgg ttacgcagcc    420
tttatcgcgg cgatgaacgc caaggccaag tccttgggca tgaccagcac ccactacgtg    480
gagcccaccg gcctgtcgat ccataacgtg tcgaccgccc gcgacctgag caagctgctg    540
gcctatgcgc gtaaattccc gatgctgagc cagctgagca ccaccaagga aaagaccgtg    600
tcgttccgca gcccaactac accttgggc ttctccaaca ccgaccacct gatcaaccgc    660
gccaactggg atatcaagct gaccaagacc ggcttcacca accaggccgg ccactgcctg    720
gtgctggtga cgagcatggg caatcgcccg gtgtcgctgg tgatcctgga tgcctttggc    780
aagttcaccc attttgccga tgccagccgt attcgtagct gggtcgagac cggcaaaggc    840
ggcgcagtgc cggatgtggc gctgcgttac aaggccgata aaaacctcaa gaatcgagcg    900
accgctacgg aagtacgtcg a                                              921

<210> SEQ ID NO 94
<211> LENGTH: 633
<212> TYPE: DNA
<213> ORGANISM: Pseudomonas fluorescens

<400> SEQUENCE: 94
atgttccgta attcctatat tcagcagaac tctgatatcc aggccgcagg cggcctggtc     60
ccgatggttg tcgagcagtc cgctcgtggc gaacgcgcct acgacatcta ctcgcgcctg    120
ctcaaggagc gagtgatctt tctggttggc ccggtagagg actacatggc caacctgatc    180
tgtgcgcagc tgctgttcct tgaagcggaa aacccggaca aggacatcca tctctacatt    240
aattcgccgg gtggttcggt gactgcgggc atgtcgatct acgacaccat gcagttcatc    300
aagccaaacg tgtcgaccac ctgtattggc caggcgtgca gcatgggcgc cttcctgctg    360
accgcgggtg ccgaaggcaa gcgtttctgc ctgccgaact cgcgcgtgat gattcaccag    420
ccactgggcg gtttccaggg ccaggcgtcg gacatcgaaa tccacgccaa ggaaatcctc    480
ttcattcgtg agcgtctcaa cacgctgatg gccaagcaca gcgggcgcac cctggaagaa    540
atcgagcgcg ataccaaccg tgacaatttc atgagcgctg aagccgccaa ggaatacggg    600
ttgatcgacg cagtgatcga caagcgcccc gca                                 633

<210> SEQ ID NO 95
<211> LENGTH: 1350
<212> TYPE: DNA
<213> ORGANISM: Pseudomonas fluorescens

<400> SEQUENCE: 95
atgagtgcgc tctacatgat tgtcggcacc ctggttgctc tgggtgtgtt ggtgaccttc     60
cacgaattcg gccacttctg ggtcgcgcgt cgttgcggcg tcaaggtatt gcgcttttcc    120
gtcggtttcg gcatgccgtt gttgcgctgg catgaccgcc gcggcactga gtttgtcatt    180
gctgctatcc cgttgggcgg ctacgtcaag atgctcgatg agcgcgaagg cgaagtgcct    240
gcagaccagt tggaccaatc cttcaatcgc aagaccgttc gtcagcgtat tgcgattgtt    300
gcggcggggc cgattgccaa ctttctgttg gcgatggtgt tcttctgggt cttggccatg    360
ctgggcagca gcaggtgcg cccggtcatt ggcgcggtca agcggacag catcgcggcc    420 aaggctggcc tgacggctgg gcaggaaatt gtatccattg atggcgaacc caccacgggc    480
```

```
tggggcgcgg tcaacttgca gttggtgcgt cgcctgggcg agagcggcac cgtcaatgtg    540
gtggtgcgcg accaggattc cagcgccgaa accccgcggg cattggcgct ggaccattgg    600
ctcaagggcg ctgatgagcc cgatccgatc aagtccctgg ggatccgccc ttggcgtccg    660
gccttgccgc cggtgctggc cgagctcgat ccgaaaggcc cagcccaggc tgctggcctg    720
aaaaccggtg atcgcttgct ggccctcgat ggccaggcgc tgggtgactg gcagcaggtg    780
gtcgacctgg tgcgtgtacg ccctgatacc aaaattgtgc tgaaagttga gcgcgagggt    840
gctcaaatcg acgtccccgt gaccttgtcg gtgcgaggcg aagccaaggc agccgggggc    900
tacctgggtg caggggtcaa aggtgtcgag tggccgccat cgatggtgcg agaggtcagc    960
tacgggcctt tggccgcgat tggcgagggt gcgaaacgca cctggaccat gagcgtgctg   1020
accctcgaat ccctcaagaa aatgttgttc ggtgagctct cggtaaaaaa cttgagtgga   1080
ccgataacca ttgctaaagt ggcgggcgct tctgcccagt cgggtgtcgc ggatttcctg   1140
aatttcctgg cttatctgag tattagcctt ggggttctga atttgctgcc cattccagta   1200
ttggatgggg ggcatctgct gttttatctg gtcgagtggg tgcgtggtcg ccccttgtcg   1260
gatcgggtgc agggttgggg gatacagatc ggtatcagtt tggtggtcgg ggtgatgttg   1320
ttagccctgg tcaacgatct gggacgtctg                                    1350

<210> SEQ ID NO 96
<211> LENGTH: 780
<212> TYPE: DNA
<213> ORGANISM: Pseudomonas fluorescens

<400> SEQUENCE: 96
atgaccgtta ccttgaaaac cgccgaagac atcgcaggca tgcgcgttgc cggcaaactg     60
gctgccgacg tgctggaaat gatcgccgaa cacgtcaagc ccggcgtcac caccgaagcg    120
ctggaccgca tctgccacaa ctatatagtc gacgtgcaaa aagccatccc tgccccgctg    180
aattacaaag gcttccccaa gtcgatctgc acctcgatca ccacgtggt ctgccacggc     240 attcccggtg acaagccact gaaggacggc gacaccctga catcgacgt cacggtgatc     300 aaggacggct accacggcga caccagccgc atgttccacg tcggcaatgt accggtgtgg    360
gccgagcgcc tgtcccaggt cacccaggaa tgcatgtaca aggccatcga aatcgtcaag    420
cccggctgcc gctgggtga catcggtgaa gtgatccaga agcacgcgga aaagaacggt     480
ttctcggtgg tgcgcgaatt ctgcggccac ggtatcggca agtgttcca cgaagagccg     540 cagatcctgc actacggccg cgccggaacc ggcatggaac tcaaggcagg catgaccttc    600
accatcgagc cgatgatcaa ccagggcaag gccgacacca aggtgctggg cgacggctgg    660
accgccatca ccaaggaccg caagctctcg gcccagtggg aacacaccct gctggtcacc    720
gacaccggct atgagatttt caccctgcgc gccgacgaca ccatcccacg cgtttcggcc    780

<210> SEQ ID NO 97
<211> LENGTH: 918
<212> TYPE: DNA
<213> ORGANISM: Pseudomonas fluorescens

<400> SEQUENCE: 97
atgaccgccg ccgtacccgc actgcccccc gaaggcaccc tcggcctgat cgccccgcc     60 ggccccgccg agctggatgt tgaaaaagcc aggcaatgga tgcgtgcccg tggctacgac    120
ctgcatattt tccccggcgt gtacgagcgc gacggctacc tggccggtag cgatgaagtg    180
```

```
cgcctgcggg atttgcatgc cgcctttgcc aaccccgata tcgatgccat cctttgcctg      240
cgtggcggct atggcacgcc ccgtttgctc gacgcgctgg acttcgacct gctgcgtgcc      300
aaccccaagc cgttcgtggg ctacagcgat atcaccgcct gcacctggc gatcaaccgc       360 tacgcgggct ttgtgacatt ccacggcccg atgctcaatg ccgacctgct cggcggcaaa      420
cagccgccca ccgagtcctc cttgttcagc ctgctacgtg gccaaagggg cgccggcagt      480
gtgctgccgc acccgatggc ctgcccgctg accacaatcg agccaggagt ggcctgtggg      540
cgcttgctgg gcggtaactt gtcgatgatc gccgcggtca tgggcacgcc gtacgaaata     600
gacgctgacg gcatcatcct gtttatcgaa gacgtcaacg aaccgctcta tcgcatcgac      660
cgtctgctga ccaacctgcg cctggctggc aagctggctc aggtcgccgg tgtgctggta     720
ggggatgtgg ctggtgtgga tagcggggca ttggcacgtc tgctgaagca gacctttgag     780
ccgctgtgcg ttccagtgct ggcaggctgg agcagtgggc attgcgaccc gaacctgaca    840
ttgccgatgg gcgccttggt gcgcctggat gcggggagc agcgggtggt gttggagcag    900
gatgtagtgt tcaaggcc                                                918

<210> SEQ ID NO 98
<211> LENGTH: 930
<212> TYPE: DNA
<213> ORGANISM: Pseudomonas fluorescens

<400> SEQUENCE: 98
atggaattca tcgaaaaagt tcgcgaaggc tacgcgccct ttggcgccta tcagacctgg      60
tatcgcgtca cgggtgacct gagcacaggc cgcacgccct ggtgatcat ccatggcggc     120 cctggttgca cccacgatta cgtcgacgcc ttcaaagacg tcgccgccag cggccatgcg    180
gtcatccact acgatcagtt gggcaacggc cgctccacgc acttgccgga aaagacgcg    240 tcgttctgga ccatcggcct gttcctcgac gagttgaaca acctgctgga ccacctgcaa    300
atcagcgaga actacgcgat cctcgggcaa tcctggggcg gcatgctcgg cagcgaacac    360
gcgatcttgc aacccaaggg cctgcgcgcg tttatccctg ccaactcccc cacctgcatg    420
cgcacctggg tcagcgaagc caaccgcctg cgcaagctgt tgcctgaagg cgtgcatgaa    480
accctgctca agcacgagca ggccggcacc taccaagacc cggcatacct ggcggcctca    540 cggatttttct atgaccagca tgtgtgccga gtcaacccgt ggcccgaaga gtgcgcgcg    600 accttcgccc aggtggatgc cgacccgacg gtgtaccacg ccatgagcgg cccgaccgaa    660
ttccacgtga tcggcagctt gaaggactgg aacgtgatcg gtcggctgtc agcgatcaag    720
gtgccaaccc tggtgatttc cggccggcac gacgaagcca caccgttggt ggtcaagccg    780
ttcctggatg agatagagaa cgtgcgctgg gcactgtttg aagactccag ccacatgtcc    840
catgtggaag aacgccaggc gtgcatgggg acggtggtga agtttctgga tgaggcgtgt    900
tcgttgccgc acaaagccct caaggccggc                                    930

<210> SEQ ID NO 99
<211> LENGTH: 885
<212> TYPE: DNA
<213> ORGANISM: Pseudomonas fluorescens

<400> SEQUENCE: 99
atgtggcgtg aaattgcccc cgaccagcag tacaacgtgc aagtcgacgg ccataacctc      60
gtggtctaca gctttggcga aggcgatgag gtgctgctgt gtctcaacgg cgggccgggc   120
ctgccgtgtg actatctgcg tgacacccat ggctggctca agcacataa cctgcgagtg    180
```

```
gttgcattcg accagcttgg cacaggcgca tcagccagac cggccgatgc cgcactgtgg    240
gaaatccgcc gttatgtcga agaagtcgag accgtgcgcc aggcgctggg cctgggccgc    300
gtgcatttgc tcgggcattc ctggggcggt tggctgggca tcgaatatgc cgtgcattat    360
cccggtgcgc tcaaaagcct gatcctggaa acaccgtcg gcgacattcc ccacctgtcc     420
caggaactgg agcgcctgcg cggcgccctg gcagcgaaa ccgtggccat gatgcaacgc     480
cacgaagcca tgggcaccct cgaccacccg cagtaccagg ccgccatcac cttgctcaac    540
taccgccacg tgtgccggct cgacgaatgg cccgagccgg tcaagcgctc cctgggcgac    600
tggaacatgg ggccttacga aaccatgcaa ggccccaacg agttcctcta tatcggcaac    660
ctcaaggact ggaaccgcct caaggaaatg gccgagttca cgatgccgat cctgatcacc    720
accggccagc acgacgaact cacccccgcc tgtgcgatgc gcatgaaact gcagcacccc    780
catgccgagt tgcatgtgtt ccccaacagc agccatatgc cgttttacga ggagccgcag    840
gcgtacttcc cggtgctgct ggactttctc gctcgccacc gaggc                    885
```

```
<210> SEQ ID NO 100
<211> LENGTH: 537
<212> TYPE: DNA
<213> ORGANISM: Pseudomonas fluorescens

<400> SEQUENCE: 100
atgtcgacct cggcccgcct gatgcttatt gtttgcgccg cgctgctcag cgcctgcgcc     60
agtcgcacac cgccgcccgc gcccgtcgcg gtcaagccta agccggtgtt caactatgcc    120
acccagaatt tctcgccagc tgccgaagac gtgctctttc gtgcgctggg cctggtcggc    180
acgccttatc gctggggcgg caacacaccg gactcgggtt ttgattgcag cggcctgatc    240
ggctttgtat tccgcgacgc tgctggcatc tcattgccgc gcaccacccg tgaactgatc    300
gtgatgcgtg cccaggacgt cagcgaacaa aacctgcaga ccggcgacct gctgttcttc    360
gccaccggtg gtggttcgcg ggtcagccat gcgggtattt atgtggggga ggggcgcttc    420
gtacacgcgc cgcaaaccgg cggtacggtg aagctggata cgctatccaa agcgtattgg    480
cagaatgcct acctgagtgc caaacgcgtg ttgccaggga tctggcgcg taacccc        537
```

```
<210> SEQ ID NO 101
<211> LENGTH: 633
<212> TYPE: DNA
<213> ORGANISM: Pseudomonas fluorescens

<400> SEQUENCE: 101
gtgcccatgc taaatcgctt cgcacccctc gtgcctctcg cactcgttac cctgttgttt     60
ggttgcgcct cccacccctca gcaggtggca gaacagcaaa aaccacaggt tcaaaatcag    120
gcaaagttcg ttgctgcaca gtctgcttct gtttatgaag aagaggtggc aaccgaaaaa    180
gaactcgcca gttctccga cagcaagcct taccagctgc cacttctggc cgacagcatc     240
cttgagcgcg gcatgtcctt gatcggtacc cgttaccgtt tcggcggcac ctcggaagcc    300
ggttttgatt gcagcggttt cattggctac ctgttctgtg aagaagccgg tatgaacctg    360
ccgcgctcca cgcgcgagat gatcaacgtg aatgcaccgt tggtcgcacg aaacaacctc    420
aagcccggtg atctgctttt ctttagtacc agtggccgcg gtcgtgtcag ccacgccggt    480
atctacctgg gcgataacca gtttattcat tccagcagcc gccgcagtgg tggtgttcgg    540
gtcgataacc tcggtgacag ctactggagc aaaaaccttca tcgaagccaa gcgcgcactc    600
```

```
gccatggccc cgacgacggt taccgctagt aag                                  633
```

<210> SEQ ID NO 102
<211> LENGTH: 1458
<212> TYPE: DNA
<213> ORGANISM: Pseudomonas fluorescens
<400> SEQUENCE: 102

```
atgatcaaat ctttgcgttc agtgttactt gccagtgttg tcttgcccct ggccttttcc     60
gtttgcgccg ctcccgtcaa taacaccctg ccacccagcg ttgcccaggc cttgcagaag    120
gccaagctgc aaaataccgc gctgtccctg gtgatgctgc cctgaacgg ccctggtacc    180
cctacggttt tcaacgccga cgtctcggtg aacccggcct ccaccatgaa gctggtcacc    240
acttacgcgg ccctggaaat gctcggcccc aaccatcagt ggaagaccga gttctacacc    300
gatggcaccc tcagcggcgg cgtgttgcgc ggcaacctgt acctcaaggg cggcggcgac    360
cccaagctga acatagaaaa actctggctg ctgatgcggg acctgcgcgc caatggcgtg    420
cagcaagtca ccggcgacct ggtgctggac cgtaacttct tcaaccagcc gcaattgccc    480
gagttcaacg acgacggcaa cgatgagaac aagccgttcc tggtcaagcc cgacgccttg    540
ctggtcaacc tcaaggccct gcgcttcgtg acccgcaatg attcggggcg ggtgatcgta    600
tcggtcgagc cgccgattgc cagcattcgc atcgacaacc aggtgaaagt caccaacgcc    660
aaacagtgca ccggtgacgt gcgctacagc ccggtgaccg ccgccgacgg cagcgtgacc    720
gtgaccgtca gcggccaact gggtgatggc tgcagctcgc agacctacct gtcgctgctc    780
gaccacgcca cctacaccgc aggcgccgtg cgggcgatct ggaaggagtt gggcggcacc    840
atccagggcc gtgatatcca ggcaccggtg cccaaggatg ccaaagtcct ggcccgggcc    900
ttctcgccgg acctggcgga gatcatccgc gacatcaaca aatacagtaa caacaccatg    960
gcccagcagt tgttcctgag cctgggtgcg cagtttcgca acgatgccga tggcgacgat   1020
gccaaggctg cgcaacgtgt cgtgcgccag tggctagcca agaaaggcat caccgcgccg   1080
cacctggtga tggaaaacgg ctccggcctg tcccgcgccg aacgggtcag cgcccgcgag   1140
atggcggcca tgctgcaagc cgcgtggaaa agcccttatg cggcggagta catcagctcg   1200
atgccgatcg ccggcaccga cggcaccatg cgtaaacgcc tgaaaaccac cgccctgcgc   1260
ggcgaagccc atgtgaagac cggcaccttg aacaccgtac gcgccatcgc cggttacagc   1320
cgcgacaaca atggcaatac ctgggcggtg gtggcgattc tcaacgactc caagccttgg   1380
ggagcctcgt cggtgctgga tcaggtgctg ctggacctgt atcgccagcc gaaggccgtt   1440
gcagccgcac cggttctc                                                  1458
```

<210> SEQ ID NO 103
<211> LENGTH: 1440
<212> TYPE: DNA
<213> ORGANISM: Pseudomonas fluorescens
<400> SEQUENCE: 103

```
atgagcgagt tgttgtcctc agtcagtgat cacctcctgg cacccggtgg cgtgaccatc     60
gaaagcctgc aaaccgtgct cggcgatctg gccgggccgg gtatcgatgc ggctgacctg    120
tatttccagg ggcagatttc cgagtcatgg gcgctggaag atgggatcgt caaggaaggc    180
agtttcaacc ttgaccaggg cgtaggcgtt cgcgcgcaat cgggtgagaa gaccggcttt    240
gcctacagca atgcgatcac cctggaggcc ttggcctgg cggcgcgtgc cgcccgttcg    300
atttcccgtg ccggccagaa tggcacggtg caggcattca gtacccagga cgtggcccag    360
```

```
ttgtatgcgc cggataaccc cttggaagtg atcagccgtg cggaaaaagt cgagctgctc      420
aagcgtatcg acgcagctac ccgcgctctg acccgcgta tccagcaagt gaccgtaagc      480
atggccggcg tgtgggagcg catccttgtg gcgtccaccg acggtgggct ggcggcggat      540
gtgcggccgc tggtgcgttt caatgtgagc gtgatcgtcg aacagaacgg gcgccgcgag      600
cgcggtggcc atggcggcgg cgggcgcacc gactaccgtt atttcctcgc tgacgaccgt      660
gccatgggct atgcccgtga ggcgctgcgc caggcattgg tcaacctgga ggcgataccg      720
gcaccggccg gcaccttgcc ggtggtgctg ggctcgggtt ggtctggcgt gttgctccac      780
gaagccgtgg gccatggcct ggaaggcgat ttcaaccgca agggcagttc cgcctatagc      840
gggcgcatgg gcgaaatggt tgcgtccaag ctgtgcacca ttgtcgatga cggcaccctg      900
gccggccgcc gtggttcgct gagtgtcgat gacgaaggta cgccgaccga atgcaccacc      960
ctgatcgaga acggcgtgct caagggctac atgcaagaca agctcaacgc ccgcctgatg     1020
ggcgtggcgc gcaccggtaa tggtcgccgt gaatcctatg cgcacctgcc aatgccgcgt     1080
atgaccaaca cctacatgct cggtggccaa agcgatccgg cagaaatcat tgcctcggtc     1140
aaacgcggta tctactgcgc caacctcggc ggcggccagg ttgatatcac cagcggcaag     1200
ttcgtgttct ccaccagcga ggcgtacctg atcgaagacg caagattac cgcgccggtc      1260 aaaggggcga cgttgattgg taacgggccg gaagccatga gcaaagtgtc gatggtcggt     1320
aacgacctgt cgctggacag cggcgtgggc acgtgcggca aggatgggca gtcggtgccg     1380
gtaggtgtcg ccagccaac cttgaaaatt gatgcgatta ccgtgggtgg cacgggatcg      1440
```

<210> SEQ ID NO 104
<211> LENGTH: 1344
<212> TYPE: DNA
<213> ORGANISM: Pseudomonas fluorescens

<400> SEQUENCE: 104

```
atgagtgcag cccaaagcgt cggtccacaa gcgttaccgg cactgcagga acaagtcgag       60
cagatccttg ccgaggccaa gcgccagggg gccagcgcct gtgaagtggc ggtgtcgctg      120
gagcaagggt tgtcgacttc ggtgcgccag cgggaagtgg aaacggttga attcaatcgt      180
gaccaagggt ttggcattac cttgtatgcg ggccagcgca aggctcggc cagcacttcc       240 gccagtggcc ctgaggcaat cgcgagacc gtcgccgcag cactggcgat tgccaagcac       300
acctccgagg atgaaagctc gggcctggcc gacaaggcgc tgatggccaa ggaggtgcag      360
gattttgacc tgttccatgc ctgggatatc accctgagc aagccatcga gctggcgctg       420
acctgcgaag cggcagcctt cgatgccgat gcccgcatca gaatgcgga cggcaccacc       480 ttgagcaccc atcagggttg tcgcgtctac ggcaacagcc atggctttat cggtggttat     540
gcctccacgc gtcacagcct cagttgcgtg atgattgccg aagccaacgg gcagatgcag      600
cgtgattact ggtacgacgt aaaccgccaa ggcgatttac tggcagaccc tgcaagcatt      660
ggccagcgtg cggcgcaacg ggctgcgagc cgcctgggcg cgcgcccggt gccgacctgc     720
gaagtgcctg tgctgttttc cgcagagttg gccggtggtt tattcggcag cttcctgggg     780
gcgatttccg gaggcaacct gtatcgcaag tcttcgttcc tggaaggcgc catcggccag    840
aagctgtttc ctgagtggct gaccatcgac gagcgcccgc atttgatgcg cgccatgggc    900
agttcgtcgt tcgacggcga tggcttggcg acctatgcca agccgtttgt cgagaaaggt    960
gagctggtgt cttatgtgct gggcacttat gccggtcgca agtgggcct gcccagtacc    1020
```

```
gccaacgcgg gcggcgttca taacctgttc gtgacccatg gcgatgaaga ccaggccgcg    1080
ttgttgcggc gtatggggcg tgggttgctg gtgactgaat tgatgggcca tggcctgaac    1140
atggtcaccg gtgactactc gcgcggtgcg gcgggcttct gggtggagaa cggcgaaatt    1200
cagttcgccg tccaggaagt gaccatcgcc ggcaatatgc gcgatatgtt caagcagatc    1260
gttgccgtgg gtaacgacct ggaactgcgc agcaatatcc gtacgggttc ggtgctgatc    1320
gaacgcatga cggtcgctgg cagc                                           1344
```

<210> SEQ ID NO 105
<211> LENGTH: 1431
<212> TYPE: DNA
<213> ORGANISM: Pseudomonas fluorescens

<400> SEQUENCE: 105

```
atgactttt  tgcgccctac cctgctgacg ctggcctgcc tgctggcctc cccggccttc     60
gctgacgacc tgccgtcact tggtgacgcc agctctgcca ttgtctcgcc gcaacaggaa    120
taccaactgg gccgcgcctg gctggcttac ctgcgcggcc aggtctcgca actcaatgac    180
ccgcaactca aggattacgt cgaaaccagc gtgtacaagc tggtggagac cagccaggtc    240
aatgaccggc gcctggaatt tatcctgatc aacagcccac agctcaacgc ctttgcggca    300
ccgggtggga tcgtcggggt caacggcggc ctgtttctca atgcacagac cgaaggcgaa    360
tacgcgtcgg tactggccca cgaactggcg cacttgtccc aacgccactt cgcccgaggc    420
gtggaagcgc aatcacgcat gcaactgccg atgatggccg ccctgcttgg cggcattatc    480
gccgccgctg cgggtgccgg ggatgccggt atcgccgcga ttgccggttc acaagccgcc    540
gcgatccagg agcagcgccg attctcgcgc cagaacgagc aggaggctga ccgcatcggc    600
atcctcaatc tggaaaaagc aggctacgac ccgcgctcca tgcccaccat gttcgaacgg    660
ctgatgcgcc aataccgctt cgacgccaag ccgccagagt tcctgctgac tcacccggtc    720
accgaatcgc gtatcgccga cacccgcaac cgcgccgaac aagccaaacc cggcggcaag    780
gaagacagcc tgcgctatca actgattcgc gcacgggtac agctcaagta cgaagacaca    840
ccaggcctgg ctgccaagcg cttccaggca cagctggatg aaaaccctaa aaatgacgtg    900
gcgcgctatg gcctggccat cgcccagatc aagggcactc aactcaagga agcacgggaa    960
agcctggcgc gctgttggc caaggcgccc aacgacatca cctacaacct ggcccaaatc   1020
gaactggaca ttaccagcaa ccgcatgccc gatgcgcagc aacgcaccga ccgaatgctc   1080
acccaatacc ccagcaacta tccgctgaat caggtgcggg tagacctgtt gcttaaacag   1140
aaccgtaccg ccgatgcaga aaaggcgctg gacgggctgc tcaaatcgcg cccggacgat   1200
ccggacgtgt ggtatcaggt cgccgaaaca cgcggcttgt ccggcaacat cattggcctg   1260
catcaggccc gtgccgaata tttcgcactg gtggggatt tccagcaagc catccagcag   1320
ttggactttg ccaagcggcg tgctggcaat aacttcccgc tgtcctcgcg catcgacgcc   1380
cgtcagcgtg aactgatcga acaggagcgc ctggtgaaag gcatgatgag c            1431
```

<210> SEQ ID NO 106
<211> LENGTH: 1059
<212> TYPE: DNA
<213> ORGANISM: Pseudomonas fluorescens

<400> SEQUENCE: 106

```
atgtgtgttc gccaaccgcg caacccgatt ttttgcctga tcccgccgta catgctcgac     60
cagatcgcac gccacggcga caaagcccaa cgggaagtcg cattacgcac gcgtgccaag    120
```

```
gacagcacgt tcgttcgtt gcgcatggtc gcggtacccg ccaaggggcc ggcccgcatg      180
gcactggccg tgggcgccga aagcaacgc tcgatctaca gtgccgaaaa caccgacagc      240
ctgcccggca agctgatccg cggcgaaggg cagcccgcca gtggcgatgc cgcggtggac      300
gaagcctatg acgcctggg cgcgaccttc gattttttg accaggtctt tgatcgcaat       360
tccatcgacg atgcgggcat ggcgctggac gccacggtgc acttcggcca ggactacaac    420
aatgcgttct ggaattcgac ccagatggtg ttcggcgatg cgaccagca gttgttcaac      480 cgctttaccg tggcactcga cgtcattggg catgagttgg cccatggcgt gactgaggat    540
gaggccaagc tgatgtactt caaccagtcc ggtgcgctga acgagtcgtt gtcggacgtg    600
ttcggttcgc tgatcaagca gtacgcgtta agcaaacgg ccgaggatgc cgactggttg      660
atcggcaagg ggttgtttac caaaaagatc aagggcacgg cgctgcgctc gatgaaggcg    720
ccaggcactg cgtttgatga caagctgctg gcaaagacc cgcagcctgg cacatggat     780 gattttgtgc aaacttacga ggacaatggg ggcgtgcata tcaattccgg cattcccaac    840
catgcgttct accaggtggc gatcaatata ggcgggttcg cctgggagcg tgccgggcgt    900
atctggtatg acgcactgcg cgattcgcgg ttgcggccca attccgggtt cttgcgtttt    960
gcgcgcatta cccacgatat tgccggccag ctttatggcg tgaacaaagc tgagcagaag   1020
gcagtcaagg aaggctggaa agcggtgggc ataaacgtt                          1059
```

<210> SEQ ID NO 107
<211> LENGTH: 885
<212> TYPE: DNA
<213> ORGANISM: Pseudomonas fluorescens

<400> SEQUENCE: 107

```
atgatgcgca tcctgctgtt cttggccact aacctggcgg tcgtactgat tgccagcgtc       60
accctgagcc tttttggctt caacgggttc atggcggcca atggggttga tctgaacctc      120
aatcagctgc tgattttctg tgcggtcttt ggttttgccg gctcgctgtt ctcgctgttc      180
atctccaagt ggatggcgaa gatgagcacc agcacccaga tcatcactca accccgcact    240
cgccatgaac aatggctgat gcaaaccgtg gagcagttgt ctcaagaagc aggcatcaaa    300
atgcccgaag tggggatttt tcctgcttat gaggccaacg cctttgccac cggctggaac    360
aagaacgacg cactggtggc tgtgagccag ggcctgctgg agcggttttc gcccgatgaa    420
gtcaaggcgg tgctggccca cgagatcggc cacgtagcca acggcgacat ggtcaccctg    480
gcactggtac agggcgtggt gaacaccttc gtgatgttct ttgcgcggat catcggcaac    540
tttgtcgaca aggtcatctt caagaacgaa gaaggccgtg gcattgccta cttcgtggcg    600
accattttcg ccgagttggt cctgggcttc ctggccagcg ccatcgtgat gtggttctcg    660
cgcaaacgcg agttccgcgc agatgaagcc ggcgcacgcc tggcgggcac cagcgcaatg    720
atcggcgcgt tgcaacgcct gcgctccgaa cagggcctgc cggtgcatat gccggacagc    780
ctgaccgcct tcggcatcaa cggcggcatc aagcagggcc tggctcgctt gttcatgagc    840
cacccgccgc tggaagagcg gattgacgca ctgcgtcgcc ggggc                     885
```

<210> SEQ ID NO 108
<211> LENGTH: 969
<212> TYPE: DNA
<213> ORGANISM: Pseudomonas fluorescens

<400> SEQUENCE: 108

```
atgcagactt ggtacccgca gatcaaaccc tacgcccggc acgatctggc tgtcgatgac    60
acccacaccc tgtatgtcga tgaaagtggc tcccccgaag gattgcctgt cgtgttcatc   120
catggcggcc ccggttccgg ttgcgacgcc cagagccgct gctatttcga cccgaacctc   180
taccatattg tcaccttcga ccagcgtggc tgtggccgct ccacgccaag ggcgagcctg   240
gagaacaaca ccacttggga cctggtcgcc gaccttgaac gcatccgcga gcacctgggc   300
atcgacaagt gggtgctgtt cggcggctcc tggggctcga ccctggccct ggcctacgcg   360
caaacccatc ccgagcgtgt gctcggcctg atcgtgcgcg gcatcttcct cgcccggccc   420
caggatattc gctggttcta ccaggagggc gcgagccgtc tgttcccgga ttactggcag   480
gactacgtgg ccccgatccc ggtggaggag cgccacgata tgattgccgc ttaccacaag   540
cggctgaccg gcaatgacca gatcgcccag atgcacgcgg ccaaagcctg gtctggctgg   600
gaaggccgca tgctgggcct gtgcccgagc ccacaacatg tggagcggtt ttccgagccg   660
cagcgcgccc tgtccatcgc acgtatcgag tgccattact tcaccaacaa ctccttcctg   720
gaacccaacc agctgattcg cgatatgcac aagatcgccc atctgcctgg cgtcatcatc   780
catggccgct acgatatgat ctgcacgctg ataacgcct gggagttgca ccaggcctgg   840
cccaacagcg agttgcaggt gatccgcgag gcggggcatg cggcatccga gccgggtatc   900
actgacgcgc tggtacgcgc gaccggcgaa atggcccggc gcttgctcga cctgccgcct   960
gaagaagca                                                             969

<210> SEQ ID NO 109
<211> LENGTH: 864
<212> TYPE: DNA
<213> ORGANISM: Pseudomonas fluorescens

<400> SEQUENCE: 109
ttgagcctgc tgctgagtga gtatccctgg gcgtttgtcg gcgtggcgct ggtgttgggc    60
ctgatcgtcg gcagctttct caatgtgttg gcgtggcgcc tgcccaaaat gctcgagcgg   120
gagtggcgtg cccaggccca tgagattctc gacttgccag ccgagcccgg tgggccggcc   180
tataacctga tgcatccgaa ctcttgctgc ccgcgctgca atcatccgat tcggccttgg   240
gaaaatatcc cggtgctcag ctacctgctg ctccgggggc attgtgccca ctgccgtgag   300
cccatcggcc tgcgttaccc tctcaccgaa ctggcctgcg cgctgatctg cgccgctgtc   360
gcctggcact tcggcttcgg ctggcaagcc ggcgcggtga tgctgctgag ctggggcttg   420
ctggggatga gcctgattga tctggaccac caattgctgc cggatgtgct ggtgctgccg   480
ctgctatggc tggggctgat cctcaacagc gctgacctgc tgacgccact gcccgatgca   540
gtatggggcg cggtcatcgg ctacatgagc ttgtggtgcc tgttctggct gttcaagctg   600
gccaccggca aagacggcat gggccatggc gacttcaaat tattggcctt gctgggagcc   660 tggggcgggct ggcagattct gccgatgacc ctgctgatgg cctcgctgct gggcgtgttt   720
gccgggctga ttttgctgcg tttgcgtaag gcccaggtgt cagcgccaat gccgttcggc   780
ccctgcctgg caattgccgg ctggattgca ttgctctggg gtggtcaaat aaccgacttc   840
tatttgcagt ctgtcggttt caga                                           864

<210> SEQ ID NO 110
<211> LENGTH: 510
<212> TYPE: DNA
<213> ORGANISM: Pseudomonas fluorescens

<400> SEQUENCE: 110
```

```
atgcctaatg cagccagtcg tttcggacgt ctgggctggc tcgtactgag cctgctggta    60
ctggtcatcg accaggtcag caaggctcac ttcgagggct ccctggaaat gttccagcaa   120
atcgtggtga tcccggatta cttcagttgg accctggcct acaacaccgg cgccgccttc   180
agcttcctgg ctgacggcgg tggctggcag cgctggctgt tcgcggtgat cgccgtggtg   240
gtcagtgccg tgctggtggt gtggctaaag cgtctgggcc gcgacgacac ctggctggcc   300
attgcgctgg cgctggtgct gggtggcgcg ctggtaacc tgtatgaccg catcgccctg   360
ggccatgtga tcgacttcat cctggtgcat tggcagaacc gccactactt cccggcgttc   420
aactttgccg acagcgccat taccgttggt gcaatcatgc tggcgctgga tatgttcaag   480
agcaagaaaa ccggagaaac cgtcaatgac                                    510
```

<210> SEQ ID NO 111
<211> LENGTH: 1908
<212> TYPE: DNA
<213> ORGANISM: Pseudomonas fluorescens

<400> SEQUENCE: 111

```
atggcaaaga atctgatcct gtggttgatc atcgcggctg tcctggtgac ggtgatgaac    60
aacttctcca gccctaacga gccgcagacc ctcaactatt ccgacttcat ccagcaagtt   120
aaggatggca aggtcgagcg cgtagcggtt gatggctacg tgattaccgg taagcgcaac   180
gatggcgaca gcttcaagac cattcgtcct gccattcagg acaacggtct catcggtgac   240
ctggtggata caaggtcgt tgtggaaggc aagcagcctg aacagcaaag catctggacc   300
cagctcctgg tggccagctt cccgatcctg gtgattatcg ccgtgttcat gttcttcatg   360
cgccagatgc aaggcggtgc gggaggcaag ggcgggccga tgagcttcgg caaaagcaag   420
gcgcgcctgc tctccgaaga ccaggtgaag accaccctgg ctgacgtcgc aggttgcgac   480
gaagccaagg aagaagtcgg tgagttggtc gagttcctgc gtgatcccgg caagttccag   540
cgcctgggtg gccgtattcc tcgcggtgtg ctgatggtgg ggcctccggg taccggtaaa   600
accttgctgg ccaaggcgat tgccggcgaa gccaaggtgc ctttcttcac gatttccggt   660
tctgacttcg tcgagatgtt tgtcggcgtc ggcgccagcc gtgttcgcga tatgttcgag   720
caggccaaga agcacgcgcc atgcatcatc ttcatcgacg aaatcgatgc cgttggtcgc   780
catcgtggcg cgggcatggg gggtggtcac gatgagcgtg agcagaccct caaccagttg   840
ctggtagaga tggatggttt cgagatgaat gacggcatta tcgtcatcgc cgcaaccaac   900
cgtcccgacg ttctcgaccc tgcgttgctg cgtccgggcc gtttcgaccg tcaggttgtg   960
gtcggcctgc cggacattcg tggtcgtgag cagatcctga agtacacat gcgcaaggtg  1020
ccaatgggtg acgacgtggc tccggctgtg atcgcccgtg gtactccgg ttttctccggt  1080
gctgatctgg cgaacctggt caacgaggct tcgctgttcg ctgcccgtac tggcaagcgc  1140
atcgttgaga tgaaagagtt cgaattggcg aaagacaaga tcatgatggg cgccgagcgc  1200
aaatccatgg tcatgtccga gaagagaag cagaacaccg cttatcacga ggccggtcac  1260
gccattgtag tcgcgttgt gcctgagcat gaccccgtct acaaagtgtc gatcattcct  1320
cgtggtcggg cactgggtgt gaccatgttc ctgccggaag aagatcgcta cagcctctcc  1380
aagcgtgcgc tgatcagcca gatctgctcg ctgtatggcg gtcgtattgc tgaggaaatg  1440
acccttggct tcgacggtgt gaccactggt gcctccaatg acatcatgcg tgccagccag  1500
atcgcacgaa acatggtgac caagtggggc ttgtcggaaa aactcggccc attgatgtac  1560
```

-continued

```
gccgaagagg aaggcgaagt gttcctgggg cgtggcggcg gtgggcaaag cgccagcttc      1620
tcgggtgaga cagccaagct gatcgactcc gaagttcgca gcatcattga ccagtgctat      1680
ggcacggcca agcagatttt gactgacaac cgtgacaagc tggacgccat ggctgatgcg      1740
ttgatgaagt acgaaaccat cgatgccgac cagatcgacg acatcatggc gggccgtacg      1800
ccgcgtgagc cgcgcgactg gaaggtggt tcgggtactt cgggcactcc gcctgtggtg       1860
cagaatgagc gccctgaaac gcctatcggc ggcccggcag ctgatcac                    1908
```

<210> SEQ ID NO 112
<211> LENGTH: 1182
<212> TYPE: DNA
<213> ORGANISM: Pseudomonas fluorescens

<400> SEQUENCE: 112

```
atgacccgaa ccattcccga acccgatctc gcgtatctgc aaaaagtgct gctggaaatg        60
ctcgccattc ccagccccac cggtttttacc gacaccatcg tgcgctacgt cgccgagcgc      120
ctggaagaac tcggcatccc gtttgaaatg acccggcgcg gcacgattcg cgccaccctc      180
aagggccaga aaacagccc tgaccgcgcc gtctccgcgc acctggacac catcggcgcc        240
gccgtgcgcg cgatcaagga caacggccgt ctgaccctgg cgccagtggg ctgctggtcg      300
agccgctttg ccgaaggcag ccgtgtcagc ctgttcaccg ataacggcgt gattcgcggc      360
agcgtgttgc cgctgatggc ttccgggcac gcgttcaaca ccgccgtgga tgaaatgccg      420
gtgagctggg accatgtgga actgcgcctg gacgcctact gcgccacgcg cgccgactgc      480
gattccctgg gaatcagcgt cggtgactac gtggcgttcg acccgctgcc cgagttcacc      540
gaaagcgggc atatcagcgc ccgccacttg gacgacaagg ccggcgtcgc cgcactgctc      600
gctgcgctca aggccatcgt tgacagtggc gaacccttgc tgatcgactg ccacccgctg      660
ttcaccatca ctgaggaaac cggcagtggc gcagcggccg ccctgccctg ggatgtgagt      720
gagtttgtcg gcatcgatat cgccccggtc gcccctggcc agcagtccag cgaacatgcg      780
gtgagcgtgg ccatgcagga ctccggcggc ccctatgact atcacctgtc ccgccacttg      840
ctgcgcctgg cgtcagacaa cgagctgccg gtgcgccgcg atctgttccg ctattacttc      900
agcgatgccc actcggcggt caccgccggc catgatattc gcaccgcgct gctggccttc      960
ggttgcgatg ccacccatgg ctatgagcgt acccacatcg acagcctcgc cgccctgagc     1020
cgcttgctgg gcgcttacat cctcagcccg ccggtgtttg ccagcgatgc gcaaccggcc     1080
cagggttccc tggaccggtt cagccatcag atcgagcatg aaacgcaaat ggagagcgac     1140
acccgtgtgc cgtcggtgga cagcttggtc ggccagaagt cc                        1182
```

<210> SEQ ID NO 113
<211> LENGTH: 1023
<212> TYPE: DNA
<213> ORGANISM: Pseudomonas fluorescens

<400> SEQUENCE: 113

```
atgctagtac tgggacttga aacctcctgc gacgaaaccg gagtcgcact atacgacagt        60
gaacgcgggc ttttggccga tgcactgttc agtcagatcg acctgcatcg cgcctatggc      120
ggcgtggtgc cggagcttgc cagccgcgat cacgtcaagc gcatgctgcc gctgatccgc      180
caggtgctgg atgaggccgg ctgtgtggca accgagatcg atgccatcgc ctacacggca      240
gggcccggat tggtcggagc cctgctggtt ggggcctctt gcgcccaggc gctggccttt      300
gcctggggca ttcctgccct cggcgtgcac catatggaag gccatttatt ggcgcccatg      360
```

```
ctggaaaaaa caccgccaga gttcccgttc gtcgctttgt tggtttcggg ggggcatacg      420
cagctggttc aggtggatgg gatcggccaa tacacgctgt gggcgagtc gctggacgat       480 gctgccggcg aagcgttcga caaaaccgcg aagatgatgg ggcttaatta tcctggcggt      540
ccggaaatcg cccgcctggc tgagaacggc gttgccggtc gctataccttt ccgcggccg     600 atgtgtgatc gtcctggctt gatgttcagt ttcagcggct tgaaaacctc tgccttgaac     660
acctggcagc acagcgttag cgccggggac gacggccaac aagcccgttg cgacatcgcg     720
ctggcgttcc agcaggctgt ggtggagact tgaccatca agtgcaagcg cgccctgaaa      780
caggcgggca tgaagcggct ggtgatcgca ggcggcgtca cgccaacaa ggcgttgcgc      840 agttccctgg aaaaaatgct cggtgacatg aatggcaatg tgttctacgc acgccctgag     900
ttctgcactg acaacggcgc gatgatcgcc tacgccggtt gccagcgcct gcaggccgga     960
cagcacgaaa gcctggcgat cagcgtgcag gcgcgctggc cgatggagca attgccgccg    1020
ttg                                                                   1023

<210> SEQ ID NO 114
<211> LENGTH: 2436
<212> TYPE: DNA
<213> ORGANISM: Pseudomonas fluorescens

<400> SEQUENCE: 114
atgcctgatc ctgttgctgc cagcttgcgt ctagcgcccg aagcgctgac tcgccctttc      60
tccgctgaac agttcagctt ctcgaccacc aatgatttgg agccctttcg cggtgtgctt     120
ggccaggaac gtgcggttga agccttgcag ttcgcgtgg ccatgccacg ccccggttac      180
aacgtgtttg tcatgggcga gccgggcacc ggccgctttt cgttcgtcaa acgctacctg     240
aaagccgaag gcaagcgcct gcaaaccccg gcggactggg tttatgtgaa taatttcgat     300
gagccccgcg agccccgcgc cctggaatta ccggtggcg ccgccgcggc gtttattgcc      360
gatatcaacg ccttggtgga taacctggtc gccaccttcc cggcggtgtt cgaacacccg     420
acttatcaac agcgtaaaag cgccatcgac cgggcgttca accagcgcta cgacaaagcg     480
ctggacgtga tcgaacgcct ggccttggaa aaagacgtgg cgctgtaccg cgacagctcc     540
aacatcgcct tcacgccgat gctcgacggc aaggcgctgg atgaagccga gttttcgcaa     600
ctgccggaag ccgatcgcga cgcttccac accgatatct ccgagctgga agaacgcctc     660
aacgaagagc tggccagcct gccgcagtgg aagcgcgagt ccaacaacca gctgcgccag     720
ttcaacgaag aaaccatcac cctggccctg agccgttgc tggcaccgtt gtcggaaaag     780
tatgcagaaa acgccggggt ctgtggctat ctgcaggcca tgcaggtgta cttgctcaaa     840
accgtggtcg agcaattggt ggacgacgcc aagaccgacg cccaggcgcg caagctgctt     900
gaggagcaat actgcccgag cctggtggtg ggccactcgg tcaacggtgg cgcgccggtg     960
gtgtttgaac cgcaccccgac ctacgacaac ctgttcggcc gtatcgaata cagcaccgac    1020
cagggcgcgc tctataccac ctaccgccag ctgcgtcccg gcgcgttgca ccgcgccaat    1080
ggcggcttcc tgattctgga agccgaaaaa atgctcagcg agccctttgt gtgggatgcg    1140
ctcaagcgtt ccctgcaatc gcgcaagctg aagatggaat cgcccctggg cgaactcggc    1200
cgcctggcca ccgtgaccct caaccccgcag atgattccct tgcaggtcaa ggtgatcatc    1260
atcggttcgc gccagttgta ttacgccctg caagacgccg accgggactt ccaggagatg    1320
ttccgcgtat tggtggactt cgacgaagac atccccatgg tcgacgagag cctggagcag    1380
```

| | |
|---|---|
| ttcgcccagt tgctcaaaac ccgtacttcg aagaaggca tggcgccgct gacctcggac | 1440 |
| gcggtggcgc gcctggcgac ttacagcgca cgcctggccg aacatcaagg ccgcttgtct | 1500 |
| gcgcgtattg gtgatttgtt ccagttggtc agcgaggcgg actttattcg ccacctggcg | 1560 |
| ggcgatgaga tgaccgatgc cgggcatatc gagcgcgccc tcaaggccaa ggccacgcgc | 1620 |
| accggccgtg tgtcggcgcg gattctcgac gacatgctcg ccggcgtcat cctcatcgac | 1680 |
| accgccggtg cggccgtggg caagtgcaac ggcctgacgg tgctggaagt gggcgactcg | 1740 |
| gcattcggcg tgccggcgcg gatttccgcc acggtgtacc cgggcggcag cggcattgtc | 1800 |
| gacatcgagc gcgaagttaa cctcggccag ccaattcact ccaagggcgt gatgatcctc | 1860 |
| accggttacc tgggcagccg ttatgcccag gaattcccgt tggccatctc cgccagtatt | 1920 |
| gccctggagc agtcctacgg ctatgtggac ggcgacagtg cgtccctggg cgaggcgtgc | 1980 |
| accttgatct cggccttgtc gaagacgccg ctcaagcaat gttttgccat caccggctcg | 2040 |
| atcaaccagt ttggtgaagt gcaggcggtg ggcggggtca acgagaagat cgaaggcttc | 2100 |
| ttccgcctct gcgaagcccg cgggttgacc ggtgagcagg ggcgatcat ccctcaggct | 2160 |
| aacgtcgcca cgctgatgct cgacgagaaa gtgttgcagg ctgtgcgtgc cgggcaattc | 2220 |
| catatctatg cggtgcgcca ggccgatgag gccttgagcc tgctggtggg cgaggatgcc | 2280 |
| ggcgagccgg acgccgaggg gcagttcccg gaaggcaccg tgaatgcgcg ggtggtggag | 2340 |
| cgcttgcggg cgattgccga gatgatcagt gaggaggatt tgaaggaggc ggagaaagag | 2400 |
| ctggcgcagc aggcgttggc agaagccaag ccgacc | 2436 |

<210> SEQ ID NO 115
<211> LENGTH: 8679
<212> TYPE: DNA
<213> ORGANISM: Pseudomonas fluorescens

<400> SEQUENCE: 115

| | |
|---|---|
| gtggcagtcg gcggcggttt gaacctcacg gtgggtggcg tcagcaccag cagtaccttt | 60 |
| gacggtgatc tcagcggcgc tggcggcttg atcaaggtcg gcaccggcac cctcacgctc | 120 |
| aacggaatca atggcatcac cggtaacacg gcgatcaacg cgggtaccct ggatgtcgag | 180 |
| ggttctctgg gcagcgcgtt ggtcaacgtg aatagcggcg gcactctcac cggcagtggc | 240 |
| tcgctattgg gtacggcgaa tatcaatagc ggcgggcacc tggcgctggg cagtggcacg | 300 |
| accttgtcgg ctggcggcct gaacatgagt gccggggcca gtctggatgt ggcgcttggc | 360 |
| gcaccgtcgc tgacttcgct gatgaatgtc ggtggcaacg tgaacctggc cggcgacctc | 420 |
| aatgtgagcg atgccggtgg cttcggcgct ggtgtgtatc gcatgatcaa ctacaccggc | 480 |
| ggcttgaccg gtgcgttgaa cgtcaacacg gtgccgctgg gttatggcct gggtgatcta | 540 |
| ctggtacaaa cctccgtggg cagccaggtc aacctggtgg tagcggcgcc gaatattcgt | 600 |
| ttctgggacg gcagcaacac ccttgccaac ggcactgttg acggtggcag cggcacctgg | 660 |
| acagcggggg gcaccaactg gacctcggcc gacggccttt ccaaccagac ctggggcggt | 720 |
| ggctttgcgg tgttccaagg tgctgcgggc actgtcagcg tggatggcgt acaaaccatc | 780 |
| accggtctgc aattcgtcac cgatggctac agcctggtca atggcaccgg tgggcagttg | 840 |
| agcaccggca gcggcaactt cgccgtgcgc gtcgacccac tggcgactgc caccctcggc | 900 |
| gtcgatatca ccggcgcggg cgtgctgaac aaactcgata ccggcacgct ggtgctcaat | 960 |
| ggcgccaaca gctacaccgg cggcaccttg ctcaatggcg gtacggtggt ggtcggcagc | 1020 |
| aacaccgcgc tgggcactgg cacgctgacc gctgcggcgg gcaccaccct ggacagcaac | 1080 |

```
gcctctgtaa ccctgggcaa tgatgcggta ctcaacggca gcctgacggt cggcggcagc    1140
aacgcattgg cgctcaatgg cgccatcagc ggcaccggtg gcctggtcaa gaatggcacg    1200
gcaggcctga cactcggcgg caccaatacc ttcctgggcc ctgtggcctt gaacgcaggc    1260
gggctgatcc tggcccgcaa tacgcgctg  ggcgcgggcg tgttgaatgc cgcaggcggt    1320
accaccttgg acgcgagcac ggcggtcacc actaccaacg cgatcaatct ggcgggcaac    1380
ctgggcatcg gcggcaccgc tgacctgacc ctcggcggcg caatcaacgg tgcaggcagc    1440
ctgaccaagg agggcacggc caatctgatc ctcagcggcg ccaacgccta cctgggtggc    1500
accaccctga acgccggtac gctgaccttg ggcagcgcca ccgcccttgg cctgggcaac    1560
ctcaccgttg gcggcgcggc gaccctggat aactcggcag cgctgagtgt gggcaatggc    1620
gtcgtgcttg acgccaacct cgccgtcacc ggcagcaacg acctgaccct gggtggcctg    1680
gtcaccggca cggctggcct gagcaaagac ggcgcggcca acctgaccct caatggcgtc    1740
aacaccttcc aaggcggcac cagcctcaac gccggcacgc tgaccctggg cacggcagca    1800
gccctgggta ccggcgcctt gaacgtaaac ggtgcagcta ctctggccaa cagcacaccg    1860
ctggtattgg ccaatgcggt caacctcaac gctgggctga ccgtgggcgg tctcaacaac    1920
aacctgaccc tggccggcgt gctggccggc agcggcagcc tggtcaaaac cggcacggcg    1980
gatgtgagcc tcaccggtac taacaccttc aacggcctgt tcgatgtgca atcaggcagc    2040
ctcaccacgc tgggcaacgg agcactgggt gtcggcgccg gggtcaacct ggcgagcggt    2100
acctccttga acctgggcgg cagcgccagc ctgggcgccc tcacgggtac cggtattgcc    2160
accgtaggcg ccggcagcac cttgagcgtc ggcaacaata atctggacag caccttcgac    2220
ggcatcgtgg caggcctcgg cgacctggcc aaagacggca caggcgcctt gaccctcggt    2280
ggcctcagcg tggtgaccgg ggacgcccag gtcaacgccg gcagcttgct cgtcaatggt    2340
tccctggcca cgccaacgt  ggcggtgggc agtggtgcca ccctcggtgg taccggtact    2400
ttgttgggca acgtgagcat cgccgacggc ggccacctgg ccgtcaattc cggcgcgacc    2460
ctgaccaccg ttcgctgct  gctcaatgcc aactccaacc tggatgcggg cctcggcgcg    2520
cccgcgacgg cggcaccgc  gctggtgcag gtcaacggca acctgaccct ggacggcacc    2580
ctcaacgtca ccgatatcgg cggcttcggt gcgggtatct accgcctgat cgactacacc    2640
ggcggcctga ccaacaacgg cctgctgctg gcagcctgc  cggtgaacat cccggccagc    2700
gacctggacc tgcaaaccgc gatcggcaac cagatcaacc tgctggtcaa cggcagcacc    2760
aacgtgcagt tctgggacgg cagccaaacc acgggcaatg caccatcga  aggcggcagc    2820 ggcacctgga gtgcaggcgg cagccaatgg accggcgtca acggcgcatt caacaccgcc    2880
tggaccccga cagctttgc  cgtgttccaa ggctcggcag gcaccgtcac ggttgacggc    2940
gcgcaagccg tcaccggttt gcagttcgtc acggatggct acaccctggc gggcggcgca    3000
gcgggcgcct tgaccctgtt caatggtgtg ggtggcaaca ccgccgtacg tgtcgatccc    3060
ggcgtcaccg ccaccctggg cgtcgcgctt aacggcggcg gcactctggc caagctcgac    3120
accggtaccc tggtgcttaa cggtgccaac agctacaccg cgcaccgc  cctggatggc    3180 ggcaccctgg tggtcggcaa taacagtgcc ctgggcagcg gcctcttgac caccgccaac    3240
ggcaccaccc tggacagcaa caccgcggtc agtctggcca atgcgctcaa cgtcaacggc    3300
agcctcaccc tcgcggcag  caacgccctg accctggccg gcaccgtggc gggcacgggc    3360
agcctgatca agaatggcat cgccaacctg accctcagtg caacaacac  ctatgccggc    3420
```

-continued

```
ccaaccgcac tcaacgcagg cggcctgatc ctggcctcca acacggccct gggcagtggc    3480
gctctgaacg cggccgctgg caccaccctc gacagcagca cggcggtcgc cctggccaac    3540
acggtcaatc tggccggcaa cctgggcatt ctgggcaccg ccgacctgag cctgaacggc    3600
ctggtcagcg gtagcggtgg gctgaccaaa accggcgcgg gcaacctcac gctcaacggc    3660
gccaacgcct acctgggcgg cacgcaattg aatgccggct ccctgaccct gggcaatgcg    3720
tcggccttgg gcagcggtgc cttggcggtc aatggggcaa ctaccctgga caccaacacg    3780
gcgttggccc tggccaataa caccagcctg aatgccgcgc tcaccgtcgg cggcagcaac    3840
gatctgagcc tcaacggtgt agtggacggc agtggttcgt tgatcaaggc cggtggcgcc    3900
aacctgacgc tcaacggcgc caacacctac agcggcggca cggcgctcag tgccggcacg    3960
ctgaccctcg gcagcaccac agccctgggc tcgggcgcgt tgaccgtcgg cggtacggcg    4020
accctggcca acagcacgcc gctggtgctg gccaatgcgg tcaatctcaa tggcgacctc    4080
actatcgctg gtagcaacaa cctgaccctg gccggtgtgc tcgctggcaa tgcggcgctg    4140
atcaaaaatg gcgcggcgga cctgctgctg accggcaaca acagcttcag cggcccgctg    4200
accgtggcgg cgggcagcgt gaccacgacg ggtaatggtg cactgggcac cacctccggc    4260
gtcactgtcg gcagcggcgc cagcctcaac ctgggtggca atgccaacct caacagcctg    4320
gccggcgacg gcgtggtaca ggtggctggc ggcaacacgc tggcggtggg tggcagcaac    4380
ctggataaca gctttggcgg cgcgctgaac ggtgccggca acctggataa aaacggcagc    4440
ggggtgctca acttgagcgg taccaacgcc atcagcggtg cggccaacgt caacggcggt    4500
accttgaatg tcaccggttc cctggccagc ggcacggtgg cagtgagcag cggcgcgacc    4560
ctggccggca gcggttcatt ggccggcgcg gtgaccgtgg ccgacggtgg gcacatcggc    4620
ctggcctccg gcagcacgtt gtcggtgggc tcgttggtgc tgggcggcaa ctcgaacctg    4680
gatgtcggtc tcggcactcc ggtgctgggt ggcggcacgg gctgctgaa tgtcggcggc    4740
aatctgaccc tggacggcaa cctcaatgtc accgatatcg gtggttttgg cagcggcgtc    4800
tacaacctta tcaactacac cggggccttg accgataacg gctggctct gggcacactg    4860
ccaggcagcg tggtgccggg cgacctgcaa gtgcagaccg cgatcaccaa caaggtcaac    4920
ctgctggtga ccgcgcccaa caccaccgtg cagttctggg atggcaacag cctgatcggc    4980
aacggtgcga ttgacggcgg caacggcacc tggagcgccg gcaataccaa ctggaccaat    5040
gtcgacggca ccctcaacca gggctggtc aacagctttg cggtgttcca aggcgcggca    5100
ggcaacgtga cggtggacgg cacgcagaac atcaccggca tgcagttcgt caccgacggc    5160
tacaccctgg gcgccggcac ggcgggggtg ctcaacctgg tcaatggcgg caccggcaac    5220
accgcggtgc gcgtcgaccc gaacgctacc gcgaccctgg gcgtaaccct caacggcgcc    5280
ggcaccctgg ccaagctcga cagcggcacc ctggtgctca acggcagcaa tggctacacc    5340
ggcggtaccg cgctcaatgg cggcaccctg gtggtgggca ataacagtgc cctgggcaca    5400
ggcgtcctga cggcggccgg tggtaccacc ctggacagca cgcggcggt cagcctggcc    5460
aatgcggccg tgctcaacgg tgcgttgacg gtgggtggca gcaacgcgct ggccctcaat    5520
ggtggcgtca gcggcagcgg cagcctggtg aaaaacggtg ccgccgcgct gacgcttaat    5580
ggcgtcaaca gctacagcgg cggcactggc ctgaacgccg gtcaattgat cctcggcaat    5640
aaagctgccc tggcagtgg agcattgacg gtgggcggcg cggcgcaact ggatggcagc    5700
accgatctgc aactgaccaa tgccctcaac ctggcggcc cgctgaccct ggccggcagc    5760
cacgacctgg ccctcaacgg cgtggtcagc ggcagcggca gcctggtgaa aaatggcaac    5820
```

```
ggcgccttgt tgctgaccgc tgccaacacc tacagcggcg gtaccacgct caacggcggc  5880
agcaccaccg gcaacaccac cagcctgcaa ggcgctatcg ccaacaacgc ggcattgacc  5940
tttgagcaag ccagcgacgg cacctacacc ggcaacctca ccggtaccgg cgtgttgaac  6000
aaaaccggca ccggcgcatt gttgctcagc ggcaacaaca cctttaccgg caacaccaac  6060
gtcaacaccg gcagcctgct ggtcaacggc accttgaaca gcgccgcggt gcaagtcgcc  6120
agcggtgcga ccctcggcgg cagcggtacc ctgggcggtg cggtgaacat ggctgacggc  6180
tcggtgctcc aggccggtgc cgcgacacca ctgtcggtgg ggtcgctggc cttgtcttcg  6240
ggcaccaccc tggacttcgc cctcggtgcg ccgggtgcct ccagtacagc ggtgaacgtg  6300
gcgggcaacc tgaccctgga cggcacgctc aacgtcagcg acacgggcgg cttcggtgtc  6360
ggtgtgtacc agctgttccg ctacggcggc agcttgaccg ataacggcct cacctttggc  6420
accttgccgg tggcgctggg caacctgagc ctgcaaacgg cgctggccaa ccagctcaac  6480
ctggtggtgc aaaccactcc agggcagatc cagttctgga acggcggcac caccaacccc  6540
gatggcagca tcagcggcgg cagcggtacc tggggcccag gcaccaactg gaccgacccc  6600
accggcaccc aagggcaggc gtccaccaat cagttcgcgg tatttggcgg gcagggcggc  6660
accgtgaccg tggtcggcaa ccaaggcttc actggcctgc aagtgctgga cgccggctac  6720
acgctggtcg ccgcgcagg cggcagcttg agcccgacca atgcggcgga tgcagcctg  6780 gcgccggtgc gggtcaattc cggcgtgacc gctcagattg atgcaccgct ggtgggaacc  6840
ggcggcatca acaagctgga tgcgggcacc ttgctgctga ctggcgccaa tacctacacc  6900
ggcggcacca ccgtcagtgg cggtacgctg gcgggcacca ccaccagcct gcgtggcagg  6960
atcctcaaca acgcgcggtt gttgttcgcc caacgcacca atggccagtt cagcggtacc  7020
ttgagcggca cgggtgcgct gatcaagcaa ggcgcaggcg cgctgttgct gaccggcaac  7080
cagccgttca gcggcaccgt ggcagtggaa gagggcgtgt tgcaagtggg taacgcggcc  7140
aacccaggcg cggtgcttgg cggccaagtc actgtggcca acggtgcggg gctgaccggt  7200
aacggcagtg tcggttcgct ggtcaacaac ggctcggtga cgcccgacgg tgcaagctg  7260 accgtggccg gcaacttcac caacgccagc accggtgcgc tgaacctggt gatcacccca  7320
tccaccaccg gctccctggc cgtgggcggc accgccaacc tgggcggtac cttgaatgtg  7380
gtcaacctgg ctccctatgc cggcgccacc acctacaccc tgctgacagc cggcgcggtc  7440
aacggcacct ttgccaccac caacctggag aacctggcgt tcctcacgac cgcgttgaac  7500
tacagcccaa cccaagtggc cctgcggtc agccgcaaca acgtcagcta cgccagcgtg  7560
gcggccaccg gtaaccaacg cggcgtggcg gcggcgttgg gcacaggtac cgcagtcggt  7620
ggcgcagcgg tgcaaaatgc actgcttaac ggtaatgcag cggcggcacg tgcggccttc  7680
gacagcttgt ccggcgaaat ccacgccagc accgccagcg ccatgcttga agattcgcgt  7740
tatgtgcgtg acgcggtcaa cgagcgcctg cgccaacccg gttgctaccg cgaggacgac  7800
ccgcgcaatg ctctggcccc cagcgagaac cacctgagca gcgccggttg ccacggcgag  7860
atggtcggtt ggatgcgcgt gctcggcacc tggggccata tgggcggtga cagcaacagc  7920
gccaagctga ccgcaacct cagtggcttc ctgctcggta ccgacaagca agtggacgac  7980
gcctggcgcg tgggcgtggc cgccggctac acccgcagcg acctggacgc caagcgccgc  8040
aattccagcg ccgatgtgga cagctaccac ctgatggcct acaccgccta ccagcaagaa  8100
gccttcgccg cacgcatggg cgtggcgtac agctggcatg acgttgaaag caaacgcaac  8160
```

| | |
|---|---|
| gtggccgtcg gtgccgaagg ccaacgcctc aaagccgatt acaaggcacg cagtgcgcag | 8220 |
| gtgttcggtg aagtcggcta caccattcaa acccctaccg tggccctgga accgttcgcc | 8280 |
| ggcctggcct acgtcaacta tgacagcgac acgatcaagg aaaaaggcgg ctcggcagcc | 8340 |
| ctgcgtggcg atgccgacca gggcatcacc tactcgacct gggcgtgcg cattggccag | 8400 |
| accatcaccc tgggcaacgg ctcgaaaatc accccacggg gcagcatcgg ctggcgccat | 8460 |
| gccttcggtg acaccaagcc cgacgccgac ctgagcttta tcaatggcgg tggctcgttc | 8520 |
| agcacccagg gcgtgccgat tgccaaagac agcgcggtgg tggaagcggg cctggactac | 8580 |
| cagatcagcc agaacggcag actgggcctg ggctattcgg ccagctctc gcgcaacgac | 8640 |
| aaggaccacg ccgtgacggt aagtttctcc ctcggtttc | 8679 |

<210> SEQ ID NO 116
<211> LENGTH: 1101
<212> TYPE: DNA
<213> ORGANISM: Pseudomonas fluorescens

<400> SEQUENCE: 116

| | |
|---|---|
| atgcgtgcac gtcaattggg cattacgttg gggttgggca tgcccggcga attgaatgcc | 60 |
| atcaccgatg ttcccggggt tcgcgtcggc catgccacgc tcaaggcgca ggtcgacggc | 120 |
| aagcaggtgc gtaccggcgt tacgctgatc cagccgcgtg ccggggaagc gcggcatcaa | 180 |
| ccgtgttttg ccggctacca cgtgctcaac ggcaatggtg acgccacggg gcttgaatgg | 240 |
| atcagcgagg cggggctgtt gaccacgccg atggcgatca ccaacactca cagtatcggg | 300 |
| gtggtacgcg acagcctgat cgccctggag cgcgagcggc tggcggaccc ggcggtgtac | 360 |
| tggtgtatgc cggtggtcat ggaaacctac gatggcctgc tcaacgatat ctggggccag | 420 |
| cacgtgcgcc cagagcatgt gcgccaggcc ctggaccagg cggaaagcgg cccggttcag | 480 |
| gaaggcgcgg tgggcggtgg caccggcatg atttgtcatg agttcaaggg cggcatcggc | 540 |
| accgcgtcac ggcggttgcc agcggagcag ggcggctgga ccgtcggcgt actggtgcag | 600 |
| gccaaccatg gcaagcgcca ggagctgcgg gtcgatggct acccggtggg ccgtcacttg | 660 |
| atggacattg cttcgccctt tgccgagcaa ggtaccccg gcatgggctc catcgtggtg | 720 |
| atcatcgcca cggacgcccc cttgctgccc caccagtgcc agcgcctggc acagcgtgcg | 780 |
| tccatcggca tcgcgcgcac cggtggaggc accgaggatt ccagtggtga cctgttcctg | 840 |
| gccttttgcca ccggtaacca ggatttgcca ccggccgact atgggcgcaa ggacctgccg | 900 |
| ctcagcaccg gcttgcagat ggtcaacaat gatcatattt cgccgctgtt cagcgcggcg | 960 |
| gcagaggcgg tggaggaggc gatcatcaac gccattctgg cgggtgaaga catgaccacc | 1020 |
| caagacggcg tcaaggtgcc gggcctggct ggcgaaaccc tcttggcagc cctgcaacag | 1080 |
| tgtggctgga gtatgtcccg g | 1101 |

<210> SEQ ID NO 117
<211> LENGTH: 2352
<212> TYPE: DNA
<213> ORGANISM: Pseudomonas fluorescens

<400> SEQUENCE: 117

| | |
|---|---|
| atgaagcgcg tcttgcaggt ttttgcggtg ctgattgtgc tggtcgccct gggcgccggt | 60 |
| tggtacgtct acagcaaaca acctacgcgc cagggcacgg tgacgctggc gcacctgcaa | 120 |
| ggctcggtca cggtgcgtta cgacgaccgt ggcgtaccgc atatccgcgc cgagaacgaa | 180 |
| gccgacctgt accgcgccct gggctatgtg cacgcccagg accgcctgtt ccagatggag | 240 |

```
atcatgcggc gcctggcccg tggcgaactg gccgaggtgc tggggcccaa gctgctggac      300
accgataagc tctttcgcag cctgcgcatc cgcgagcgtg ccttaagcta tgtggagcat      360
atggaccctg gctcagcctc gtccaaggcc ctgcaagcct acctggacgg gatcaatcag      420
tatcaggaca gccacgccag ccccatggag ttcgatgtgc tgggcatcgc caagcgcccg      480
tttaccgccg aagacagcat cagcgtcgcc gggtacatgg cctacagctt gccgcggcc       540 tttcgcaccg agccggtgct gacctatgtg cgtgaccggc tgggcagcga ctacttgaag      600
gtcttcgatc tcgactggca acccaagggc gcactcaacc tggcggccag cgattggcag      660
acccttggcg ccatcgccgc cctgagcgaa caggccctgg ccgacaacgg cctgccgcag      720
ttcgaaggca gcaatgcctg gccgtcagc ggcagccata cccaaagtgg caagccgttg       780
ctggcgggtg accctcatat ccgttttttcg gtgccttcgg tctggtacga ggcgcaactg     840
tcggcgccag gcttcgagct atacggctac acaacgcgc tggtaccggt ggcgttcctg       900
gggcacaacc tggacttcgg ctggagcctg accatgttcc agaacgacga cctcgacctg      960
gtcgccgaga aggtcaaccc aaacaacccc aaccaggtct ggtatcacga ccaatgggtg      1020
gacatgagca gcagcgagca gcagatccag gtcaagggcc aggcgccggt gaccctcacc      1080
ctgcgccgct cgccccacgg cccgatcatc aacgatgtgc tcggtgagaa cgccggcagc      1140
acaccgattg ccatgtggtg ggcgttcctc gacagcgaaa accgatcct cgatggtttc       1200 tatcagctca accgtgccga taccctggcc aaggcgcgtg ccgcggccgc gaaggtctcg      1260
gcgccgggcc tgaacatcgt gtgggcaaac gccaagggcg atatcggctg gtgggcggcg     1320
gcgcagttgc cgatccgccc ggccggcgtc aacccggcgt tcatcctcga cggcagtacc      1380
gcccaggccg acaagctggg tttctacccc ttcagtgcca cccccagga agaaaacccg       1440 ccgcgcggct atgtggtgtc cgccaatgcc cagccagcat cgcccaccgg catgccgatc      1500
cccggctatt acaacctggc ggatcgtggc cagcagttga acgtgcagtt gagcgacaaa      1560
agcgtgaagt gggatgtgac caacagccag gccctgcaac tgggcaccac caccgcctac      1620
ggcacgcgcc tgctggcgcc gctgttgccg gtgctgcgcg aggtggtcaa ggacccggcg      1680
caactcaaat tggtggaaca gcttgccaac tggaagggtg actacccgct ggactccacc      1740
agcgccacgc tgttcaacca gttgctgttc aacctcagcg acgcgacctt tcaccccaaa      1800
ctcggcgatg ccttgttcaa gaccttgctc ggcacccgcg tgatcgacgc cgcattgccc      1860
cgcctggccg catcggcaga ctcgccctgg tggaacggca accgcgccga taccgtcaag      1920
ctcgcctggg acaacagcct ggcccactc aaggcgacgt tcggcgatga cccggcgcaa      1980
tggcagtggg gcaaggcgca caccctgacc cacggccacc cgctgggcct gcaaaagccg      2040
ctggataaaa ttttcaacgt cggccgttc ccggcgccgg gcagccatga ggttccgaac       2100
aaccagaccg cgctgattgg cccggcaccg tggccggtga cctacggccc gtcgacacgg      2160
cgcctgatcg acttcgccga cccgacccac gccctcacca tcaacccggt ggggcaaagc      2220
ggtgtgccgt tgatacgca ctatggcgac caggcgcaga gctatatcga gggaaggtac       2280
gagcaggcgc acttcagtga tgaggaagtg acggccaata cccgcggcac cttgaaactg      2340
ctgcccgccc ga                                                          2352

<210> SEQ ID NO 118
<211> LENGTH: 2964
<212> TYPE: DNA
<213> ORGANISM: Pseudomonas fluorescens
```

<400> SEQUENCE: 118

```
atgccccgt ctccacaacg cctcgcgctc gccatcaccc tgttggccgg cggtggtttc      60
atcgaagcag ccgcagccaa gaccctgcag atcgacacgc ctaccaccca ggggcaaacc     120
ctgggtggca gtgatacgtt gaccacgtcg gcgcctggca gcattacaac ctccggggta     180
gcagtgacgc tcaaggacgg cacccgcagt gcggggtgg tggtgactaa cgcgggcaag     240
ctggtctcca gtggcggccg gggtatcgac agttcgggca gtgtcagcgg ggagcgcagg     300
tacagcattt acaaccttgc cggtggggtg atccaaggcg ccaatgatgc gttgcgcatc     360
aacagtaacg ttgccagcgg cagcgtgctg atcgacaaca gcggaccat tcgctcggcc     420
accggccaag ggctggacct ggatgcgctg cgcagcagta acgtcaccac cacgatcatc     480
aaccgtgccg gtggcttgat cgcggggag ccagcgacg gcatgaagac cggcgccaac     540
gcttctatca ctaactacgg cgagatctcc actggcgaca ccttctcccg cgatgacaag     600
ttcgatggcg tggacatcga ctccgccagc ggcgtgacgg tcaccaatta cggcctgatt     660
tccggtggcc gccatggcat caccacggac gagggcgcca cgctgaccaa ctacggcacg     720
gtgatcggcc gcaacggctc gggctttggt tccgatggcg acggcactgt ggtcaaccac     780
ggcaccatca taggcgcgtt ctccggcctg caaccggatg cgacggtga cggtgtggac     840
atcgacaaga tcgcccatat cgaaaattac ggtgttatcc agggtgtagg cgccggggt     900
gtcgacaaga acgcttcgc caacggcagc gaagggatcg ccctgggcgg tggctctctc     960
tacaacgcca aggcgcgct gatcagtggt gccagcaatg ccatcctggt ggacgacggc    1020
agcgacgggc cggggctcgc ggccaccacc ctggagaacc acggcacgat tgaaggcctg    1080
gatggctttg gcgtgaagtt cgtcggcaac tatgccgaca cggtcatcaa cagcggcacc    1140
ataagcggca gtaatggcct ggctctggat ttgggcggcg gcgatgacca gctgatcttg    1200
cgtaacggca gccgctttat cggcacggtg gacgcggca gcggttacga ccgactgacc    1260
ctggacgacg tcgccggtgg cagttttggc gacagccgca acctcgaacg gttggaggtc    1320
aagcaaggca cctggacgtt gaccggccag ggtgacttca gcgacggcgg cgagatttcc    1380
agcggtgcca cgctggtcaa ccaaggcggc attgccggta acgtgacggt cgacgcaggc    1440
ggtgtgtatg ccggcggcg ctcggtgggc agcctgctgg tcaacggcac tctgcagacc    1500
aacaccgtat tgggtaccgc cagcatcagc cgtgacttgc gcatgggcag cggctcgacc    1560
ctcgcctatg gcgtcaacgc cgacggcagt agcgcaccga tcaaggtcgg cggcaccgct    1620
taccttaatg gggcgacgct gacggtcaac cccggcgaag gcacctaccc ctggcaaagc    1680
cactacagcg tgctgcaagc cggcagcatc aatggcacgt ttggcaaggt caccagcgac    1740
tacgccttcc tgaccccgac cctggattac agcgccactc aggtcggcct tacgtacacc    1800
cgtaacgaca tcgccttcaa ccagttcgcc agcaccggca acggcgccag cgccgccaac    1860
agcctggcgg gcctgggcac gaccaacccg ctgtacaacg ccctgctcaa taccaccacc    1920
ggcacagccg gtgccgctat cgagcaactg gcgggcagca gcaccgccaa cctcaccagc    1980
gccaccctca atgccagtgc gcaagtgggc aacagcatgc tcgccgccat gcacaaggtg    2040
ggcggcggtg cgggactgct ggtagggctc aatgacaaag atacaccggt actgccgcc    2100
accggcgtgc ccgccgaggt gcgcaacctc aatgacccga atgcccgcgg ccgactgtgg    2160
ctgcaaggca tcggcagcta cggcaagctt gatggcgagc acggcagcaa cggcttgacc    2220
caacgcacca aggcacagt gctcggcgcc gattgggcg tggacagcga ctggcgcttg    2280
ggtgtgctag ggggttactc caagaccgac ctggacacca ccggtgtcga cggcagcgtc    2340
```

```
gacagctggc acgccggcgt ctatgccctg cgccagagcg gcccattggc gttgcgactg    2400
ggtgcggcct acagcgggca ccagggcgac agtaaacgca cgctggcctt cagcggtttt    2460
aacgaccgcg ccaaaggcga ctatgacgcc aacagccagc aggcttttgc ggaactgggc    2520
tacgccctgg gcagcggtcg cttgagcgca gaaccgttcg ccaacctcgg ctaccagcgc    2580
taccagcgcg acggctataa cgaaaaaggc ggcgccgctg cgttgcatgt cgacggccag    2640
acccaggaca acttcagcag caccttcggc ctgcgcctgg cccacctgag ccagctgaac    2700
aacggtgtca gcctcacacc ccgtgccagc gtcggctgga agcacaccta tggcgatgtc    2760
gacagcacca cacgccaggc tttcctggcc ggtggcacag ccttcaatgt gcaaggcagc    2820
gctctggatc gggatagcct gctgctggag gcgagcctgg atgtaggttt atccgcccgc    2880
catcgcctgg gcctgggcta taccggtgaa gtgggcagca cagccgcaa ccacgcgctc     2940 acaggccaat ggcagatgag tttt                                           2964
```

<210> SEQ ID NO 119
<211> LENGTH: 1806
<212> TYPE: DNA
<213> ORGANISM: Pseudomonas fluorescens

<400> SEQUENCE: 119

```
atgagtacgc agcctttgac ccatggaacg gttccccagc gcctggcgca cacccgtgaa      60
ctgatgcgcc gcgaaggcat tcatgccctg ctggtgccat cggcggaccc gcacctgtcc     120
gaatatttgc cggggttactg gcaagggcgt cagtggttgt ccggctttca tggttcggtg     180
ggcaccctga tcgtcacggc ggagtttgcc ggggtctggg cggacagccg ttactgggaa     240
caggcgacca aggaactcaa gggcagcggt atcgagttgg tgaagctgca accgggtcag     300
cctgggccgc tggagtggtt ggcggagcaa accctgagg gtgccgtggt ggcggtggac      360
ggcgcggtca tggccgtggc ctcggcacg accctgggtg gcaagttggc cgagcgtggc      420
gcgcgtctgc gtaccgatat cgatgtactc aatgatgtct ggcaagaccg cccggcgctg     480
ccgaaccagc cgatctatca gcatctgccg ccccaggcca cggtcagtcg tggcgagaaa     540
ctggccgctt tgcgcgccag tttgaaagac aagggcgccg actggcattt catcgcgacg     600
ctggatgaca tcgcctggct attcaacctg cgcggcgctg atgtgtcgtt caatccggtg     660
tttgtgtcct ttgccttgat caatcagcag caggcgactt tgtttgtggc gttgggcaag     720
gtcgatgcgc tctgcgggc ggtgcttgag caggatggcg tgaccctgcg tgattacagc      780
gaggtggcgc acgcgctgcg agcggtaccg gcgggcgcaa gcttgcaagt agacccggcc     840
cgcgtcaccg ccggcttgct ggaaaacctc gacgcgggcg tcaagctggt tgaaagcctc    900
aaccccacca cactgccaa atcccgcaag agcctggcag acgcggaaca tatccgccaa      960
gccatggagc aggatggtgc ggcgctgtgc gaattctttg cctggctcga cagtgccctg    1020
ggccgcgagc gcattaccga actgacgatt gacgaacacc tgaccgctgc gcgtaccgc     1080 cgcccaggct atgtatcgct aagcttcaac accattgccg ccttcaatgc caacggcgcg    1140
atgccgcatt accacgccac cgaagaagag catgcgctga tcgaaggtga tggcttgctg    1200
ttgatcgact cggcggcca gtacctgggc ggaaccacgg acatcacgcg gatggtgccc    1260
atcggtagac cgagtgagga acagaagcgc gattgcacgc gggtactcaa gggcgtgatt    1320
gccctgtccc gtgcgcagtt ccccaaaggc attctttcac cgttgctgga tgccattgcc    1380
cgggcaccga tctgggcaga aggcgtggac tacggtcacg gtacaggcca cggcgtaggt    1440
```

| | |
|---|---:|
| tatttcctca acgtgcatga gggcccgcag gtgattgcct atcaagccgc tgcggcgcca | 1500 |
| caaacggcga tgcagccagg gatgattacg tcaattgagc cgggtactta tcgccctggc | 1560 |
| cgttggggcg tgcgcattga aacctggtg ttgaaccgtg aagcgggcaa gaccgagttt | 1620 |
| ggcgaattcc tcaagttcga aaccctgacc ctgtgcccga ttgatacccg gtgcttggag | 1680 |
| ccgtcgttgc tgacggcgga tgagcgtgaa tggttcaacg cgtatcacgc ccaggtgcgt | 1740 |
| gagcgtttga cccgctgct caatggtgca gcgcttgagt ggttgcaggt gcgcactgcg | 1800 |
| gcgatt | 1806 |

<210> SEQ ID NO 120
<211> LENGTH: 2112
<212> TYPE: DNA
<213> ORGANISM: Pseudomonas fluorescens

<400> SEQUENCE: 120

| | |
|---|---:|
| atgcgttatc aattgccccc gcgtcgaatc agcatgaagc atctgttccc cagcaccgcc | 60 |
| ctcgcttttt tcattggtct cggcttcgcg tcgatgtcga ccaatacgtt cgcagccaat | 120 |
| agctgggaca accttcagcc tgatcgcgat gaggtgattg ccagccttaa cgtcgtcgag | 180 |
| ttgcttaagc gccatcacta cagcaagccg ccgctggacg acgctcgctc agtgatcatc | 240 |
| tacgacagct acctcaagct gctggacccg tcgcgcagct acttcctggc cagcgatatc | 300 |
| gctgagttcg acaagtggaa gacgcaattc gacgacttcc tcaagagcgg cgacctgcag | 360 |
| cctggcttca ccatctacaa gcgctaccta gaccgcgtca aagcgcgtct ggacttcgcc | 420 |
| ctgggtgagc tgaacaaagg cgtcgacaag ctcgatttca cccagaaaga aaccttctg | 480 |
| gtggaccgca aggacgcccc ttggctgacc agcaccgcag ccctagacga cctgtggcgc | 540 |
| aaacgcgtca aggacgaagt gctgcgcttg aagatcgccg gcaaagagcc caaggccatt | 600 |
| caagagctgt tgaccaagcg ctacaaaaac cagctggcgc gcctggacca gacccgtgcc | 660 |
| gaggatatct ccaggccta catcaacacc tttgcgatgt cctacgaccc gcacaccaat | 720 |
| tatctgtcgc cagataacgc ggaaaatttc gatatcaata tgagtctgtc cctggaaggc | 780 |
| atcggtgccg tcctgcaaag cgacaatgac caggtgaaga ttgtacgtct ggtgccggca | 840 |
| ggcccggctg acaaaaccaa gcaagtggca ccggccgaca agatcatcgg cgtggcccag | 900 |
| gccgacaaag gatggtcga tgtggtcggc tggcgcctgg acgaagtggt caagctgatc | 960 |
| cgtgggccta aaggcagcgt ggtgcgcctg gaagtgattc cgcacaccaa tgcaccgaac | 1020 |
| gaccagacca gcaagatcgt gtccatcacc cgtgaagcgg tgaagctcga agaccaggcc | 1080 |
| gtgcagaaga aagtcctcaa cctcaagcag gatggcaagg actacaagct gggggtgatt | 1140 |
| gaaatcccgg ccttctacct ggacttcaag gcgttccgtg ccggtgatcc ggactacaag | 1200 |
| tccaccaccc gcgacgtgaa gaaaatcctc acagaactgc agaaagagaa agtcgacggc | 1260 |
| gtggtcatcg acctgcgcaa caacggcggc ggctccctgc aggaagccac cgagctgacc | 1320 |
| agcctgttta tcgacaaggg cccgaccgtg ttggtacgca acgctgacgg ccgtgtcgac | 1380 |
| gtgctcgaag acgagaaccc gggggccttc tacaaagggc cgatggcgct gctggtcaac | 1440 |
| cgcctctcgg cctcggcctc ggagatttc gccggtgcca tgcaggacta ccaccgtgca | 1500 |
| ctgatcatcg gcggccagac cttcggcaaa ggcaccgtgc agaccatcca gccgctgaac | 1560 |
| catggcgagc ttaagctgac actggccaag ttctaccggg tctccgggca gagcacccag | 1620 |
| catcagggcg tactgccgga tatcgatttc ccgtcgatca tcgacaccaa ggaaattggc | 1680 |
| gaaagcgccc tgcctgaagc catgccgtgg gacaccatcc gccctgcgat caagccggcg | 1740 |

```
tcggatccgt tcaagccgtt cctggcacag ctgaaggctg accacgacac ccgctctgcc      1800
aaggatgccg agttcgtgtt tatccgcgac aagctggccc tggccaagaa gctgatggaa      1860
gagaagaccg tcagcctcaa cgaagcggat cgccgtgcac agcactccag catcgagaat      1920
cagcaactgg tgctggaaaa cacccgccgc aaggccaaag gtgaagaccc gctcaaagag      1980
ctgaagaaag aagatgaaga cgcgctgccg accgaggcgg ataaaaccaa gccggaagac      2040
gacgcctact tggccgagac tggccggatc ctgctggatt acctgaagat caccaagcag      2100
gtggccaagc ag                                                          2112

<210> SEQ ID NO 121
<211> LENGTH: 3072
<212> TYPE: DNA
<213> ORGANISM: Pseudomonas fluorescens

<400> SEQUENCE: 121
ttgctcgcga aaacgtcaa cgataacgcg ggcaacctgg atgcacgcgg cgtctgtgag        60
tgcttcgcga gcaagctcgc tcctacaggg ggaataacaa taatagggag tgtgcacatg      120
atcaccgatt caccacgttt caaacccttc accgcaggtt ccttgctctt gctgtccgtt      180
gcggcacagg cgcaatacat cgagaccggc caaccgggta accctgccag ctggcgctcg      240
gccgagtacc agagcgactg gggcctgggc cgtatgaaag ccgatgaagc ctacgccgcc      300
gggatcagcg gccagggcgt gaaaatcggc gcgctggact cagggttcga tgccaatcac      360
cccgaagccg ccaaagaccg tttccacccg gtcaccgcca ctggcaccta tgtcgatggc      420
agcgccttca gcaccaccgg cgcgctcaac ccgaacaacg attcccacgg cacccacgtc      480
accggcacca tggcgccgc ccgcgacggc gtgggtatgc atggcgttgc ttacaacgcg      540
caagtctttg tgggcaacac caacgccaac gacagcttcc tgttcggccc cacgccagac      600
cccaaatact tcaagaccgt gtacaccgca ctggtggatt ccggcgtgcg cgccatcaac      660
aacagctggg gcagccagcc caaggacgtc agctaccaga ccctggacaa catgcatgcg      720
gcgtacgccc agcattacaa ccgcggcacc tggcttgacg cggcagcgga cgtggccaag      780
gcgggcgtga tcaacgtgtt cagcgccggc aacagcggct atgccaacgc cagcgtgcgc      840
tcggccttgc cgtatttcca gccggaactg gaaggccact ggctggccgt atccgggctg      900
gataaagcca ataaccagaa atacaacaag tgcggcgttg ccaagtactg gtgtatttct      960
acccccggcg cgctgatcaa cagcactatt cccgacgggg ggtatgggt gaagtccggc      1020 acctcgatgt cagcgcccca tgccactggc gcgttggcgc tggtgatgga acgttatccc      1080
tacatgacca acgagcaagc cttgcaggtg ctgctgacca ccgccacgca gctcgacggc      1140
tcgatcaccc aggcgcctaa cgccatcgtc ggctggggcg tgcctgacct gggccggggcg      1200 atgcacggtc ctgggcaatt gctcgggccc atggaggtca acctggccgc cgggcagggc      1260
gatgtgtgga gcaacggcat ctccgaccag gcgctgcttc agcgccaggc cgaggaccgc      1320
gccgagcaca cggcctggca gcaaaccctg atcgacaagg gctggcaaaa cggcgtgggc      1380
gccactgcca gccagcagga ccagaccgac tacgccatcg gcaatgcccg cgaccaggcc      1440
gccgccaacc gcgtgtacga aggcagcctg atcaaggccg gtgccggcag tctggtgctc      1500
agcggcgaca gcacctatcg cggtgcgacc ctggtcaacg gcggtctgtt ggccgtcaat      1560
ggctcgttga cttcggcggt gacggtcaat gacagcggca ccctgggtgg ttccggacgt      1620
atcgccgcgt tgtcggtaaa cagtggcggc cgtgtggcgc caggcaattc ggtgggtaca      1680
```

```
ttgcaggtgg cggggatgt aaacctcggc gccggctcga cctatgccgt ggaactgacg    1740
cccaccagca gcgaccgcat tgtcgccggc ggccaggcta ttctgggcgg cggtaccgtt    1800
acgctggcgc tggaaaacag ccccaccttg ctcagccaga gcgaggccca agcctgatc     1860 ggccggcagt actcgattct cgaggcgcg ggcggcattc agggccagtt cgggcaagtg    1920
ctgcccaact acctgttcct cggtggcact ctggactacg ccgccaatgc cgtgcaactg    1980 aacgtgggc gcaacgacgc cagcttcgcc agcgtcggcg ccacccgcaa ccagcgcaac    2040
gtcgcagccg ccgccgagca attgggcgcc ggcaactcgg tgtatgaaag cctgctgcag    2100
tcgcaatcgg tcgccgtggc ccagcagggc ttgcagcaac tgtccgggga aatctacccg    2160
gctgtgggtg cgatgctgat caacgacagc ctgcaactgc gtaatgccgt gggcgagcgc    2220
ctgcgccatg tgccagtgac cggtgaaagc aacctgtggt tcaaagcact gggcgcctgg    2280
ggcaagaccg acagacgcac tgaaacggcg ggttccacta cctccatcgg tggcctgttg    2340
gcgggcgtgg atggcgcgct ggatgagcag acccgcgtgg tgtggtcgc cggttacagc    2400 gacagctcct tgaacatggg cagcggtacc cattcatcgg catccatcga cagctaccac    2460
tttggcgcgt acgccgggcg cgagctgggt gattggcgcc tgagcgtcgg cggtgcctac    2520
agctggcatc gcgcgatgt gaagcgcgac ctgcaatggg gggatgtcag cggcaagcaa    2580
aaaaccaagc tggacgcgac cacggcgcag gtcttcaccg aagccgcgta ccgcatccgc    2640 ctgcaagcg tggccctgga gccgttcgcc aacctggcct atgtgcatct gaacagcgag    2700
tccttccacg aaaaaggcga tgccgcggcc ctggagcgcg gcagcgaccg gcgtgacgcg    2760
gtgctcagca ccttggcgt acgtgccctg aaaaccctgg ctctcaatga ccaccagcaa    2820
ctagacctgt ccggttcgtt gggctggcaa cacagcctga cggcggtgga gtccgaagag    2880
cacttggcgt ttgtcgcggg cgggccttca tttgccgtgc gcagtgcgcc attgctgcgc    2940
gacgctgcct tggtgggcgt gcaggccagc ctggcgctga atgcatcgac acgggtcaac    3000
ctggattaca acggccaact gggtgggcgc gcgaaaaccc agggcgtggg tttgagcttg    3060
aactggcagt tc                                                         3072
```

<210> SEQ ID NO 122
<211> LENGTH: 1023
<212> TYPE: DNA
<213> ORGANISM: Pseudomonas fluorescens

<400> SEQUENCE: 122

```
atggatttc tggccgaata cgcgagcttt ctggcgaaga ccgtcaccct ggtggtcgct      60
attctggtgg tactgatcag ctttgcagcc ttgcgcagta aaggtcgtcg taaatccgcc     120
ggccaattgc aggtcagcaa gctgaatgat ttttacaagg gattgcgcga gcgcctggag    180
tcgagcctgc tcgacaaaga ccagctcaag gccctgcgca gtccgaaag caaagccgaa     240 aagaagaaag acaagaagaa gcccgaggcc aagccacggg tattcgtgct ggatttcgac    300
ggtgacatca aggcctcggc caccgaaagc ctgccatg aaatcaccgc gctgctgagc    360
ctggccacgc ccaaggatga agtggtgctg cgcctggaaa gcggcggcgg catggtgcac    420
agctatggcc tggcctcttc gcaattggcg cgtatccgcc aggccggcgt gccattgact    480
gtgtgcatcg acaaagtggc ggccagcggc ggctacatga tggcgtgcat cggcgagaag    540
atcatcagcg ctccccttcgc cattctcggt tccattggcg tggtggcgca gttgcccaac    600
gtcaatcgcg tgctgaaaaa gcacgacatc gactttgaag tgctgactgc cggtgaatac    660
aagcgcacgc tcacagtgtt cggcgaaaac accgagaagg gccggagaa gttccaggaa    720
```

```
gacctggaca ttacccacca gttgttcaag aacttcgttt cgcgctaccg cccacagttg      780
gcgattgacg aggtggctac cggtgaagtg tggctgggcg tcgccgcact cgacaagcaa      840
ctggtcgatg agctgcaaac cagcgacgaa tacctggcca ccaaggccaa gaccgccgaa      900
gtgttccacc tgcactatgc cgagcgtaag agcctgcaag agcgcgtagg cctggcagcc      960
agcggttcgg tggaccgggt gctgttgacc tggtggagcc gcttgaccca gcaacggttc     1020
tgg                                                                   1023
```

<210> SEQ ID NO 123
<211> LENGTH: 2439
<212> TYPE: DNA
<213> ORGANISM: Pseudomonas fluorescens

<400> SEQUENCE: 123

```
atggcctcgc cagccctctt acatttctt ccccggttcg gcgttgccgc ggcagtggtc       60
agtgccttgg gcctggccgg ttgccagctc cagaacaccc aggacaccct gccgccgtt      120 gctggcgtgc agccgatcaa gggcctggca cagaatgtgt cggtgcgccg caatgcccaa     180
ggcatgccgc tgatcgaaag caacactttc cacgacgctc tgttcagcct cggttacgtg     240
cacgccagcg accgcatcac ccagatggtc actctgcgcc tgctggctca gggccgtctg     300
gcggaaatgt cggccccgca agtgctggat gtcgaccgct tcatgcgggc ggtcaacctc     360
aagaaaagcg ctggcgagtt gtacaatgcc tcatcgccac gcctcagacg cttcttgaa     420 gtgtatgccc gaggcgtcaa cgcctacctg ttccgctacc gcgacaagct gccggcggac     480
ctggcccaga gcggctacaa gcccgagtac tggaagccgg aagattcggc gctgctgttc     540
tgcctgctca atttcagcca gtcgagcaac ctgcaggggg agctctcgtc cctggtgctg     600
gcgcaaaagg tcggcgtcga caaactcgcc tggctcaccc caagcgcacc ggacgaacct     660
gtcccgctgg ccgaagccga caagctcaaa ggcgtcaacc tgagccagat caccggcctc     720
gccgggctgg aaaccgtagg ccagcaattg cgcagcctca cgccctgag cgtcaccacc     780 tcaagcaact gggccattgg cccgcaacgc agccgcagcg ccaagagcct gttggccaac     840
gacatcgccg cgcagccaca agcaccgtcg ccgtggaact acgtgcagat cgtgcgcccc     900
aaataccagg ccgccggtgc ttcgattgcc ggcctgccga ccctgctctc cggtttcaac     960
ggcaaagtgg cgtggagcat gagcgcggtc aagggcgaca cccaggacct gttcctggag    1020
aaggtcaaac gccagggcaa cgcgctgtac tacgagaaca cggcaaatg gctgccggcc    1080 ggcgtgcgca acgaaacctt cttcatcaag ggccagcgct cgattcgcga agtggtgtac    1140
gaaacccgcc acggcgccct gctcaacagc agccaggcgc tcaccagcgg tcttggcctg    1200
gccttgcaaa ccgccgactt caaggacgac aagagcctgg atgcattctt cgacctgtcc    1260
cgcgcacaaa acgctggcaa agcctcggat gccacccgcg agattcgcgc catagccttg    1320
aacatgatct cgccgacgc cagcaacatc ggctggcaag tcaccggccg cttccccaac    1380
cgccgagaag gcgaaggcct gttgccatcg ccgggctggg acacgcgctt tgactgggac    1440
ggctacgccg acgcgatgct gcacccgtac gaccaagacc cggccagggg ctggatcggc    1500
accgccaacc agcgcaccgc accgcgtggc tacggcatgc aactgtccaa cgcctgggat    1560
gcaccggagc gcagcgaacg cctggcgcaa ctggcaacg ctggcaagca tgacagccgc    1620
agcctgatcg ccatgcaata cgaccagacc accctcttcg ccgccaagct caagaacatg    1680
ttccaggcgc cgggtatggc cctgcccctc aagcaggcca tcgatgcatt gccggcagcg    1740
```

```
gaacgcgcca aggcccgcga agcgctcgac cgcctgatgg ccttcgatgg tcgactggcg    1800
accacctcgg ctgacgcggc gatctatgaa ctgttcctgc aagaaagcgc ccggcagatc    1860
ttcctcgaca aactcggccc ggaaaacagc gccagctgga aagccttcgt cagcaacgtc    1920
agcctgtcct actcggccat cgccgaccac ctgctgggcc gtgaagacag cccattctgg    1980
gatgacacgc gtaccgcgca aaagaagac aaacccgcga tcctggcccg caccctggcc    2040
gccgccatca ctactggcga cagccaattg ggcgccgatc acaaggcctg gcagtggggc    2100
aagctgcaca gcaccacatg gaaaaatacc agcggccagg tcatccgcgg ccccttcgcc    2160
agcggtggcg atcacaacac cctgaacccg gcaccgtaca cctggggcca ggatttcaac    2220
gcgacccaag tatcggcgct gcgcatgatc atcgacttcg gccaggcgga accaatgatg    2280
ggccagagcg gcatcggcca atccggcaac ccggccagcc cgaactatgc caacggcatc    2340
gacccgtcgt tgaaggcgca atatctgagc tttccgatgc agccgcagaa ctttgagaag    2400
gtgtacggca agacaaggtt gaccctgacg cctggtaag                          2439
```

```
<210> SEQ ID NO 124
<211> LENGTH: 1434
<212> TYPE: DNA
<213> ORGANISM: Pseudomonas fluorescens

<400> SEQUENCE: 124
```

```
atgtcgatac cacgttttgaa gtcttactta tccatagtcg ccacagtgct ggtgctgggt      60
caggccttac ctgcgcaagc ggtcgagttg cctgacttca cccaactggt ggagcaggcc     120
tcgcctgccg tggtgaacat cagtaccacg cagaagctgc cggatcgcaa agtctcgaac     180
cagcagatgc ccgacctgga aggcttgccg ccatgctgc gcgagttctt cgaacgaggg      240
atgccgcaac cacgctcccc ccgtggcggc ggtggccagc gcgaagccca atccctgggc     300
tccggcttca tcatttcgcc tgacggctat atcctcacca caaccacgt gattgccgat      360 gccgacgaga ttctcgtgcg cctggccgac cgcagtgaac tcaaggccaa gctgattggc     420
accgatccac gttccgacgt ggccttgctt aaaatcgagg gcaaggactt gccggtgctt     480
aagctgggca gtcccagga cctgaaggcc ggtcagtggg tggtcgcgat cggttcgccg     540
ttcggctttg accacaccgt tacccaaggc atcgtcagcg ccatcggtcg cagcctgccg     600
aacgaaaact acgtaccgtt catccagacc gacgtgccga tcaacccggg taactccggt     660
ggcccgctgt tcaacctggc cggcgaagtg gtggggatca actcgcagat ctacacccgc     720
tccggcggct tcatgggcgt gtcttttcgcg atcccaatcg atgtggccat ggacgtctcc     780
aatcagctca aaagcggcgg caaggtcagc cgcggctggt tgggcgtggt aatccaggaa    840
gtgaacaagg acctggctga gtccttcggt ctcgacaagc cggccggtgc cctggttgcg     900
cagattcagg acaatggccc tgcggccaaa ggcggcctga agtcggtga cgtcatcctg      960 agcatgaacg ccagccgat catcatgtcg gcagacttgc ctcatttggt cggcgcgctc     1020
aaggccggcg gcaaagccaa gctggaagtg attcgtgatg gcaagcgcca gaacgtcgaa    1080
ctgaccgtag gtgccatccc ggaagaaggc gcgaccctgg atgccctggg caacgccaag    1140
cccggtgccg agcgcagcag taaccgcctg ggtatcgccg tggttgaact gaccgccgag    1200
cagaagaaaa ccttcgacct gcaaagcggt gtggtgatca aggaagttca ggacggccca    1260
gccgccttga tcggcctgca accgggtgac gtgatcactc acttgaacaa ccaggcaatc    1320
gataccacca aggaattcgc cgacatcgcc aaggcgttgc cgaagaatcg ctcggtgtcg    1380
atgcgcgtcc tgcgtcaagg ccgtgccagc ttcattacct tcaagctggc tgag         1434
```

<210> SEQ ID NO 125
<211> LENGTH: 1287
<212> TYPE: DNA
<213> ORGANISM: Pseudomonas fluorescens

<400> SEQUENCE: 125

| | | | |
|---|---|---|---|
| atgcgcgaag cgttgaatca aggcctgatc gacttcctca aggcctcccc tactcctttt | 60 |
| catgccactg ccgccctggc ccagcgcctg aagccgccg gctaccagcg tctcgacgag | 120 |
| cgcgacacct gggccaccga ggccaacggt cgctactacg tgacccgcaa cgattcctcg | 180 |
| atcatcgcct tcaagctcgg ccgccaatcg ccgctgcaag atggtatccg catggtcggc | 240 |
| gcccacaccg acagcccgtg cctgcgggtc aagccccagc cggagctgca acgccagggc | 300 |
| ttctggcaac tgggtgtgga agtctacggc ggcgcgctgc tggcaccctg gttcgaccgc | 360 |
| gacctgtccc tggccgggcg tgtcaccttc cgccgcgatg caaggtcga gagccaactg | 420 |
| atcgacttca agctgccgat cgccatcatt cccaacctgg ccattcacct caaccgtgaa | 480 |
| gccaaccaag gctgggcgat caatgcccag accgagctgc cgccgatcct cgcgcagttt | 540 |
| gccggtgacg agcgcgtgga ctttcgcgcc gtgctcaccg agcagttggc ccgcgagcat | 600 |
| gggttgaacg ccgatgtggt gctcgactac gagctgagtt tctacgacac ccaaagtgcc | 660 |
| gccgtgatcg gcctcaatgg cgactttatc gctggtgcgc cctgacaa cctgctgtcg | 720 |
| tgctacgccg gtttgcaggc cttgctcacc agcgacaccg atgaaacctg cgtgctggtg | 780 |
| tgcaacgacc acgaagaagt cggttcctgc tcagcctgcg gtgccgatgg cccgatgctg | 840 |
| gaacagaccc tgcgtcgcct gctgcccgaa ggtgaagaat cgtacgcac cattcagaaa | 900 |
| tccctgctgg tgtcggcaga caacgcccac ggcgtgcacc ccaactacgc cgagaaacac | 960 |
| gacgccaacc acggtccgaa actcaacgcc ggcccggtga tcaaggtcaa cagcaaccag | 1020 |
| cgctacgcca ccaacagcga aaccgccggg ttcttccgcc acctgtgcat ggcccaggaa | 1080 |
| gtgccagtgc agagcttcgt ggtgcgcagc gacatgggct gtggctcgac catcggcccc | 1140 |
| atcaccgcca gccacctagg cgtgcgcacg gtggacatcg gcttgccgac ctttgccatg | 1200 |
| cactctatcc gcgagctgtg cggcagccat gacctggcgc acctggtcaa ggtgttgggg | 1260 |
| gcgttctacg ccagtcgcga tttgccc | 1287 |

<210> SEQ ID NO 126
<211> LENGTH: 3288
<212> TYPE: DNA
<213> ORGANISM: Pseudomonas fluorescens

<400> SEQUENCE: 126

| | | | |
|---|---|---|---|
| gtgtcgattc atgtcgcgtt gcaccacgtt acgcattacc gctacgaccg tgctgttgaa | 60 |
| ctcggcccac agatcgttcg gctacgcccg gcggcccata gccgtacgcg gatcttgtct | 120 |
| tacgcgctca agtgctgcc tgagcagcac ttcatcaatt ggcagcagga cccgcagggc | 180 |
| aactacctgg cgcgcttggt attcccggaa aagaccgatg agttgcgcat tgaggtcgac | 240 |
| ctcgtcgccg aaatggcggt attcaacccg ttcgattttt tcctcgaacc ctacgccgaa | 300 |
| aaaatccct tcagctacgc cgccgatgag cagcgcgagt tggcgccata cttggaaacc | 360 |
| ttgccgctga cgccaaagtt tgccgcctat ttggccggca tcgaccgcac gccgctgccc | 420 |
| gctgtggatt cctggtggg cctcaatcag cgtctggccg cggatatcgg ttacctgatc | 480 |
| cgcatggaac cgggcgtaca aaccccggaa ttcaccttgg gcgccgcatc cggctcctgc | 540 |

```
cgggattcgg cctggctgct ggtgcaattg ctgcgcaacc tggggttggc ggcgcggttt    600
gtgtcgggct atttgatcca gctcaccgcc gacgtcaaag cccttgatgg cccgtccggc    660
accgaagtcg acttcaccga cctgcacgcc tggtgcgagg tgtacttgcc cggcgcgggc    720
tggatcggcc tggacgccac ctccgggctg ttcgccggtg aagggcatat ccccttggcc    780
tgtagccctg atccttcgtc cgccgcaccg atcagcgggc tggtggaacc ctgcgagtgc    840
gaattcaccc acgagatgtc ggtggagcgc atttgggaag cgccacgggt gaccaagccc    900
tataccgaag aacaatggct ggcgatccag gccctgggcc ggcagattga tggcgacctg    960
ctcaaggacg acgtacgcct gaccatgggc ggcgagccaa ccttcgtctc tatcgacgac   1020
cccgacggtg ccgagtggaa caccgcagcc ctgggcccgg acaagcgtcg cctgtcggcc   1080
gagctgttcc agcgcctgcg ccagcactat gcgcccaagg gcctggtgca tttcggccaa   1140
ggcaagtggt accccggcga gcaactgccg cgctggtcgc tcaattgcta ctggcgccgc   1200
gacggcgtgc cgatctggca caacagtgcg ctgattgccg atgagcaaga ggactatggc   1260
gccgatgggg tgatggccgg gcgttttcctg gccagcgtcg ccgagcgcct caaactaccg   1320
gcgcgctttg tgttcccggc gttcgaagac aatttctact acctatggcg cgaaggggcg   1380
ctgccccaga acgtcactgc ccaggacccg cgcctgagcg acgacctgga gcgtgaacgc   1440
ctgcgtaaag tgttcagcca gggcctggat aaagtcatcg ccaggtgct gccgctggca   1500
cgtactgcgg ccaatgaccg ctggcagagt gggcgttggt acctgcgcga taaccattgc   1560
cgcctggtgc cgggggattc gccgctgggc tatcgcctgc cgctcgcctc gcagccctgg   1620
gtgactgcgc cggagtatcc gtttgtgcat ccgaccgacc ctaaccagga tcagccggat   1680
ctgccgacca gcgcccagtt gcaaaaccat ggcgagcccg cgccggttga tgatcgtgtg   1740
cccaagattg acgagtccgc cgactggctg accgtaccg cgctgtgcgc cgaagcacgg   1800
gaagggcgcc tgtatctgtt tatgccgccg ctggagcgcg tcgaggacta cctggaactg   1860
gtgaccgcta tcgaggccac cgccgaagag ctgcattgcc cggtactgct ggagggctac   1920
gagccgccag cggatacgcg cctgagcaat ttccgagtga cgccagaccc tggtgtcatc   1980
gaggtcaacg tacagccgtc cgccacctgg gacgagttgg tagaacgcac cgaattcctc   2040
tacgaagagg cccggcaaac ccgcctgacc accgagaagt tcatgatcga cgggcgccat   2100
accggcaccg gtggcggtaa ccacttcgtg ctcggcggcg cgacgcccaa ggattcgccc   2160
ttcctgcgcc ggccggacct gctacgcagc ctgatcagct actggcacaa ccaccgtcg   2220
ttgtcctatt tgttctccgg cctgtttatc ggccccacct cccaggcgcc ccgggtagat   2280
gaggcgcgca acgatgcgct gtatgaactg gaaatcgcct tcgcgcagat gccggagcca   2340
ggcgaggagt gcccgccgtg gctggtggac cgcctgttgc gcaacctgct gatcgacgtg   2400
acgggtaata cccatcgcgc cgaattctgt atcgacaaac tttactcacc cgacggcgcc   2460
actggccgcc tggggctgct ggaactgcgc gcctttgaaa tgccccccca tgcgcgcatg   2520
agcctgaccc agcagttgtt gctgcgggcg ctggtcgcgc ggttctggcg cgagccctat   2580
gcgccgccga agctggcgcg ctggggcact gagctgcatg accgtttcct gttgccgcac   2640
tttatcgagc aggactttgc cgacgtgatc gtcgagctga acgcggccgg ctatccgctg   2700
cgggccgaat ggttcgcggc gcatctggag tttcgtttcc ccaaggtggg cgactacgcc   2760
gtcagcggta tcgaactgga actgcgccag gccttggagc cttggcatgt gctgggcgag   2820
gagggggcg tgggtggcac ggtgcgctat gtggattcgt ccctggagcg cctgcaagtg   2880
aagttgagcg ggttgccgcc gcaacgctac ctgctgacct gcaatggcgt gccggtgccg   2940
```

```
ctgcaagcga ccggccgcgt cggcgagttc gtggcgggcg tgcgttaccg cgcctggcag    3000
ccggccaact gcctgcaacc gaccatcccc gtgcatgcgc cactggtatt tgacctgctc    3060
gacacctgga tgcagcgttc gttgggcggc tgccaatacc atgtggcgca cccaggcggg    3120
cgcaattacg acagcctgcc ggtgaatgcc aatgaggcgg agagccggcg catggcgcgg    3180 ttttccgct  tgggcatag  cccgggcaag ctgccagtgc cgactgtaac ggtaaacgat    3240
gaattgccaa tgacgctgga tttgcggcgt ttcaaaaaaa ataaggaa                 3288

<210> SEQ ID NO 127
<211> LENGTH: 1974
<212> TYPE: DNA
<213> ORGANISM: Pseudomonas fluorescens

<400> SEQUENCE: 127
atggcgcgtt gttgtgttgc ctggcaagcc tggggaccgc ccaggctgca ccctatgtgg      60
aaaccggcaa actgggcgac gccgccagct ggcgcagcaa tgagttcaag gccgactggg     120
ggcctgggcg ccgtgcacgc cgacaccgcc tatgcggctg gctataccgg caagggcgtc     180
aagctgggga tcttcgacca gccggtatac gcccagcacc cggagttcgc cagccctgac     240
aaggtggtga cgattgtcac cgagggcatt cgccaataca ccgacccata tcccggtg      300 aaggcgggcg acgcgttccg ctacgacggc acgccgtcca aggactccaa cggcaaactg     360
ggtaaccacg gcacccacgt cggcggcatt gcggccggta accgcgatgg cgggccgatg     420
catggcgtgg cgttcaacgc acagatcctc accgccgaaa acggtgaccc ggggccggaa     480
gacgggatca tccttggcaa cgacggcgcc gtgtacaagg ccgttggga  tgggctggtc     540 gccagtggcg cacgcatcat caacaacagt tggggcatcg gcatcggtga tcagtacgcc     600
aaaggcggcc gtgatccggc gttccccaac ttcaccgtca acgaggccca ggcgcagttc     660
aataccatcc ggccgatcct tggcacccta gcaggtggtg cgtaccaagg cgccatcgac     720
gcggcccgca gcggtgtgct gaccatcttt gccgcaggca atgactacaa cctcaacaac     780
ccggatgcga tttccggcct tgcgtatttt gtgccagaga tcgcgcctaa ctggctgtcc     840
gtcgcggccc tccagcagaa cccgaatacc gccagcccg  atccgtacgt gatcagtacg     900
ttctcctcgc gttgtggtta tgcggcgagc ttttgcgtgt cggcacccgg caccaagatc     960
tacagttcga tcatcaacgg taccgacctg agcaacctca ccaccgactg gccaacaaa     1020 aacggcacct ccatggccgc acctcacgtg gcgggcgccg cagcggtgct gatggagcgc    1080
ttccagtaca tgagcggcga ccagatttcc accgtgctca agaccaccgc caccgacctc    1140
ggcgcgccgg gcatcgactc gttgtacggc tggggcatga tcaacctggg caaagcggtc    1200 aacgcccag  ggatgtttat caccgctgag gatatcccgg ccgagttccg tatcgacggc    1260
gcctacggca gcggccagtt cgtcgcggac ctgccgggtg tcggcgcggt ggtggatgcc    1320
ggcaaaccca ctcagcgtgt gtgcgacgac gtgcactgcg gcgggatgt  gtggagcaat    1380 gacatctcgg gccatggcgg cctgaccaag cagggcatcg gtaccttggt gctcaccggc    1440
gccaatacct acagcgggcc gacgcgggtc aaccagggct tgctggcgat caacggttcg    1500
gttacctccg acgtcactgt gagccagagc ggcgtggtcg gtggttcggg cgtatcggt    1560 tcgctgagcg cgaacagcgg cggcaccgtg gcgccgggca attccatcgg caccttgaac    1620
gtggcgggca acgtcaactt tgaacccggt tccacctacg cggtagaact gtcgccacc    1680 agcagcgatc gcatcgtcgc cggcggcacg gccaccctca acggcggcac cgtgaccctg    1740
```

```
gccctggaaa atagcccgac cttgttgagc gccacccagg cccaaagcct gatcggccgt    1800
cagtacaaca tcctgcaagc ggcaggtggc gtcaccggca gtttcgcggc agtggtgccc    1860
aactacctgt tgtcggcgg caccttgaac tacgccgcca acggtgtgca actggatgtg     1920
gacgcacaac gctcgccatg tggcgcagcc aacaagcgcc aggcgcgcgt gaga           1974

<210> SEQ ID NO 128
<211> LENGTH: 3726
<212> TYPE: DNA
<213> ORGANISM: Pseudomonas fluorescens

<400> SEQUENCE: 128
atggacgtag caggtaatgg cttcactgtg tcgcaacgca atcgcacccc ccgtttcaag     60
accacacccc tcacacccat agcactcggc ctggccttat ggctgggcca cggttccgtg    120
gccagggcag acgacaaccc ttacaccccg caggtactgg aatcggcgtt caggacagcc    180
gtcgcctcat tcggccctga gactgccgtg tacaaaaacc tcaggtttgc ctacgccgat    240
atcgtcgatc ttgcggccaa ggacttgcgc gcccagtccg gcaagttcga ttcggccctc    300
aagcaaaact atgagctgca acccgagaac ctgaccatcg cgccatgct cggcgacacc     360 cgtcggccac tggactacgc ctcgcgcctg gattactacc gcagccggct gttcagcaac    420
agcggccgct acaccaccaa tatcctggac ttttccaagg ccattatcgc caacttgccg    480
gccgccaagc cttacaccta cgtagagcca ggcgttagca gcaacctcaa tgggcagttg    540
aacgccggcc agtcctgggc tggcgcaacc cgtgactgga cgccaacgc gcaaacctgg     600 aagacccccg aagctcaggt caactctggc ctggaccgca ccaacgcgta ctacgcctat    660
gccttgggca tcaccggtaa gggggtgaat gtcggcgtgc tggactcggg catcttcacc    720
gaacactccg agttccaggg caagaatgcc caggccagg accgggtgca ggcggtgacc     780
tccacgggcg agtactacgc cacccatccg cgctaccgcc ttgaagtgcc cagtggtgag    840
ttcaagcagg gtgagcattt cagtatccca ggggaatacg acccggcgtt caacgacggg    900
catggcacgg agatgtccgg ggtgctggcc gccaaccgca acggcacggg tatgcacggc    960
attgccttcg acgccaacct gtttgtcgcc aacactggcg gcagcgacaa cgaccgctac   1020
caaggctcca acgacctcga ctacaacgca ttcatggcca gctacaacgc cctggcggcg   1080
aagaacgtgg cgatcgtcaa ccagagttgg gggcagagtt cgcgcgatga cgtggagaac   1140
cacttcggca acgtcggcga cagcgccgcg caaaacctgc gcgacatgac cgccgcctat   1200
cgcccgttct gggacaaggc ccatgccggg cacaaaacct ggatggacgc catggccgat   1260
gcggcccggc aaaacacgtt catccagatc atctcggcgg gcaacgacag ccacggtgcc   1320
aacccggaca ccaattcgaa cctgccgttc ttcaaaccgg atatcgaagc taagttcctc   1380
tccatcactg gctacgacga aactagcgcc caggtctaca accgctgcgg tacgtccaag   1440
tggtggtgcg tgatgggcat atcgggcatt ccatctgccg gccccgaggg cgaaatcatc   1500
ccgaatgcca acggcacctc ggccgccgca ccgagcgttt ccggggcctt ggcgctagtg   1560
atgcaacgct tcccctacat gaccgccagc caggcgcggg acgtgttgct gaccacctcc   1620
agcctgcaag cgccgatgg cccggacacg ccggttggca cgctgaccgg tggccgcacc   1680
tacgacaacc tgcaaccggt gcatgatgcc gcgccgggtt tgccgcaagt gccgggtgtg   1740
gtcagtggct ggggcttgcc caacctgcaa aaagccatgc aagggccggg gcagttcctc   1800
ggtgcggtgg cagtggcgtt gcccagtggt acccgcgata tctgggccaa cccgatttcc   1860
gatgaagcca ttcgcgcccg ccgcgtagaa gacgctgccg aacaggctac ctgggccgcc   1920
```

```
accaagcagc aaaaaggctg gctcagtggc ctgcccgcca atgcctcggc cgacgatcag    1980
tttgaatacg acatcggtca tgcccgggag caggcaacac tcacccgcgg ccaggacgtg    2040
ctcaccggca gcacctacgt cggtagcctg tcaagtccg gggatggcga gttggtgctg     2100
gaaggccaga acacctattc gggcagtact tgggtacgcg gaggcaaatt gtcggtggac    2160
ggcgcattga cctctgccgt gacggtagat agcagcgccg tgggcacgcg caatgccgat    2220
aacggcgtga tgaccacact gggcggcacc ctggccggca acggcacggt gggcgccttg    2280
accgtcaaca acggtgggcg agtggcccct gggcattcga taggcacact gcgcaccggc    2340
gatgtcacgt tcaaccccgg gttcggtgtat gccgtcgaag tcggggccga tggccgcagc    2400
gaccagttgc agagcagcgg ggtggcgacc ctcaatggcg gtgtggtgag cgtgtcccta    2460
gagaacagcc ccaacctgtt gaccgccacc gaggcgcgca gcttgctggg ccagcagttc    2520
aatatcctca gcgccagcca aggtatccag gggcagtttg cagcgttcgc ccccaactac    2580
ctgttcattg gcactgcgct gaactatcaa ccgaaccagt tgaccctggc gatagcccgc    2640
aaccagacca ccttcgccag cgtcgcgcaa acccgcaatg agcggtcggt ggcgacggta    2700
gccgagacat tggcgctgg cagcccggtc tacgaaagcc tgctggcgtc ggattccgct     2760
gcccaggcgc gggagggctt caaacaactt tcagggcaac tgcattcgga cgtggctgca    2820
gcgcaaatgg ctgacagccg ctacctgcgt gaagcggtca acgctcgcct gcaacaggcg    2880
caggcactgg actccagcgc gcagatcgac agccgtgaca acggcggctg ggtacagctg    2940
cttggtggac gcaacaacgt cagtggtgac aacaacgcca gcggctactc ctcgtccacc    3000
agcggcgtac tgctgggcct ggacaccgag gtgaacgacg gctggcgcgt gggcgcggcg    3060
accggttata cccaaagcca cctcaacggc cagtcggcgt cggcggacag cgacaactat    3120
cacctgtcgg tctatggcgg caaacgcttc gaggcgattg ccctgcgcct gggcggtgcc    3180
agcacctggc accgtctgga cacttcgcga cgggtggcct atgccaatca gtcggaccat    3240
gccaaggccg actacaacgc gcgtaccgac caagtgtttg ccgagatcgg ttacacccag    3300
tggaccgtgt ttgaaccctt cgccaacctc acgtacctga actatcaaag cgactcgttc    3360
aaggaaaaag gcggtgccgc agccttgcat gccagccagc aaagccagga cgcgacactc    3420 tccacccctgg gcgtgcgtgg tcacactcag ttgccgctca cgtccacctc ggcggtgacc    3480
ctgcgcggtg agctgggttg ggagcaccag ttcggtgata ccgatcgtga agcttctctg    3540
aagtttgccg gtagtgacac ggccttcgcc gtaaacagcg tgcctgtggc cagggatggt    3600
gcggtgatca aagccagtgc ggagatggcc ttgaccaagg acacccttgt gtcgttgaac    3660
tacagtggct tgctctccaa ccggggtaac aacaacggga tcaatgccgg gtttaccttc    3720
ctgttc                                                              3726
```

<210> SEQ ID NO 129
<211> LENGTH: 2418
<212> TYPE: DNA
<213> ORGANISM: Pseudomonas fluorescens

<400> SEQUENCE: 129

```
atgagcgacc agcaagaatt tccagattac gacctcaacg attacgccga ccccgaaaac    60
gctgaagccc cctcgtccaa tactggcctg gccttgcctg gcaaaaacct gccggacaag    120
gtttacatca tcccgatcca caaccggccg ttttttcccgg cccaagtgtt gccggtgatc    180
gtcaatgaag aaccctgggc cgaaaccctg gagctggtga gcaaatccga ccaccattcc    240
```

```
cttgcgctgt ttttcatgga cacgccgccc gatgacccac ggcacttcga cacctccgcc      300
ctgccgctgt acggcaccct ggtgaaggtg caccacgcca gccgcgagaa cggcaagctg      360
cagttcgtgg ctcagggcct gacccgcgtg cgcatcaaga cctggctcaa gcaccaccgc      420
ccaccgtacc tggtggaggt tgaatacccg caccagccca gcgagccgac cgatgaggtc      480
aaggcctacg gcatggcgct gatcaatgcg atcaaggaac tgctgcccct caacccgctg      540
tacagcgaag agttgaagaa ctacctcaac cgcttcagcc ccaacgaccc gtcgccgctt      600
accgacttcg ccgccgccct cacctcggcg accggtaatg agctgcagga agtgctggac      660
tgcgtgccca tgctcaagcg catggaaaaa gtgctgccga tgttgcgcaa agaggtagaa      720
gtcgcgcgcc tgcaaaaaga actctccgcc gaggtaaacc gcaagatcgg cgagcaccag      780
cgagagttct tcctcaagga acaactcaaa gtcatccaac aggagctggg cctgaccaag      840
gacgatcgca gcgccgacgt cgaacagttc gaacagcgcc tgcaaggcaa ggtgttgccg      900
gcccaggcac agaagcgcat cgatgaagag ctgaacaaac tgtcgatcct ggaaaccggt      960
tcgccggaat acgccgtcac gcgcaactac ctggactggg ccacctcggt gccgtggggc     1020
gtgtacggcg cagacaaact cgacctcaag cacgcgcgca aagtgctcga caagcaccat     1080
gcgggcctgg atgacatcaa gagccgcatc ctcgaattcc tcgccgtggg cgcctacaag     1140
ggcgaagtcg ccggttccat cgtgttgctg gtgggcccgc cgggcgtggg caagaccagt     1200
gtgggcaagt ccatcgccga atccctgggg cggccgttct atcgcttcag tgtcggcggc     1260
atgcgcgacg aggccgagat caagggccac cggcgcacct acatcggcgc cctgcccggc     1320
aagctggtgc aggcgttgaa agacgtggaa gtgatgaacc cggtgatcat gctcgacgag     1380
atcgataaga tgggccagag cttccagggc gacccggcgt cggcgctgct ggaaaccctg     1440
gacccggaac agaacgtcga attcctcgac cactacctgg atctgcgcct ggacctgtcc     1500
aaagtgctgt tcgtgtgcac cgccaacacc ctggactcga tcccgggccc gttgctggac     1560
cgcatgaagt gattcgcct gtcgggctat atcaccgaag aaaaagtcgc catcgccaag     1620
cgccacctgt ggcccaagca gttggaaaaa gccggcgtgg ccaaaaacag cctgaccatc     1680
agtgatggtg ccttgcgcgc gttgatcgac ggttatgcgc gagaggccgg cgtgcgtcag     1740
ttggagaagc aactgggcaa gctggtgcgc aaggcggtgg tcaagctgct ggatgaaccg     1800
gactcggtga tcaagatcgg caacaaggac ctggaaagct ccctgggcat gcccgtgttc     1860
cgtaatgaac aagtgctgtc cggcaccggc gtgattaccg gctggcctg gaccagcatg     1920 ggcggcgcca ccttgccgat cgaagcgacg cgcatccaca cgctcaaccg cggcttcaag     1980
ctcaccgggc agttgggtga agtgatgaaa gagtccgccg aaatcgccta cagctacatc     2040
agttcaaacc ttaagtcgtt tggcggcgat gcgaagttct tcgatgaagc cttcgtccac     2100
ttgcacgtac cggaaggcgc cacccccaaa gacgcccga gtgctggcgt gaccatggcc     2160
agtgcgttgc tgtccctggc ccgcaaccaa ccgccgaaaa aaggcgtggc gatgaccggc     2220
gaactgacct tgaccgggca tgtactgccg attggcggag tgcgcgagaa ggtgattgcg     2280
gcgcggcgcc agaagattca cgagttgatc ttgccggagc ccaaccgtgg cagctttgag     2340
gagttgccgg attatttgaa ggaaggcatg acggtgcact tgccaagcg gtttgcggat     2400 gtggcgaagg tgctcttc                                                 2418
```

<210> SEQ ID NO 130
<211> LENGTH: 2655
<212> TYPE: DNA
<213> ORGANISM: Pseudomonas fluorescens

<400> SEQUENCE: 130

```
atgcgcaccg aacaaccgaa gatgatttac ctgaaggact atcaggcgcc ggactacctg      60
atcgacgaga cgcacctgac cttcgagttg ttcgaggacc acagcctggt ccacgcgcag     120
ctggtgatgc gccgcaaccc cgagcgtggt accggcctgc caccgctggt gctcgatggc     180
cagcagcttg agttgctgag cgtcaccctc gcggatcagg aactgaccgc cgccgattac     240
cagctgaccg acagccacct gaccctgcag cccccgagtg aaaccttcac cctggacacc     300
acggtcaaga tccacccgga aaccaacacc gcactggaag gcttgtacaa atccagcggt     360
atgttctgca cccagtgcga ggccgaaggt ttccgcaaga tcacctatta cctcgaccgc     420
ccggatgtga tgagcgtgtt caccaccacg gtgatcgccg agcaacacag ctacccggtg     480
ctgctgtcca acggcaaccc gattgccagc ggccctggtg aagacggccg gcactgggcg     540
acctgggaag acccgttcaa aaagccggcc tacctgtttg cgctggtggc cggtgacctg     600
tggtgcgtcg aagacagctt taccaccatg accaaccgcg aagtcgcgct gcgcatctac     660
gtcgagccgg aaaatatcga caagtgccag cacgccatga ccagcctgaa aaaatccatg     720
cgctgggacg aagagaccta cggccgcgag tacgacctcg acatcttcat gatcgttgcg     780
gtcaacgact tcaacatggg cgccatggag aacaagggcc tcaacatctt caactccagc     840
gccgtgctgg cccgcgccga aaccgctaca gacgccgctc accagcgcgt cgaagccatc     900
gtcgcccacg aatacttcca caactggtcg ggtaaccgcg tgacctgccg cgactggttc     960
cagctgtcgc tcaaggaagg cttcaccgtg ttccgtgact cgggcttctc tgccgacatg    1020
aactcggcca cggtcaagcg catccaggac gtggcgtact tgcgtaccca tcagttcgct    1080
gaagatgccg gccccatggc ccatgccgtg cgccccgaca gctttatcga gatctccaac    1140
ttctacaccc tgaccgtgta tgaaaagggc tcggaagtgg tcggcatgat ccacaccttg    1200
ctcggcgccg agggctttcg caaaggcagc gacctgtatt cgaacgcca tgacggccag    1260
gccgtgacct gcgacgactt catcaaggcc atggaagacg ccaatggcgc cgacctcagc    1320
cagttcaagc gctggtacag ccaggccggc accccgcgcc tggcggtcag cgaggcctac    1380
gacgcagcgg ccaagaccta cagcctgacc ttccgccaga gttgcccgcc cactccggac    1440
aaggtcgaga aactgccctt tgtgatcccg gtggagctgg gcttgctgga cgggcagggc    1500
gccggcattg ccttgcgcct ggccggtgaa gcgacggcgg cgacacttc gcgggtaatc    1560
tcggtgaccg aagcggagca gacgtttacc ttcgtcgaca tcgctgaaaa accccttgcct    1620
tcgttgctgc gtggtttctc ggcgccggtg aagctcagct tcccctacag ccgtgatcaa    1680
ctgatgttcc tgatgcagca cgacagcgac ggtttcaacc gctgggatgc cggccagcaa    1740
ttggccgtgc aggtgctgca ggagctgatc ggccagcatc aggcgggcca gccgctgaag    1800
ctcgatcaac gcttgatcga cgcgctgcgc acggtgttga gcgatgaaag cctggaccag    1860
gccatggtcg ccgaaatgct ctcgctgccg agcgaagcct acctcaccga aatcagcgaa    1920
gtggcggatg tggacgccat ccacgctgcc cgcgagtttg cccgcaagca actggccgac    1980
aacctgttcg aagggttgtg gctgcgctac caggccaacc gcgagctgtc caagcaaacg    2040
ccatatgtgg cagaggccga gcacttcgcc cggcgtgcgc tgcagaacat cgcgctgtcg    2100
tacttgatgc tcagcggcaa gccagaagta ttggcggcca ccctggatca gttcgacacc    2160
agcgataaca tgaccgaacg cctgacggcg ttggcggtgc tggtgaactc gccgtttgaa    2220
gcagagaaag cccaggcctt ggcggtgttt gccgaaaact tcaaggacaa cccgctggtc    2280
```

```
atggaccaat ggttcagcgt acaggccggc agcaccttgc cgggcgggct ggcgcgggtc    2340
aaggcgttga tgcagcaccc ggcgttcacc atcaagaacc ccaacaaggt acgcgcgctg    2400
gtgggcgcat ttgccgggca gaacctgatc aacttccatg cggcggatgg ctcgggttac    2460
cggttcctgg cggatctggt gatccagctc aataccttga acccgcagat tgcctcgcgc    2520
caactggcgc cgctgacccg ctggcgtaaa tacgacagcg cacggcaggc gctgatgaaa    2580
gcggagctgg agcgcatcct gggcgcgggt gagctgtcca gcgatgtgtt tgaggtggtc    2640
agcaagagcc tggcg                                                    2655
```

<210> SEQ ID NO 131
<211> LENGTH: 1080
<212> TYPE: DNA
<213> ORGANISM: Pseudomonas fluorescens

<400> SEQUENCE: 131

```
gtggccgtca cgccgaacca gcgcgccgtg ccggcgccg tcgagcaatt gggcgcgggc      60
aacggtgtgt atgaaagctt gctgctggca cccacgcc cctcggccca gggcgcgttc     120
cagcaactga gcggcgaggt ttacccggcg ctggaaaccg cgctggtcaa tgacagccgc    180
tacgtgcgcg aagccgtggg cgaacgcctg cgcaacggtg aaatgggcgc tgccagccaa    240
gccatcgaca gccgtggcaa cgtgtgggtc aaggcactgg gcgcatgggg caagaccgac    300
agccgcaacg caccgcgggc tacaccacc tccatcggcg catgctcgc cggtgtggac      360 ggtgccctcg atgacgccac acgcattggc ctggtggccg gctacagcga cacgtcgctg    420
aacatgggca gcggcacccca cagccgcgct tcggtcgaca gctaccattt cggcgcctat    480
gccgggcatg aaatcggcgc ctggcgcctg agtggcggcg cgacctacag ctggcaccgc    540
gccgatgtca aacgcgacct gcaatacggc gacgtcagcg gcaagcaaaa ggccaaggtc    600
gatgcccaca gcacccaggt gttcaccgaa gctgcgtacc gcatcaacct gcaaccgctg    660
gccctggagc cgttcgccaa tctggcctac gtgcacctgg caactgacag cttcaaagag    720
aagggcgacg ccgccgcgct gagaagtggc gatgacagcc gtgacctggt gctcagcacc    780
ctgggtatgc gcgccttgaa gaccttcaat atcaacgatc accagcaact ggaagtctcc    840 ggcacccttgg gctggcagca aacctgagc agcaccgatt cggagcagca cctggcgttt    900
gcctcgggcg cccttcgtt cgctgtggaa agtgcgccaa tggtgcgcga tgctgcgttg    960
gtcggggcac gggtcagcct ggcattgagc aaggatgcgc gggtgaactt cgattacaac   1020
ggcctgctgg ccagcaagga gaaggtgcac ggcgtcggct tgagcctgga ttgggcgttc   1080
```

<210> SEQ ID NO 132
<211> LENGTH: 1149
<212> TYPE: DNA
<213> ORGANISM: Pseudomonas fluorescens

<400> SEQUENCE: 132

```
atgaccgtgg ccttgacctc catcaagatc agcaccgact tcgacagcgg caacattcag     60
gtcctggatg ccagcgacgc ttatcagttg ttgctggcaa tcaaacccga caccgcagc    120 gatcactacc aatggttcca cttcaaggcc gaaggcatgc acgtgggca cacccacacc    180 tttcgcttga gcaacgcagg cgcgctcgtcc tacaagcatg cctggagcgg ttacaacgcc    240
gtggcgtcct atgaccatat caactggttc cgggtaccga cacgttttga tggcgagatc    300
ctgcacatca ctctccagac ccggcaaaag tacgcctggt ttgcctactt cgagccctac    360
agccgtgaac gccacgactg gttgatcgag caagccctga agtacgccgg agtcacccctg    420
```

```
ctggccaccg gcaagagcgc tgaaggccgc gatatccaac tgctgcgccg tggcaaaggg      480
atcgaaggcc ggcgcaaggt gtggatcatc gcccagcagc accccggcga acacatggcc      540
gaatggttta tggagggcgt gattgagcgc ctgcaaaaag acggcgacga cgaactgaaa      600
aaactgctgg ccgtcgccga tctgtacctg gtgccgaacg tgaacccgga cggtgccttc      660
catggccacc tgcgcaccaa tgccatgggc caggacctca accgcgcctg caaagcgcc      720 agccaggaac tcagcccga gtcctgttc gtccagcaac agatggaaaa atacggcgtg      780
gatatgttcc tcgacataca cggcgatgaa gaaatcccct acgtgttcac cgccggctgc      840
gaaggcaacc tggctacac cccgcgtatc gaagccctgg aaaaacactt ccgcagccat      900
ttgagccacc tgacccggga cttccagacc acccacggct acacccgcga cctgcctggc      960
caagccaaca tgaccctggc ctgcaacgcg gtggggaaa agtacgactg cctgtccctg     1020
accctggaaa tgcccttcaa ggacaacgac gacgcgccca acctgcgaac tggctggtca     1080
ggcgatcgtt cgaaacagtt gggcaaggac gtattgagca gcatcgccga tatcgtcggg     1140
cgtttgcgc                                                             1149

<210> SEQ ID NO 133
<211> LENGTH: 1293
<212> TYPE: DNA
<213> ORGANISM: Pseudomonas fluorescens

<400> SEQUENCE: 133
atgcttcgcg ccttgataac ccttgctctt gtctgcctgc tccaaccggc gtttgccgat       60
gagcgcgcac aaacccaaca acagttggac gctacgcgtc aggacattac cgagctgaaa      120
aagctgctcg gcaagctcca ggaagaaaaa tccggggtgc agaaagacct gcgcggcacg      180
gaaaccgaaa tgggcaagct ggagaagcag gtccaggagc tgcaaaaaga actaaagaag      240
agcgagtcgg aactggagcg actcgacgct gagaaaaaaa aactccagag cgcacgcgtt      300
gaacagcaac gtctgatcgc gatccaggcc cgtgccgcgt accagagcgg ccgccaggag      360
tacctcaagc tgctgctcaa ccagcagaat ccggaaaaat cgcccgtac cctcacctat      420 tacgattacc tgagccaggc gcgcctggcg caattgaagg ggtttaacga aaccctgcgc      480
caattggcca atgtcgaaca ggaaatcgcc gaccagcaat cccagctgct cgaccagaaa      540
accgccctgg acacccagcg cgaccagctc gataaagtac gcaaggaacg ccagcaggcc      600
ctggccaagc tcaacagcga cgtaaaagcc cgcgacgcca agctccaggc ccgcgagcag      660
gaccaggcca acctggccaa agtcctcaag accatcgaag aaaccctggc ccgccaggca      720
cgcgaggccg aagaagcgcg gcaaaaagcg ctgatcgccc agcaggaagc cgaaaaaag      780 cgtcagcgtg aggctgaact ggctgccacc ccgacgctc cggccccgcg caaacccgcg      840
cgcgcagccc ctggcccgct ggtttccagc agtggcgagt cgttcggcgg ccctttgct      900 tcagcgcgcg gcaaacttcc atggccggtt gatggtcgat tactggcacg ctttggggaa      960 accgtggcg atgacacccg cgccaagtgg gatggcgtga tgatcagcgc ctctgccggc     1020
agccaggtcc acgccgtgca tggtggccgc gtggtgtttg ccgattggtt gcggggcgcc     1080
ggcttgctgg tgattcttga ccacggtaat ggctatttga gcctttacgg ccacaatcag     1140
acattactca gtcggcagg tgatgttgta aaagccggtg aatccatctc cactgtcggt     1200
aacagtggtg gccaggacac cccggcgctg tacttcgcta ttcgtcagca gggccgcccg     1260 agcgacctg cacaatggtg ccggtcccaa gga                                  1293
```

<210> SEQ ID NO 134
<211> LENGTH: 1440
<212> TYPE: DNA
<213> ORGANISM: Pseudomonas fluorescens

<400> SEQUENCE: 134

```
atgttcgaac accacgccac gctcaagaaa cacttcagcg ccctgcgcac caccgccgaa      60
ttttttctccc tgcgctacgt acgcgaatcc ggccagtacc tgtcggtgcg caagaacgtc     120
gccgagccgc ctcacctggg ccatgacgaa ggcgcgatgc tcaccgtgcg tctcaacggg     180
gtagaagcct acgccgcgac caacgatatt tcccttgccg gcctgcaagc cgcccttgag     240
cgtgctgaac agcaagcccg gttgatcaag ccccacgccc tgctcgacct gcaccagcag     300
ccggtgtcca gcgacgtcgc cgactacctg tcgcccgacc tcgaccagcc cttcccatcc     360
ctgagcgact gctaccaatt gctcggcgat gagtccgccg ccgtgcccaa ggatgagcgc     420
ctggtgagct gggaagtcag cctgggaacc acgcgggtcg aacagatcta cctcaacagc     480
gccggcgcgc aattgcgtca ggcccagcgc tttgtctttc cgggcctgag tgtgaccgcc     540
ttcgacggca acgacagcca gaccgtacc ctgggcggca ccaacttcgg ccagcaaggc     600
agtgccggcg tgatccagcg ctttggcctg gtgggcgccg cccgcaaagt ggccgacgaa     660
gccctgcaat gctgctcgc accgaatacg ccccacggcc cgcgtgacct gctgctgatg     720
cccgaccaga tgatcctgca gatccacgag tccatcggcc atccgctgga ctggatcgc     780
atcctcggtg acgagcgcaa ttacgccggc accagtttg tgaaagccag cgacttcggc     840
cacctgcaat atggctcacc gctgcttaat gtcaccttcg acccggacat ccccgaacag     900
cttgccagtt acggccatga cgacgacggc acgcctgcca gcaagcaatt tctgattcgc     960
gagggcctgc tgctcaagcc attgggcggg gccttgtcgc aatttcgcgc caacctgcca    1020
ggcgttgcca acagccgcgc ctgcggctgg aaccgtgcgc ccatcgaccg catggccaac    1080
ctgaatatcg agcctggcga taaagcctc gcgcaactgg tgggcggcat cgagaacggc    1140
atcctgatgt cgaccaaccg ttcgtggtcc atcgacgatg cgcgcaacaa gttccagttc    1200
ggctgcgagt ggggccagtt gatcgaaaac ggcgaactca agggcgtggt gaagaacccc    1260
aactaccggg cgatttccgc gcagttctgg cgcaagctca gcgcggtggg cgacgccagc    1320
accttcaagg tgttgggcac gccaaactgc ggcaaaggcg aacccaacca ggtgatccgc    1380
gtcggccatg cgtcgccggc ctgtgtattc agcaatgtcg atgtatttgg gggagatgcc    1440
```

<210> SEQ ID NO 135
<211> LENGTH: 711
<212> TYPE: DNA
<213> ORGANISM: Pseudomonas fluorescens

<400> SEQUENCE: 135

```
atgcgaatga acggtcttac acaccaatgg gttttggggt tgctcggcgc ggttgcgagc      60
agtgccgtgg ttgccgccag cagcggccag gacagtgccc gggaggaaat tgccgcccag     120
gcaaaaatcc tcgaacccag cctgttggaa accgccgcg atatccacgc ccatcccgaa     180
ctgggcaata ccgaaacccg caccgccgag ttggtcgcca acagttgcg cgaactcggc     240
cttgaagtaa agaccggggt ggcccgcact ggcgtcgtcg ccatcttgaa aggtgccctg     300
cccggcccga ccgtggccct gcgcgccgac atggatgcgc tgccggtcaa ggaagtcgcc     360
gacctgcccct tcgcctccaa agccaagggc acctacctgg caaggaagt cgacgtgatg     420
cacgcctgcg gccacgacgc acataccgct atcctgctga gcactgcgaa gattcttacg     480
```

```
gggatgcgcg agcgcctgcc cggcaccgtg gtgtttattt tccaaccggc cgaagaaggc    540
cccagcgact ttatccccga cggcaagaac acttggggcg cgaagatgat ggtgcaggaa    600
ggcgtaatga aagcgcccaa gccggatgcg gtgtttggcc tgcacgtatg ggccggtgtg    660
cctgccgggg caaatcgcct atcgcccggg cccgactttg ccagctccg a              711
```

<210> SEQ ID NO 136
<211> LENGTH: 720
<212> TYPE: DNA
<213> ORGANISM: Pseudomonas fluorescens

<400> SEQUENCE: 136

```
atgcggtgtt tggcctgcac gtatgggccg gtgtgcctgc cggggcaaat cgcctatcgc     60
ccgggcccga ctttggccag ctccgatgac ctgcgcatca aaatcctcgg caaacagacc    120
cacgccggcc gccctggga cggtatcgac ccgatcaccg tcggcgcgca aaccattgtc    180
ggcctgcaga ccgtggtcag ccgccgtacc gatatttcgt cattcccctc tgtggtgagc    240
atcggcacca tcaacggtgg cactcgctac aacatcatcc ccgagtcggt ggacatgagc    300
ggcacccttc gctcctacga ctacggcatt cgtcagaagc tgcatgcaga cgtgcgtcaa    360
accgtagaga aaatcgccga aagcggtggc gccaaggccg aagtgacaat catcgagaag    420
tacgacccca ccatcaacaa cccggcgctg accgagaaaa tgctgccgag cctgcgttgg    480
gcggctcagg atgatgtggt gcaaggccca ttggtaggtg gcgccgaaga cttctcgttc    540
tatgccaagg aagcgccggg gctgtttgtg ttcctggggg tgaccccaag ggaccaggac    600
atgagcaagg cggcgccgaa tcacaaccca gggttctttg tggatgagtc ggcattggtg    660
gtgggcgtga ggacactggc gtcgttggcg acggattacc tttacaccca cacccccctg    720
```

<210> SEQ ID NO 137
<211> LENGTH: 870
<212> TYPE: DNA
<213> ORGANISM: Pseudomonas fluorescens

<400> SEQUENCE: 137

```
ctggcgactc tggttgtgaa caacatgcgt ggtatcgtca aggttgcagc cgtcaaggct     60
ccaggcttcg cgaccgtcg caaggccatg ctgcaggaca tcgccgtatt gactggcggt    120
accgttatct ccgaagagat cggcctgagc ctggaaagcg ccaccctgga aaacctgggt    180
agcgccaagc gcgtgaccat ctccaaggaa aacaccatca tcgttgacgg tgctggcgtt    240
gaaggcgaca tcgagtcccg catcgcgcag atccgtgccc aggttgctga acctcctcg    300 gactacgacc gtgaaaaact gcaagagcgc ctggccaagc tgtccggcgg cgttgcggtg    360
atcaaggttg gcgctggttc cgaagttgaa atgaaagaga agaaggcccg cgttgaagac    420
gccttgcacg caacccgtgc agccgttgaa gaaggcgtgg tacctggcgg tggcgttgcg    480
ctgatccgtg ctctggaagc cctgaccaac ctgaccggcg acaatgccga ccagaacgtt    540
ggtatcgctg tgctgcgtcg tgccgttgaa gcaccgctgc gccagatcgc tgccaactcc    600
ggcgacgagc caagcgttgt ggtcaacgaa gtcaagaacg gcaaaggtaa ctacggttac    660
aacgctgcga ctggcgtcta cggcgacatg atcgaaatgg gcatcctgga tccaaccaag    720
gtgactcgtt cggcgctgca agcagcagcc tccatcggtg gcttgatcct gaccaccgaa    780
gctgccatcg ctgacaagcc gaaggctgaa ggcgcagctg gcgcggtat gccagacatg    840 ggcggcatgg gtggcatggg cggcatgatg                                     870
```

METHOD FOR RAPIDLY SCREENING MICROBIAL HOSTS TO IDENTIFY CERTAIN STRAINS WITH IMPROVED YIELD AND/OR QUALITY IN THE EXPRESSION OF HETEROLOGOUS PROTEINS

CROSS-REFERENCE TO RELATED APPLICATIONS

This application claims the benefit of U.S. Provisional Application No. 60/914,361, filed Apr. 27, 2007, which is hereby incorporated in its entirety by reference herein.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 342528_SequenceListing.txt, a creation date of Apr. 21, 2008 and a size of 216 KB. The sequence listing filed via EFS-Web is part of the specification and is herein incorporated by reference in its entirety.

FIELD OF THE INVENTION

This invention is in the field of protein production, particularly to identifying optimal host cells for large-scale production of properly processed heterologous proteins.

BACKGROUND OF THE INVENTION

More than 150 recombinantly produced proteins and polypeptides have been approved by the U.S. Food and Drug Administration (FDA) for use as biotechnology drugs and vaccines, with another 370 in clinical trials. Unlike small molecule therapeutics that are produced through chemical synthesis, proteins and polypeptides are most efficiently produced in living cells. However, current methods of production of recombinant proteins in bacteria often produce improperly folded, aggregated or inactive proteins, and many types of proteins require secondary modifications that are inefficiently achieved using known methods.

Numerous attempts have been developed to increase production of properly folded proteins in recombinant systems. For example, investigators have changed fermentation conditions (Schein (1989) Bio/Technology, 7:1141-1149), varied promoter strength, or used overexpressed chaperone proteins (Hockney (1994) Trends Biotechnol. 12:456-463), which can help prevent the formation of inclusion bodies.

Strategies have been developed to excrete proteins from the cell into the supernatant. For example, U.S. Pat. No. 5,348,867; U.S. Pat. No. 6,329,172; PCT Publication No. WO 96/17943; PCT Publication No. WO 02/40696; and U.S. Application Publication 2003/0013150. Other strategies for increased expression are directed to targeting the protein to the periplasm. Some investigations focus on non-Sec type secretion (see for e.g. PCT Publication No. WO 03/079007; U.S. Publication No. 2003/0180937; U.S. Publication No. 2003/0064435; and, PCT Publication No. WO 00/59537). However, the majority of research has focused on the secretion of exogenous proteins with a Sec-type secretion system.

A number of secretion signals have been described for use in expressing recombinant polypeptides or proteins. See, for example, U.S. Pat. No. 5,914,254; U.S. Pat. No. 4,963,495; European Patent No. 0 177 343; U.S. Pat. No. 5,082,783; PCT Publication No. WO 89/10971; U.S. Pat. No. 6,156,552; U.S. Pat. Nos. 6,495,357; 6,509,181; 6,524,827; 6,528,298; 6,558,939; 6,608,018; 6,617,143; U.S. Pat. Nos. 5,595,898; 5,698,435; and 6,204,023; U.S. Pat. No. 6,258,560; PCT Publication Nos. WO 01/21662, WO 02/068660 and U.S. Application Publication 2003/0044906; U.S. Pat. No. 5,641,671; and European Patent No. EP 0 121 352.

Heterologous protein production often leads to the formation of insoluble or improperly folded proteins, which are difficult to recover and may be inactive. Furthermore, the presence of specific host cell proteases may degrade the protein of interest and thus reduce the final yield. There is no single factor that will improve the production of all heterologous proteins. As a result, there is a need in the art for identifying improved large-scale expression systems capable of secreting and properly processing recombinant polypeptides to produce transgenic proteins in properly processed form.

SUMMARY OF THE INVENTION

The present invention provides compositions and methods for rapidly identifying a host cell population capable of producing at least one heterologous polypeptide according to a desired specification with improved yield and/or quality. The compositions comprise two or more host cell populations that have been genetically modified to increase the expression of one or more target genes involved in protein production, decrease the expression of one or more target genes involved in protein degradation, express a heterologous gene that affects the protein product, or a combination. The ability to express a polypeptide of interest in a variety of modified host cells provides a rapid and efficient means for determining an optimal host cell for the polypeptide of interest. The desired specification will vary depending on the polypeptide of interest, but includes yield, quality, activity, and the like.

It is recognized that the host cell populations may be modified to express many combinations of nucleic acid sequences that affect the expression levels of endogenous sequences and/or exogenous sequences that facilitate the expression of the polypeptide of interest. In one embodiment, two or more of the host cell populations has been genetically modified to increase the expression of one or more target genes involved in one or more of the proper expression, processing, and/or translocation of a heterologous protein of interest. In another embodiment, the target gene is a protein folding modulator. In another embodiment, the protein folding modulator is selected from the list in Table 1.

In another embodiment, one or more of the host cell populations has been genetically modified to decrease the expression of one or more target genes involved in proteolytic degradation. In another embodiment, the target gene is a protease. In another embodiment, the protease is selected from the list in Table 2.

In one embodiment, nucleotide sequences encoding the proteins of interest are operably linked to a *P. fluorescens* Sec system secretion signal as described herein. One or more of the strains in the array may express the heterologous protein of interest in a periplasm compartment. In certain embodiments, one or more strains may also secrete the heterologous protein extracellularly through an outer cell wall.

Host cells include eukaryotic cells, including yeast cells, insect cells, mammalian cells, plant cells, etc., and prokaryotic cells, including bacterial cells such as *P. fluorescens*, *E. coli*, and the like.

As indicated, the library of host cell populations can be rapidly screened to identify certain strain(s) with improved yield and/or quality of heterologously expressed protein. The strain arrays are useful for screening for improved expression of any protein of interest, including therapeutic proteins, hormones, a growth factors, extracellular receptors or ligands, proteases, kinases, blood proteins, chemokines, cytokines, antibodies and the like.

DETAILED DESCRIPTION

Figure 1A:
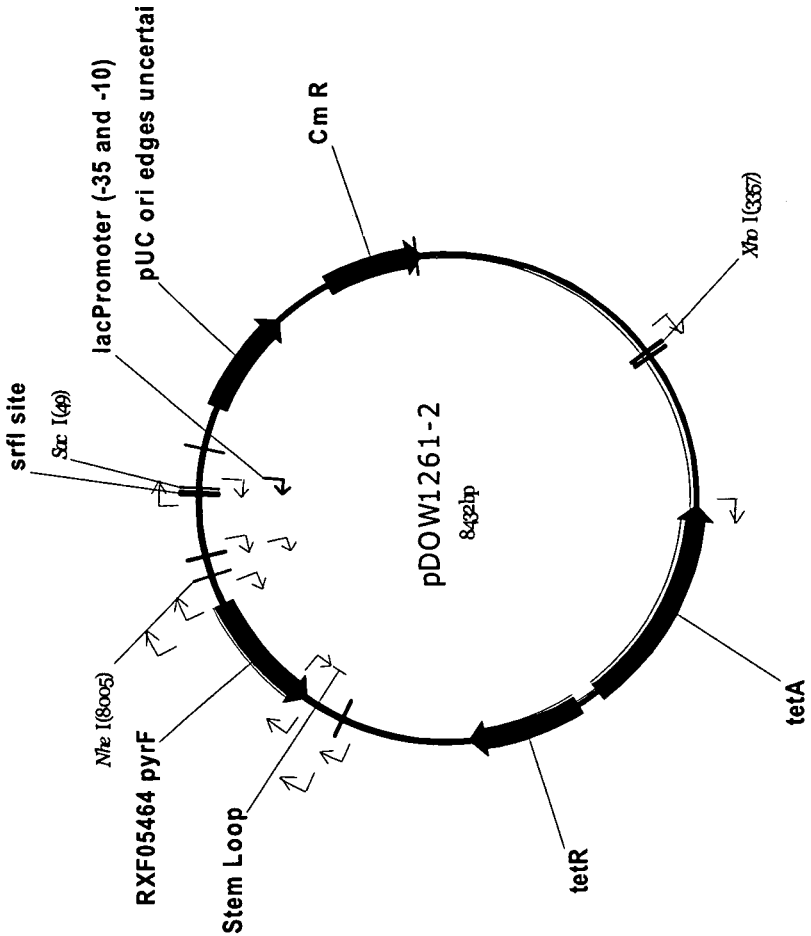
FIG. 1A depicts plasmid pDOW1261-2 used for engineering genomic deletion in *P. fluorescens*.

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements.

Many modifications and other embodiments of the inventions set forth herein will come to mind to one skilled in the art to which these inventions pertain having the benefit of the teachings presented in the foregoing descriptions and the associated drawings.

Therefore, it is to be understood that the inventions are not to be limited to the specific embodiments disclosed and that modifications and other embodiments are intended to be included within the scope of the invention. Although specific terms are employed herein, they are used in a generic and descriptive sense only and not for purposes of limitation.

Overview

Compositions and methods for identifying an optimal host strain, e.g, a *Pseudomonas fluorescens* host strain, for producing high levels of properly processed heterologous polypeptides in a host cell are provided. In particular, a library (or "array") of host strains is provided, wherein each strain (or "population of host cells") in the library has been genetically modified to modulate the expression of one or more target genes in the host cell. An "optimal host strain" can be identified or selected based on the quantity, quality, and/or location of the expressed protein of interest compared to other populations of phenotypically distinct host cells in the array. Thus, an optimal host strain is the strain that produces the polypeptide of interest according to a desired specification. While the desired specification will vary depending on the polypeptide being produced, the specification includes the quality and/or quantity of protein, whether the protein is sequestered or secreted, protein folding, and the like.

"Heterologous," "heterologously expressed," or "recombinant" generally refers to a gene or protein that is not endogenous to the host cell or is not endogenous to the location in the native genome in which it is present, and has been added to the cell by infection, transfection, microinjection, electroporation, microprojection, or the like.

One or more of the host cell populations in the array is modified to modulate the expression of one or more target genes in the host cell. By "target gene" is intended a gene that affects heterologous protein production in a host cell. Target genes that affect heterologous protein production include genes encoding proteins that modulate expression, activity, solubility, translocation, proteolytic degradation and/or cleavage of the heterologous protein. For example, a target gene may encode at least one of a host cell protease, a protein folding modulator, a transcription factor, a translation factor, a secretion modulator, or any other protein involved in the proper transcription, translation, processing, and/or translocation of a heterologous protein of interest. A "target protein" refers to the protein or polypeptide resulting from expression of the target gene. Expression and/or activity of a target gene or genes is increased or decreased, depending on the function of the target gene or protein. For example, expression of one or more host cell proteases may be decreased, whereas expression of one or more protein folding modulators may be increased.

The arrays described herein are useful for rapidly identifying an optimal host cell for production of a heterologous protein or peptide of interest. Heterologous protein production often leads to the formation of insoluble or improperly folded proteins, which are difficult to recover and may be inactive. Furthermore, the presence of specific host cell proteases may degrade the protein of interest and thus reduce the final yield. There is no single host cell population that will optimally produce all polypeptides or proteins of interest. Thus, using the compositions and methods of the invention, an optimal host cell can be rapidly and efficiently identified from the library of modified cell populations. The optimal host strain can then be used to produce sufficient amounts of the protein of interest or for commercial production. Likewise, a host strain can be modified for expression of the protein of interest based on the optimal host strain.

In one embodiment, the method includes obtaining an array comprising at least a first and a second population of *P. fluorescens* cells, wherein each population is selected from the group consisting of (i) a population of *P. fluorescens* cells that has been genetically modified to reduce the expression of at least target gene involved in protein degradation; (ii) a population of *P. fluorescens* cells that has been genetically modified to increase the expression of at least one target gene involved in protein production; and, (iii) a population of *P. fluorescens* cells that has been genetically modified to reduce the expression of at least one target gene involved in protein degradation and to increase the expression of at least one target gene involved in protein production; introducing into at least one cell of each population an expression construct comprising at least one gene encoding at least one heterologous protein of interest; maintaining said cells under conditions sufficient for the expression of said protein of interest in at least one population of cells; and selecting the optimal population of cells in which the heterologous protein of interest is produced; wherein each population in the array is non-identical and wherein each population is physically separate from one from another; wherein the heterologous protein of interest exhibits one or more of improved expression, improved activity, improved solubility, improved translocation, or reduced proteolytic degradation or cleavage in the optimal population of cells compared to other populations in the array.

The array may further comprise a population of host cells (e.g., *P. fluorescens* host cells) that has not been genetically modified to alter the expression of a host cell protease or a protein folding modulator. This population may be a wild-type strain, or may be a strain that has been genetically modified to alter the expression of or more genes not involved in protein production, processing, or translocation (e.g., may be genetically modified to express, for example, a selectable marker gene).

In one embodiment, each population of *P. fluorescens* host cells is phenotypically distinct (i.e., "non-identical") one from another. By "phenotypically distinct" is intended that each population produces a measurably different amount of one or more target proteins. In this embodiment, each strain has been genetically modified to alter the expression of one or more different target genes. Where the expression of more than one target gene is modulated in a population of host cells, then the combination of target genes is phenotypically distinct from other populations in the library. An array comprising a plurality of phenotypically distinct populations of host cells according to the present invention is one that provides a diverse population from which to select one or more strains useful for producing a heterologous protein or peptide of interest. It will be understood by one of skill in the art that such an array may also comprise replicates (e.g., duplicates, triplicates, etc.) of any one or more populations of host cells.

Arrays

Provided herein is an array of host cell populations (i.e. "strain array") which can be rapidly screened to identify certain strain(s) with improved yield and/or quality of heterologous protein. As used herein, the term "strain array" refers to a plurality of addressed or addressable locations (e.g., wells, such as deep well or microwells). The location of each of the microwells or groups of microwells in the array is typically known, so as to allow for identification of the optimal host cell for expression of the heterologous protein of interest.

The strain array comprises a plurality of phenotypically distinct host strains. The arrays may be low-density arrays or high-density arrays and may contain about 2 or more, about 4 or more, about 8 or more, about 12 or more, about 16 or more, about 20 or more, about 24 or more, about 32 or more, about 40 or more, about 48 or more, about 64 or more, about 72 or more, about 80 or more, about 96 or more, about 192 or more, about 384 or more host cell populations.

The host cell populations of the invention can be maintained and/or screened in a multi-well or deep well vessel. The vessel may contain any desired number of wells, however, a miniaturized cell culture microarray platform is useful for screening each population of host cells individually and simultaneously using minimal reagents and a relatively small number of cells. A typical multi-well, microtiter vessel useful in this assay is a multi-well plate including, without limitation, 10-well plates, 28-well plates, 96-well plates, 384-well plates, and plates having greater than 384 wells. Alternatively, an array of tubes, holders, cartridges, minitubes, microfuge tubes, cryovials, square well plates tubes, plates, slants, or culture flasks may also be used, depending on the volume desired.

The vessel may be made of any material suitable for culturing and/or screening a host cell of interest, e.g., *Pseudomonas*. For example, the vessel can be a material that can be easily sterilized such as plastic or other artificial polymer material, so long as the material is biocompatible. Any number of materials can be used, including, but not limited to, polystyrene; polypropylene; polyvinyl compounds (e.g. polyvinylchloride); polycarbonate (PVC); polytetrafluoroethylene (PTFE); polyglycolic acid (PGA); cellulose; glass; fluoropolymers, fluorinated ethylene propylene, polyvinylidene, polydimethylsiloxane, silicon, and the like.

Automated transformation of cells and automated colony pickers will facilitate rapid screening of desired cells. The arrays may be created and/or screened using a spotter device (e.g., automated robotic devices) as known in the art.

Target Genes

The strain array of the present invention comprises a plurality of phenotypically and genotypically distinct host cell populations, wherein each population in the array has been genetically modified to modulate the expression of one or more target genes in the host cell. By "target gene" is intended a gene that affects heterologous protein production in a host cell. A target gene may encode a host cell protease or an endogenous or exogenous protein folding modulator, transcription factor, translation factor, secretion modulator, or any other gene involved in the proper expression, processing, and/or translocation of a heterologous protein of interest. A "target protein" refers to the protein or polypeptide resulting from expression of the target gene. Expression and/or activity of a target gene or genes is increased or decreased, depending on the function of the target gene or protein. A target gene can be endogenous to the host cell, or can be a gene that is heterologously expressed in each of the host cell populations in the array.

In one embodiment, the target gene or genes is at least one protein folding modulator, putative protein folding modulator, or a cofactor or subunit of a folding modulator. In some embodiments, the target gene or genes can be selected from a chaperone protein, a foldase, a peptidyl prolyl isomerase and a disulfide bond isomerase. In some embodiments, the target gene or genes can be selected from htpG, cbpA, dnaJ, dnaK and fkbP. Exemplary protein folding modulators from *P. fluorescens* are listed in Table 1.

In other embodiments, the target gene comprises at least one putative protease, a protease-like protein, or a cofactor or subunit of a protease. For example, the target gene or genes can be a serine, threonine, cysteine, aspartic or metallopeptidase. In one embodiment, the target gene or genes can be selected from hslV, hslU, clpA, clpB and clpX. The target gene can also be a cofactor of a protease. Exemplary proteases from *P. fluorescens* are listed in Table 2. Proteases from a variety of organisms can be found in the MEROPS Peptidase Database maintained by the Welcome Trust Sanger Institute, Cambridge, UK (Rawlings et. al., 2006, Nucleic Acids Research 34 (Database issue): D270 2).

Protein Folding Modulators

Another major obstacle in the production of heterologous proteins in host cells is that the cell often is not adequately equipped to produce either soluble or active protein. While the primary structure of a protein is defined by its amino acid sequence, the secondary structure is defined by the presence of alpha helices or beta sheets, and the ternary structure by covalent bonds between adjacent protein stretches, such as disulfide bonds. When expressing heterologous proteins, particularly in large-scale production, the secondary and tertiary structure of the protein itself is of critical importance. Any significant change in protein structure can yield a functionally inactive molecule, or a protein with significantly reduced biological activity. In many cases, a host cell expresses protein folding modulators (PFMs) that are necessary for proper production of active heterologous protein. However, at the high levels of expression generally required to produce usable, economically satisfactory biotechnology products, a cell often cannot produce enough native protein folding modulator or modulators to process the heterologously-expressed protein.

In certain expression systems, overproduction of heterologous proteins can be accompanied by their misfolding and segregation into insoluble aggregates. In bacterial cells these aggregates are known as inclusion bodies. In *E. coli*, the network of folding modulators/chaperones includes the Hsp70 family. The major Hsp70 chaperone, DnaK, efficiently prevents protein aggregation and supports the refolding of damaged proteins. The incorporation of heat shock proteins into protein aggregates can facilitate disaggregation. However, proteins processed to inclusion bodies can, in certain cases, be recovered through additional processing of the insoluble fraction. Proteins found in inclusion bodies typically have to be purified through multiple steps, including denaturation and renaturation. Typical renaturation processes for inclusion body targeted proteins involve attempts to dissolve the aggregate in concentrated denaturant and subsequent removal of the denaturant by dilution. Aggregates are frequently formed again in this stage. The additional processing adds cost, there is no guarantee that the in vitro refolding will yield biologically active product, and the recovered proteins can include large amounts of fragment impurities.

The recent realization that in vivo protein folding is assisted by molecular chaperones, which promote the proper isomerization and cellular targeting of other polypeptides by transiently interacting with folding intermediates, and by foldases, which accelerate rate-limiting steps along the folding pathway, has provided additional approaches to combat the problem of inclusion body formation (see for e.g. Thomas J G et al. (1997) *Appl Biochem Biotechnol* 66:197-238).

In certain cases, the overexpression of chaperones has been found to increase the soluble yields of aggregation-prone proteins (see Baneyx, F. (1999) *Curr. Opin. Biotech.* 10:411-421 and references therein). The beneficial effect associated with an increase in the intracellular concentration of these chaperones appears highly dependent on the nature of the overproduced protein, and may not require overexpression of the same protein folding modulator(s) for all heterologous proteins.

Protein folding modulators, including chaperones, disulfide bond isomerases, and peptidyl-prolyl cis-trans isomerases (PPIases) are a class of proteins present in all cells which aid in the folding, unfolding and degradation of nascent polypeptides.

Chaperones act by binding to nascent polypeptides, stabilizing them and allowing them to fold properly. Proteins possess both hydrophobic and hydrophilic residues, the former are usually exposed on the surface while the latter are buried within the structure where they interact with other hydrophilic residues rather than the water which surrounds the molecule. However in folding polypeptide chains, the hydrophilic residues are often exposed for some period of time as the protein exists in a partially folded or misfolded state. It is during this time when the forming polypeptides can become permanently misfolded or interact with other misfolded proteins and form large aggregates or inclusion bodies within the cell. Chaperones generally act by binding to the hydrophobic regions of the partially folded chains and preventing them from misfolding completely or aggregating with other proteins. Chaperones can even bind to proteins in inclusion bodies and allow them to disaggregate (Ranson et. al. 1998). The GroES/EL, DnaKJ, Clp, Hsp90 and SecB families of folding modulators are all examples of proteins with chaperone like activity.

Another important type of folding modulator is the disulfide bond isomerases. These proteins catalyze a very specific set of reactions to help folding polypeptides form the proper intra-protein disulfide bonds. Any protein that has more than two cysteines is at risk of forming disulfide bonds between the wrong residues. The disulfide bond formation family consists of the Dsb proteins which catalyze the formation of disulfide bonds in the non-reducing environment of the periplasm. When a periplasmic polypeptide misfolds disulfide bond isomerase, DsbC is capable of rearranging the disulfide bonds and allowing the protein to reform with the correct linkages.

The proline residue is unique among amino acids in that the peptidyl bond immediately preceding it can adopt either a cis or trans conformation. For all other amino acids this is not favored due to steric hindrance. Peptidyl-prolyl cis-trans isomerases (PPIases) catalyze the conversion of this bond from one form to the other. This isomerization may aid in protein folding, refolding, assembly of subunits and trafficking in the cell (Dolinski, et. al. 1997).

In addition to the general chaperones which seem to interact with proteins in a non-specific manner, there are also chaperones which aid in the folding of specific targets. These protein-specific chaperones form complexes with their targets, preventing aggregation and degradation and allowing time for them to assemble into multi-subunit structures. The PapD chaperone is one well known example of this type (Lombardo et. al. 1997).

Folding modulators also include, for example, HSP70 proteins, HSP110/SSE proteins, HSP40 (DNAJ-related) proteins, GRPE-like proteins, HSP90 proteins, CPN60 and CPN10 proteins, Cytosolic chaperoning, HSP100 proteins, Small HSPs, Calnexin and calreticulin, PDI and thioredoxin-related proteins, Peptidyl-prolyl isomerases, Cyclophilin PPIases, FK-506 binding proteins, Parvulin PPIases, Individual chaperoning, Protein specific chaperones, or intramolecular chaperones. Folding modulators are generally described in "Guidebook to Molecular Chaperones and Protein-Folding Catalysts" (1997) ed. M. Gething, Melbourne University, Australia.

The best characterized molecular chaperones in the cytoplasm of *E. coli* are the ATP-dependent DnaK-DnaJ-GrpE and GroEL-GroES systems. Based on in vitro studies and homology considerations, a number of additional cytoplasmic proteins have been proposed to function as molecular chaperones in *E. coli*. These include ClpB, HtpG and IbpA/B, which, like DnaK-DnaJ-GrpE and GroEL-GroES, are heat-shock proteins (Hsps) belonging to the stress regulon. The trans conformation of X-Pro bonds is energetically favored in nascent protein chains; however, approximately 5% of all prolyl peptide bonds are found in a cis conformation in native proteins. The trans to cis isomerization of X-Pro bonds is rate limiting in the folding of many polypeptides and is catalyzed in vivo by peptidyl prolyl cis/trans isomerases (PPIases). Three cytoplasmic PPIases, SlyD, SlpA and trigger factor (TF), have been identified to date in *E. coli*. TF, a 48 kDa protein associated with 50S ribosomal subunits that has been postulated to cooperate with chaperones in *E. coli* to guarantee proper folding of newly synthesized proteins. At least five proteins (thioredoxins 1 and 2, and glutaredoxins 1, 2 and 3, the products of the trxA, trxc, grxA, grxB and grxC genes, respectively) are involved in the reduction of disulfide bridges that transiently arise in cytoplasmic enzymes. Thus, target genes can be disulfide bond forming proteins or chaperones that allow proper disulfide bond formation.

TABLE 1

*P. fluorescens* strain MB214 protein folding modulators

| ORF ID | GENE | FUNCTION | FAMILY | LOCATION |
|---|---|---|---|---|
| | | GroES/EL | | |
| RXF02095.1 | groES | Chaperone | Hsp10 | Cytoplasmic |
| RXF06767.1::Rxf02090 | groEL | Chaperone | Hsp60 | Cytoplasmic |
| RXF01748.1 | ibpA | Small heat-shock protein (sHSP) IbpA PA3126; Acts as a holder for GroESL folding | Hsp20 | Cytoplasmic |
| RXF03385.1 | hscB | Chaperone protein hscB | Hsp20 | Cytoplasmic |
| | | Hsp70 (DnaK/J) | | |
| RXF05399.1 | dnaK | Chaperone | Hsp70 | Periplasmic |
| RXF06954.1 | dnaK | Chaperone | Hsp70 | Cytoplasmic |
| RXF03376.1 | hscA | Chaperone | Hsp70 | Cytoplasmic |
| RXF03987.2 | cbpA | Curved dna-binding protein, dnaJ like activity | Hsp40 | Cytoplasmic |
| RXF05406.2 | dnaJ | Chaperone protein dnaJ | Hsp40 | Cytoplasmic |
| RXF03346.2 | dnaJ | Molecular chaperones (DnaJ family) | Hsp40 | Non-secretory |
| RXF05413.1 | grpE | heat shock protein GrpE PA4762 | GrpE | Cytoplasmic |
| | | Hsp100 (Clp/Hsl) | | |
| RXF04587.1 | clpA | atp-dependent clp protease atp-binding subunit clpA | Hsp100 | Cytoplasmic |
| RXF08347.1 | clpB | ClpB protein | Hsp100 | Cytoplasmic |
| RXF04654.2 | clpX | atp-dependent clp protease atp-binding subunit clpX | Hsp100 | Cytoplasmic |
| RXF04663.1 | clpP | atp-dependent Clp protease proteolytic subunit (ec 3.4.21.92) | MEROPS peptidase family S14 | Cytoplasmic |
| RXF01957.2 | hslU | atp-dependent hsl protease atp-binding subunit hslU | Hsp100 | Cytoplasmic |
| RXF01961.2 | hslV | atp-dependent hsl protease proteolytic subunit | MEROPS peptidase subfamily T1B | Cytoplasmic |
| | | Hsp33 | | |
| RXF04254.2 | yrfI | 33 kDa chaperonin (Heat shock protein 33 homolog) (HSP33). | Hsp33 | Cytoplasmic |
| | | Hsp90 | | |
| RXF05455.2 | htpG | Chaperone protein htpG | Hsp90 | Cytoplasmic |
| | | SecB | | |
| RXF02231.1 | secB | secretion specific chaperone SecB | SecB | Non-secretory |
| | | Disulfide Bond Isomerases | | |
| RXF07017.2 | dsbA | disulfide isomerase | DSBA oxido-reductase | Cytoplasmic |
| RXF08657.2 | dsbA/dsbC/dsbG/fernA | disulfide isomerase | DSBA oxido-reductase | Cytoplasmic |
| RXF01002.1 | dsbA/dsbC | disulfide isomerase | DSBA oxido-reductase/Thioredoxin | Periplasmic |
| RXF03307.1 | dsbC | disulfide isomerase | glutaredoxin/Thioredoxin | Periplasmic |
| RXF04890.2 | dsbG | disulfide isomerase | glutaredoxin/Thioredoxin | Periplasmic |
| | | Peptidyl-prolyl cis-trans isomerases | | |
| RXF03768.1 | ppiA | Peptidyl-prolyl cis-trans isomerase A (ec 5.2.1.8) | PPIase: cyclophilin type | Periplasmic |
| RXF05345.2 | ppiB | Peptidyl-prolyl cis-trans isomerase B. | PPIase: cyclophilin type | Cytoplasmic |
| RXF06034.2 | fklB | Peptidyl-prolyl cis-trans isomerase FklB. | PPIase: FKBP type | OuterMembrane |
| RXF06591.1 | fklB/fkbP | fk506 binding protein Peptidyl-prolyl cis-trans isomerase (EC 5.2.1.8) | PPIase: FKBP type | Periplasmic |
| RXF05753.2 | fklB; fkbP | Peptidyl-prolyl cis-trans isomerase (ec 5.2.1.8) | PPIase: FKBP type | Outer Membrane |
| RXF01833.2 | slyD | Peptidyl-prolyl cis-trans isomerase SlyD. | PPIase: FKBP type | Non-secretory |
| RXF04655.2 | tig | Trigger factor, ppiase (ec 5.2.1.8) | PPIase: FKBP type | Cytoplasmic |

TABLE 1-continued

*P. fluorescens* strain MB214 protein folding modulators

| ORF ID | GENE | FUNCTION | FAMILY | LOCATION |
|---|---|---|---|---|
| RXF05385.1 | yaad | Probable FKBP-type 16 kDa peptidyl-prolyl cis-trans isomerase (EC 5.2.1.8) (PPiase) (Rotamase). | PPIase: FKBP type | Non-secretory |
| RXF00271.1 | | Peptidyl-prolyl cis-trans isomerase (ec 5.2.1.8) | PPIase: FKBP type | Non-secretory |
| pili assembly chaperones (papD like) | | | | |
| RXF06068.1 | cup | Chaperone protein cup | pili assembly papD | Periplasmic |
| RXF05719.1 | ecpD | Chaperone protein ecpD | pili assembly papD | Signal peptide |
| RXF03406.2 | ecpD; csuC | Chaperone protein ecpD | pili assembly papD | Signal peptide |
| RXF04296.1 | ecpD; cup | Chaperone protein ecpD | pili assembly papD | Periplasmic |
| RXF04553.1 | ecpD; cup | Chaperone protein ecpD | pili assembly papD | Periplasmic |
| RXF04554.2 | ecpD; cup | Chaperone protein ecpD | pili assembly papD | Periplasmic |
| RXF05310.2 | ecpD; cup | Chaperone protein ecpD | pili assembly papD | Periplasmic |
| RXF05304.1 | ecpD; cup | Chaperone protein ecpD | pili assembly papD | Periplasmic |
| RXF05073.1 | gltF | Gram-negative pili assembly chaperone periplasmic function | pili assembly papD | Signal peptide |

Protease

Unwanted degradation of heterologously-expressed protein presents an obstacle to the efficient use of certain expression systems. When a cell is modified to produce large quantities of a target protein, the cell is placed under stress and often reacts by inducing or suppressing other proteins. The stress that a host cell undergoes during production of heterologous proteins can increase expression of, for example, specific proteins or cofactors to cause degradation of the overexpressed heterologous protein. The increased expression of compensatory proteins can be counterproductive to the goal of expressing high levels of active, full-length heterologous protein. Decreased expression or lack of adequate expression of other proteins can cause misfolding and aggregation of the heterologously-expressed protein. While it is known that a cell under stress will change its profile of protein expression, not all heterologously expressed proteins will modulate expression of the same proteins in a particular host cell.

Thus, the optimal host strain, e.g., *P. fluorescens* host strain, can be identified using an array comprising a plurality of host cell populations that have been genetically engineered to decrease the expression of one or more protease enzymes. In one embodiment, one or more host cell populations is modified by reducing the expression of, inhibiting or removing at least one protease from the genome. The modification can also be to more than one protease. In a related embodiment, the cell is modified by reducing the expression of a protease cofactor or protease protein. In another embodiment, the host cell is modified by inhibition of a promoter for a protease or related protein, which can be a native promoter. Alternatively, the gene modification can be to modulate a protein homologous to the target gene.

The array comprising the modified host strains can be screened by expressing the heterologous protein(s) of interest and assessing the quality and/or quantity of protein production as discussed infra. Alternatively, an isolate of the heterologous protein of interest can be independently incubated with lysate collected from each of the protease-deficient host cell populations and the level of proteolytic degradation can be used to identify the optimal host cell. In this embodiment, the optimal host cell population is that which results in the least amount of heterologous protein degradation. Thus, in one embodiment, lysate from the optimal host cell population can be degraded by less than about 50% of the heterologous protein, less than about 45%, less than about 40%, less than about 35%, less than about 30%, less than about 25%, less than about 20%, less than about 10%, less than about 5%, less than about 4%, about 3%, about 2%, about 1%, or less of the protein.

Exemplary target protease genes include those proteases classified as Aminopeptidases; Dipeptidases; Dipeptidyl-peptidases and tripeptidyl peptidases; Peptidyl-dipeptidases; Serine-type carboxypeptidases; Metallocarboxypeptidases; Cysteine-type carboxypeptidases; Omegapeptidases; Serine proteinases; Cysteine proteinases; Asp artic proteinases; Metallo proteinases; or Proteinases of unknown mechanism.

Aminopeptidases include cytosol aminopeptidase (leucyl aminopeptidase), membrane alanyl aminopeptidase, cystinyl aminopeptidase, tripeptide aminopeptidase, prolyl aminopeptidase, arginyl aminopeptidase, glutamyl aminopeptidase, x-pro aminopeptidase, bacterial leucyl aminopeptidase, thermophilic aminopeptidase, clostridial aminopeptidase, cytosol alanyl aminopeptidase, lysyl aminopeptidase, x-trp aminopeptidase, tryptophanyl aminopeptidase, methionyl aminopeptidas, d-stereospecific aminopeptidase, aminopeptidase ey. Dipeptidases include x-his dipeptidase, x-arg dipeptidase, x-methyl-his dipeptidase, cys-gly dipeptidase, glu-glu dipeptidase, pro-x dipeptidase, x-pro dipeptidase, met-x dipeptidase, non-stereospecific dipeptidase, cytosol non-specific dipeptidase, membrane dipeptidase, beta-ala-his dipeptidase. Dipeptidyl-peptidases and tripeptidyl peptidases include dipeptidyl-peptidase i, dipeptidyl-peptidase ii, dipeptidyl peptidase iii, dipeptidyl-peptidase iv, dipeptidyl-dipeptidase, tripeptidyl-peptidase I, tripeptidyl-peptidase II. Peptidyl-dipeptidases include peptidyl-dipeptidase a and peptidyl-dipeptidase b. Serine-type carboxypeptidases include lysosomal pro-x carboxypeptidase, serine-type D-ala-D-ala carboxypeptidase, carboxypeptidase C, carboxypeptidase D. Metallocarboxypeptidases include carboxypeptidase a, carboxypeptidase B, lysine(arginine) carboxypeptidase, gly-X carboxypeptidase, alanine carboxypeptidase, muramoylpentapeptide carboxypeptidase, carboxypeptidase h, glutamate carboxypeptidase, carboxypeptidase M, muramoyltetrapeptide carboxypeptidase, zinc d-ala-d-ala carboxypeptidase, carboxypeptidase A2, membrane pro-x carboxypeptidase, tubulinyl-tyr carboxypeptidase, carboxypeptidase t. Omega-peptidases include acylaminoacyl-peptidase, peptidyl-glycinamidase, pyroglutamyl-peptidase I, beta-aspartyl-peptidase, pyroglutamyl-peptidase II, n-formylmethionyl-peptidase, pteroylpoly-[gamma]-glutamate carboxypeptidase, gamma-glu-X carboxypeptidase, acylmuramoyl-ala peptidase. Serine proteinases include chymotrypsin, chymotrypsin c, metridin, trypsin, thrombin, coagulation factor Xa, plasmin, enteropeptidase, acrosin, alpha-lytic protease, glutamyl, endopeptidase, cathepsin G, coagulation factor viia, coagulation factor ixa, cucumisi, prolyl oligopeptidase, coagulation factor xia, brachyurin, plasma kallikrein, tissue kallikrein, pancreatic elastase, leukocyte elastase, coagulation factor xiia, chymase, complement component clr55, complement component cls55, classical-complement pathway c3/c5 convertase, complement factor I, complement factor D, alternative-complement pathway c3/c5 convertase, cerevisin, hypodermin C, lysyl endopeptidase, endopeptidase 1a, gamma-reni, venombin ab, leucyl endopeptidase, tryptase, scutelarin, kexin, subtilisin, oryzin, endopeptidase k, thermomycolin, thermitase, endopeptidase SO, T-plasminogen activator, protein C, pancreatic endopeptidase E, pancreatic elastase ii, IGA-specific serine endopeptidase, U-plasminogen, activator, venombin A, furin, myeloblastin, semenogelase, granzyme A or cytotoxic T-lymphocyte proteinase 1, granzyme B or cytotoxic T-lymphocyte proteinase 2, streptogrisin A, treptogrisin B, glutamyl endopeptidase II, oligopeptidase B, limulus clotting factor c, limulus clotting factor, limulus clotting enzyme, omptin, repressor lexa, bacterial leader peptidase I, togavirin, flavirin. Cysteine proteinases include cathepsin B, papain, ficin, chymopapain, asclepain, clostripain, streptopain, actinide, cathepsin 1, cathepsin H, calpain, cathepsin t, glycyl, endopeptidase, cancer procoagulant, cathepsin S, picornain 3C, picornain 2A, caricain, ananain, stem bromelain, fruit bromelain, legumain, histolysain, interleukin 1-beta converting enzyme. Aspartic proteinases include pepsin A, pepsin B, gastricsin, chymosin, cathepsin D, neopenthesin, renin, retropepsin, pro-opiomelanocortin converting enzyme, aspergillopepsin I, aspergillopepsin II, penicillopepsin, rhizopuspepsin, endothiapepsin, mucoropepsin, candidapepsin, saccharopepsin, rhodotorulapepsin, physaropepsin, acrocylindropepsin, polyporopepsin, pycnoporopepsin, scytalidopepsin a, scytalidopepsin b, xanthomonapepsin, cathepsin e, barrierpepsin, bacterial leader peptidase I, pseudomonapepsin, plasmepsin. Metallo proteinases include atrolysin a, microbial collagenase, leucolysin, interstitial collagenase, neprilysin, envelysin, iga-specific metalloendopeptidase, procollagen N-endopeptidase, thimet oligopeptidase, neurolysin, stromelysin 1, meprin A, procollagen C-endopeptidase, peptidyl-lys metalloendopeptidase, astacin, stromelysin, 2, matrilysin gelatinase, aeromonolysin, pseudolysin, thermolysin, bacillolysin, aureolysin, coccolysin, mycolysin, beta-lytic metalloendopeptidase, peptidyl-asp metalloendopeptidase, neutrophil collagenase, gelatinase B, leishmanolysin, saccharolysin, autolysin, deuterolysin, serralysin, atrolysin B, atrolysin C, atroxase, atrolysin E, atrolysin F, adamalysin, horrilysin, ruberlysin, bothropasin, bothrolysin, ophiolysin, trimerelysin I, trimerelysin II, mucrolysin, pitrilysin, insulysin, O-syaloglycoprotein endopeptidase, russellysin, mitochondrial, intermediate, peptidase, dactylysin, nardilysin, magnolysin, meprin B, mitochondrial processing peptidase, macrophage elastase, choriolysin, toxilysin. Proteinases of unknown mechanism include thermopsin and multicatalytic endopeptidase complex.

TABLE 2

*P. fluorescens* strain MB214 proteases

| Family | ORF ID | Gene | Function | Location |
|---|---|---|---|---|
| Aspartic Peptidases | | | | |
| A8 (signal peptidase II family) | RXF05383.2 | | Lipoprotein signal peptidase (ec 3.4.23.36) | Cytoplasmic Membrane |
| A24 (type IV prepilin peptidase family) | RXF05379.1 | | type 4 prepilin peptidase pild (ec 3.4.99.—) | Cytoplasmic Membrane |
| Cysteine Peptidases | | | | |
| C15 (pyroglutamyl peptidase I family) | RXF02161.1 | | Pyrrolidone-carboxylate peptidase (ec 3.4.19.3) | Cytoplasmic |
| C40 | RXF01968.1 | | invasion-associated protein, P60 | Signal peptide |
| | RXF04920.1 | | invasion-associated protein, P60 | Cytoplasmic |
| | RXF04923.1 | | phosphatase-associated protein papq | Signal peptide |
| C56 (PfpI endopeptidase family) | RXF01816.1 | | protease I (ec 3.4.—.—) | Non-secretory |
| Metallopeptidases | | | | |
| M1 | RXF08773.1 | | Membrane alanine aminopeptidase (ec 3.4.11.2) | Non-secretory |
| M3 | RXF00561.2 | prlC | Oligopeptidase A (ec 3.4.24.70) | Cytoplasmic |
| | RXF04631.2 | | Zn-dependent oligopeptidases | Cytoplasmic |
| M4 (thermolysin family) | RXF05113.2 | | Extracellular metalloprotease precursor (ec 3.4.24.—) | Extracellular |
| M41 (FtsH endopeptidase family) | RXF05400.2 | | Cell division protein ftsH (ec 3.4.24.—) | Cytoplasmic Membrane |
| M10 | RXF04304.1 | | Serralysin (ec 3.4.24.40) | Extracellular |
| | RXF04500.1 | | Serralysin (ec 3.4.24.40) | Extracellular |
| | RXF01590.2 | | Serralysin (ec 3.4.24.40) | Extracellular |
| | RXF04495.2 | | Serralysin (ec 3.4.24.40) | Extracellular |
| | RXF02796.1 | | Serralysin (ec 3.4.24.40) | Extracellular |

TABLE 2-continued

P. fluorescens strain MB214 proteases

| Family | ORF ID | Gene | Function | Location |
|---|---|---|---|---|
| M14 (carboxypeptidase A family) | RXF09091.1 | | Zinc-carboxypeptidase precursor (ec 3.4.17.—) | Cytoplasmic |
| M16 (pitrilysin family) | RXF03441.1 | | Coenzyme pqq synthesis protein F (ec 3.4.99.—) | Non-secretory |
| | RXF01918.1 | | zinc protease (ec 3.4.99.—) | Signal peptide |
| | RXF01919.1 | | zinc protease (ec 3.4.99.—) | Periplasmic |
| | RXF03699.2 | | processing peptidase (ec 3.4.24.64) | Signal peptide |
| M17 (leucyl aminopeptidase family) | RXF00285.2 | | Cytosol aminopeptidase (ec 3.4.11.1) | Non-secretory |
| M18 | RXF07879.1 | | Aspartyl aminopeptidase (ec 3.4.11.21) | Cytoplasmic |
| M20 | RXF00811.1 | dapE | Succinyl-diaminopimelate desuccinylase (ec 3.5.1.18) | Cytoplasmic |
| | RXF04052.2 | | Xaa-His dipeptidase (ec 3.4.13.3) | Signal peptide |
| | RXF01822.2 | | Carboxypeptidase G2 precursor (ec 3.4.17.11) | Signal peptide |
| | RXF09831.2:: RXF04892.1 | | N-acyl-L-amino acid amidohydrolase (ec 3.5.1.14) | Signal peptide |
| M28 (aminopeptidase Y family) | RXF03488.2 | | Alkaline phosphatase isozyme conversion protein precursor (ec 3.4.11.—) | OuterMembrane |
| M42 (glutamyl aminopeptidase family) | RXF05615.1 | | Deblocking aminopeptidase (ec 3.4.11.—) | Non-secretory |
| M22 | RXF05817.1 | | O-sialoglycoprotein endopeptidase (ec 3.4.24.57) | Extracellular |
| | RXF03065.2 | | Glycoprotease protein family | Non-secretory |
| M23 | RXF01291.2 | | Cell wall endopeptidase, family M23/M37 | Signal peptide |
| | RXF03916.1 | | Membrane proteins related to metalloendopeptidases | Signal peptide |
| | RXF09147.2 | | Cell wall endopeptidase, family M23/M37 | Signal peptide |
| M24 | RXF04693.1 | | Methionine aminopeptidase (ec 3.4.11.18) | Cytoplasmic |
| | RXF03364.1 | | Methionine aminopeptidase (ec 3.4.11.18) | Non-secretory |
| | RXF02980.1 | | Xaa-Pro aminopeptidase (ec 3.4.11.9) | Cytoplasmic |
| | RXF06564.1 | | Xaa-Pro aminopeptidase (ec 3.4.11.9) | Cytoplasmic |
| M48 (Ste24 endopeptidase family) | RXF05137.1 | | Heat shock protein HtpX | Cytoplasmic Membrane |
| | RXF05081.1 | | Zinc metalloprotease (ec 3.4.24.—) | Signal peptide |
| M50 (S2P protease family) | RXF04692.1 | | Membrane metalloprotease | Cytoplasmic Membrane |
| Serine Peptidases | | | | |
| S1 (chymotrypsin family) | RXF01250.2 | | protease do (ec 3.4.21.—) | Periplasmic |
| | RXF07210.1 | | protease do (ec 3.4.21.—) | Periplasmic |
| S8 (subtilisin family) | RXF06755.2 | | serine protease (ec 3.4.21.—) | Non-secretory |
| | RXF08517.1 | | serine protease (ec 3.4.21.—) | Extracellular |
| | RXF08627.2 | | extracellular serine protease (ec 3.4.21.—) | Signal peptide |
| | RXF06281.1 | | Extracellular serine protease precursor (ec 3.4.21.—) | Non-secretory |
| | RXF08978.1 | | extracellular serine protease (ec 3.4.21.—) | OuterMembrane |
| | RXF06451.1 | | serine protease (ec 3.4.21.—) | Signal peptide |
| S9 (prolyl oligopeptidase family) | RXF02003.2 | | Protease ii (ec 3.4.21.83) | Periplasmic |
| | RXF00458.2 | | Hydrolase | Non-secretory |
| S11 (D-Ala-D-Ala carboxypeptidase A family) | RXF04657.2 | | D-alanyl-D-alanine-endopeptidase (ec 3.4.99.—) | Periplasmic |
| | RXF00670.1 | | D-alanyl-D-alanine carboxypeptidase (ec 3.4.16.4) | Cytoplasmic Membrane |
| S13 (D-Ala-D-Ala peptidase C family) | RXF00133.1 | | D-alanyl-meso-diaminopimelate endopeptidase (ec 3.4.—.—) | OuterMembrane |
| | RXF04960.2 | | D-alanyl-meso-diaminopimelate endopeptidase (ec 3.4.—.—) | Signal peptide |
| S14 (ClpP endopeptidase family) | RXF04567.1 | clpP | atp-dependent Clp protease proteolytic subunit (ec 3.4.21.92) | Non-secretory |
| | RXF04663.1 | clpP | atp-dependent Clp protease proteolytic subunit (ec 3.4.21.92) | Cytoplasmic |
| S16 (lon protease family) | RXF04653.2 | | atp-dependent protease La (ec 3.4.21.53) | Cytoplasmic |
| | RXF08653.1 | | atp-dependent protease La (ec 3.4.21.53) | Cytoplasmic |

TABLE 2-continued

P. fluorescens strain MB214 proteases

| Family | ORF ID | Gene | Function | Location |
|---|---|---|---|---|
| | RXF05943.1 | | atp-dependent protease La (ec 3.4.21.53) | Cytoplasmic |
| S24 (LexA family) | RXF00449.1 | | LexA repressor (ec 3.4.21.88) | Non-secretory |
| | RXF03397.1 | | LexA repressor (ec 3.4.21.88) | Cytoplasmic |
| S26 (signal peptidase I family) | RXF01181.1 | | Signal peptidase I (ec 3.4.21.89) | Cytoplasmic Membrane |
| S33 | RXF05236.1 | pip3 | Proline iminopeptidase (ec 3.4.11.5) | Non-secretory |
| | RXF04802.1 | pip1 | Proline iminopeptidase (ec 3.4.11.5) | Non-secretory |
| | RXF04808.2 | pip2 | Proline iminopeptidase (ec 3.4.11.5) | Cytoplasmic |
| S41 (C-terminal processing peptidase family) | RXF06586.1 | | Tail-specific protease (ec 3.4.21.—) | Signal peptide |
| | RXF01037.1 | | Tail-specific protease (ec 3.4.21.—) | Signal peptide |
| S45 | RXF07170.1 | pacB2 | Penicillin acylase (ec 3.5.1.11) | Signal peptide |
| | RXF06399.2 | pacB1 | Penicillin acylase ii (ec 3.5.1.11) | Signal peptide |
| S49 (protease IV family) | RXF06993.2 | | possible protease sohb (ec 3.4.—.—) | Non-secretory |
| | RXF01418.1 | | protease iv (ec 3.4.—.—) | Non-secretory |
| S58 (DmpA aminopeptidase family) | RXF06308.2 | | D-aminopeptidase (ec 3.4.11.19) | Cytoplasmic Membrane |
| Threonine Peptidases | | | | |
| T1 (proteasome family) | RXF01961.2 | hslV | atp-dependent protease hslV (ec 3.4.25.—) | Cytoplasmic |
| T3 (gamma-glutamyltransferase family) | RXF02342.1 | ggt1 | Gamma-glutamyltranspeptidase (ec 2.3.2.2) | Periplasmic |
| | RXF04424.2 | ggt2 | Gamma-glutamyltranspeptidase (ec 2.3.2.2) | Periplasmic |
| Unclassified Peptidases | | | | |
| U32 | RXF00428.1 | | protease (ec 3.4.—.—) | Cytoplasmic |
| | RXF02151.2 | | protease (ec 3.4.—.—) | Cytoplasmic |
| U61 | RXF04715.1 | | Muramoyltetrapeptide carboxypeptidase (ec 3.4.17.13) | Non-secretory |
| U62 | RXF04971.2 | pmbA | PmbA protein | Cytoplasmic |
| | RXF04968.2 | | TldD protein | Cytoplasmic |
| Non MEROPS Proteases | | | | |
| | RXF00325.1 | | Repressor protein C2 | Non-secretory |
| | RXF02689.2 | | Microsomal dipeptidase (ec 3.4.13.19) | Cytoplasmic |
| | RXF02739.1 | | membrane dipeptidase (3.4.13.19) | Signal peptide |
| | RXF03329.2 | | Hypothetical Cytosolic Protein | Cytoplasmic |
| | RXF02492.1 | | Xaa-Pro dipeptidase (ec 3.4.13.9) | Cytoplasmic |
| | RXF04047.2 | | caax amino terminal protease family | Cytoplasmic Membrane |
| | RXF08136.2 | | protease (transglutaminase-like protein) | Cytoplasmic |
| | RXF09487.1 | | Zinc metalloprotease (ec 3.4.24.—) | Non-secretory |

Additional Protein Modification Enzymes

In another embodiment, the target gene comprises a gene involved in proper protein processing and/or modification. Common modifications include disulfide bond formation, glycosylation, acetylation, acylation, phosphorylation, and gamma-carboxylation, all of which can regulate protein folding and biological activity. A non-exhaustive list of several classes of enzymes involved in protein processing is found in Table 3. One of skill in the art will recognize how to identify a target gene useful in the host cell chosen for the array, or useful with the heterologous protein of interest, from among the classes of protein modification enzymes listed in Table 3. The target gene may be endogenous to the host cell utilized, may be endogenous to the organism from which the heterologous protein of interest is derived, or may be known to facilitate proper processing of a heterologously expressed protein of interest. It is also recognized that any gene involved in protein production can be targeted according to desired specifications for the heterologous protein of interest.

TABLE 3

Classes of enzymes involved in protein processing

| Class | Examples |
|---|---|
| Glycosyltransferases (EC 2.4.1.18) | α-glucan-branching glycosyltransferase<br>enzymatic branching factor<br>branching glycosyltransferase<br>enzyme Q<br>glucosan transglycosylase<br>glycogen branching enzyme<br>amylose isomerase<br>plant branching enzyme<br>α-1,4-glucan:α-1,4-glucan-6-glycosyltransferase<br>starch branching enzyme<br>UDP-N-acetyl-D-galactosamine:polypeptide N-acetylgalactosaminyltransferase<br>GDP-fucose protein O-fucosyltransferase 2<br>O-GlcNAc transferase |

TABLE 3-continued

Classes of enzymes involved in protein processing

| Class | Examples |
|---|---|
| Histone acetyltransferase (EC 2.3.1.48) | nucleosome-histone acetyltransferase<br>histone acetokinase<br>histone acetylase<br>histone transacetylase<br>histone deacetylase |
| Protein kinase (EC 2.7) | non-specific serine/threonine protein kinase<br>Fas-activated serine/threonine kinase<br>Goodpasture antigen-binding protein kinase<br>IκB kinase<br>cAMP-dependent protein kinase<br>cGMP-dependent protein kinase<br>protein kinase C<br>polo kinase<br>cyclin-dependent kinase<br>mitogen-activated protein kinase<br>mitogen-activated protein kinase kinase kinase<br>receptor protein serine/threonine kinase<br>dual-specificity kinase |
| Phosphatase (EC 3.1.3.48) | protein-tyrosine-phosphatase<br>phosphotyrosine phosphatase<br>phosphoprotein phosphatase (phosphotyrosine)<br>phosphotyrosine histone phosphatase<br>protein phosphotyrosine phosphatase<br>tyrosylprotein phosphatase<br>phosphotyrosine protein phosphatase<br>phosphotyrosylprotein phosphatase<br>tyrosine O-phosphate phosphatase<br>PPT-phosphatase<br>PTPase<br>[phosphotyrosine]protein phosphatase<br>PTP-phosphatase |

Methods for Modulating the Expression of Target Genes

One or more host cell populations of the array can be modified by any technique known in the art, for example by a technique wherein at least one target gene is knocked out of the genome, or by mutating at least one target gene to reduce expression of the gene, by altering at least one promoter of at least one target gene to reduce expression of the target gene, or by coexpressing (with the heterologous protein or polypeptide of interest) the target gene or an inhibitor of the target gene in the host genome. As discussed supra, the target gene can be endogenous to the host cell populations in the array, or can be heterologously expressed in each of the host cell populations.

The expression of target genes can be increased, for example, by introducing into at least one cell in a host population an expression vector comprising one or more target genes involved in protein production. The target gene expression can also be increased, for example, by mutating a promoter of a target gene. A host cell or organism that expresses a heterologous protein can also be genetically modified to increase the expression of at least one target gene involved in protein production and decrease the expression of at least one target gene involved in protein degradation.

The genome may be modified to modulate the expression of one or more target genes by including an exogenous gene or promoter element in the genome or in the host with an expression vector, by enhancing the capacity of a particular target gene to produce mRNA or protein, by deleting or disrupting a target gene or promoter element, or by reducing the capacity of a target gene to produce mRNA or protein. The genetic code can be altered, thereby affecting transcription and/or translation of a target gene, for example through substitution, deletion ("knock-out"), co-expression, or insertion ("knock-in") techniques. Additional genes for a desired protein or regulatory sequence that modulate transcription of an existing target sequence can also be inserted.

Genome Modification

The genome of the host cell can be modified via a genetic targeting event, which can be by insertion or recombination, for example homologous recombination. Homologous recombination refers to the process of DNA recombination based on sequence homology. Homologous recombination permits site-specific modifications in endogenous genes and thus novel alterations can be engineered into a genome (see, for example Radding (1982) Ann. Rev. Genet. 16: 405; U.S. Pat. No. 4,888,274).

Various constructs can be prepared for homologous recombination at a target locus. Usually, the construct can include at least 10 bp, 20 bp, 30 bp, 40 bp, 50 bp, 70 bp, 100 bp, 500 bp, 1 kbp, 2 kbp, 4 kbp, 5 kbp, 10 kbp, 15 kbp, 20 kbp, or 50 kbp of sequence homologous with the identified locus. Various considerations can be involved in determining the extent of homology of target gene sequences, such as, for example, the size of the target locus, availability of sequences, relative efficiency of double cross-over events at the target locus and the similarity of the target sequence with other sequences.

The modified gene can include a sequence in which DNA substantially isogenic flanks the desired sequence modifications with a corresponding target sequence in the genome to be modified. The "modified gene" is the sequence being introduced into the genome to alter the expression of a protease or a protein folding modulator in the host cell. The "target gene" is the sequence that is being replaced by the modified gene. The substantially isogenic sequence can be at least about 95%, 97-98%, 99.0-99.5%, 99.6-99.9%, or 100% identical to the corresponding target sequence (except for the desired sequence modifications). The modified gene and the targeted gene can share stretches of DNA at least about 10, 20, 30, 50, 75, 150 or 500 base pairs that are 100% identical.

Nucleotide constructs can be designed to modify the endogenous, target gene product. The modified gene sequence can have one or more deletions, insertions, substitutions or combinations thereof designed to disrupt the function of the resultant gene product. In one embodiment, the alteration can be the insertion of a selectable marker gene fused in reading frame with the upstream sequence of the target gene.

The genome can also be modified using insertional inactivation. In this embodiment, the genome is modified by recombining a sequence in the gene that inhibits gene product formation. This insertion can either disrupt the gene by inserting a separate element, or remove an essential portion of the gene. In one embodiment, the insertional deletion also includes insertion of a gene coding for resistance to a particular stressor, such as an antibiotic, or for growth in a particular media, for example for production of an essential amino acid.

The genome can also be modified by use of transposons, which are genetic elements capable of inserting at sites in prokaryote genomes by mechanisms independent of homologous recombination. Transposons can include, for example, Tn7, Tn5, or Tn10 in *E. coli*, Tn554 in *S. aureus*, IS900 in *M. paratuberculosis*, IS492 from *Pseudomonas atlantica*, IS116 from *Streptomyces* and IS900 from *M. paratuberculosis*. Steps believed to be involved in transposition include cleavage of the end of the transposon to yield 3' OH; strand transfer, in which transposase brings together the 3'OH exposed end of transposon and the identified sequence; and a single step transesterification reaction to yield a covalent linkage of the transposon to the identified DNA. The key reaction performed by transposase is generally thought to be nicking or strand exchange, the rest of the process is done by host enzymes.

In one embodiment, the expression or activity of a target gene or protein is increased by incorporating a genetic sequence encoding the target protein or homolog thereof into the genome by recombination. In another embodiment, a promoter is inserted into the genome to enhance the expression of the target gene or homolog. In another embodiment, the expression or activity of a target gene or homolog thereof is decreased by recombination with an inactive gene. In another embodiment, a sequence that encodes a different gene, which can have a separate function in the cell or can be a reporter gene such as a resistance marker or an otherwise detectable marker gene, can be inserted into the genome through recombination. In yet another embodiment, a copy of at least a portion of the target gene that has been mutated at one or more locations is inserted into the genome through recombination. The mutated version of the target gene may not encode a protein, or the protein encoded by the mutated gene may be rendered inactive, the activity may be modulated (either increased or decreased), or the mutant protein can have a different activity when compared to the native protein.

There are strategies to knock out genes in bacteria, which have been generally exemplified in E. coli. One route is to clone a gene-internal DNA fragment into a vector containing an antibiotic resistance gene (e.g. ampicillin). Before cells are transformed via conjugative transfer, chemical transformation or electroporation (Puehler, et al. (1984) Advanced Molecular Genetics New York, Heidelberg, Berlin, Tokyo, Springer Verlag), an origin of replication, such as the vegetative plasmid replication (the oriV locus) is excised and the remaining DNA fragment is re-ligated and purified (Sambrook, et al. (2000) Molecular cloning: A laboratory manual, third edition Cold Spring Harbor, N.Y., Cold Spring Harbor Laboratory Press). Alternatively, antibiotic-resistant plasmids that have a DNA replication origin can be used. After transformation, the cells are plated onto e.g. LB agar plates containing the appropriate antibiotics (e.g. 200 micrograms/mL ampicillin). Colonies that grow on the plates containing the antibiotics presumably have undergone a single recombination event (Snyder, L., W. Champness, et al. (1997) Molecular Genetics of Bacteria Washington D.C., ASM Press) that leads to the integration of the entire DNA fragment into the genome at the homologous locus. Further analysis of the antibiotic-resistant cells to verify that the desired gene knock-out has occurred at the desired locus is e.g. by diagnostic PCR (McPherson, M. J., P. Quirke, et al. (1991) PCR: A Practical Approach New York, Oxford University Press). Here, at least two PCR primers are designed: one that hybridizes outside the DNA region that was used for the construction of the gene knock-out; and one that hybridizes within the remaining plasmid backbone. Successful PCR amplification of the DNA fragment with the correct size followed by DNA sequence analysis will verify that the gene knock-out has occurred at the correct location in the bacterial chromosome. The phenotype of the newly constructed mutant strain can then be analyzed by, e.g., SDS polyacrylamide gel electrophoresis (Simpson, R. J. (2003) Proteins and Proteomics—A Laboratory Manual. Cold Spring Harbor, N.Y., Cold Spring Harbor Laboratory Press).

An alternate route to generate a gene knock-out is by use of a temperature-sensitive replicon, such as the pSC101 replicon to facilitate gene replacement (Hamilton, et al. (1989) Journal of Bacteriology 171(9): 4617-22). The process proceeds by homologous recombination between a gene on a chromosome and homologous sequences carried on a plasmid temperature sensitive for DNA replication. After transformation of the plasmid into the appropriate host, it is possible to select for integration of the plasmid into the chromosome at 44° C. Subsequent growth of these cointegrates at 30° C. leads to a second recombination event, resulting in their resolution. Depending on where the second recombination event takes place, the chromosome will either have undergone a gene replacement or retain the original copy of the gene.

Other strategies have been developed to inhibit expression of particular gene products. For example, RNA interference (RNAi), particularly using small interfering RNA (siRNA), has been extensively developed to reduce or even eliminate expression of a particular gene product. siRNAs are short, double-stranded RNA molecules that can target complementary mRNAs for degradation. RNAi is the phenomenon in which introduction of a double-stranded RNA suppresses the expression of the homologous gene. dsRNA molecules are reduced in vivo to 21-23 nt siRNAs which are the mediators of the RNAi effect. Upon introduction, double stranded RNAs get processed into 20-25 nucleotide siRNAs by an RNase III-like enzyme called Dicer (initiation step). Then, the siRNAs assemble into endoribonuclease-containing complexes known as RNA-induced silencing complexes (RISCs), unwinding in the process. The siRNA strands subsequently guide the RISCs to complementary RNA molecules, where they cleave and destroy the cognate RNA (effecter step). Cleavage of cognate RNA takes place near the middle of the region bound by the siRNA strand. RNAi has been successfully used to reduce gene expression in a variety of organisms including zebrafish, nematodes (C. elegans), insects (Drosophila melanogaster), planaria, cnidaria, trypanosomes, mice and mammalian cells.

The genome can also be modified by mutation of one or more nucleotides in an open reading frame encoding a target gene. Techniques for genetic mutation, for instance site directed mutagenesis, are well known in the art. Some approaches focus on the generation of random mutations in chromosomal DNA such as those induced by X-rays and chemicals.

Coexpression

In one embodiment, one or more target genes in the host cell can be modified by including one or more vectors that encode the target gene(s) to facilitate coexpression of the target gene with the heterologous protein or peptide. In another embodiment, the host cell is modified by enhancing a promoter for a target gene, including by adding an exogenous promoter to the host cell genome.

In another embodiment, one or more target genes in the host cell is modified by including one or more vectors that encode an inhibitor of a target gene, such as a protease inhibitor to inhibit the activity of a target protease. Such an inhibitor can be an antisense molecule that limits the expression of the target gene, a cofactor of the target gene or a homolog of the target gene. Antisense is generally used to refer to a nucleic acid molecule with a sequence complementary to at least a portion of the target gene. In addition, the inhibitor can be an interfering RNA or a gene that encodes an interfering RNA. In Eukaryotic organisms, such an interfering RNA can be a small interfering RNA or a ribozyme, as described, for example, in Fire, A. et al. (1998) Nature 391:806-11, Elbashir et al. (2001) Genes & Development 15(2):188-200, Elbashir et al. (2001) Nature 411(6836):494-8, U.S. Pat. No. 6,506,559 to Carnegie Institute, U.S. Pat. No. 6,573,099 to Benitec, U.S. patent application Nos. 2003/0108923 to the Whitehead Inst., and 2003/0114409, PCT Publication Nos. WO03/006477, WO03/012052, WO03/023015, WO03/056022, WO03/064621 and WO03/070966.

The inhibitor can also be another protein or peptide. The inhibitor can, for example, be a peptide with a consensus sequence for the target protein. The inhibitor can also be a protein or peptide that can produce a direct or indirect inhibitory molecule for the target protein in the host. For example, protease inhibitors can include Amastatin, E-64, Antipain, Elastatinal, APMSF, Leupeptin, Bestatin, Pepstatin, Benzamidine, 1,10-Phenanthroline, Chymostatin, Phosphoramidon, 3,4-dichloroisocoumarin, TLCK, DFP, TPCK. Over 100 naturally occurring protein protease inhibitors have been identified so far. They have been isolated in a variety of organisms from bacteria to animals and plants. They behave as tight-binding reversible or pseudo-irreversible inhibitors of proteases preventing substrate access to the active site through steric hindrance. Their size are also extremely variable from 50 residues (e.g BPTI: Bovine Pancreatic Trypsin Inhibitor) to up to 400 residues (e.g alpha-1PI: alpha-1 Proteinase Inhibitor). They are strictly class-specific except proteins of the alpha-macroglobulin family (e.g alpha-2 macroglobulin) which bind and inhibit most proteases through a molecular trap mechanism.

An exogenous vector or DNA construct can be transfected or transformed into the host cell. Techniques for transfecting and transforming eukaryotic and prokaryotic cells respectively with exogenous nucleic acids are well known in the art. These can include lipid vesicle mediated uptake, calcium phosphate mediated transfection (calcium phosphate/DNA co-precipitation), viral infection, particularly using modified viruses such as, for example, modified adenoviruses, microinjection and electroporation. For prokaryotic transformation, techniques can include heat shock mediated uptake, bacterial protoplast fusion with intact cells, microinjection and electroporation. Techniques for plant transformation include Agrobacterium mediated transfer, such as by A. tumefaciens, rapidly propelled tungsten or gold microprojectiles, electroporation, microinjection and polyethylene glycol mediated uptake. The DNA can be single or double stranded, linear or circular, relaxed or supercoiled DNA. For various techniques for transfecting mammalian cells, see, for example, Keown et al. (1990) Processes in Enzymology Vol. 185, pp. 527-537.

An expression construct encoding a target gene or an enhancer or inhibitor thereof can be constructed as described below for the expression constructs comprising the heterologous protein or polypeptide of interest. For example, the constructs can contain one, or more than one, internal ribosome entry site (IRES). The construct can also contain a promoter operably linked to the nucleic acid sequence encoding at least a portion of the target gene, or a cofactor of the target gene, a mutant version of at least a portion of the target gene, or in some embodiments, an inhibitor of the target gene. Alternatively, the construct can be promoterless. In cases in which the construct is not designed to incorporate into the cellular DNA/genome, the vector typically contains at least one promoter element. In addition to the nucleic acid sequences, the expression vector can contain selectable marker sequences. The expression constructs can further contain sites for transcription initiation, termination, and/or ribosome binding sites. The identified constructs can be inserted into and can be expressed in any prokaryotic or eukaryotic cell, including, but not limited to bacterial cells, such as P. fluorescens or E. coli, yeast cells, mammalian cells, such as CHO cells, or plant cells.

The construct can be prepared in accordance with processes known in the art. Various fragments can be assembled, introduced into appropriate vectors, cloned, analyzed and then manipulated further until the desired construct has been achieved. Various modifications can be made to the sequence, to allow for restriction analysis, excision, identification of probes, etc. Silent mutations can be introduced, as desired. At various stages, restriction analysis, sequencing, amplification with the polymerase chain reaction, primer repair, in vitro mutagenesis, etc. can be employed. Processes for the incorporation of antibiotic resistance genes and negative selection factors will be familiar to those of ordinary skill in the art (see, e.g., WO 99/15650; U.S. Pat. No. 6,080,576; U.S. Pat. No. 6,136,566; Niwa, et al., J. Biochem. 113:343-349 (1993); and Yoshida, et al., Transgenic Research, 4:277-287 (1995)).

The construct can be prepared using a bacterial vector, including a prokaryotic replication system, e.g. an origin recognizable by a prokaryotic cell such as P. fluorescens or E. coli. A marker, the same as or different from the marker to be used for insertion, can be employed, which can be removed prior to introduction into the host cell. Once the vector containing the construct has been completed, it can be further manipulated, such as by deletion of certain sequences, linearization, or by introducing mutations, deletions or other sequences into the homologous sequence. In one embodiment, the target gene construct and the heterologous protein construct are part of the same expression vector, and may or may not be under the control of the same promoter element. In another embodiment, they are on separate expression vectors. After final manipulation, the construct can be introduced into the cell.

Cell Growth Conditions

The cell growth conditions for the host cells described herein include that which facilitates expression of the protein of interest in at least one strain in the array (or at least a proportion of cells thereof), and/or that which facilitates fermentation of the expressed protein of interest. As used herein, the term "fermentation" includes both embodiments in which literal fermentation is employed and embodiments in which other, non-fermentative culture modes are employed. Growth, maintenance, and/or fermentation of the populations of host cells in the array may be performed at any scale. However, where multiple populations of host cells are screened simultaneously, the scale will be limited by the number of different populations and the capacity to grow and test multiple populations of host cells. In one embodiment, the fermentation medium may be selected from among rich media, minimal media, and mineral salts media. In another embodiment either a minimal medium or a mineral salts medium is selected. In still another embodiment, a minimal medium is selected. In yet another embodiment, a mineral salts medium is selected.

Mineral salts media consists of mineral salts and a carbon source such as, e.g., glucose, sucrose, or glycerol. Examples of mineral salts media include, e.g., M9 medium, Pseudomonas medium (ATCC 179), Davis and Mingioli medium (see, B D Davis & E S Mingioli (1950) in J. Bact. 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. No organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A preferred mineral salts medium will contain glucose as the carbon source. In comparison to mineral salts media, minimal media can also contain mineral salts and a carbon source, but can be supplemented with, e.g., low levels of amino acids, vitamins, peptones, or other ingredients, though these are added at very minimal levels.

In one embodiment, media can be prepared using the components listed in Table 4 below. The components can be added in the following order: first $(NH_4)HPO_4$, $KH_2PO_4$ and citric acid can be dissolved in approximately 30 liters of distilled water; then a solution of trace elements can be added, followed by the addition of an antifoam agent, such as Ucolub N 115. Then, after heat sterilization (such as at approximately 121° C.), sterile solutions of glucose $MgSO_4$ and thiamine-HCL can be added. Control of pH at approximately 6.8 can be achieved using aqueous ammonia. Sterile distilled water can then be added to adjust the initial volume to 37l minus the glycerol stock (123 mL). The chemicals are commercially available from various suppliers, such as Merck.

TABLE 4

Medium composition

| Component | Initial concentration |
|---|---|
| $KH_2PO_4$ | 13.3 g $l^{-1}$ |
| $(NH_4)_2HPO_4$ | 4.0 g $l^{-1}$ |
| Citric Acid | 1.7 g $l^{-1}$ |
| $MgSO_4$—$7H_2O$ | 1.2 g $l^{-1}$ |
| Trace metal solution | 10 ml $l^{-1}$ |
| Thiamin HCl | 4.5 mg $l^{-1}$ |
| Glucose-$H_2O$ | 27.3 g $l^{-1}$ |
| Antifoam Ucolub N115 | 0.1 ml $l^{-1}$ |
| Feeding solution | |
| $MgSO_4$—$7H_2O$ | 19.7 g $l^{-1}$ |
| Glucose-$H_2O$ | 770 g $l^{-1}$ |
| $NH_3$ | 23 g |
| Trace metal solution | |

6 g $l^{-1}$ Fe(III) citrate 1.5 g $l^{-1}$ $MnCl_2$—$4H_2O$
0.8 g $l^{-1}$ $ZmCH_2COOI_2$—$2H_2O$ 0.3 g $l^{-1}$ $H_3BO_3$
0.25 g $l^{-1}$ $Na_2MoO_4$—$2H_2O$ 0.25 g $l^{-1}$ $CoCl_2$ $6H_2O$
0.15 g $l^{-1}$ $CuCl_2$ $2H_2O$ 0.84 g $l^{-1}$ ethylene
Dinitrilo-tetracetic acid $Na_2$ sah $2H_2O$
(Tritriplex III, Merck)

In the present invention, growth, culturing, and/or fermentation of the transformed host cells is performed within a temperature range permitting survival of the host cells, preferably a temperature within the range of about 4° C. to about 55° C., inclusive. Thus, e.g., the terms "growth" (and "grow," "growing"), "culturing" (and "culture"), and "fermentation" (and "ferment," "fermenting"), as used herein in regard to the host cells of the present invention, inherently means "growth," "culturing," and "fermentation," within a temperature range of about 4° C. to about 55° C., inclusive. In addition, "growth" is used to indicate both biological states of active cell division and/or enlargement, as well as biological states in which a non-dividing and/or non-enlarging cell is being metabolically sustained, the latter use of the term "growth" being synonymous with the term "maintenance."

The host cells of the array should be grown and maintained at a suitable temperature for normal growth of that cell type. Such normal growth temperatures may be readily selected based on the known growth requirements of the selected host cell. Preferably, during the establishment of the culture and particularly during course of the screening, the cell culture is incubated in a controlled $CO_2/N_2$ humidity suitable for growth of the selected cells before and after transformation with the heterologous protein or polypeptide of interest. The humidity of the incubation is controlled to minimize evaporation from the culture vessel, and permit the use of smaller volumes. Alternatively, or in addition to controlling humidity, the vessels may be covered with lids in order to minimize evaporation. Selection of the incubation temperature depends primarily upon the identity of the host cells utilized. Selection of the percent humidity to control evaporation is based upon the selected volume of the vessel and concentration and volume of the cell culture in the vessel, as well as upon the incubation temperature. Thus, the humidity may vary from about 10% to about 80%. It should be understood that selection of a suitable conditions is well within the skill of the art.

Screening

The strain array described herein can be screened for the optimal host cell population in which to express a heterologous protein of interest. The optimal host cell population can be identified or selected based on the quantity, quality, and/or location of the expressed protein of interest. In one embodiment, the optimal host cell population is one that results in an increased yield of the protein or polypeptide of interest within the host cell compared to other populations of phenotypically distinct host cells in the array.

The increased production alternatively can be an increased level of properly processed protein or polypeptide per gram of protein produced, or per gram of host protein. The increased production can also be an increased level of recoverable protein or polypeptide produced per gram of heterologous protein or per gram of host cell protein. The increased production can also be any combination of an increased level of total protein, increased level of properly processed or properly folded protein, or increased level of active or soluble protein. In this embodiment, the term "increased" or "improved" is relative to the level of protein or polypeptide that is produced, properly processed, soluble, and/or recoverable when the protein or polypeptide of interest is expressed in one or more other populations of host cells in the array. The increased production may optimize the efficiency of the cell or organism by for example, decreasing the energy expenditure, increasing the use of available resources, or decreasing the requirements for growth supplements in growth media. The increased production may also be the result of a decrease in proteolyic degradation of the expressed protein.

In one embodiment, at least one strain in the array produces at least 0.1 mg/ml correctly processed protein. A correctly processed protein has an amino terminus of the native protein. In another embodiment, at least one strain produces 0.1 to 10 mg/ml correctly processed protein in the cell, including at least about 0.2, about 0.3, about 0.4, about 0.5, about 0.6, about 0.7, about 0.8, about 0.9 or at least about 1.0 mg/ml correctly processed protein. In another embodiment, the total correctly processed protein or polypeptide of interest produced by at least one strain in the array is at least 1.0 mg/ml, at least about 2 mg/ml, at least about 3 mg/ml, about 4 mg/ml, about 5 mg/ml, about 6 mg/ml, about 7 mg/ml, about 8 mg/ml, about 10 mg/ml, about 15 mg/ml, about 20 mg/ml, about 25 mg/ml, about 30 mg/ml, about 35 mg/ml, about 40 mg/ml, about 45 mg/ml, at least about 50 mg/ml, or greater. In some embodiments, the amount of correctly processed protein produced is at least about 5%, about 10%, about 15%, about 20%, about 25%, about 30%, about 40%, about 50%, about 60%, about 70%, about 80%, about 90%, about 95%, about 96%, about 97%, about 98%, at least about 99%, or more of total heterologous protein in a correctly processed form.

An improved expression of a protein or polypeptide of interest can also refer to an increase in the solubility of the protein. The protein or polypeptide of interest can be produced and recovered from the cytoplasm, periplasm or extracellular medium of the host cell. The protein or polypeptide can be insoluble or soluble. The protein or polypeptide can include one or more targeting (e.g., signal or leader) sequences or sequences to assist purification, as discussed supra.

The term "soluble" as used herein means that the protein is not precipitated by centrifugation at between approximately 5,000 and 20,000× gravity when spun for 10-30 minutes in a buffer under physiological conditions. Soluble proteins are not part of an inclusion body or other precipitated mass. Similarly, "insoluble" means that the protein or polypeptide can be precipitated by centrifugation at between 5,000 and 20,000× gravity when spun for 10-30 minutes in a buffer under physiological conditions. Insoluble proteins or polypeptides can be part of an inclusion body or other precipitated mass. The term "inclusion body" is meant to include any intracellular body contained within a cell wherein an aggregate of proteins or polypeptides has been sequestered.

In another embodiment, the optimal host cell population produces an increased amount of the protein of interest that is transported to the periplasm or secreted into the extracellular space of the host cell. In one embodiment, at least one strain in the array produces at least 0.1 mg/ml protein in the periplasmic compartment. In another embodiment, at least one strain produces 0.1 to 10 mg/ml periplasmic protein in the cell, or at least about 0.2, about 0.3, about 0.4, about 0.5, about 0.6, about 0.7, about 0.8, about 0.9 or at least about 1.0 mg/ml periplasmic protein. In one embodiment, the total protein or polypeptide of interest produced by at least one strain in the array is at least 1.0 mg/ml, at least about 2 mg/ml, at least about 3 mg/ml, about 4 mg/ml, about 5 mg/ml, about 6 mg/ml, about 7 mg/ml, about 8 mg/ml, about 10 mg/ml, about 15 mg/ml, about 20 mg/ml, at least about 25 mg/ml, or greater. In some embodiments, the amount of periplasmic protein produced is at least about 5%, about 10%, about 15%, about 20%, about 25%, about 30%, about 40%, about 50%, about 60%, about 70%, about 80%, about 90%, about 95%, about 96%, about 97%, about 98%, about 99%, or more of total protein or polypeptide of interest produced.

At least one strain in the array of the invention can also lead to increased yield of the protein or polypeptide of interest. In one embodiment, at least one strain produces a protein or polypeptide of interest as at least about 5%, at least about 10%, about 15%, about 20%, about 25%, about 30%, about 40%, about 45%, about 50%, about 55%, about 60%, about 65%, about 70%, about 75%, or greater of total cell protein (tcp). "Percent total cell protein" is the amount of protein or polypeptide in the host cell as a percentage of aggregate cellular protein. Methods for the determination of the percent total cell protein are well known in the art.

In a particular embodiment, at least one host cell population in the array can have a heterologous protein production level of at least 1% tcp and a cell density of at least 40 mg/ml, when grown (i.e. within a temperature range of about 4° C. to about 55° C., including about 10° C., about 15° C., about 20° C., about 25° C., about 30° C., about 35° C., about 40° C., about 45° C., and about 50° C.) in a mineral salts medium. In a particularly preferred embodiment, the expression system will have a protein or polypeptide expression level of at least 5% tcp and a cell density of at least 40 g/L, when grown (i.e. within a temperature range of about 4° C. to about 55° C., inclusive) in a mineral salts medium.

In practice, heterologous proteins targeted to the periplasm are often found in the broth (see European Patent No. EP 0 288 451), possibly because of damage to or an increase in the fluidity of the outer cell membrane. The rate of this "passive" secretion may be increased by using a variety of mechanisms that permeabilize the outer cell membrane, including: colicin (Miksch et al. (1997) *Arch. Microbiol.* 167: 143-150); growth rate (Shokri et al. (2002) *App Miocrobiol Biotechnol* 58:386-392); TolIII overexpression (Wan and Baneyx (1998) *Protein Expression Purif.* 14: 13-22); bacteriocin release protein (Hsiung et al. (1989) *Bio/Technology* 7: 267-71), colicin A lysis protein (Lloubes et al. (1993) *Biochimie* 75: 451-8) mutants that leak periplasmic proteins (Furlong and Sundstrom (1989) Developments in Indus. *Microbio.* 30: 141-8); fusion partners (Jeong and Lee (2002) *Appl. Environ. Microbio.* 68: 4979-4985); or, recovery by osmotic shock (Taguchi et al. (1990) *Biochimica Biophysica Acta* 1049: 278-85). Transport of engineered proteins to the periplasmic space with subsequent localization in the broth has been used to produce properly folded and active proteins in *E. coli* (Wan and Baneyx (1998) *Protein Expression Purif.* 14: 13-22; Simmons et al. (2002) *J. Immun. Meth.* 263: 133-147; Lundell et al. (1990) *J. Indust. Microbio.* 5: 215-27).

The method may also include the step of purifying the protein or polypeptide of interest from the periplasm or from extracellular media. The heterologous protein or polypeptide can be expressed in a manner in which it is linked to a tag protein and the "tagged" protein can be purified from the cell or extracellular media.

In some embodiments, the protein or polypeptide of interest can also be produced by at least one strain in the array in an active form. The term "active" means the presence of biological activity, wherein the biological activity is comparable or substantially corresponds to the biological activity of a corresponding native protein or polypeptide. In the context of proteins this typically means that a polynucleotide or polypeptide comprises a biological function or effect that has at least about 20%, about 50%, preferably at least about 60-80%, and most preferably at least about 90-95% activity compared to the corresponding native protein or polypeptide using standard parameters. However, in some embodiments, it may be desirable to produce a polypeptide that has altered or improved activity compared to the native protein (e.g. one that has altered or improved immunoreactivity, substrate specificity, etc). An altered or improved polypeptide may result from a particular conformation created by one or more of the host cell populations of the array.

The determination of protein or polypeptide activity can be performed utilizing corresponding standard, targeted comparative biological assays for particular proteins or polypeptides which can be used to assess biological activity.

The recovery of active protein or polypeptide of interest may also be improved in the optimal host strain compared to one or more other strains in the array of the invention. Active proteins can have a specific activity of at least about 20%, at least about 30%, at least about 40%, about 50%, about 60%, at least about 70%, about 80%, about 90%, or at least about 95% that of the native protein or polypeptide from which the sequence is derived. Further, the substrate specificity ($k_{cat}/K_m$) is optionally substantially similar to the native protein or polypeptide. Typically, $k_{cat}/K_m$ will be at least about 30%, about 40%, about 50%, about 60%, about 70%, about 80%, at least about 90%, at least about 95%, or greater. Methods of assaying and quantifying measures of protein and polypeptide activity and substrate specificity ($k_{cat}/K_m$), are well known to those of skill in the art.

Measurement of Protein Activity

The activity of the heterologously-expressed protein or polypeptide of interest can be compared with a previously established native protein or polypeptide standard activity. Alternatively, the activity of the protein or polypeptide of interest can be determined in a simultaneous, or substantially simultaneous, comparative assay with the native protein or polypeptide. For example, in vitro assays can be used to determine any detectable interaction between a protein or polypeptide of interest and a target, e.g. between an expressed enzyme and substrate, between expressed hormone and hormone receptor, between expressed antibody and antigen, etc. Such detection can include the measurement of calorimetric changes, proliferation changes, cell death, cell repelling, changes in radioactivity, changes in solubility, changes in molecular weight as measured by gel electrophoresis and/or gel exclusion methods, phosphorylation abilities, antibody specificity assays such as ELISA assays, etc. In addition, in vivo assays include, but are not limited to, assays to detect physiological effects of the heterologously expressed protein or polypeptide in comparison to physiological effects of the native protein or polypeptide, e.g. weight gain, change in electrolyte balance, change in blood clotting time, changes in clot dissolution and the induction of antigenic response. Generally, any in vitro or in vivo assay can be used to determine the active nature of the protein or polypeptide of interest that allows for a comparative analysis to the native protein or polypeptide so long as such activity is assayable. Alternatively, the proteins or polypeptides produced in at least one strain in the array of the present invention can be assayed for the ability to stimulate or inhibit interaction between the protein or polypeptide and a molecule that normally interacts with the protein or polypeptide, e.g. a substrate or a component of a signal pathway with which the native protein normally interacts. Such assays can typically include the steps of combining the protein with a substrate molecule under conditions that allow the protein or polypeptide to interact with the target molecule, and detect the biochemical consequence of the interaction with the protein and the target molecule.

Assays that can be utilized to determine protein or polypeptide activity are described, for example, in Ralph, P. J., et al. (1984) *J. Immunol.* 132:1858 or Saiki et al. (1981) *J. Immunol.* 127:1044, Steward, W. E. II (1980) The Interferon Systems. Springer-Verlag, Vienna and New York, Broxmeyer, H. E., et al. (1982) Blood 60:595, *Molecular Cloning: A Laboratory Manua"*, 2d ed., Cold Spring Harbor Laboratory Press, Sambrook, J., E. F. Fritsch and T. Maniatis eds., 1989, and *Methods in Enzymology: Guide to Molecular Cloning Techniques*, Academic Press, Berger, S. L. and A. R. Kimmel eds., 1987, A K Patra et al., *Protein Expr Purif,* 18(2): p/182-92 (2000), Kodama et al., *J. Biochem.* 99: 1465-1472 (1986); Stewart et al., *Proc. Natl. Acad. Sci. USA* 90: 5209-5213 (1993); (Lombillo et al., *J. Cell Biol.* 128:107-115 (1995); (Vale et al., *Cell* 42:39-50 (1985). Activity can be compared between samples of heterologously expressed protein derived from one or more of the other host cell populations in the array, or can be compared to the activity of a native protein, or both. Activity measurements can be performed on isolated protein, or can be performed in vitro in the host cell.

In another embodiment, protein production and/or activity may be monitored directly in the culture by fluorescence or spectroscopic measurements on, for example, a conventional microscope, luminometer, or plate reader. Where the protein of interest is an enzyme whose substrate is known, the substrate can be added to the culture media wherein a fluorescent signal is emitted when the substrate is converted by the enzyme into a product. In one embodiment, the expression construct encoding the heterologous protein or polypeptide of interest further encodes a reported protein. By "reporter protein" is meant a protein that by its presence in or on a cell or when secreted in the media allows the cell to be distinguished from a cell that does not contain the reporter protein. Production of the heterologous protein of interest results in a detectable change in the host cell population. The reporter molecule can be firefly luciferase and GFP or any other fluorescence molecule, as well as beta-galactosidase gene (beta.gal) and chloramphenicol and acetyltransferase gene (CAT). Assays for expression produced in conjunction with each of these reporter gene elements are well-known to those skilled in the art.

The reporter gene can encode a detectable protein or an indirectly detectable protein, or the reporter gene can be a survival gene. In a preferred embodiment, the reporter protein is a detectable protein. A "detectable protein" or "detection protein" (encoded by a detectable or detection gene) is a protein that can be used as a direct label; that is, the protein is detectable (and preferably, a cell comprising the detectable protein is detectable) without further manipulation. Thus, in this embodiment, the protein product of the reporter gene itself can serve to distinguish cells that are expressing the detectable gene. In this embodiment, suitable detectable genes include those encoding autofluorescent proteins.

As is known in the art, there are a variety of autofluorescent proteins known; these generally are based on the green fluorescent protein (GFP) from *Aequorea* and variants thereof, including, but not limited to, GFP, (Chalfie, et al. (1994) *Science* 263(5148):802-805); enhanced GFP (EGFP; Clontech—Genbank Accession Number U55762)), blue fluorescent protein (BFP; Quantum Biotechnologies, Inc., Montreal, Canada); Stauber (1998) *Biotechniques* 24(3):462-471; Heim and Tsien (1996) *Curr. Biol.* 6:178-182), enhanced yellow fluorescent protein (EYFP; Clontech Laboratories, Inc., Palo Alto, Calif.) and red fluorescent protein. In addition, there are recent reports of autofluorescent proteins from *Renilla* and *Ptilosarcus* species. See WO 92/15673; WO 95/07463; WO 98/14605; WO 98/26277; WO 99/49019; U.S. Pat. No. 5,292,658; U.S. Pat. No. 5,418,155; U.S. Pat. No. 5,683,888; U.S. Pat. No. 5,741,668; U.S. Pat. No. 5,777,079; U.S. Pat. No. 5,804,387; U.S. Pat. No. 5,874,304; U.S. Pat. No. 5,876,995; and U.S. Pat. No. 5,925,558; all of which are expressly incorporated herein by reference.

Isolation of Protein or Polypeptide of Interest

To measure the yield, solubility, conformation, and/or activity of the protein of interest, it may be desirable to isolate the protein from one or more strains in the array. The isolation may be a crude, semi-crude, or pure isolation, depending on the requirements of the assay used to make the appropriate measurements. The protein may be produced in the cytoplasm, targeted to the periplasm, or may be secreted into the culture or fermentation media. To release proteins targeted to the periplasm, treatments involving chemicals such as chloroform (Ames et al. (1984) *J. Bacteriol.,* 160: 1181-1183), guanidine-HCl, and Triton X-100 (Naglak and Wang (1990) *Enzyme Microb. Technol.,* 12: 603-611) have been used. However, these chemicals are not inert and may have detrimental effects on many heterologous protein products or subsequent purification procedures. Glycine treatment of *E. coli* cells, causing permeabilization of the outer membrane, has also been reported to release the periplasmic contents (Ariga et al. (1989) J. Ferm. Bioeng., 68: 243-246). The most widely used methods of periplasmic release of heterologous protein are osmotic shock (Nosal and Heppel (1966) *J. Biol. Chem.,* 241: 3055-3062; Neu and Heppel (1965) *J. Biol. Chem.,* 240:3685-3692), hen eggwhite (HEW)-lysozyme/ethylenediamine tetraacetic acid (EDTA) treatment (Neu and Heppel (1964) *J. Biol. Chem.,* 239: 3893-3900; Witholt et al. (1976) *Biochim. Biophys. Acta,* 443: 534-544; Pierce et al. (1995) ICheme Research. Event, 2: 995-997), and combined HEW-lysozyme/osmotic shock treatment (French et al. (1996) *Enzyme and Microb. Tech.,* 19: 332-338). The French method involves resuspension of the cells in a fractionation buffer followed by recovery of the periplasmic fraction, where osmotic shock immediately follows lysozyme treatment.

Typically, these procedures include an initial disruption in osmotically-stabilizing medium followed by selective release in non-stabilizing medium. The composition of these media (pH, protective agent) and the disruption methods used (chloroform, HEW-lysozyme, EDTA, sonication) vary among specific procedures reported. A variation on the HEW-lysozyme/ EDTA treatment using a dipolar ionic detergent in place of EDTA is discussed by Stabel et al. (1994) *Veterinary Microbiol.*, 38: 307-314. For a general review of use of intracellular lytic enzyme systems to disrupt *E. coli*, see Dabora and Cooney (1990) in *Advances in Biochemical Engineering/ Biotechnology*, Vol. 43, A. Fiechter, ed. (Springer-Verlag: Berlin), pp. 11-30.

Conventional methods for the recovery of proteins or polypeptides of interest from the cytoplasm, as soluble protein or refractile particles, involved disintegration of the bacterial cell by mechanical breakage. Mechanical disruption typically involves the generation of local cavitation in a liquid suspension, rapid agitation with rigid beads, sonication, or grinding of cell suspension (*Bacterial Cell Surface Techniques*, Hancock and Poxton (John Wiley & Sons Ltd, 1988), Chapter 3, p. 55).

HEW-lysozyme acts biochemically to hydrolyze the peptidoglycan backbone of the cell wall. The method was first developed by Zinder and Arndt (1956) *Proc. Natl. Acad. Sci. USA*, 42: 586-590, who treated *E. coli* with egg albumin (which contains HEW-lysozyme) to produce rounded cellular spheres later known as spheroplasts. These structures retained some cell-wall components but had large surface areas in which the cytoplasmic membrane was exposed. U.S. Pat. No. 5,169,772 discloses a method for purifying heparinase from bacteria comprising disrupting the envelope of the bacteria in an osmotically-stabilized medium, e.g., 20% sucrose solution using, e.g., EDTA, lysozyme, or an organic compound, releasing the non-heparinase-like proteins from the periplasmic space of the disrupted bacteria by exposing the bacteria to a low-ionic-strength buffer, and releasing the heparinase-like proteins by exposing the low-ionic-strength-washed bacteria to a buffered salt solution.

Many different modifications of these methods have been used on a wide range of expression systems with varying degrees of success (Joseph-Liazun et al. (1990) *Gene*, 86: 291-295; Carter et al. (1992) *Bio/Technology*, 10: 163-167). Efforts to induce recombinant cell culture to produce lysozyme have been reported. EP 0 155 189 discloses a means for inducing a recombinant cell culture to produce lysozymes, which would ordinarily be expected to kill such host cells by means of destroying or lysing the cell wall structure.

U.S. Pat. No. 4,595,658 discloses a method for facilitating externalization of proteins transported to the periplasmic space of bacteria. This method allows selective isolation of proteins that locate in the periplasm without the need for lysozyme treatment, mechanical grinding, or osmotic shock treatment of cells. U.S. Pat. No. 4,637,980 discloses producing a bacterial product by transforming a temperature-sensitive lysogen with a DNA molecule that codes, directly or indirectly, for the product, culturing the transformant under permissive conditions to express the gene product intracellularly, and externalizing the product by raising the temperature to induce phage-encoded functions. Asami et al. (1997) *J. Ferment. and Bioeng.*, 83: 511-516 discloses synchronized disruption of *E. coli* cells by T4 phage infection, and Tanji et al. (1998) *J. Ferment. and Bioeng.*, 85: 74-78 discloses controlled expression of lysis genes encoded in T4 phage for the gentle disruption of *E. coli* cells.

Upon cell lysis, genomic DNA leaks out of the cytoplasm into the medium and results in significant increase in fluid viscosity that can impede the sedimentation of solids in a centrifugal field. In the absence of shear forces such as those exerted during mechanical disruption to break down the DNA polymers, the slower sedimentation rate of solids through viscous fluid results in poor separation of solids and liquid during centrifugation. Other than mechanical shear force, there exist nucleolytic enzymes that degrade DNA polymer. In *E. coli*, the endogenous gene endA encodes for an endonuclease (molecular weight of the mature protein is approx. 24.5 kD) that is normally secreted to the periplasm and cleaves DNA into oligodeoxyribonucleotides in an endonucleolytic manner. It has been suggested that endA is relatively weakly expressed by *E. coli* (Wackernagel et al. (1995) *Gene* 154: 55-59).

If desired, the proteins produced using one or more strains in the array of this invention may be isolated and purified to substantial purity by standard techniques well known in the art, including, but not limited to, ammonium sulfate or ethanol precipitation, acid extraction, anion or cation exchange chromatography, phosphocellulose chromatography, hydrophobic interaction chromatography, affinity chromatography, nickel chromatography, hydroxylapatite chromatography, reverse phase chromatography, lectin chromatography, preparative electrophoresis, detergent solubilization, selective precipitation with such substances as column chromatography, immunopurification methods, and others. For example, proteins having established molecular adhesion properties can be reversibly fused with a ligand. With the appropriate ligand, the protein can be selectively adsorbed to a purification column and then freed from the column in a relatively pure form. The fused protein is then removed by enzymatic activity. In addition, protein can be purified using immunoaffinity columns or Ni-NTA columns. General techniques are further described in, for example, R. Scopes, *Protein Purification*: Principles and Practice, Springer-Verlag: N.Y. (1982); Deutscher, *Guide to Protein Purification*, Academic Press (1990); U.S. Pat. No. 4,511,503; S. Roe, *Protein Purification Techniques: A Practical Approach* (Practical Approach Series), Oxford Press (2001); D. Bollag, et al., Protein Methods, Wiley-Lisa, Inc. (1996); AK Patra et al., *Protein Expr Purif*, 18(2): p/182-92 (2000); and R. Mukhija, et al., *Gene* 165(2): p. 303-6 (1995). See also, for example, Ausubel, et al. (1987 and periodic supplements); Deutscher (1990) "Guide to Protein Purification," *Methods in Enzymology* vol. 182, and other volumes in this series; Coligan, et al. (1996 and periodic Supplements) *Current Protocols in Protein Science* Wiley/ Greene, N.Y.; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See also, for example, Hochuli (1989) *Chemische Industrie* 12:69-70; Hochuli (1990) "Purification of Recombinant Proteins with Metal Chelate Absorbent" in Setlow (ed.) *Genetic Engineering, Principle and Methods* 12:87-98, Plenum Press, NY; and Crowe, et al. (1992) QIAexpress: The High Level Expression & Protein Purification System QUIAGEN, Inc., Chatsworth, Calif.

Detection of the expressed protein is achieved by methods known in the art and include, for example, radioimmunoassays, Western blotting techniques or immunoprecipitation.

Certain proteins expressed by the strains in the array of this invention may form insoluble aggregates ("inclusion bodies"). Several protocols are suitable for purification of proteins from inclusion bodies. For example, purification of inclusion bodies typically involves the extraction, separation and/or purification of inclusion bodies by disruption of the host cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension is typically lysed using 2-3 passages through a French Press. The cell suspension can also be homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies can be solubilized, and the lysed cell suspension typically can be centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art.

The heterologously-expressed proteins present in the supernatant can be separated from the host proteins by standard separation techniques well known to those of skill in the art. For example, an initial salt fractionation can separate many of the unwanted host cell proteins (or proteins derived from the cell culture media) from the protein or polypeptide of interest. One such example can be ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of a protein or polypeptide of interest can be used to isolated it from proteins of greater and lesser size using ultrafiltration through membranes of different pore size (for example, Amicon or Millipore membranes). As a first step, the protein mixture can be ultrafiltered through a membrane with a pore size that has a lower molecular weight cut-off than the molecular weight of the protein of interest. The retentate of the ultrafiltration can then be ultrafiltered against a membrane with a molecular cut off greater than the molecular weight of the protein of interest. The protein or polypeptide of interest will pass through the membrane into the filtrate. The filtrate can then be chromatographed as described below.

The expressed proteins or polypeptides of interest can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Renaturation and Refolding

Where heterologously expressed protein is produced in a denatured form, insoluble protein can be renatured or refolded to generate secondary and tertiary protein structure conformation. Protein refolding steps can be used, as necessary, in completing configuration of the heterologous product. Refolding and renaturation can be accomplished using an agent that is known in the art to promote dissociation/association of proteins. For example, the protein can be incubated with dithiothreitol followed by incubation with oxidized glutathione disodium salt followed by incubation with a buffer containing a refolding agent such as urea.

The protein or polypeptide of interest can also be renatured, for example, by dialyzing it against phosphate-buffered saline (PBS) or 50 mM Na-acetate, pH 6 buffer plus 200 mM NaCl. Alternatively, the protein can be refolded while immobilized on a column, such as the Ni NTA column by using a linear 6M-1M urea gradient in 500 mM NaCl, 20% glycerol, 20 mM Tris/HCl pH 7.4, containing protease inhibitors. The renaturation can be performed over a period of 1.5 hours or more. After renaturation the proteins can be eluted by the addition of 250 mM imidazole. Imidazole can be removed by a final dialyzing step against PBS or 50 mM sodium acetate pH 6 buffer plus 200 mM NaCl. The purified protein can be stored at 4° C. or frozen at −80° C.

Other methods include, for example, those that may be described in M H Lee et al., *Protein Expr. Purif.*, 25(1): p. 166-73 (2002), W. K. Cho et al., *J. Biotechnology*, 77(2-3): p. 169-78 (2000), Ausubel, et al. (1987 and periodic supplements), Deutscher (1990) "Guide to Protein Purification," *Methods in Enzymology* vol. 182, and other volumes in this series, Coligan, et al. (1996 and periodic Supplements) *Current Protocols in Protein Science* Wiley/Greene, N.Y., S. Roe, *Protein Purification Techniques: A Practical Approach* (Practical Approach Series), Oxford Press (2001); D. Bollag, et al., Protein Methods, Wiley-Lisa, Inc. (1996)

Expression Vectors

A heterologous protein of interest can be produced in one or more of the host cells disclosed herein by introducing into each strain an expression vector encoding the heterologous protein of interest. In one embodiment, the vector comprises a polynucleotide sequence encoding the protein of interest operably linked to a promoter capable of functioning in the chosen host cell, as well as all other required transcription and translation regulatory elements.

The term "operably linked" refers to any configuration in which the transcriptional and any translational regulatory elements are covalently attached to the encoding sequence in such disposition(s), relative to the coding sequence, that in and by action of the host cell, the regulatory elements can direct the expression of the coding sequence.

The heterologous protein of interest can be expressed from polynucleotides in which the heterologous polypeptide coding sequence is operably linked to transcription and translation regulatory elements to form a functional gene from which the host cell can express the protein or polypeptide. The coding sequence can be a native coding sequence for the heterologous polypeptide, or may be a coding sequence that has been selected, improved, or optimized for use in the selected expression host cell: for example, by synthesizing the gene to reflect the codon use bias of a host species. In one embodiment of the invention, the host species is a *P. fluore-*

*scens*, and the codon bias of *P. fluorescens* is taken into account when designing the polypeptide coding sequence. The gene(s) are constructed within or inserted into one or more vector(s), which can then be transformed into the expression host cell.

Other regulatory elements may be included in a vector (also termed "expression construct"). The vector will typically comprise one or more phenotypic selectable markers and an origin of replication to ensure maintenance of the vector and to, if desirable, provide amplification within the host. Additional elements include, but are not limited to, for example, transcriptional enhancer sequences, translational enhancer sequences, other promoters, activators, translational start and stop signals, transcription terminators, cistronic regulators, polycistronic regulators, or tag sequences, such as nucleotide sequence "tags" and "tag" polypeptide coding sequences, which facilitates identification, separation, purification, and/or isolation of an expressed polypeptide.

In another embodiment, the expression vector further comprises a tag sequence adjacent to the coding sequence for the protein or polypeptide of interest. In one embodiment, this tag sequence allows for purification of the protein. The tag sequence can be an affinity tag, such as a hexa-histidine affinity tag. In another embodiment, the affinity tag can be a glutathione-S-transferase molecule. The tag can also be a fluorescent molecule, such as YFP or GFP, or analogs of such fluorescent proteins. The tag can also be a portion of an antibody molecule, or a known antigen or ligand for a known binding partner useful for purification.

A protein-encoding gene according to the present invention can include, in addition to the protein coding sequence, the following regulatory elements operably linked thereto: a promoter, a ribosome binding site (RBS), a transcription terminator, and translational start and stop signals. Useful RBSs can be obtained from any of the species useful as host cells in expression systems according to the present invention, preferably from the selected host cell. Many specific and a variety of consensus RBSs are known, e.g., those described in and referenced by D. Frishman et al., Gene 234(2):257-65 (8 Jul. 1999); and B. E. Suzek et al., Bioinformatics 17(12):1123-30 (December 2001). In addition, either native or synthetic RBSs may be used, e.g., those described in: EP 0207459 (synthetic RBSs); O. Ikehata et al., Eur. J. Biochem. 181(3):563-70 (1989) (native RBS sequence of 5'-AAGGAAG-3'). Further examples of methods, vectors, translation and transcription elements, and other elements useful in the present invention are described in, e.g.: U.S. Pat. No. 5,055,294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox.

Transcription of the DNA encoding the heterologous protein of interest is increased by inserting an enhancer sequence into the vector or plasmid. Typical enhancers are cis-acting elements of DNA, usually about from 10 to 300 bp in size that act on the promoter to increase its transcription. Examples include various *Pseudomonas* enhancers.

Generally, the heterologous expression vectors will include origins of replication and selectable markers permitting transformation of the host cell and a promoter derived from a highly-expressed gene to direct transcription of a downstream structural sequence. Such promoters can be derived from operons encoding the enzymes such as 3-phosphoglycerate kinase (PGK), acid phosphatase, or heat shock proteins, among others. Where signal sequences are used, the heterologous coding sequence is assembled in appropriate phase with translation initiation and termination sequences, and the signal sequence capable of directing compartmental accumulation or secretion of the translated protein. Optionally the heterologous sequence can encode a fusion enzyme including an N-terminal identification polypeptide imparting desired characteristics, e.g., stabilization or simplified purification of expressed heterologous product. The fusion polypeptide can also comprise one or more target proteins or inhibitors or enhances thereof, as discussed supra.

Vectors are known in the art for expressing heterologous proteins in host cells, and any of these may be used for expressing the genes according to the present invention. Such vectors include, e.g., plasmids, cosmids, and phage expression vectors. Examples of useful plasmid vectors include, but are not limited to, the expression plasmids pBBR1MCS, pDSK519, pKT240, pML122, pPS10, RK2, RK6, pRO1600, and RSF1010. Other examples of such useful vectors include those described by, e.g.: N. Hayase, in Appl. Envir. Microbiol. 60(9):3336-42 (September 1994); A. A. Lushnikov et al., in Basic Life Sci. 30:657-62 (1985); S. Graupner & W. Wackemagel, in Biomolec. Eng. 17(1):11-16. (October 2000); H. P. Schweizer, in Curr. Opin. Biotech. 12(5):439-45 (October 2001); M. Bagdasarian & K. N. Timmis, in Curr. Topics Microbiol. Immunol. 96:47-67 (1982); T. Ishii et al., in FEMS Microbiol. Lett. 116(3):307-13 (Mar. 1, 1994); I. N. Olekhnovich & Y. K. Fomichev, in Gene 140(1):63-65 (Mar. 11, 1994); M. Tsuda & T. Nakazawa, in Gene 136(1-2):257-62 (Dec. 22, 1993); C. Nieto et al., in Gene 87(1):145-49 (Mar. 1, 1990); J. D. Jones & N. Gutterson, in Gene 61(3):299-306 (1987); M. Bagdasarian et al., in Gene 16(1-3):237-47 (December 1981); H. P. Schweizer et al., in Genet. Eng. (NY) 23:69-81 (2001); P. Mukhopadhyay et al., in J. Bact. 172(1): 477-80 (January 1990); D. O. Wood et al., in J. Bact. 145(3): 1448-51 (March 1981); and R. Holtwick et al., in Microbiology 147(Pt 2):337-44 (February 2001).

Further examples of expression vectors that can be useful in a host cell of the invention include those listed in Table 5 as derived from the indicated replicons.

TABLE 5

Examples of Useful Expression Vectors

| Replicon | Vector(s) |
| --- | --- |
| PPS10 | PCN39, PCN51 |
| RSF1010 | PKT261-3 |
|  | PMMB66EH |
|  | PEB8 |
|  | PPLGN1 |
|  | PMYC1050 |
| RK2/RP1 | PRK415 |
|  | PJB653 |
| PRO1600 | PUCP |
|  | PBSP |

The expression plasmid, RSF1010, is described, e.g., by F. Heffron et al., in Proc. Nat'l Acad. Sci. USA 72(9):3623-27 (September 1975), and by K. Nagahari & K. Sakaguchi, in J. Bact. 133(3):1527-29 (March 1978). Plasmid RSF1010 and derivatives thereof are particularly useful vectors in the present invention. Exemplary useful derivatives of RSF1010, which are known in the art, include, e.g., pKT212, pKT214, pKT231 and related plasmids, and pMYC1050 and related plasmids (see, e.g., U.S. Pat. Nos. 5,527,883 and 5,840,554 to Thompson et al.), such as, e.g., pMYC1803. Plasmid pMYC1803 is derived from the RSF1010-based plasmid pTJS260 (see U.S. Pat. No. 5,169,760 to Wilcox), which carries a regulated tetracycline resistance marker and the replication and mobilization loci from the RSF1010 plasmid.

Other exemplary useful vectors include those described in U.S. Pat. No. 4,680,264 to Puhler et al.

In one embodiment, an expression plasmid is used as the expression vector. In another embodiment, RSF1010 or a derivative thereof is used as the expression vector. In still another embodiment, pMYC1050 or a derivative thereof, or pMYC4803 or a derivative thereof, is used as the expression vector.

The plasmid can be maintained in the host cell by inclusion of a selection marker gene in the plasmid. This may be an antibiotic resistance gene(s), where the corresponding antibiotic(s) is added to the fermentation medium, or any other type of selection marker gene known in the art, e.g., a prototrophy-restoring gene where the plasmid is used in a host cell that is auxotrophic for the corresponding trait, e.g., a biocatalytic trait such as an amino acid biosynthesis or a nucleotide biosynthesis trait, or a carbon source utilization trait.

The promoters used in accordance with the present invention may be constitutive promoters or regulated promoters. Common examples of useful regulated promoters include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an *E. coli* organism.

Common examples of non-lac-type promoters useful in expression systems according to the present invention include, e.g., those listed in Table 6.

TABLE 6

| Examples of non-lac Promoters | |
|---|---|
| Promoter | Inducer |
| $P_R$ | High temperature |
| $P_L$ | High temperature |
| Pm | Alkyl- or halo-benzoates |
| Pu | Alkyl- or halo-toluenes |
| Psal | Salicylates |

See, e.g.: J. Sanchez-Romero & V. De Lorenzo (1999) Manual of Industrial Microbiology and Biotechnology (A. Demain & J. Davies, eds.) pp. 460-74 (ASM Press, Washington, D.C.); H. Schweizer (2001) Current Opinion in Biotechnology, 12:439-445; and R. Slater & R. Williams (2000 Molecular Biology and Biotechnology (J. Walker & R. Rapley, eds.) pp. 125-54 (The Royal Society of Chemistry, Cambridge, UK)). A promoter having the nucleotide sequence of a promoter native to the selected bacterial host cell may also be used to control expression of the transgene encoding the target polypeptide, e.g., a *Pseudomonas* anthranilate or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter, or whether derived from the same or different organisms.

Regulated promoters utilize promoter regulatory proteins in order to control transcription of the gene of which the promoter is a part. Where a regulated promoter is used herein, a corresponding promoter regulatory protein will also be part of an expression system according to the present invention. Examples of promoter regulatory proteins include: activator proteins, e.g., *E. coli* catabolite activator protein, MalT protein; AraC family transcriptional activators; repressor proteins, e.g., *E. coli* LacI proteins; and dual-function regulatory proteins, e.g., *E. coli* NagC protein. Many regulated-promoter/promoter-regulatory-protein pairs are known in the art. In one embodiment, the expression construct for the target protein(s) and the heterologous protein of interest are under the control of the same regulatory element.

Promoter regulatory proteins interact with an effector compound, i.e. a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although an effector compound can be used throughout the cell culture or fermentation, in a preferred embodiment in which a regulated promoter is used, after growth of a desired quantity or density of host cell biomass, an appropriate effector compound is added to the culture to directly or indirectly result in expression of the desired gene(s) encoding the protein or polypeptide of interest.

By way of example, where a lac family promoter is utilized, a lacI gene can also be present in the system. The lacI gene, which is (normally) a constitutively expressed gene, encodes the Lac repressor protein (LacD protein) which binds to the lac operator of these promoters. Thus, where a lac family promoter is utilized, the lacI gene can also be included and expressed in the expression system. In the case of the lac promoter family members, e.g., the tac promoter, the effector compound is an inducer, preferably a gratuitous inducer such as IPTG (isopropyl-D-1-thiogalactopyranoside, also called "isopropylthiogalactoside").

For expression of a protein or polypeptide of interest, any plant promoter may also be used. A promoter may be a plant RNA polymerase II promoter. Elements included in plant promoters can be a TATA box or Goldberg-Hogness box, typically positioned approximately 25 to 35 basepairs upstream (5') of the transcription initiation site, and the CCAAT box, located between 70 and 100 basepairs upstream. In plants, the CCAAT box may have a different consensus sequence than the functionally analogous sequence of mammalian promoters (Messing et al. (1983) In: *Genetic Engineering of Plants*, Kosuge et al., eds., pp. 211-227). In addition, virtually all promoters include additional upstream activating sequences or enhancers (Benoist and Chambon (1981) *Nature* 290:304-310; Gruss et al. (1981) *Proc. Nat. Acad. Sci.* 78:943-947; and Khoury and Gruss (1983) *Cell* 27:313-314) extending from around −100 bp to −1,000 bp or more upstream of the transcription initiation site.

Expression Systems

It may be desirable to target the protein or polypeptide of interest to the periplasm of one or more of the populations of host cells in the array, or into the extracellular space. In one embodiment, the expression vector further comprises a nucleotide sequence encoding a secretion signal sequence polypeptide operably linked to the nucleotide sequence encoding the protein or polypeptide of interest. In some embodiments, no modifications are made between the signal sequence and the protein or polypeptide of interest. However, in certain embodiments, additional cleavage signals are incorporated to promote proper processing of the amino terminal of the polypeptide.

The vector can have any of the characteristics described above. In one embodiment, the vector comprising the coding sequence for the protein or polypeptide of interest further comprises a signal sequence, e.g., a secretion signal sequence.

Therefore, in one embodiment, this isolated polypeptide is a fusion protein of the secretion signal and a protein or polypeptide of interest. However, the secretion signal can also be cleaved from the protein when the protein is targeted to the periplasm. In one embodiment, the linkage between the Sec system secretion signal and the protein or polypeptide is modified to increase cleavage of the secretion signal.

The CHAMPION™ pET expression system provides a high level of protein production. Expression is induced from the strong T7lac promoter. This system takes advantage of the high activity and specificity of the bacteriophage T7 RNA polymerase for high level transcription of the gene of interest. The lac operator located in the promoter region provides tighter regulation than traditional T7-based vectors, improving plasmid stability and cell viability (Studier and Moffatt (1986) *J Molecular Biology* 189(1): 113-30; Rosenberg, et al. (1987) *Gene* 56(1): 125-35). The T7 expression system uses the T7 promoter and T7 RNA polymerase (T7 RNAP) for high-level transcription of the gene of interest. High-level expression is achieved in T7 expression systems because the T7 RNAP is more processive than native *E. coli* RNAP and is dedicated to the transcription of the gene of interest. Expression of the identified gene is induced by providing a source of T7 RNAP in the host cell. This is accomplished by using a BL21 *E. coli* host containing a chromosomal copy of the T7 RNAP gene. The T7 RNAP gene is under the control of the lacUV5 promoter which can be induced by IPTG. T7 RNAP is expressed upon induction and transcribes the gene of interest.

The pBAD expression system allows tightly controlled, titratable expression of protein or polypeptide of interest through the presence of specific carbon sources such as glucose, glycerol and arabinose (Guzman, et al. (1995) J Bacteriology 177(14): 4121-30). The pBAD vectors are uniquely designed to give precise control over expression levels. Heterologous gene expression from the pBAD vectors is initiated at the araBAD promoter. The promoter is both positively and negatively regulated by the product of the araC gene. AraC is a transcriptional regulator that forms a complex with L-arabinose. In the absence of L-arabinose, the AraC dimer blocks transcription. For maximum transcriptional activation two events are required: (i) L-arabinose binds to AraC allowing transcription to begin, and, (ii) The cAMP activator protein (CAP)-cAMP complex binds to the DNA and stimulates binding of AraC to the correct location of the promoter region.

The trc expression system allows high-level, regulated expression in *E. coli* from the trc promoter. The trc expression vectors have been optimized for expression of eukaryotic genes in *E. coli*. The trc promoter is a strong hybrid promoter derived from the tryptophane (trp) and lactose (lac) promoters. It is regulated by the lacO operator and the product of the lacIQ gene (Brosius, J. (1984) Gene 27(2): 161-72).

Transformation of the host cells with the vector(s) disclosed herein may be performed using any transformation methodology known in the art, and the bacterial host cells may be transformed as intact cells or as protoplasts (i.e. including cytoplasts). Exemplary transformation methodologies include poration methodologies, e.g., electroporation, protoplast fusion, bacterial conjugation, and divalent cation treatment, e.g., calcium chloride treatment or CaCl/Mg2+ treatment, or other well known methods in the art. See, e.g., Morrison, *J. Bact.*, 132:349-351 (1977); Clark-Curtiss & Curtiss, *Methods in Enzymology*, 101:347-362 (Wu et al., eds, 1983), Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

Proteins of Interest

The methods and compositions of the present invention are useful for identifying a *P. fluorescens* strain that is optimal for producing high levels of a properly processed protein or polypeptide of interest. The arrays are useful for screening for production of a protein or polypeptide of interest of any species and of any size. However, in certain embodiments, the protein or polypeptide of interest is a therapeutically useful protein or polypeptide. In some embodiments, the protein can be a mammalian protein, for example a human protein, and can be, for example, a growth factor, a cytokine, a chemokine or a blood protein. The protein or polypeptide of interest can be processed in a similar manner to the native protein or polypeptide. In certain embodiments, the protein or polypeptide of interest is less than 100 kD, less than 50 kD, or less than 30 kD in size. In certain embodiments, the protein or polypeptide of interest is a polypeptide of at least about 5, 10, 15, 20, 30, 40, 50 or 100 or more amino acids.

The coding sequence for the protein or polypeptide of interest can be a native coding sequence for the polypeptide, if available, but will more preferably be a coding sequence that has been selected, improved, or optimized for use in an expressible form in the strains of the array: for example, by optimizing the gene to reflect the codon use bias of a *Pseudomonas* species such as *P. fluorescens* or other suitable organism. For gene optimization, one or more rare codons may be removed to avoid ribosomal stalling and minimize amino acid misincorporation. One or more gene-internal ribosome binding sites may also be eliminated to avoid truncated protein products. Long stretches of C and G nucleotides may be removed to avoid RNA polymerase slippage that could result in frame-shifts. Strong gene-internal stem-loop structures, especially the ones covering the ribosome binding site, may also be eliminated.

In other embodiments, the protein when produced also includes an additional targeting sequence, for example a sequence that targets the protein to the periplasm or the extracellular medium. In one embodiment, the additional targeting sequence is operably linked to the carboxy-terminus of the protein. In another embodiment, the protein includes a secretion signal for an autotransporter, a two partner secretion system, a main terminal branch system or a fimbrial usher porin.

The gene(s) that result are constructed within or are inserted into one or more vectors, and then transformed into each of the host cell populations in the array. Nucleic acid or a polynucleotide said to be provided in an "expressible form" means nucleic acid or a polynucleotide that contains at least one gene that can be expressed by the one or more of the host cell populations of the invention.

Extensive sequence information required for molecular genetics and genetic engineering techniques is widely publicly available. Access to complete nucleotide sequences of mammalian, as well as human, genes, cDNA sequences, amino acid sequences and genomes can be obtained from GenBank. GenBank is maintained by the National Institutes of Health, Bethesda, Md., and can be accessed at ncbi.nlm.nih.gov/Entrez within the NIH website. Additional information can also be obtained from GeneCards, an electronic encyclopedia integrating information about genes and their products and biomedical applications, made available by the Department of Molecular Genetics, the Weizmann Institute of Science, Rehovot, Israel. Nucleotide sequence information also can be obtained from the EMBL Nucleotide Sequence Database made available on the worldwide web by the European Bioinformatics Institute (Hinxton, Cambridge, UK) or from the DNA Databank of Japan (Research Organization of Information and Systems, National Institute of Genetics, Center for Information Biology and DNA Data Bank of Japan, 1111 Yata, Mishima, Shizuoka 411-8540, Japan). Additional sites for information on amino acid sequences include the Protein Information Resource website established by the National Biomedical Research Foundation, which includes Swiss-Prot.

Examples of proteins that can be expressed in this invention include molecules such as, e.g., renin, a growth hormone, including human growth hormone; bovine growth hormone; growth hormone releasing factor; parathyroid hormone; thyroid stimulating hormone; lipoproteins; $\alpha$-1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated polypeptide; a microbial protein, such as beta-lactamase; Dnase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-$\beta$; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-$\beta$, including TGF-$\beta$1, TGF-$\beta$2, TGF-$\beta$3, TGF-$\beta$4, or TGF-$\beta$5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

In certain embodiments, the protein or polypeptide can be selected from IL-1, IL-1a, IL-1b, IL-2, IL-3, IL-4, IL-5, IL-6, IL-7, IL-8, IL-9, IL-10, IL-11, IL-12, IL-12elasti, IL-13, IL-15, IL-16, IL-18, IL-18BPa, IL-23, IL-24, VIP, erythropoietin, GM-CSF, G-CSF, M-CSF, platelet derived growth factor (PDGF), MSF, FLT-3 ligand, EGF, fibroblast growth factor (FGF; e.g., $\alpha$-FGF (FGF-1), $\beta$-FGF (FGF-2), FGF-3, FGF-4, FGF-5, FGF-6, or FGF-7), insulin-like growth factors (e.g., IGF-1, IGF-2); tumor necrosis factors (e.g., TNF, Lymphotoxin), nerve growth factors (e.g., NGF), vascular endothelial growth factor (VEGF); interferons (e.g., IFN-$\alpha$, IFN-$\beta$, IFN-$\gamma$); leukemia inhibitory factor (LIF); ciliary neurotrophic factor (CNTF); oncostatin M; stem cell factor (SCF); transforming growth factors (e.g., TGF-$\alpha$, TGF-$\beta$1, TGF-$\beta$2, TGF-$\beta$3); TNF superfamily (e.g., LIGHT/TNFSF14, STALL-1/TNFSF13B (BLy5, BAFF, THANK), TNFalpha/TNFSF2 and TWEAK/TNFSF12); or chemokines (BCA-1/BLC-1, BRAK/Kec, CXCL16, CXCR3, ENA-78/LIX, Eotaxin-1, Eotaxin-2/MPIF-2, Exodus-2/SLC, Fractalkine/Neurotactin, GROalpha/MGSA, HCC-1, I-TAC, Lymphotactin/ATAC/SCM, MCP-1/MCAF, MCP-3, MCP-4, MDC/STCP-1/ABCD-1, MIP-1.quadrature., MIP-1.quadrature., MIP-2.quadrature./GRO.quadrature., MIP-3.quadrature./Exodus/LARC, MIP-3/Exodus-3/ELC, MIP-4/PARC/DC-CK1, PF-4, RANTES, SDF1, TARC, TECK, microbial toxins, ADP ribosylating toxins, microbial or viral antigens).

In one embodiment of the present invention, the protein of interest can be a multi-subunit protein or polypeptide. Multisubunit proteins that can be expressed include homomeric and heteromeric proteins. The multisubunit proteins may include two or more subunits that may be the same or different. For example, the protein may be a homomeric protein comprising 2, 3, 4, 5, 6, 7, 8, 9, 10, 11, 12 or more subunits. The protein also may be a heteromeric protein including 2, 3, 4, 5, 6, 7, 8, 9, 10, 11, 12, or more subunits. Exemplary multisubunit proteins include: receptors including ion channel receptors; extracellular matrix proteins including chondroitin; collagen; immunomodulators including MHC proteins, full chain antibodies, and antibody fragments; enzymes including RNA polymerases, and DNA polymerases; and membrane proteins.

In another embodiment, the protein of interest can be a blood protein. The blood proteins expressed in this embodiment include but are not limited to carrier proteins, such as albumin, including human and bovine albumin, transferrin, recombinant transferrin half-molecules, haptoglobin, fibrinogen and other coagulation factors, complement components, immunoglobulins, enzyme inhibitors, precursors of substances such as angiotensin and bradykinin, insulin, endothelin, and globulin, including alpha, beta, and gamma-globulin, and other types of proteins, polypeptides, and fragments thereof found primarily in the blood of mammals. The amino acid sequences for numerous blood proteins have been reported (see, S. S. Baldwin (1993) Comp. Biochem Physiol. 106b:203-218), including the amino acid sequence for human serum albumin (Lawn, L. M., et al. (1981) Nucleic Acids Research, 9:6103-6114.) and human serum transferrin (Yang, F. et al. (1984) Proc. Natl. Acad. Sci. USA 81:2752-2756).

In another embodiment, the protein of interest can be an enzyme or co-factor. The enzymes and co-factors expressed in this embodiment include but are not limited to aldolases, amine oxidases, amino acid oxidases, aspartases, B12 dependent enzymes, carboxypeptidases, carboxyesterases, carboxylyases, chemotrypsin, CoA requiring enzymes, cyanohydrin synthetases, cystathione synthases, decarboxylases, dehydrogenases, alcohol dehydrogenases, dehydratases, diaphorases, dioxygenases, enoate reductases, epoxide hydrases, fumerases, galactose oxidases, glucose isomerases, glucose oxidases, glycosyltrasferases, methyltransferases, nitrile hydrases, nucleoside phosphorylases, oxidoreductases, oxynitilases, peptidases, glycosyltrasferases, peroxidases, enzymes fused to a therapeutically active polypeptide, tissue plasminogen activator; urokinase, reptilase, streptokinase; catalase, superoxide dismutase; Dnase, amino acid hydrolases (e.g., asparaginase, amidohydrolases); carboxypeptidases; proteases, trypsin, pepsin, chymotrypsin, papain, bromelain, collagenase; neuramimidase; lactase, maltase, sucrase, and arabinofuranosidases.

In another embodiment, the protein of interest can be a single chain, Fab fragment and/or full chain antibody or fragments or portions thereof. A single-chain antibody can include the antigen-binding regions of antibodies on a single stably-folded polypeptide chain. Fab fragments can be a piece of a particular antibody. The Fab fragment can contain the antigen binding site. The Fab fragment can contain 2 chains: a light chain and a heavy chain fragment. These fragments can be linked via a linker or a disulfide bond.

In other embodiments, the protein of interest is a protein that is active at a temperature from about 20 to about 42° C. In one embodiment, the protein is active at physiological temperatures and is inactivated when heated to high or extreme temperatures, such as temperatures over 65° C.

In one embodiment, the protein of interest is a protein that is active at a temperature from about 20 to about 42° C., and/or is inactivated when heated to high or extreme temperatures, such as temperatures over 65° C.; is, or is substantially homologous to, a native protein, such as a native mammalian or human protein and not expressed from nucleic acids in concatameric form, where the promoter is not a native promoter in to the host cell used in the array but is derived from another organism, such as *E. coli*.

Host Cell

In one embodiment the invention provides an array of *P. fluorescens* host cells from which to optimally produce a heterologous protein or peptide of interest. *P. fluorescens* has been demonstrated to be an improved platform for production of a variety of proteins and several efficient secretion signals have been identified from this organism (see, U.S. Application Publication Number 2006/0008877, herein incorporated by reference in its entirety).

The Pseudomonads system offers advantages for commercial expression of polypeptides and enzymes, in comparison with other bacterial expression systems. In particular, *P. fluorescens* has been identified as an advantageous expression system. *P. fluorescens* encompasses a group of common, non-pathogenic saprophytes that colonize soil, water and plant surface environments. Commercial enzymes derived from *P. fluorescens* have been used to reduce environmental contamination, as detergent additives, and for stereoselective hydrolysis. *P. fluorescens* is also used agriculturally to control pathogens. U.S. Pat. No. 4,695,462 describes the expression of recombinant bacterial proteins in *P. fluorescens*.

However, it is contemplated that alternate host cells, or even a multiplicity of different host cells, can be used to generate an array comprising a plurality of phenotypically distinct host cells that have been genetically modified to modulate the expression of one or more target genes, as discussed supra. The host cell can be any organism in which target genes can be altered. Methods of identifying target genes homologous to those listed in Tables 1 and 2 are known in the art. Further, one of skill in the art would understand how to identify target genes that are native to or useful in a host cell of interest. Many of these proteins are well known in the art. See, for example, U.S. Patent Application Publication No. 2006/0110747).

Host cells can be selected from "Gram-negative Proteobacteria Subgroup 18." "Gram-negative Proteobacteria Subgroup 18" is defined as the group of all subspecies, varieties, strains, and other sub-special units of the species *Pseudomonas fluorescens*, including those belonging, e.g., to the following (with the ATCC or other deposit numbers of exemplary strain(s) shown in parenthesis): *Pseudomonas fluorescens* biotype A, also called biovar 1 or biovar I (ATCC 13525); *Pseudomonas fluorescens* biotype B, also called biovar 2 or biovar II (ATCC 17816); *Pseudomonas fluorescens* biotype C, also called biovar 3 or biovar III (ATCC 17400); *Pseudomonas fluorescens* biotype F, also called biovar 4 or biovar IV (ATCC 12983); *Pseudomonas fluorescens* biotype G, also called biovar 5 or biovar V (ATCC 17518); *Pseudomonas fluorescens* biovar VI; *Pseudomonas fluorescens* Pf0-1; *Pseudomonas fluorescens* Pf-5 (ATCC BAA-477); *Pseudomonas fluorescens* SBW25; and *Pseudomonas fluorescens* subsp. *cellulosa* (NCIMB 10462).

The host cell can be selected from "Gram-negative Proteobacteria Subgroup 19." "Gram-negative Proteobacteria Subgroup 19" is defined as the group of all strains of *Pseudomonas fluorescens* biotype A. A particularly preferred strain of this biotype is *P. fluorescens* strain MB101 (see U.S. Pat. No. 5,169,760 to Wilcox), and derivatives thereof. An example of a preferred derivative thereof is *P. fluorescens* strain MB214, constructed by inserting into the MB101 chromosomal asd (aspartate dehydrogenase gene) locus, a native *E. coli* PlacI-lacI-lacZYA construct (i.e. in which PlacZ was deleted).

Additional *P. fluorescens* strains that can be used in the present invention include *Pseudomonas fluorescens* Migula and *Pseudomonas fluorescens* Loitokitok, having the following ATCC designations: [NCIB 8286]; NRRL B-1244; NCIB 8865 strain CO1; NCIB 8866 strain $CO_2$; 1291 [ATCC 17458; IFO 15837; NCIB 8917; LA; NRRL B-1864; pyrrolidine; PW2 [ICMP 3966; NCPPB 967; NRRL B-899]; 13475; NCTC 10038; NRRL B-1603 [6; IFO 15840]; 52-1C; CCEB 488-A [BU 140]; CCEB 553 [EM 15/47]; IAM 1008 [AHH-27]; IAM 1055 [AHH-23]; 1 [IFO 15842]; 12 [ATCC 25323; NIH 11; den Dooren de Jong 216]; 18 [IFO 15833; WRRL P-7]; 93 [TR-10]; 108 [52-22; IFO 15832]; 143 [IFO 15836; PL]; 149 [2-40-40; IFO 15838]; 182 [IFO 3081; PJ 73]; 184 [IFO 15830]; 185 [W2 L-1]; 186 [IFO 15829; PJ 79]; 187 [NCPPB 263]; 188 [NCPPB 316]; 189 [PJ227; 1208]; 191 [IFO 15834; PJ 236; 22/1]; 194 [Klinge R-60; PJ 253]; 196 [PJ 288]; 197 [PJ 290]; 198 [PJ 302]; 201 [PJ 368]; 202 [PJ 372]; 203 [PJ 376]; 204 [IFO 15835; PJ 682]; 205 [PJ 686]; 206 [PJ 692]; 207 [PJ 693]; 208 [PJ 722]; 212. [PJ 832]; 215 [PJ 849]; 216 [PJ 885]; 267 [B-9]; 271 [B-1612]; 401 [C71A; IFO 15831; PJ 187]; NRRL B-3178 [4; IFO. 15841]; KY 8521; 3081; 30-21; [IFO 3081]; N; PYR; PW; D946-B83 [BU 2183; FERM-P 3328]; P-2563 [FERM-P 2894; IFO 13658]; IAM-1126 [43F]; M-1; A506 [A5-06]; A505 [A5-05-1]; A526 [A5-26]; B69; 72; NRRL B-4290; PMW6 [NCIB 11615]; SC 12936; A1 [IFO 15839]; F 1847 [CDC-EB]; F 1848 [CDC 93]; NCIB 10586; P17; F-12; AmMS 257; PRA25; 6133D02; 6519E01; Ni; SC15208; BNL-WVC; NCTC 2583 [NCIB 8194]; H13; 1013 [ATCC 11251; CCEB 295]; IFO 3903; 1062; or Pf-5.

In one embodiment, the host cell can be any cell capable of producing a protein or polypeptide of interest, including a *P. fluorescens* cell as described above. The most commonly used systems to produce proteins or polypeptides of interest include certain bacterial cells, particularly *E. coli*, because of their relatively inexpensive growth requirements and potential capacity to produce protein in large batch cultures. Yeasts are also used to express biologically relevant proteins and polypeptides, particularly for research purposes. Systems include *Saccharomyces cerevisiae* or *Pichia pastoris*. These systems are well characterized, provide generally acceptable levels of total protein production and are comparatively fast and inexpensive. Insect cell expression systems have also emerged as an alternative for expressing recombinant proteins in biologically active form. In some cases, correctly folded proteins that are post-translationally modified can be produced. Mammalian cell expression systems, such as Chinese hamster ovary cells, have also been used for the expression of proteins or polypeptides of interest. On a small scale, these expression systems are often effective. Certain biologics can be derived from proteins, particularly in animal or human health applications. In another embodiment, the host cell is a plant cell, including, but not limited to, a tobacco cell, corn, a cell from an *Arabidopsis* species, potato or rice cell.

In another embodiment, the host cell can be a prokaryotic cell such as a bacterial cell including, but not limited to, an *Escherichia* or a *Pseudomonas* species. Typical bacterial cells are described, for example, in "Biological Diversity: Bacteria and Archaeans," a chapter of the On-Line Biology Book, provided by Dr. M. J. Farabee of the Estrella Mountain Community College, Arizona, USA. In certain embodiments, the host cell can be a Pseudomonad cell, and can typically be a *P. fluorescens* cell. In other embodiments, the host cell can also be an *E. coli* cell. In another embodiment the host cell can be a eukaryotic cell, for example an insect cell, including but not limited to a cell from a *Spodoptera, Trichoplusia, Drosophila* or an *Estigmene* species, or a mammalian cell, including but not limited to a murine cell, a hamster cell, a monkey cell, a primate cell or a human cell.

In one embodiment, the host cell can be a member of any of the bacterial taxa. The cell can, for example, be a member of any species of eubacteria. The host can be a member of any one of the taxa: Acidobacteria, Actinobacteira, Aquificae, Bacteroidetes, Chlorobi, Chlamydiae, Choroflexi, Chrysiogenetes, Cyanobacteria, Deferribacteres, Deinococcus, Dictyoglomi, Fibrobacteres, Firmicutes, Fusobacteria, Gemmatimonadetes, Lentisphaerae, Nitrospirae, Planctomycetes, Proteobacteria, Spirochaetes, Thermodesulfobacteria, Thermomicrobia, Thermotogae, Thermus (Thermales), or Verrucomicrobia. In an embodiment of a eubacterial host cell, the cell can be a member of any species of eubacteria, excluding Cyanobacteria.

The bacterial host can also be a member of any species of Proteobacteria. A proteobacterial host cell can be a member of any one of the taxa Alphaproteobacteria, Betaproteobacteria, Gammaproteobacteria, Deltaproteobacteria, or Epsilonproteobacteria. In addition, the host can be a member of any one of the taxa Alphaproteobacteria, Betaproteobacteria, or Gammaproteobacteria, and a member of any species of Gammaproteobacteria.

In one embodiment of a Gamma Proteobacterial host, the host will be member of any one of the taxa Aeromonadales, Alteromonadales, Enterobacteriales, Pseudomonadales, or Xanthomonadales; or a member of any species of the Enterobacteriales or Pseudomonadales. In one embodiment, the host cell can be of the order Enterobacteriales, the host cell will be a member of the family Enterobacteriaceae, or may be a member of any one of the genera *Erwinia, Escherichia*, or *Serratia*; or a member of the genus *Escherichia*. Where the host cell is of the order Pseudomonadales, the host cell may be a member of the family Pseudomonadaceae, including the genus *Pseudomonas*. Gamma Proteobacterial hosts include members of the species *Escherichia coli* and members of the species *Pseudomonas fluorescens*.

Other *Pseudomonas* organisms may also be useful. Pseudomonads and closely related species include Gram-negative Proteobacteria Subgroup 1, which include the group of Proteobacteria belonging to the families and/or genera described as "Gram-Negative Aerobic Rods and Cocci" by R. E. Buchanan and N. E. Gibbons (eds.), Bergey's Manual of Determinative Bacteriology, pp. 217-289 (8th ed., 1974) (The Williams & Wilkins Co., Baltimore, Md., USA) (hereinafter "Bergey (1974)"). Table 7 presents these families and genera of organisms.

TABLE 7

Families and Genera Listed in the Part, "Gram-Negative Aerobic Rods and Cocci" (in Bergey (1974))

| | |
|---|---|
| Family I. *Pseudomonaceae* | *Gluconobacter* |
| | *Pseudomonas* |
| | *Xanthomonas* |
| | *Zoogloea* |
| Family II. *Azotobacteraceae* | *Azomonas* |
| | *Azotobacter* |
| | *Beijerinckia* |
| | *Derxia* |
| Family III. *Rhizobiaceae* | *Agrobacterium* |
| | *Rhizobium* |
| Family IV. *Methylomonadaceae* | *Methylococcus* |
| | *Methylomonas* |
| Family V. *Halobacteriaceae* | *Halobacterium* |
| | *Halococcus* |
| Other Genera | *Acetobacter* |
| | *Alcaligenes* |
| | *Bordetella* |
| | *Brucella* |
| | *Francisella* |
| | *Thermus* |

"Gram-negative Proteobacteria Subgroup 1" also includes Proteobacteria that would be classified in this heading according to the criteria used in the classification. The heading also includes groups that were previously classified in this section but are no longer, such as the genera *Acidovorax, Brevundimonas, Burkholderia, Hydrogenophaga, Oceanimonas, Ralstonia*, and *Stenotrophomonas*, the genus *Sphingomonas* (and the genus *Blastomonas*, derived therefrom), which was created by regrouping organisms belonging to (and previously called species of) the genus *Xanthomonas*, the genus *Acidomonas*, which was created by regrouping organisms belonging to the genus *Acetobacter* as defined in Bergey (1974). In addition hosts can include cells from the genus *Pseudomonas, Pseudomonas enalia* (ATCC 14393), *Pseudomonas nigrifaciensi* (ATCC 19375), and *Pseudomonas putrefaciens* (ATCC 8071), which have been reclassified respectively as *Alteromonas haloplanktis, Alteromonas nigrifaciens*, and *Alteromonas putrefaciens*. Similarly, e.g., *Pseudomonas acidovorans* (ATCC 15668) and *Pseudomonas testosteroni* (ATCC 11996) have since been reclassified as *Comamonas acidovorans* and *Comamonas testosteroni*, respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida*. "Gram-negative Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram-negative Proteobacteria Subgroup 1" include: 1) *Azotobacter* group bacteria of the genus *Azorhizophilus;* 2) Pseudomonadaceae family bacteria of the genera *Cellvibrio, Oligella*, and *Teredinibacter;* 3) Rhizobiaceae family bacteria of the genera *Chelatobacter, Ensifer, Liberibacter* (also called "*Candidatus Liberibacter*"), and *Sinorhizobium*; and 4) Methylococcaceae family bacteria of the genera *Methylobacter, Methylocaldum, Methylomicrobium, Methylosarcina*, and *Methylosphaera*.

In another embodiment, the host cell is selected from "Gram-negative Proteobacteria Subgroup 2." "Gram-negative Proteobacteria Subgroup 2" is defined as the group of Proteobacteria of the following genera (with the total numbers of catalog-listed, publicly-available, deposited strains thereof indicated in parenthesis, all deposited at ATCC, except as otherwise indicated): *Acidomonas* (2); *Acetobacter* (93); *Gluconobacter* (37); *Brevundimonas* (23); *Beyerinckia* (13); *Derxia* (2); *Brucella* (4); *Agrobacterium* (79); *Chelatobacter* (2); *Ensifer* (3); *Rhizobium* (144); *Sinorhizobium* (24); *Blastomonas* (1); *Sphingomonas* (27); *Alcaligenes* (88); *Bordetella* (43); *Burkholderia* (73); *Ralstonia* (33); *Acidovorax* (20); *Hydrogenophaga* (9); *Zoogloea* (9); *Methylobacter* (2); *Methylocaldum* (1 at NCIMB); *Methylococcus* (2); *Methylomicrobium* (2); *Methylomonas* (9); *Methylosarcina* (1); *Methylosphaera*; *Azomonas* (9); *Azorhizophilus* (5); *Azotobacter* (64); *Cellvibrio* (3); *Oligella* (5); *Pseudomonas* (1139); *Francisella* (4); *Xanthomonas* (229); *Stenotrophomonas* (50); and *Oceanimonas* (4).

Exemplary host cell species of "Gram-negative Proteobacteria Subgroup 2" include, but are not limited to the following bacteria (with the ATCC or other deposit numbers of exemplary strain(s) thereof shown in parenthesis): *Acidomonas methanolica* (ATCC 43581); *Acetobacter aceti* (ATCC 15973); *Gluconobacter oxydans* (ATCC 19357); *Brevundimonas diminuta* (ATCC 11568); *Beijerinckia indica* (ATCC 9039 and ATCC 19361); *Derxia gummosa* (ATCC 15994); *Brucella melitensis* (ATCC 23456), *Brucella abortus* (ATCC 23448); *Agrobacterium tumefaciens* (ATCC 23308), *Agrobacterium radiobacter* (ATCC 19358), *Agrobacterium rhizogenes* (ATCC 11325); *Chelatobacter heintzii* (ATCC 29600); *Ensifer adhaerens* (ATCC 33212); *Rhizobium leguminosarum* (ATCC 10004); *Sinorhizobium fredii* (ATCC 35423); *Blastomonas natatoria* (ATCC 35951); *Sphingomonas paucimobilis* (ATCC 29837); *Alcaligenes faecalis* (ATCC 8750); *Bordetella pertussis* (ATCC 9797); *Burkholderia cepacia* (ATCC 25416); *Ralstonia pickettii* (ATCC 27511); *Acidovorax facilis* (ATCC 11228); *Hydrogenophaga flava* (ATCC 33667); *Zoogloea ramigera* (ATCC 19544); *Methylobacter luteus* (ATCC 49878); *Methylocaldum gracile* (NCIMB 11912); *Methylococcus capsulatus* (ATCC 19069); *Methylomicrobium agile* (ATCC 35068); *Methylomonas methanica* (ATCC 35067); *Methylosarcina fibrata* (ATCC 700909); *Methylosphaera hansonii* (ACAM 549); *Azomonas agilis* (ATCC 7494); *Azorhizophilus paspali* (ATCC 23833); *Azotobacter chroococcum* (ATCC 9043); *Cellvibrio mixtus* (UQM 2601); *Oligella urethralis* (ATCC 17960); *Pseudomonas aeruginosa* (ATCC 10145), *Pseudomonas fluorescens* (ATCC 35858); *Francisella tularensis* (ATCC 6223); *Stenotrophomonas maltophilia* (ATCC 13637); *Xanthomonas campestris* (ATCC 33913); and *Oceanimonas doudoroffii* (ATCC 27123).

In another embodiment, the host cell is selected from "Gram-negative Proteobacteria Subgroup 3." "Gram-negative Proteobacteria Subgroup 3" is defined as the group of Proteobacteria of the following genera: *Brevundimonas; Agrobacterium; Rhizobium; Sinorhizobium; Blastomonas; Sphingomonas; Alcaligenes; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

In another embodiment, the host cell is selected from "Gram-negative Proteobacteria Subgroup 4." "Gram-negative Proteobacteria Subgroup 4" is defined as the group of Proteobacteria of the following genera: *Brevundimonas; Blastomonas; Sphingomonas; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

In another embodiment, the host cell is selected from "Gram-negative Proteobacteria Subgroup 5." "Gram-negative Proteobacteria Subgroup 5" is defined as the group of Proteobacteria of the following genera: *Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

The host cell can be selected from "Gram-negative Proteobacteria Subgroup 6." "Gram-negative Proteobacteria Subgroup 6" is defined as the group of Proteobacteria of the following genera: *Brevundimonas; Blastomonas; Sphingomonas; Burkholderia; Ralstonia; Acidovorax; Hydrogenophaga; Azomonas; Azorhizophilus; Azotobacter; Cellvibrio; Oligella; Pseudomonas; Teredinibacter; Stenotrophomonas; Xanthomonas*; and *Oceanimonas*.

The host cell can be selected from "Gram-negative Proteobacteria Subgroup 7." "Gram-negative Proteobacteria Subgroup 7" is defined as the group of Proteobacteria of the following genera: *Azomonas; Azorhizophilus; Azotobacter; Cellvibrio; Oligella; Pseudomonas; Teredinibacter; Stenotrophomonas; Xanthomonas*; and *Oceanimonas*.

The host cell can be selected from "Gram-negative Proteobacteria Subgroup 8." "Gram-negative Proteobacteria Subgroup 8" is defined as the group of Proteobacteria of the following genera: *Brevundimonas; Blastomonas; Sphingomonas; Burkholderia; Ralstonia; Acidovorax; Hydrogenophaga; Pseudomonas; Stenotrophomonas; Xanthomonas*; and *Oceanimonas*.

The host cell can be selected from "Gram-negative Proteobacteria Subgroup 9." "Gram-negative Proteobacteria Subgroup 9" is defined as the group of Proteobacteria of the following genera: *Brevundimonas; Burkholderia; Ralstonia; Acidovorax; Hydrogenophaga; Pseudomonas; Stenotrophomonas*; and *Oceanimonas*.

The host cell can be selected from "Gram-negative Proteobacteria Subgroup 10." "Gram-negative Proteobacteria Subgroup 10" is defined as the group of Proteobacteria of the following genera: *Burkholderia; Ralstonia; Pseudomonas; Stenotrophomonas*; and *Xanthomonas*.

The host cell can be selected from "Gram-negative Proteobacteria Subgroup 11." "Gram-negative Proteobacteria Subgroup 11" is defined as the group of the genera: *Pseudomonas; Stenotrophomonas*; and *Xanthomonas*. The host cell can be selected from "Gram-negative Proteobacteria Subgroup 12." "Gram-negative Proteobacteria Subgroup 12" is defined as the group of Proteobacteria of the following genera: *Burkholderia; Ralstonia; Pseudomonas*. The host cell can be selected from "Gram-negative Proteobacteria Subgroup 13." "Gram-negative Proteobacteria Subgroup 13" is defined as the group of Proteobacteria of the following genera: *Burkholderia; Ralstonia; Pseudomonas*; and *Xanthomonas*. The host cell can be selected from "Gram-negative Proteobacteria Subgroup 14." "Gram-negative Proteobacteria Subgroup 14" is defined as the group of Proteobacteria of the following genera: *Pseudomonas* and *Xanthomonas*. The host cell can be selected from "Gram-negative Proteobacteria Subgroup 15." "Gram-negative Proteobacteria Subgroup 15" is defined as the group of Proteobacteria of the genus *Pseudomonas*.

The host cell can be selected from "Gram-negative Proteobacteria Subgroup 16." "Gram-negative Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas alcaligenes* (ATCC 14909); *Pseudomonas anguilliseptica* (ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomonas oleovorans* (ATCC 8062); *Pseudomonas pseudoalcaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphila*; *Pseudomonas alginovora*; *Pseudomonas andersonii*; *Pseudomonas aspleni* (ATCC 23835); *Pseudomonas azelaica* (ATCC 27162); *Pseudomonas beyerinckii* (ATCC 19372); *Pseudomonas borealis*; *Pseudomonas boreopolis* (ATCC 33662); *Pseudomonas brassicacearum*; *Pseudomonas butanovora* (ATCC 43655); *Pseudomonas cellulosa* (ATCC 55703); *Pseudomonas aurantiaca* (ATCC 33663); *Pseudomonas chlororaphis* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens*; *Pseudomonas diterpeniphila*; *Pseudomonas elongata* (ATCC 10144); *Pseudomonas flectens* (ATCC 12775); *Pseudomonas azotoformans*; *Pseudomonas brenneri*; *Pseudomonas cedrella*; *Pseudomonas corrugata* (ATCC 29736); *Pseudomonas extremorientalis*; *Pseudomonas fluorescens* (ATCC 35858); *Pseudomonas gessardii*; *Pseudomonas libanensis*; *Pseudomonas mandelii* (ATCC 700871); *Pseudomonas marginalis* (ATCC 10844); *Pseudomonas migulae*; *Pseudomonas mucidolens* (ATCC 4685); *Pseudomonas orientalis*; *Pseudomonas rhodesiae*; *Pseudomonas synxantha* (ATCC 9890); *Pseudomonas tolaasii* (ATCC 33618); *Pseudomonas veronii* (ATCC 700474); *Pseudomonas frederiksbergensis*; *Pseudomonas geniculata* (ATCC 19374); *Pseudomonas gingeri*; *Pseudomonas graminis*; *Pseudomonas grimontii*; *Pseudomonas halodenitrificans*; *Pseudomonas halophila*; *Pseudomonas hibiscicola* (ATCC 19867); *Pseudomonas huttiensis* (ATCC 14670); *Pseudomonas hydrogenovora*; *Pseudomonas jessenii* (ATCC 700870); *Pseudomonas kilonensis*; *Pseudomonas lanceolata* (ATCC 14669); *Pseudomonas lini*; *Pseudomonas marginata* (ATCC 25417); *Pseudomonas mephitica* (ATCC 33665); *Pseudomonas denitrificans* (ATCC 19244); *Pseudomonas pertucinogena* (ATCC 190); *Pseudomonas pictorum* (ATCC 23328); *Pseudomonas psychrophila*; *Pseudomonas filva* (ATCC 31418); *Pseudomonas monteilii* (ATCC 700476); *Pseudomonas mosselii*; *Pseudomonas oryzihabitans* (ATCC 43272); *Pseudomonas plecoglossicida* (ATCC 700383); *Pseudomonas putida* (ATCC 12633); *Pseudomonas reactans*; *Pseudomonas spinosa* (ATCC 14606); *Pseudomonas balearica*; *Pseudomonas luteola* (ATCC 43273); *Pseudomonas stutzeri* (ATCC 17588); *Pseudomonas amygdali* (ATCC 33614); *Pseudomonas avellanae* (ATCC 700331); *Pseudomonas caricapapayae* (ATCC 33615); *Pseudomonas cichorii* (ATCC 10857); *Pseudomonas ficuserectae* (ATCC 35104); *Pseudomonas fuscovaginae*; *Pseudomonas meliae* (ATCC 33050); *Pseudomonas syringae* (ATCC 19310); *Pseudomonas viridiflava* (ATCC 13223); *Pseudomonas thermocarboxydovorans* (ATCC 35961); *Pseudomonas thermotolerans*; *Pseudomonas thivervalensis*; *Pseudomonas vancouverensis* (ATCC 700688); *Pseudomonas wisconsinensis*; and *Pseudomonas xiamenensis*.

The host cell can be selected from "Gram-negative Proteobacteria Subgroup 17." "Gram-negative Proteobacteria Subgroup 17" is defined as the group of Proteobacteria known in the art as the "fluorescent Pseudomonads" including those belonging, e.g., to the following *Pseudomonas* species: *Pseudomonas azotoformans*; *Pseudomonas brenneri*; *Pseudomonas cedrella*; *Pseudomonas corrugata*; *Pseudomonas extremorientalis*; *Pseudomonas fluorescens*; *Pseudomonas gessardii*; *Pseudomonas libanensis*; *Pseudomonas mandelii*; *Pseudomonas marginalis*; *Pseudomonas migulae*; *Pseudomonas mucidolens*; *Pseudomonas orientalis*; *Pseudomonas rhodesiae*; *Pseudomonas synxantha*; *Pseudomonas tolaasii*; and *Pseudomonas veronii*.

Other suitable hosts include those classified in other parts of the reference, such as Gram (+) Proteobacteria. In one embodiment, the host cell is an *E. coli*. The genome sequence for *E. coli* has been established for *E. coli* MG1655 (Blattner, et al. (1997) The complete genome sequence of *Escherichia coli* K-12, Science 277(5331): 1453-74) and DNA microarrays are available commercially for *E. coli* K12 (MWG Inc, High Point, N.C.). *E. coli* can be cultured in either a rich medium such as Luria-Bertani (LB) (10 g/L tryptone, 5 g/L NaCl, 5 g/L yeast extract) or a defined minimal medium such as M9 (6 g/L $Na_2HPO_4$, 3 g/L $KH_2PO_4$, 1 g/L $NH_4Cl$, 0.5 g/L NaCl, pH 7.4) with an appropriate carbon source such as 1% glucose. Routinely, an over night culture of *E. coli* cells is diluted and inoculated into fresh rich or minimal medium in either a shake flask or a fermentor and grown at 37° C.

A host cell can also be of mammalian origin, such as a cell derived from a mammal including any human or non-human mammal. Mammals can include, but are not limited to primates, monkeys, porcine, ovine, bovine, rodents, ungulates, pigs, swine, sheep, lambs, goats, cattle, deer, mules, horses, monkeys, apes, dogs, cats, rats, and mice.

A host cell may also be of plant origin. Cells from any plant can be selected in which to screen for the production of a heterologous protein of interest. Examples of suitable plant include, but are not limited to, alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassaya, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radiscchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. In some embodiments, plants useful in the method are *Arabidopsis*, corn, wheat, soybean, and cotton.

Kits

The present invention also provides kits useful for identifying a host strain, e.g. a *P. fluorescens* host strain, optimal for producing a heterologous protein or polypeptide of interest. The kit comprises a plurality of phenotypically distinct host cells, wherein each population has been genetically modified to increase the expression of one or more target genes involved in protein production, to decrease the expression of one or more target genes involved in protein degradation, or both. The array may further comprise one or more populations of cells that have not been genetically modified to modulate the expression of either a gene involved in protein production or a gene involved in protein degradation. These kits may also comprise reagents sufficient to facilitate growth and maintenance of the cell populations as well as reagents and/or constructs for expression of a heterologous protein or polypeptide of interest. The populations of host cells may be provided in the kit in any manner suitable for storage, transport, and reconstitution of cell populations. The cell populations may be provided live in a tube, on a plate, or on a slant, or may be preserved either freeze-dried or frozen in a tube or vial. The cell populations may contain additional components in the storage media such as glycerol, sucrose, albumin, or other suitable protective or storage agents.

The following examples are offered by way of illustration and not by way of limitation.

EXPERIMENTAL EXAMPLES

Overview

Heterologous protein production often leads to the formation of insoluble or improperly folded proteins, which are difficult to recover and may be inactive. Furthermore, the presence of specific host cell proteases may degrade the protein of interest and thus reduce the final yield. There is no single factor that will improve the production of all heterologous proteins. Thus, a method was sought to identify factors specific to a particular heterologous protein from a pool of likely candidates.

Using Systems Biology tools, the *P. fluorescens* genome was mined to identify host cell protein folding modulator and protease genes. Then, global gene expression analyses were performed to prioritize upregulated targets, and, thereafter, novel protein production strains were constructed. As a result, a "Pfēnex Strain Array" was assembled consisting of a plurality of phenotypically distinct *P. fluorescens* host strains that are deficient in host-cell proteases or allow the co-overexpression of protein folding modulators. This strain array can be used to screen for factors that specifically enhance the yield or quality of certain heterologous proteins. Providing a plurality of phenotypically distinct host strains increases the chance of success of identifying a host strain that will increase the production of any individual heterologous protein of interest.

This invention provides an improvement in the production of heterologous proteins in *Pseudomonas fluorescens*. Having available a library of host strains in the same genetic background allows the rapid screening and identification of factors that increase the yield and/or quality of heterologously expressed proteins. The genome sequence of *P. fluorescens* has been annotated and targeted host cell folding modulators and proteases have been identified. Folding modulators assist in the proper folding of proteins and include chaperones, chaperoning, peptidyl-proline isomerases (PPIases), and disulfide bond formation proteins. Proteases can degrade the protein of interest and thus affect heterologous protein yield and quality. Using background knowledge from the literature and DNA microarray analyses to identify likely targets, a list of about 80 target genes was assembled. In host cells that have the same genetic background, these genes were either removed from the genome or cloned into plasmids to enable co-overexpression along with heterologous proteins. The resulting strains were arrayed in 96-well format and, after transformation of plasmids that express the heterologous protein of interest, were screened for improved protein yield and/or quality.

Example 1

Identification of Folding Modulator Genes in the Genome of *P. fluorescens* Strain MB214

Folding modulators are a class of proteins present in all cells which aid in the folding, unfolding and degradation of nascent and heterologous polypeptides. Folding modulators include chaperones, chaperoning, peptidyl-prolyl cis-trans isomerases, and proteins involved in protein disulfide bond formation. As a first step to construct novel production strains with the ability to help fold heterologous proteins, the *P. fluorescens* genome was mined to identify host cell folding modulator genes.

Each of the 6,433 predicted ORFs of the *P. fluorescens* MB214 genome was analyzed for the possibility that they encoded a folding modulator using the following method. Several folding modulators of interest had already been identified by Dow researchers by analysis of the genome annotation (Ramseier et. al. 2001). Homologs of these starting proteins were identified using protein/protein BLAST with the starting protein as the query and a database of all MB214 translated ORFs as the subject. Those translated ORFs which matched the query proteins with significant homology were added to the list for further analysis. Significant homology is defined here as having an e-score of 1e-30 or less with allowances made for human judgment based on the length and quality of the alignment. The intention of this study was to be very inclusive to maximize the chance that all potential folding modulators would be identified.

More ORFs were added to the list based on their curated function from the previous annotation containing the keyword "chaperone". Finally, the ORFs were analyzed by the protein signature family searching program InterProScan (Quevillon et. al. 2005) against the InterPro Database version 7.0 (Mulder et. al. 2005). The ORFs were assigned protein families by the InterProScan software as well as Gene Ontology (GO) categories associated with those families (Gene Ontology Consortium. 2004). Using these automatic GO assignments, all of the ORFs which had been assigned the GO terms "GO:0006457 Biological Process: protein folding" or "GO:0003754 Molecular Function: chaperone activity" were added to the list for further analysis.

The list was then analyzed to remove ORFs which had a low probability of encoding folding modulators. Again, the intent of this study was to be very inclusive but many of the ORFs assigned to the list by these semi-automated methods could be easily identified as not coding for folding modulators based on limited criteria and human judgment.

The most common reason for excluding a certain ORF was the weak evidence that this ORF is actually a folding modulator, i.e. ORFs which had been assigned to the list based on the previous annotation where the reasoning for annotating the ORF as a folding modulator was either unclear or contradictory. InterProScan is actually a conglomerate of different programs and some of these programs are considered to be more reliable than others. If an ORF was assigned to the list based solely on the output of the ScanRegExp or ProfileScan components then it was removed. The final list of *P. fluorescens* folding modulators has 43 members and is shown in Table 1.

Example 2

Identification of Protease Genes in the Genome of *P. fluorescens* Strain MB214

Proteases are enzymes that hydrolyze peptide bonds and are necessary for the survival of all living creatures. However, their role in the cell means that proteases can be detrimental to recombinant protein yield and/or quality in any heterologous protein expression system, which also includes the Pfenex Expression Technology™. As a first step to construct novel production strains that have protease genes removed from the genome, the *P. fluorescens* genome was mined to identify host cell protease genes.

Each of the 6,433 predicted ORFs of the *P. fluorescens* MB214 genome were analyzed for the possibility that they encoded a protease using the following method. The MEROPS database is manually curated by researchers at the Wellcome Trust Sanger Institute, Cambridge, UK (Rawlings et. al., 2006, Nucleic Acids Research 34 (Database issue): D270-2). It is a comprehensive list of proteases discovered both through laboratory experiments as well as by homology to known protease families. One of the strengths of the database is the MEROPS hierarchical classification scheme. In this system, homologs which share the same function are grouped together into families. Families are grouped into clans based on evolutionary relatedness that again are based on similar structural characteristics. The method makes great use of the database to identify protease homologs within the *P. fluorescens* genome.

Homologs to the MEROPS database were identified using protein/protein BLAST with each MB214 translated ORF as the query and a database of all of the MEROPS proteins as the subject. Those translated ORFs, which matched the query proteins with significant homology, were added to the list for further analysis. Significant homology in this case is defined here as having an e-score of $1e^{-60}$ or less with allowances made for human judgment based on the length and quality of the alignment. This step yielded 109 potential proteases for the list.

The ORFs were also analyzed by the protein signature family searching program InterProScan (Quevillon et. al. 2005) against the InterPro Database version 7.0 (Mulder et. al. 2005). The ORFs were assigned protein families by the InterProScan software as well as Gene Ontology (GO) categories associated with those families (Gene Ontology Consortium. 2004). Using these automatic GO assignments, all of the ORFs which had been assigned a GO name that contained the strings "peptidase", "protease" or "proteolysis" were added to the list for further analysis. This step yielded an additional 70 potential proteases that had not been identified in the previous step.

More ORFs were added to the list based on their curated function from the previous annotation (Ramseier et. al. 2001) containing the keywords "peptidase" or "protease". This step yielded 32 potential proteases that again had not been identified in the previous steps.

The list was then analyzed to remove ORFs which had a low probability of encoding proteases. Again, the intent of this study was to be very inclusive but many of the ORFs assigned to the list by these semi-automated methods could be easily identified as not coding for proteases based on limited criteria and human judgment. The two most common reasons for excluding genes were the weak evidence that a certain ORF is actually a protease, or that a particular gene showed greatest homology with another protein known to be protease homolog but not a protease itself. The final list of *P. fluorescens* proteases has 90 members and is shown in Table 2.

Example 3

In Silico Cellular Location Prediction of the Folding Modulator and Protease Proteins One of the strengths of the Pfenex Expression Technology™ is its ability to control the cellular compartment to which a particular heterologous protein can be segregated. Thus, the cellular compartments where the identified host cell folding modulator and protease proteins are located were predicted. To make these predictions, two programs were chosen. PsortB 2.0 combines the results of 12 separate algorithms, which predict the subcellular location of a given peptide. The majority of the algorithms rely on detecting homology between the query protein and proteins of known subcellular localization. PsortB also includes algorithms such as HMMTOP and SignalP, which detect the presence of transmembrane folding domains or type I secretion signal sequences, respectively, using Hidden Markov Models (HMM). In addition to the PsortB results, SignalP HMM was used to predict the presence of type I secretion signal sequences. This was necessary because the output of PsortB can be vague when a signal sequence is detected but no other specific information indicating the subcellular location is given. In these cases, PsortB indicates that the subcellular localization of the protein is unknown, because it really could segregate to any one of the cytoplasmic membrane, periplasm, outer membrane or extracellular compartments. However, it is informative enough to know that the protein is probably not located in the cytoplasm to make it worth noting that in the table. Thus, Table 2 lists the results of the PsortB algorithm except in cases where that result was unknown. In these cases the result of SignalP HMM alone is given with "Signal Peptide" indicating that a signal peptide was detected and "Non Secretory" indicating that no signal peptide was detected.

Example 4

Construction of Plasmids that Enable the Co-Overexpression of Folding Modulators Folding modulator genes were cloned into a plasmid derivative of pCN (Nieto et al. 1990), which is compatible with another plasmid that routinely is used to express the heterologous protein of interest (Squires et al. 2004; Chew et al. 2005). The construction of a mannitol-inducible grpE-dnaKJ-containing plasmid is exemplified. Other folding modulators—either as a single gene or as multiple genes when organized in operons—were cloned similarly as outlined below.

Employing genomic DNA isolated from *P. fluorescens* MB214 (DNeasy; Qiagen, Valencia, Calif.) as a template and primers RC199 (5-ATATACTAGTAGGAGGTAACTTATGGCT-GACGAACAGACGCA-3') (SEQ ID NO:1) and RC200 (5'-ATATTCTAGATTACAGGTCGCCGAAGAAGC-3') (SEQ ID NO:2), the grpE-dnaKJ genes were amplified using PfuTurbo (Stratagene, La Jolla, Calif.) as per the manufacturer's recommendations. The resulting 4 kb PCR product was digested with SpeI and XbaI (restriction sites underlined in the primers above) and ligated into pDOW2236 which is a derivative of pDOW1306-6 (Schneider et al. 2005b) to create pDOW2240 containing the grpE-dnaKJ operon under control of the tac promoter. Plasmid pDOW2240 was then digested with SpeI and Hind III and the resulting grpE-dnaKJ-containing 4.0 kb DNA fragment was gel-purified using Qiaquick (Qiagen, Valencia, Calif.) and ligated into pDOW2247, which is a derivative of pCN carrying the *P. fluorescens* mannitol-regulated promoter (Schneider et al. 2005a), that was also digested with SpeI and HindIII. The resulting plasmid, pDOW3501, contained the grpE-dnaKJ operon under the control of the mannitol promoter. Plasmid pDOW3501 was then transformed into DC388 and other uracil-auxotrophic strains by selecting on M9 glucose plates supplemented with 250 ug/ml uracil.

Example 5

Figure 1B:
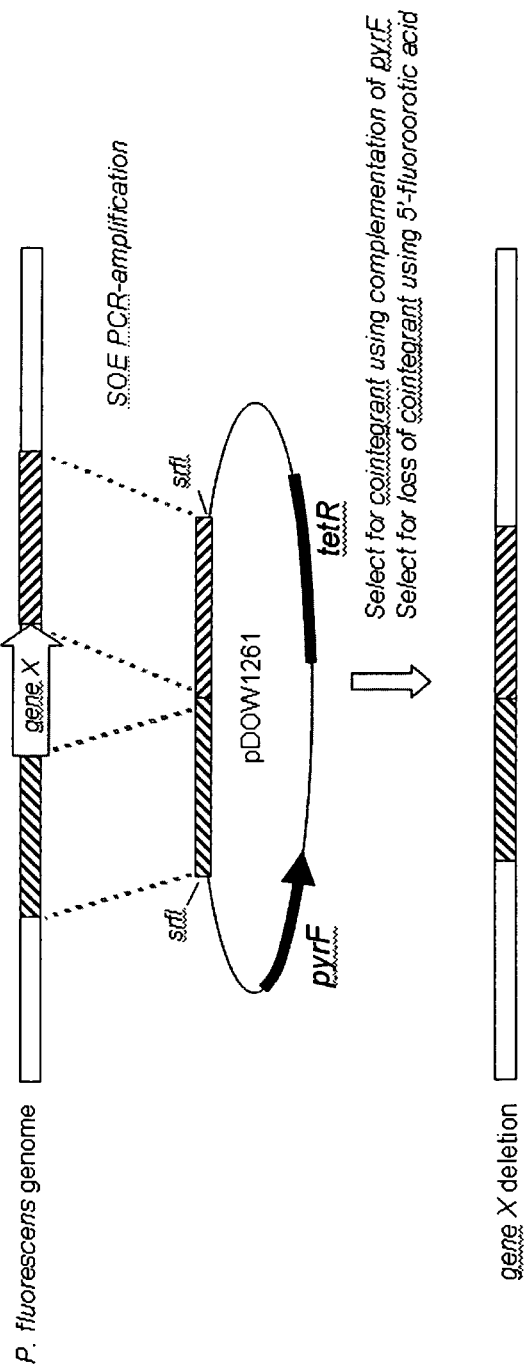
FIG. 1B is a schematic drawing of the constructions of a gene X deletion.

Construction of *P. fluorescens* Strains with Genomic Deletions of Protease Genes Plasmids that enabled the creation of genomic deletions were constructed by amplification of 500-1000 bp DNA fragments both 5' and 3' of the gene to be deleted. The resulting 5' PCR product typically ends with the translational initiation codon (ATG or GTG or TGT) of the gene to be deleted while the 3' PCR product typically begins with the stop codon (TAA or TGA or TAG) of the gene to be deleted. These two PCR products were fused together through an additional amplification step then cloned into pDOW1261 (FIG. 1) (Chew et al. 2005) using SOE PCR (Horton et al. 1990).

Example 6

Figure 2:
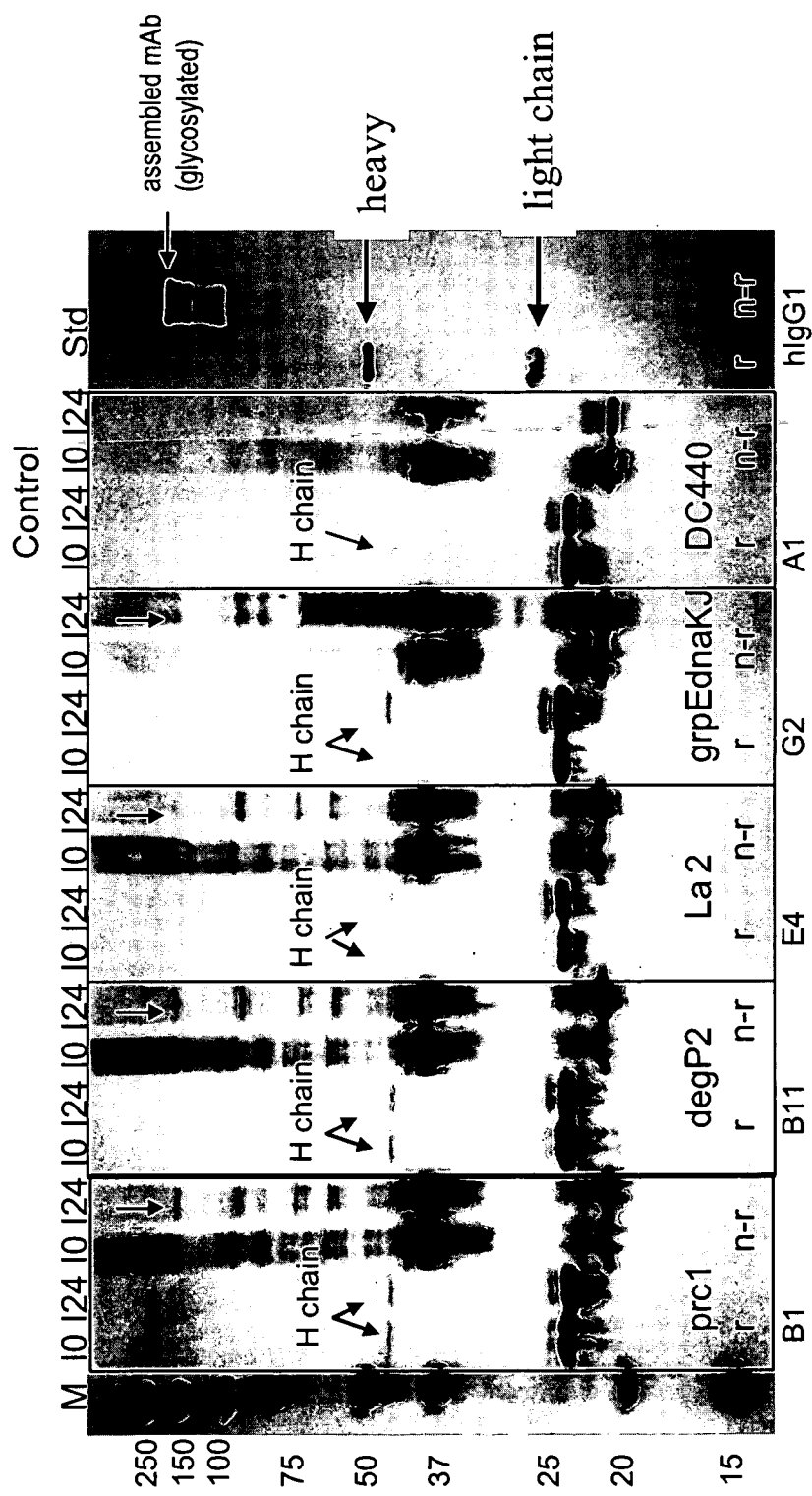
FIG. 2 is a Western blot analysis of soluble cells fractions prepared at 0 and 24 hours post-induction (I0 and I24, respectively) in Δprc1, ΔdegP2, ΔLa2 and the grpEdnaKJ co-expression strains (Example 6). The top arrows point to the fully assembled monoclonal antibody in the co-expressed strains but not in the control (DC440). r=recombinant; n-r=nonrecombinant.

High-Through-Put Growth and Analysis of Heterologous Protein Expression in *P. fluorescens* Strains Plasmid pDOW2787 encodes the monoclonal antibody (m-Ab) gal2; the heavy chain is expressed with a Pbp secretion leader and under control of the tac promoter. The light chain is expressed with an OprF secretion leader and under control of the mannitol promoter. The plasmid was electroporated into competent cells of 63 strains carrying either a directed gene deletion or pDOW2247 carrying a folding modulator for co-expression, and five control strains containing a wild type strain. Cells were cultured in replicate deep-well blocks containing growth medium with glycerol by shaking at 300 rpm. Protein expression was induced at 24 hrs with 0.1 mM isopropyl β-D-thiogalactopyranoside (IPTG) and 1% mannitol. At 24 hrs post-induction, aliquots were lysed, antigen-binding of the antigen was measured to quantitate amounts of active antibody. The value was divided by $OD_{600}$ to measure cell specific activity. Strains Δprc1, ΔdegP2, ΔLa2, ΔclpP, and Δprc2, Δprc2, the grpEdnaKJ co-expression strain, Δtig, ΔclpX, and Δlon were all 2.4-fold or more higher than the control strains, which was statistically significant ($p<0.5$). Soluble cells fractions were prepared from Δprc1, ΔdegP2, ΔLa2 and the grpEdnaKJ co-expression strain and subjected to Western analysis (FIG. 2). A band with a size consistent with fully assembled antibody was detected in the four test strains, but not in the control.

REFERENCES

Chew, L. C., T. M. Ramseier, D. M. Retallack, J. C. Schneider, C. H. Squires and H. W. Talbot (2005). *Pseudomonas fluorescens*. Production of Recombinant Proteins. Novel *Microbial and Eucaryotic Expression Systems*. G. Gellissen. Weinheim, WILEY-VCH: 45-66

Dolinski, K, Heitman, J. 1997. Peptidyl-prolyl isomerases—an overview of the cyclophilin, FKBP and parvulin families. in Guidebook to Molecular Chaperones and Protein-Folding Catalysts. Gething M-J. Ed. Oxford University Press Inc., New York: 359-369

Gardy, J. L., M. R. Laird, F. Chen, S. Rey, C. J. Walsh, M. Ester, and F. S. L. Brinkman 2005 PSORTb v.2.0: expanded prediction of bacterial protein subcellular localization and insights gained from comparative proteome analysis. Bioinformatics 21(5):617-623.

Gene Ontology Consortium. 2004. The Gene Ontology (GO) database and informatics resource. Nucleic Acids Research 32:D258-D261.

Gething M-J. Ed. 1997. Guidebook to Molecular Chaperones and Protein-Folding Catalysts. Oxford University Press Inc., New York.

Horton, R. M., Z. Cai, S, N. Ho and L. R. Pease (1990). "Gene splicing by overlap extension: tailor-made genes using the polymerase chain reaction." *BioTechniques* 8(5): 528-30, 532, 534-5

Lombardo, M-J, Thanassi, D G, Hultgren, S J. 1997. *Escherichia coli* PapD. in Guidebook to Molecular Chaperones and Protein-Folding Catalysts. Gething M-J. Ed. Oxford University Press Inc., New York: 463-465

Mulder N J, Apweiler R, Attwood T K, Bairoch A, Bateman A, Binns D, Bradley P, Bork P, Bucher P, Cerutti L, Copley R, Courcelle E, Das U, Durbin R, Fleischmann W, Gough J, Haft D, Harte N, Hulo N, Kahn D, Kanapin A, Krestyaminova M, Lonsdale D, Lopez R, Letunic I, Madera M, Maslen J, McDowall J, Mitchell A, Nikolskaya A N, Orchard S, Pagni M, Ponting C P, Quevillon E, Selengut J, Sigrist C J, Silventoinen V, Studholme D J, Vaughan R, Wu C H. 2005. InterPro, Progress and Status in 2005. Nucleic Acids Res. 33, Database Issue:D201-5.

Nieto, C., E. Femandez-Tresguerres, N. Sanchez, M. Vicente and R. Diaz (1990). "Cloning vectors, derived from a naturally occurring plasmid of *Pseudomonas savastanoi*, specifically tailored for genetic manipulations in *Pseudomonas*." Gene 87(1): 145-9.

Quevillon E., Silventoinen V., Pillai S., Harte N., Mulder N., Apweiler R., Lopez R. (2005) InterProScan: protein domains identifier. Nucleic Acids Research 33: W116-W120.

Ramseier T M, S. C., Payne J, Chew L, Rothman L D, Subramanian M. 2001. The *Pseudomonas fluorescens* MB214 Genome Sequence. CRI CRI2001001442; BIOTECH 01-007. The Dow Chemical Company.

Ranson, N A, White, H E, Saibil, H R. 1998. Chaperonins Biochem. J. 333, 233-242.

Rawlings, N. D., Morton, F. R. & Barrett, A. J. 2006. MEROPS: the peptidase database. Nucleic Acids Res 34, D270-D272.

Schneider, J. C., A. F. Jenings, D. M. Mun, P. M. McGovern and L. C. Chew (2005a). "Auxotrophic markers pyrF and proC can replace antibiotic markers on protein production plasmids in high-cell-density *Pseudomonas fluorescens* fermentation." Biotechnology Progress 21(2): 343-348.

Schneider, J. C., B. Rosner and A. Rubio (2005b). Mannitol Induced Promoter Systems in Bacterial Host Cells. USA, The Dow Chemical Company.

Squires, C. H., D. M. Retallack, L. C. Chew, T. M. Ramseier, J. C. Schneider and H. W. Talbot (2004). "Heterologous protein production in *P. fluorescens*." BioProcess International 2(11): 54-56, 58-59

Table of SEQ ID NOS:

| PROTEIN FOLDING MODULATOR (RXF#) | SEQ ID NO: | PROTEASE (RXF#) | SEQ ID NO: |
|---|---|---|---|
| RXF02095.1 | 3 | RXF00133.1 | 46 |
| RXF06767.1 | 4 | RXF00285.2 | 47 |
| RXF01748.1 | 5 | RXF00325.1 | 48 |
| RXF03385.1 | 6 | RXF00428.1 | 49 |
| RXF05399.1 | 7 | RXF00449.1 | 50 |
| RXF06954.1 | 8 | RXF00458.2 | 51 |
| RXF03376.1 | 9 | RXF00561.2 | 52 |
| RXF03987.2 | 10 | RXF00670.1 | 53 |
| RXF05406.2 | 11 | RXF00811.1 | 54 |
| RXF03346.2 | 12 | RXF01037.1 | 55 |
| RXF05413.1 | 13 | RXF01181.1 | 56 |
| RXF04587.1 | 14 | RXF01250.2 | 57 |
| RXF08347.1 | 15 | RXF01291.2 | 58 |
| RXF04654.2 | 16 | RXF01418.1 | 59 |
| RXF04663.1 | 17 | RXF01590.2 | 60 |
| RXF01957.2 | 18 | RXF01816.1 | 61 |
| RXF01961.2 | 19 | RXF01822.2 | 62 |
| RXF04254.2 | 20 | RXF01918.1 | 63 |
| RXF05455.2 | 21 | RXF01919.1 | 64 |
| RXF02231.1 | 22 | RXF01961.2 | 65 |
| RXF07017.2 | 23 | RXF01968.1 | 66 |
| RXF08657.2 | 24 | RXF02003.2 | 67 |
| RXF01002.1 | 25 | RXF02151.2 | 68 |
| RXF03307.1 | 26 | RXF02161.1 | 69 |
| RXF04890.2 | 27 | RXF02342.1 | 70 |
| RXF03768.1 | 28 | RXF02492.1 | 71 |
| RXF05345.2 | 29 | RXF02689.2 | 72 |
| RXF06034.2 | 30 | RXF02739.1 | 73 |
| RXF06591.1 | 31 | RXF02796.1 | 74 |
| RXF05753.2 | 32 | RXF02980.1 | 75 |
| RXF01833.2 | 33 | RXF03065.2 | 76 |
| RXF04655.2 | 34 | RXF03329.2 | 77 |
| RXF05385.1 | 35 | RXF03364.1 | 78 |
| RXF00271.1 | 36 | RXF03397.1 | 79 |
| RXF06068.1 | 37 | RXF03441.1 | 80 |
| RXF05719.1 | 38 | RXF03488.2 | 81 |
| RXF03406.2 | 39 | RXF03699.2 | 82 |
| RXF04296.1 | 40 | RXF03916.1 | 83 |
| RXF04553.1 | 41 | RXF04047.2 | 84 |
| RXF04554.2 | 42 | RXF04052.2 | 85 |
| RXF05310.2 | 43 | RXF04304.1 | 86 |
| RXF05304.1 | 44 | RXF04424.2 | 87 |
| RXF05073.1 | 45 | RXF04495.2 | 88 |
| RXF02090 | 137 | RXF04500.1 | 89 |
| | | RXF04567.1 | 90 |
| | | RXF04631.2 | 91 |
| | | RXF04653.2 | 92 |
| | | RXF04657.2 | 93 |
| | | RXF04663.1 | 94 |
| | | RXF04692.1 | 95 |
| | | RXF04693.1 | 96 |
| | | RXF04715.1 | 97 |
| | | RXF04802.1 | 98 |
| | | RXF04808.2 | 99 |
| | | RXF04920.1 | 100 |
| | | RXF04923.1 | 101 |
| | | RXF04960.2 | 102 |
| | | RXF04968.2 | 103 |
| | | RXF04971.2 | 104 |
| | | RXF05081.1 | 105 |
| | | RXF05113.2 | 106 |
| | | RXF05137.1 | 107 |
| | | RXF05236.1 | 108 |
| | | RXF05379.1 | 109 |
| | | RXF05383.2 | 110 |
| | | RXF05400.2 | 111 |
| | | RXF05615.1 | 112 |
| | | RXF05817.1 | 113 |
| | | RXF05943.1 | 114 |
| | | RXF06281.1 | 115 |
| | | RXF06308.2 | 116 |
| | | RXF06399.2 | 117 |
| | | RXF06451.1 | 118 |
| | | RXF06564.1 | 119 |
| | | RXF06586.1 | 120 |
| | | RXF06755.2 | 121 |
| | | RXF06993.2 | 122 |
| | | RXF07170.1 | 123 |
| | | RXF07210.1 | 124 |
| | | RXF07879.1 | 125 |
| | | RXF08136.2 | 126 |
| | | RXF08517.1 | 127 |
| | | RXF08627.2 | 128 |
| | | RXF08653.1 | 129 |
| | | RXF08773.1 | 130 |
| | | RXF08978.1 | 131 |
| | | RXF09091.1 | 132 |
| | | RXF09147.2 | 133 |
| | | RXF09487.1 | 134 |
| | | RXF09831.2 | 135 |
| | | RXF04892.1 | 136 |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for identifying an optimal population of *Pseudomonas fluorescens* (*P. fluorescens*) host cells for expression of at least one heterologous protein of interest comprising:
   a) assembling a strain array comprising at least four populations of *P. fluorescens* host cells, wherein each population of *P. fluorescens* host cells in the strain array is selected from the group consisting of:
      i) a population of *P. fluorescens* host cells that has been genetically modified to reduce the expression of at least one target gene encoding a protease, wherein the protease is an aminopeptidase, a dipeptidase, a dipeptidyl-peptidase, a tripeptidyl peptidase, a peptidyl-dipeptidase, a serine-type carboxypeptidase, a metallocarboxypeptidase, a cysteine-type carboxypeptidase, an omegapeptidase, a serine proteinase, a threonine proteinase, a cysteine proteinase, an aspartic proteinase, or a metalloproteinase;
      ii) a population of *P. fluorescens* host cells that has been genetically modified to increase the expression of at least one target gene encoding a protein that modulates protein processing, folding or translocation, wherein the protein that modulates protein processing, folding or translocation is a chaperone, a disulfide bond isomerase, a peptidyl-prolyl cis-trans isomerase, a GroES/EL folding modulator, a DnaKJ folding modulator, a Clp folding modulator, an Hsp90 folding modulator, a SecB folding modulator, a PapD chaperone, an HSP70 protein, an HSP110/SSE protein, an HSP40 (DNAJ-related) protein, a GRPE-like protein, an HSP90 protein, a CPN60 protein, a CPN10 protein, an HSP100 protein, a small HSP, a calnexin, a calreticulin, a PDI-related protein, a thioredoxin-related protein, a cyclophilin PPIase, a FK-506 binding protein, or parvulin PPIase; and,
      iii) a population of *P. fluorescens* host cells that has been genetically modified to reduce the expression of at least one target gene encoding a protease, wherein the protease is an aminopeptidase, a dipeptidase, a dipeptidyl-peptidase, a tripeptidyl peptidase, a peptidyl-dipeptidase, a serine-type carboxypeptidase, a metallocarboxypeptidase, a cysteine-type carboxypeptidase, an omegapeptidase, a serine proteinase, a threonine proteinase, a cysteine proteinase, an aspartic proteinase, or a metalloproteinase, and to increase the expression of at least one target gene encoding a protein that modulates protein processing, folding or translocation, wherein the protein that modulates protein processing, folding or translocation is a chaperone, a disulfide bond isomerase, a peptidyl-prolyl cis-trans isomerase, a GroES/EL folding modulator, a DnaKJ folding modulator, a Clp folding modulator, an Hsp90 folding modulator, a SecB folding modulator, a PapD chaperone, an HSP70 protein, an HSP110/SSE protein, an HSP40 (DNAJ-related) protein, a GRPE-like protein, an HSP90 protein, a CPN60 protein, a CPN10 protein, an HSP100 protein, a small HSP, a calnexin, a calreticulin, a PDI-related protein, a thioredoxin-related protein, a cyclophilin PPIase, a FK-506 binding protein, or parvulin PPIase;
   wherein each population of *P. fluorescens* host cells in the strain array is non-identical and wherein each population of *P. fluorescens* host cells in the strain array is physically separate one from another;
   b) introducing into at least one cell of each of the at least four populations of *P. fluorescens* host cells in the strain array an expression cassette comprising at least one gene encoding the at least one heterologous protein of interest,
   wherein when the population of *P. fluorescens* host cells into which the expression cassette is introduced has been genetically modified to reduce the expression of at least one target gene encoding a protease as set forth in (i), the gene encoding the heterologous protein of interest does not encode the protease of (i),
   and wherein when the population of *P. fluorescens* host cells into which the expression cassette is introduced has been genetically modified to increase the expression of at least one target gene encoding a protein that modulates protein processing, folding or translocation as set forth in (ii), the gene encoding the heterologous protein of interest does not encode the protein that modulates protein processing, folding or translocation of (ii),
   and wherein when the population of *P. fluorescens* host cells has been genetically modified to reduce the expression of at least one target gene encoding a protease, and to increase the expression of at least one target gene encoding a protein that modulates protein processing, folding or translocation as set forth in (iii), the gene encoding the heterologous protein of interest does not encode the protease of (i) or the protein that modulates protein processing, folding or translocation of (ii);
   c) maintaining the populations of *P. fluorescens* host cells in the strain array under conditions sufficient for the expression of said heterologous protein of interest encoded by the gene encoding the at least one heterologous protein of interest, in the at least four populations of *P. fluorescens* host cells in the strain array, and expressing said heterologous protein of interest encoded by the gene encoding the at least one heterologous protein of interest, in the at least four populations of *P. fluorescens* host cells in the strain array; and,
   d) selecting the optimal population of *P. fluorescens* host cells in the strain array in which the heterologous protein of interest encoded by the gene encoding the at least one heterologous protein of interest is produced, by simultaneous screening of the at least four populations of *P. fluorescens* host cells in the strain array;
   wherein the heterologous protein of interest encoded by the gene encoding the at least one heterologous protein of interest exhibits one or more of improved expression, improved activity, improved solubility, improved translocation, or reduced proteolytic degradation in the optimal population of *P. fluorescens* host cells compared to other populations of *P. fluorescens* host cells in the strain array.

2. The method of claim 1, wherein said protease is encoded by SEQ ID NO: 110, SEQ ID NO: 109, SEQ ID NO: 69, SEQ ID NO: 66, SEQ ID NO: 100, SEQ ID NO: 101, SEQ ID NO: 61, SEQ ID NO: 130, SEQ ID NO: 52, SEQ ID NO: 91, SEQ ID NO: 106, SEQ ID NO: 111, SEQ ID NO: 86, SEQ ID NO: 89, SEQ ID NO: 60, SEQ ID NO: 88, SEQ ID NO: 74, SEQ ID NO: 132, SEQ ID NO: 80, SEQ ID NO: 63, SEQ ID NO: 64, SEQ ID NO: 82, SEQ ID NO: 47, SEQ ID NO: 125, SEQ ID NO: 54, SEQ ID NO: 85, SEQ ID NO: 62, SEQ ID NOS: 135 and 136, SEQ ID NO: 81, SEQ ID NO: 112, SEQ ID NO: 113, SEQ ID NO: 76, SEQ ID NO: 58, SEQ ID NO: 83, SEQ ID NO: 133, SEQ ID NO: 96, SEQ ID NO: 78, SEQ ID NO: 75, SEQ ID NO: 119, SEQ ID NO: 107, SEQ ID NO: 105, SEQ ID NO: 95, SEQ ID NO: 57, SEQ ID NO: 124, SEQ ID NO: 121, SEQ ID NO: 127, SEQ ID NO: 128, SEQ ID NO: 115, SEQ ID NO: 131, SEQ ID NO: 118, SEQ ID NO: 67, SEQ ID NO: 51, SEQ ID NO: 93, SEQ ID NO: 53, SEQ ID NO: 46, SEQ ID NO: 102, SEQ ID NO: 90, SEQ ID NO: 94, SEQ ID NO: 92, SEQ ID NO: 129, SEQ ID NO: 114, SEQ ID NO: 50, SEQ ID NO: 79, SEQ ID NO: 56, SEQ ID NO: 108, SEQ ID NO: 98, SEQ ID NO: 99, SEQ ID NO: 120, SEQ ID NO: 55, SEQ ID NO: 123, SEQ ID NO: 117, SEQ ID NO: 122, SEQ ID NO: (59), SEQ ID NO: 116, SEQ ID NO: 19, SEQ ID NO: 70, SEQ ID NO: 87, SEQ ID NO: 49, SEQ ID NO: 68, SEQ ID NO: 97, SEQ ID NO: 104, SEQ ID NO: 103, SEQ ID NO: 48, SEQ ID NO:72, SEQ ID NO: 73, SEQ ID NO: 77, SEQ ID NO: 71, SEQ ID NO:84, SEQ ID NO:126, or SEQ ID NO:134.

3. The method of claim 1, wherein the protein that modulates protein processing, folding or translocation is a protein folding modulator.

4. The method of claim 3, wherein the protein folding modulator is encoded by SEQ ID NO: 3, SEQ ID NOS: 4 and 137, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, or SEQ ID NO: 45.

5. The method of claim 1, wherein the array further comprises at least one population of *P. fluorescens* host cells that has not been genetically modified to increase the expression of said target gene encoding a protein that modulates protein processing, folding or translocation or to reduce the expression of the target gene encoding a protease.

6. The method of claim 1, wherein each of said at least four *P. fluorescens* host cell populations has been genetically modified to increase the expression of two or more target genes, said target genes each encoding a different protein that modulates protein processing, folding or translocation.

7. The method of claim 1, wherein each of said at least four *P. fluorescens* host cell populations has been genetically modified to reduce the expression of two or more target genes, said target genes each encoding a different protease.

8. The method of claim 1, wherein said array is in a format that allows high throughput screening of said array.

9. The method of claim 8, wherein said format is a 96-well format.

10. The method of claim 1, wherein said expression cassette further comprises a signaling peptide operably linked to the heterologous protein of interest.

11. The method of claim 10, wherein said signaling peptide is a secretion signal peptide.

12. The method of claim 10, wherein said signaling peptide is native to the *Pseudomonas fluorescens* host cell into which the expression cassette is introduced according to step (b).

13. The method of claim 1, wherein the array comprises at least one population of *P. fluorescens* host cells that has not been genetically modified to alter the expression of a host cell protease or a protein folding modulator.

* * * * *